United States Patent
Bacon et al.

(10) Patent No.: US 10,035,809 B2
(45) Date of Patent: Jul. 31, 2018

(54) SUBSTITUTED 2,3,4,5,7,9,13,13A-OCTAHYDRO-1,5-METHANOPYRIDO[1',2':4,5]PYRAZINO[1,2-A][1,3]DIAZEPINES AND METHODS FOR TREATING VIRAL INFECTIONS

(71) Applicant: Gilead Sciences, Inc., Foster City, CA (US)

(72) Inventors: Elizabeth M. Bacon, Burlingame, CA (US); Zhenhong R. Cai, Palo Alto, CA (US); Xiaowu Chen, Hillsborough, CA (US); Jeromy J. Cottell, Redwood City, CA (US); Manoj C. Desai, Foster City, CA (US); Mingzhe Ji, Union City, CA (US); Haolun Jin, Foster City, CA (US); Scott E. Lazerwith, Burlingame, CA (US); Michael R. Mish, Foster City, CA (US); Philip Anthony Morganelli, Oakland, CA (US); Hyung-Jung Pyun, Fremont, CA (US); James G. Taylor, Burlingame, CA (US); Teresa Alejandra Trejo Martin, Belmont, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/599,151

(22) Filed: May 18, 2017

(65) Prior Publication Data
US 2017/0260204 A1    Sep. 14, 2017

Related U.S. Application Data

(63) Continuation of application No. 15/349,934, filed on Nov. 11, 2016, now Pat. No. 9,732,092, which is a continuation of application No. 14/815,504, filed on Jul. 31, 2015, now Pat. No. 9,663,528, which is a continuation of application No. 14/133,858, filed on Dec. 19, 2013, now Pat. No. 9,216,996.

(60) Provisional application No. 61/845,803, filed on Jul. 12, 2013, provisional application No. 61/788,397, filed on Mar. 15, 2013, provisional application No. 61/745,375, filed on Dec. 21, 2012.

(51) Int. Cl.
| | |
|---|---|
| A61K 31/4985 | (2006.01) |
| C07D 487/04 | (2006.01) |
| C07D 498/14 | (2006.01) |
| A61K 31/537 | (2006.01) |
| C07D 471/22 | (2006.01) |
| A61K 31/529 | (2006.01) |
| A61K 31/551 | (2006.01) |
| A61K 31/553 | (2006.01) |
| C07D 471/18 | (2006.01) |
| A61K 45/06 | (2006.01) |
| C07D 498/18 | (2006.01) |
| C07D 487/14 | (2006.01) |
| A61K 31/498 | (2006.01) |

(52) U.S. Cl.
CPC .......... C07D 498/14 (2013.01); A61K 31/498 (2013.01); A61K 31/529 (2013.01); A61K 31/537 (2013.01); A61K 31/551 (2013.01); A61K 31/553 (2013.01); A61K 45/06 (2013.01); C07D 471/18 (2013.01); C07D 471/22 (2013.01); C07D 487/14 (2013.01); C07D 498/18 (2013.01)

(58) Field of Classification Search
CPC .......................... A61K 31/4985; C07D 487/04
USPC .......................................... 514/250; 544/346
See application file for complete search history.

(56) References Cited

U.S. PATENT DOCUMENTS

| | | | |
|---|---|---|---|
| 5,814,639 | A | 9/1998 | Liotta et al. |
| 5,914,331 | A | 6/1999 | Liotta et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 6,043,230 | A | 3/2000 | Arimilli et al. |

(Continued)

FOREIGN PATENT DOCUMENTS

| | | |
|---|---|---|
| DE | 2244012 A1 | 3/1973 |
| DE | 2552871 A1 | 7/1976 |

(Continued)

OTHER PUBLICATIONS

Agrawal, et al. (2012) "Probing Chelation Motifs in HIV Integrase Inhibitors" Proc. Natl. Acad. Sci. U.S.A.; 109(7): 2251-2256.

(Continued)

Primary Examiner — Douglas M Willis

(57) ABSTRACT

Compounds for use in the treatment of human immunodeficiency virus (HIV) infection are disclosed. The compounds have the following Formula (I):

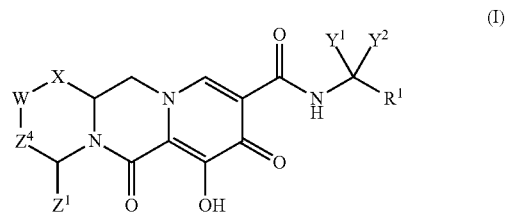

including stereoisomers and pharmaceutically acceptable salts thereof, wherein $R^1$, X, W, $Y^1$, $Y^2$, $Z^1$, and $Z^4$ are as defined herein. Methods associated with preparation and use of such compounds, as well as pharmaceutical compositions comprising such compounds, are also disclosed.

3 Claims, No Drawings

(56) References Cited

U.S. PATENT DOCUMENTS

| | | |
|---|---|---|
| 6,620,841 B1 | 9/2003 | Fujishita et al. |
| 6,642,245 B1 | 11/2003 | Liotta et al. |
| 6,703,396 B1 | 3/2004 | Liotta et al. |
| 7,176,220 B2 | 2/2007 | Satoh et al. |
| 7,419,969 B2 | 9/2008 | Naidu et al. |
| 7,550,463 B2 | 6/2009 | Yoshida |
| 7,635,704 B2 | 12/2009 | Satoh et al. |
| 7,858,788 B2 | 12/2010 | Yoshida et al. |
| 8,129,385 B2 | 3/2012 | Johns et al. |
| 8,148,374 B2 | 4/2012 | Desai et al. |
| 8,188,271 B2 | 5/2012 | Yoshida et al. |
| 8,410,103 B2 | 4/2013 | Johns et al. |
| 8,592,397 B2 | 11/2013 | Dahl et al. |
| 8,598,185 B2 | 12/2013 | Dahl et al. |
| 8,633,219 B2 | 1/2014 | Matsuzaki et al. |
| 8,716,264 B2 | 5/2014 | Dahl et al. |
| 8,778,943 B2 | 7/2014 | Johns et al. |
| 8,841,310 B2 | 9/2014 | Stoffels |
| 8,981,103 B2 | 3/2015 | Ando et al. |
| 8,987,441 B2 | 3/2015 | Takahashi et al. |
| 9,018,192 B2 | 4/2015 | Dahl et al. |
| 9,051,337 B2 | 6/2015 | Johns et al. |
| 9,216,996 B2 | 12/2015 | Jin et al. |
| 9,457,036 B2 | 10/2016 | Dahl et al. |
| 9,545,414 B2 | 1/2017 | Dahl et al. |
| 9,663,528 B2 | 5/2017 | Desai et al. |
| 9,682,084 B2 | 6/2017 | Carra et al. |
| 9,708,342 B2 | 7/2017 | Carra et al. |
| 9,732,092 B2 | 8/2017 | Jin et al. |
| 2005/0054645 A1 | 3/2005 | Miyazaki et al. |
| 2005/0137224 A1 | 6/2005 | Shima et al. |
| 2006/0086401 A1 | 4/2006 | Sato |
| 2007/0072831 A1 | 3/2007 | Cai et al. |
| 2007/0117848 A1 | 5/2007 | Puerta et al. |
| 2007/0219243 A1 | 9/2007 | Kearney et al. |
| 2008/0020010 A1 | 1/2008 | Nair et al. |
| 2008/0139579 A1 | 6/2008 | Morrissette et al. |
| 2008/0161271 A1 | 7/2008 | Yoshida et al. |
| 2008/0200435 A1 | 8/2008 | Stoffels |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318702 A1 | 12/2009 | Matsuda et al. |
| 2010/0068695 A1 | 3/2010 | Kiyama et al. |
| 2010/0285122 A1 | 11/2010 | Oliyai et al. |
| 2012/0022251 A1 | 1/2012 | Sumino et al. |
| 2012/0108564 A1 | 5/2012 | Miyazaki et al. |
| 2012/0232117 A1 | 9/2012 | Bae et al. |
| 2013/0006485 A1 | 1/2013 | Kwasniewski |
| 2013/0243857 A1 | 9/2013 | Oliyai et al. |
| 2014/0011995 A1 | 1/2014 | Sumino et al. |
| 2014/0094605 A1 | 4/2014 | Yoshida et al. |
| 2014/0142070 A1 | 5/2014 | Delaet et al. |
| 2014/0213556 A1 | 7/2014 | Dahl et al. |
| 2014/0221355 A1 | 8/2014 | Lazerwith et al. |
| 2014/0221356 A1 | 8/2014 | Jin et al. |
| 2014/0221378 A1 | 8/2014 | Miyazaki et al. |
| 2014/0243521 A1 | 8/2014 | Yoshida et al. |
| 2014/0256937 A1 | 9/2014 | Akiyama |
| 2014/0349971 A1 | 11/2014 | Stoffels |
| 2015/0111856 A1 | 4/2015 | Dahl et al. |
| 2015/0150810 A1 | 6/2015 | Oliyai et al. |
| 2015/0232479 A1 | 8/2015 | Johns et al. |
| 2015/0283135 A1 | 10/2015 | Stoffels |
| 2016/0137666 A1 | 5/2016 | Johns et al. |
| 2016/0194335 A1 | 7/2016 | Jin et al. |
| 2016/0207939 A1 | 7/2016 | Johns et al. |
| 2016/0304535 A1 | 10/2016 | Johns et al. |
| 2017/0000807 A1 | 1/2017 | Koziara et al. |
| 2017/0027967 A1 | 2/2017 | Koziara et al. |
| 2017/0079999 A1 | 3/2017 | Dahl et al. |
| 2017/0114074 A1 | 4/2017 | Jin et al. |
| 2017/0197985 A1 | 7/2017 | Carra et al. |

FOREIGN PATENT DOCUMENTS

| | | |
|---|---|---|
| DE | 2658401 A1 | 7/1978 |
| EP | 0154199 A2 | 9/1985 |
| EP | 0378067 A2 | 7/1990 |
| EP | 0456073 A2 | 11/1991 |
| EP | 1422218 A1 | 5/2004 |
| EP | 1544199 A1 | 6/2005 |
| EP | 1874117 A1 | 1/2008 |
| EP | 2412709 A1 | 2/2012 |
| EP | 2465580 A1 | 6/2012 |
| EP | 2527007 A1 | 11/2012 |
| EP | 2602260 A1 | 6/2013 |
| GB | 2345058 A | 6/2000 |
| WO | WO-1994/017090 A1 | 8/1994 |
| WO | WO-1999/005142 A1 | 2/1999 |
| WO | WO-1999/25345 A1 | 5/1999 |
| WO | WO-2000/027823 A1 | 5/2000 |
| WO | WO-2003/030897 A1 | 4/2003 |
| WO | WO-2003/035077 A1 | 5/2003 |
| WO | WO-2004/004657 A2 | 1/2004 |
| WO | WO-2004/024078 A2 | 3/2004 |
| WO | WO-2005/016927 A1 | 2/2005 |
| WO | WO-2005/042533 A2 | 5/2005 |
| WO | WO-2005/074513 A2 | 8/2005 |
| WO | WO-2005/110399 A2 | 11/2005 |
| WO | WO-2005/110414 A1 | 11/2005 |
| WO | WO-2005/112930 A1 | 12/2005 |
| WO | WO-2005/113508 A1 | 12/2005 |
| WO | WO-2005/113509 A1 | 12/2005 |
| WO | WO-2006/028523 A2 | 3/2006 |
| WO | WO-2006/030807 A1 | 3/2006 |
| WO | WO-2006/066414 A1 | 6/2006 |
| WO | WO-2006/088173 A1 | 8/2006 |
| WO | WO-2006/116764 A1 | 11/2006 |
| WO | WO-2007/014352 A2 | 2/2007 |
| WO | WO-2007/049675 A1 | 5/2007 |
| WO | WO-2007/079260 A1 | 7/2007 |
| WO | WO-2007/089030 A1 | 8/2007 |
| WO | WO-2007-092681 A1 | 8/2007 |
| WO | WO-2007/102499 A1 | 9/2007 |
| WO | WO-2007/102512 A1 | 9/2007 |
| WO | WO-2008/002959 A2 | 1/2008 |
| WO | WO-2008/033836 A2 | 3/2008 |
| WO | WO-2008/048538 A1 | 4/2008 |
| WO | WO-2009/006199 A1 | 1/2009 |
| WO | WO-2009/006203 A1 | 1/2009 |
| WO | WO-2009/018320 A1 | 2/2009 |
| WO | WO-2009/018350 A1 | 2/2009 |
| WO | WO-2009/036161 A1 | 3/2009 |
| WO | WO-2009/103950 A1 | 8/2009 |
| WO | WO-2010/011812 A1 | 1/2010 |
| WO | WO-2010/011813 A1 | 1/2010 |
| WO | WO-2010/011814 A1 | 1/2010 |
| WO | WO-2010/011815 A1 | 1/2010 |
| WO | WO-2010/011816 A1 | 1/2010 |
| WO | WO-2010/011818 A1 | 1/2010 |
| WO | WO-2010/011819 A1 | 1/2010 |
| WO | WO-2010/068253 A1 | 6/2010 |
| WO | WO-2010/068262 A1 | 6/2010 |
| WO | WO-2010/110231 A1 | 9/2010 |
| WO | WO-2010/110409 A1 | 9/2010 |
| WO | WO-2010/147068 A1 | 12/2010 |
| WO | WO-2011/094150 A1 | 8/2011 |
| WO | WO-2011/105590 A1 | 9/2011 |
| WO | WO-2011/119566 A1 | 9/2011 |
| WO | WO-2012/009009 A2 | 1/2012 |
| WO | WO-2012/018065 A1 | 2/2012 |
| WO | WO-2012/039414 A1 | 3/2012 |
| WO | WO-2012/106534 A2 | 8/2012 |
| WO | WO-2012/151361 A1 | 11/2012 |
| WO | WO-2012/151567 A1 | 11/2012 |
| WO | WO-2013/038407 A1 | 3/2013 |
| WO | WO-2013/054862 A1 | 4/2013 |
| WO | WO-2013/087581 A1 | 6/2013 |
| WO | WO-2014/008636 A1 | 1/2014 |
| WO | WO-2014/011769 A1 | 1/2014 |
| WO | WO-2014/014933 A1 | 1/2014 |
| WO | WO-2014/018449 A1 | 1/2014 |

(56) References Cited

FOREIGN PATENT DOCUMENTS

| | | |
|---|---|---|
| WO | WO-2014/022707 A1 | 2/2014 |
| WO | WO-2014/074675 A1 | 5/2014 |
| WO | WO-2014/093941 A1 | 6/2014 |
| WO | WO-2014/099586 A1 | 6/2014 |
| WO | WO-2014/100077 A1 | 6/2014 |
| WO | WO-2014/100323 A1 | 6/2014 |
| WO | WO-2014/104279 A1 | 7/2014 |
| WO | WO-2014/200880 A1 | 12/2014 |
| WO | WO-2015/006731 A1 | 1/2015 |
| WO | WO-2015/006733 A1 | 1/2015 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |
| WO | WO-2015/110897 A2 | 7/2015 |
| WO | WO-2015/195656 A2 | 12/2015 |
| WO | WO-2015/196116 A1 | 12/2015 |
| WO | WO-2015/196137 A1 | 12/2015 |

OTHER PUBLICATIONS

Agrawal, et al., Protocols for Oligonucleotide Conjugates, Eds, Humana Press; New Jersey, 1994; vol. 26 pp. 1-72.
AIDS treatment Guidelines (2013)—"AIDS info Guidelines for the Use of Antiretroviral Agents in HIV-1-Infected Adults and Adolescents," [downloaded from http://aidsinfo.nih.gov/guidelines on Mar. 15, 2013], 267 pages.
Akiyama, et al. (2013) "Discovery of Novel HIV Integrase Inhibitors Part 2. Selection and Evaluation of an Azabicylic Carbamoyl Pyridone as apre-Clinical Candidate" Poster, American Chemical Society National Meeting and Exposition; Apr. 7-11; New Orleans, LA.
Andrews, C. et al. (2014) "Long-Acting Integrase Inhibitor Protects Macaques from Intrarectal Simian/Human Immunodeficiency Virus," Science 343:1151-1154.
Atsushi M. et al. (2001) "Regioselective Oxygenations of S—Trans Dienes, Silyl Dienol Ethers (SDEs), by Triphenyl Phosphite Ozonide (TPPO) and It's Mechanistic Study" The Journal of Organic Chemistry 66(10): 3548-3553.
Barrow J. C. et al (2000) "Preparation and Evaluation of 1, 3-diaminocyclopentane-linked dihydropyrimidinone derivatives as selective alphala-receptor antagonists" Bioorganic & Medicinal Chemistry Letters, Pergamon, Amsterdam, NL 10(17): 1917-1920.
Bisel, P. et al. (1998) "Diastereoselective .alpha.-iminoamine rearrangement: asymmetric synthesis of (R)-(-)- and (S)-(-)-2-benzyl-2-hydroxycyclohexanone" Tetrahedron: Asymmetry 9:4027-4034.
Brehm et. al. (1954) "The Relative Acidifying Influence of Oxygen and Sulfur Atoms on α—Hydrogen Atoms" 76:5389-5391.
Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6, 2013; Atlanta, GA.
Brocklehurst C.E. et al. (2011) "Diastereoisomeric Salt Formation and Enzyme-Catalyzed Kinetic Resolution as Complementary Methods for the Chiral Separation of cis -/ trans—Enantiomers of 3-Aminocyclohexanol" Organic Process Research and Development, 15(1): 294-300.
Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.
Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.
Castagna, A. et al. (2014) "Dolutegravir in Antiretroviral-Experienced Patients With Raltegravir-and/or Elvitegravir-Resistant HIV-1: 24-Week Results of the Phase III Viking-3 Study" Infectious Diseases Society of America Journal of InfectiousDiseases 210:354-62.
Castellino, S., et al., (2013), "Metabolism, Excretion, and Mass Balance of the HIV-1 Integrase Inhibitor Dolutegravir in Humans", Antimicrobial Agents and Chemother., 57:3536-46.
Chen, D. et al. (2003) "New C19-diterpenoid alkaloids from the roots of Aconitum transsecutum" Abstract, Huaxue Xuebao 61(6):901-906.
Chen, S. et al. (2014) "Evaluation of the effect of UGT1A1 polymorphisms on dolutegravir pharmacokinetics" Pharmacogenomics, 15(1):9-16.
Chorell, E et al. (2012) "Design and Synthesis of Fluorescent Pilicides and Curlicides: Bioactive Tools to Study Bacterial Virulence Mechanisms" Chemistry—A European Journal, 18(15): 4522-4532.
Clotet, G. et al. (2014) "Once-daily dolutegravir versus darunavir plus ritonavir in antiretroviral-naive adults with HIV-1 infection (Flamingo) 48 week results from the randomised open-label phase 3b study", Lancet, 383:2222-31.
Cohen, J. et al. (2014) "A Bid to Thwart HIV With Shot of Long-Lasting Drug" Science 343:1067.
Cottrell, M. et al. (2013) "Clinical Pharmacokinetic, Pharmacodynamic and Drug-Interaction Profile of the Integrase Inhibitor Dolutegravir" Clin Pharmacokinet 52:981-994.
Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.
Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From Spring-2 (ING113086) and Single (ING114467)"Poster No. CUPE 282, 7.sup.th IAS Conference on HIV Pathogenesis, Treatment and Prevention; Jun. 30-Jul. 3; Kuala Lumpur, Malaysia.
Dauvergne J. et al. (2004) "Synthesis of 4-azacyclopent-2-enones and 5,5-dialkyl-4-azacyclopent-2-enones" Tetrahedron, Elsevier Science Publishers 60(11): 2559-2567.
Deanda, F. et al. (2013) "Dolutegravir Interactions with HIV-1 Integrase-DNA: Structural Rationale for Drug Resistance and Dissociation Kinetics" PLOS One 8(10): e77448 1-12.
Disclosed Anonymously. (2014) "Preparation of Methyl 3-(benzyloxy)-5-992,4-difluorobenzyl)carbamoyl)-1-(2,2-dimethoxy ethyl)-4-oxol,4-dihydropyridine-2-carboxylate" an IP.com Prior Art Database Technical Disclosure, the whole document.
Disclosed Anonymously. (2014) "Process for the Preparation of 4H-Pyran-4-One Derivatives" an IP.com Prior Art Database Technical Disclosure, //priorart.ip.com/IPCOM/000235923.
Enright, B. et al. (2010) "Assessment of Hydroxypropyl Methylcellulose, Propylene Glycol, Polysorbate 80, and Hydroxypropyl-.beta.-Cyclodextrin for Use in Developmental and Reproductive Toxicology Studies" Birth Defects Research (Part B) 89:504-516.
European Search Report dated Mar. 31, 2015 for EP application No. 13815937.1.
FDA DTG Pharmacology Review—Center for Drug Evaluation and Research; DTG PharmTox Review 2013, 103 pages.
FDA_DDI Guidance for Industry—Drug Interaction Studies -Study Design, Data Analysis, Implications for Dosing, and Labeling Recommendations, 79 pages.
Feinberg, J. et al. (2013) "Once-Daily Dolutegravir (DTG) is Superior to Darunavir/Ritonavir (DRV)/f) in Antiretroviral-Naive Adults: 48 Week Results from Flamingo (ING114915)" Presentation, 53.sup.rd ICAAC Interscience Conference on AntimicrobialAgents and Chemotherapy; Sep. 10-13; Denver CO.
Gad, S. et al.(2006) "Nonclinical Vehicle Use in Studies by Multiple Routes in Multiple Species" International Journal of Toxicology 25:499-521.
Gao, Y. et al. (2007) "Attenuating Pregnane X Receptor (PXR Activiatin: A Molecular Modeling Approach" Xenobiotica 37(2):124-138.

(56) References Cited

OTHER PUBLICATIONS

Gein, V. L., et al. (1992) "Synthesis of 4-Substituted 1-Methyl-5-Aryl- and 1,5-Diaryltetrahydropyrrole-2,3-Diones and their Antiviral Action" translated from Khimik-farmatsevticheskii Zhurnal; 25(12):37-40.

Gould, S. et al. (2005) "2-Hydroxypropyl-.beta.-cyclodextrin (HP-.beta.-CD): A toxicology review" Food and Chemical Toxicology 43:1451-1459.

Gouverneur, V. et al. (1998) "New Acylnitroso Compounds for the Asymmetric Oxyamination of Dienes" Tetrahedron 54:10537-10554.

Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.

Guitierez, M., "Drug safety profile of integrase strand transfer inhibitors," Expert Opin. Drug Saf. (2014) 13(4):431-445.

Hare, S. et al. (2011) "Structural and Functional Analyses of the Second-Generation Integrase Strand Transfer Inhibitor Dolutegravir (S/GSK1349572)" Molecular Pharmacology 80(4):565-572.

Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).

Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.

Hurt et al., (2014), "Resistance to HIV Integrase Strand Transfer Inhibitors Among Clinical Specimens in the United States, 2009-2012", Clin Infect Dis., 58:423-31.

Hurt, C. et al. (2013) "Characterization of Resistance to Integrase Strand Transfer Inhibitors among Clinical Specimens in the United States, 2009-2012" Poster 591; 20th Conference on Retroviruses and Opportunistic Infections; Mar. 3-6; Atlanta, GA.

International Preliminary Report on Patentability dated Jun. 23, 2015 for PCT/US2013/076367.

Intl Search Report—Written Opinion dated Sep. 18, 2006 for PCT/US2006/016604.

Intl. Search Report—Written Opinion dated Feb. 9, 2016 for PCT/US2015/026017.

Intl. Search Report dated Mar. 12, 2014 for PCT/US2013/076367.

Johns, B. et al., (2013), "HIV Integrase Inhibitors", Successful Strategies for Discovery of Antiviral Drugs, 32(6):149-88.

Johns, B., et al., "Carbamoyl Pyridone HIV-1 Integrase Inhibitors 3. A Diastereomeric Approach to Chiral Nonracemic Tricyclic Ring Systems and the Discovery of S/GSK1349572 (Dolutegravir) and S/GSK1265744," J. Med. Chem. 54 pages.

Johns, B., et al., (2010) "Discovery of S/GSK1349572: A Once Daily Next Generation Integrase Inhibitor with a Superior Resistance Profile", 17th Conference on Retroviruses and Opportunistic Infections Feb. 16-19, 2010, San Francisco, CA, USA (18 pages).

Johns, B., et al., (2013) "Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744)," J. Med. Chem. 54 pages.

Johns, B., et al., (2013) "Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744)," J. Med. Chem. 56:5901-5916.

Kawasuji, T. et al.(2007) "3-Hydroxy-1,5-dihydro-pyrrol-2-one Derivatives as Advanced Inhibitors of HIV Integrase" Bioorganic & Medicinal Chemistry; 15:5487-5492.

Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.

Kliewer, S. et al. (2002) "The Nuclear Pregnane X Receptor: A Key Regulator of Xenobiotic Metabolism" Endocrine Reviews 23(5):687-702.

Kobayashi, M. et al. (2011) "In Vitro Antiretroviral Properties of S/GSK1349572, a Next-Generation HIV Integrase Inhibitor" Antimicrob Agents and Chemother 55(2):813-21.

Krow, G. et al. (2008) "Selectfluor as a Nucleofuge in the Reactions of Azabicyclo[n. 2.1]alkane.beta.-Halocarbamic Acid Esters (n = 2,3)" J. Org. Chem. 73:2122-2129.

Lepist, E. et al. (2011) "Effect of Cobicistat and Ritonavir on Proximal Renal Tubular Cell Uptake and Efflux Tansporters" Poster A1-1724; 51.sup.st Interscience Conference on Antimicrobial Agents and Chemotherapy; Sep. 17-20; Chicago, IL.

Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.

Llyod J. et al. (2009) "Dihydropyrazolopyrimidines containing benzimidazoles as KV1.5 potassium channel antagonistics" Bioorganic & Medicinal Chemistry Letters 19(18): 5469-5473.

Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference onAntimicrobial Agents and Chemotherapy; Sep. 10-13; Denver, CO.

Maggi, P., (2014) "The Problem of Renal Function Monitoring in Patients Treated With the Novel . Antiretroviral Drugs", HIV Clinical Trials, HIV Clin Trials;15(3):87-91.

Malet, I., et al., (2014) "New raltegravir resistance pathways induce broad cross-resistance to all currently used integrase inhibitors", J Antimicrob Chemother, 69: 2118-2122.

Margolis et al. (2014) '744 and Rilpivirine as Two Drug Oral Maintenance Therapy: LAI116482 (LATTE) Week 48 Results38 Presentation; 21st Conference on Retroviruses and Opportunistic Infections; Mar. 3-6; Boston, MA.

Menendez-Arias, L., Alvarez, M., "Antiretroviral therapy and drug resistance in human immunodeficiency virus type 2 infection," Antiviral Res. (2013), http://dx.doi.org/10.1016/j.antiviral.2013.12.001.

Metifiot, M. et al. (2013) "HIV Integrase Inhibitors: 20-Year Landmark and Challenges" Advances in Pharmacology 67:75-105.

Min, S. S et al.(2010) "Pharmacokinetics and Safety of S/GSK1349572, a Next-Generation HIV Integrase Inhibitor, in Healthy Volunteers" Antimicrob Agents and Chemother 54(1):254-258.

Min, S. et al.(2011) "Antiviral activity, safety, and pharmacokinetics/pharmacodynamics of dolutegravir as 10-day monotherapy in HIV-1-infected adults" AIDS 25(14):1737-1745.

Mulvihill M.J. et al. (1998) "Enzymatic resolution of aminocyclopentenols as precursors to D-and L-carbocyclic nucleosides" The Journal of Organic Chemistry, American Chemistry Society, US, 63(10): 3357-3363.

Nair, V. et al. (2014) "Pharmacokinetics and Dose-range Finding Toxicity of a Novel anti-HIV Active Integrase Inhibitor" Supplementary Materials.

Nichols, G. et al (2013) "Phase 3 Assessment of Dolutegravir (DTG) 50 mg Twice Daily (BID) in HIV-1—Infected Subjects With Raltegravir (RAL) and/or Elvitegravir (EVG) Resistance in Viking-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.

Nichols, G. et al. (2012) "Antiviral Activity of Dolutegravir in Subjects With Failure on an Integrase Inhibitor-Based Regimen: Week 24 Phase 3 Results From Viking-3" Presentation O232; 11th International Congress on Drug Therapy in HIV Infection;Nov. 11-15; Glasgow, UK.

Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.

Office Action dated Mar. 30, 2015 for Pakistan Appl. No. 908/2013.

(56) References Cited

OTHER PUBLICATIONS

Opposition Decision in European patent application No. 02749384.0, dated Mar. 12, 2015.
Pace, P., et al. (2007) "Dihydroxypyrimidine-4-carboxamides as Novel Potent and Selective HIV Integrase Inhibitors" J. Med. Chem; 50:2225-2239.
Palella, et al. (1998) Declining Morbidity and Mortality among Patients with Advanced Human Immunodefiency Virus Infectio. New England. Journal of Medicine 338:853-860.
Panel on 25 Antiretroviral Guidelines for Adults and Adolescents. Guidelines for the use of antiretroviral agents in HIV-1-infected adults and adolescents. Department ofHealth and Human Services. Available at http:/ /aidsinfo.nih.gov/ContentFiles/AdultandAdolescentGL.pdf. Section accessed Mar. 14, 2013.
Park, B. et al. (2001) "Metabolism of Fluorine-Containing Drugs" Annu. Rev. Pharmacol. Toxicol. 41:443-70.
Patel, P. et al. (2014) "Relative Bioavailability of a Paediatric Granule Formulation of the HIV Integrase Inhibitor, Dolutegravir, in Healthy Adult Subjects" Antiviral Therapy.
Patel, P., et al., "Pharmacokinetics of the HIV integrase inhibitor S/GSK1349572 co-administered with acid-reducing agents and multivitamins in healthy volunteers," J Antimicrob Chemother (2011); 66: 1567-1572.
PCT/US2013/076367 dated Dec. 19, 2013, [259 pages].
Peng, C. et al. (2002) "Norditerpenoid alkaloids from the roots of Aconitum hemsleyanum Pritz. var. pengzhouense" Abstract, Chinese Chemical Letters 13(3):233-236.
Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.
Plamen A. et al. (2012) "Biomimetic Synthesis, antibacterial activity and structure-activity properties of the pyroglutamate core of oxazolomycin" Organic & Biomolecular Chemistry, 10(17): 3472-3485.
Poster 595, Huang, W., et al., Impact of Raltegravir/Elvitegravir Selected Mutationson Dolutegravir Cross-Resistance, 1 page.
Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar.3-6; Atlanta, GA.
PXR Background and data, 2 pages.
Quashie et al., "Evolution of HIV integrase resistance mutations," Curr Opin Infect Dis (2013) 26:43-49.
Quashie, P. et al. (2013) "Evolution of HIV integrase resistance mutations" Curr Opin Infect Dis 26:43-49.
Raffi F. et al., (2013) "Once-daily dolutegravir versus raltegravir in antiretroviral-naive adults with HIV-1 infection: 48 week results from the randomised, double-blind, non-inferiority Spring-2 study," www.thelancet.com Published online Jan. 8, 2013 http://dx.doi.org/10.1016/S0140-6736(12)61853-4, 9 pages.
Raffi, F. et al. (2013) "Once-daily Dolutegravir (DTG; S/GSK1349572) is Non-inferior to Raltegravir (RAL) in Antiretroviral-naive Adults. 48 Week Results from Spring-2 (ING113086)" Presentation THLBB04; XIX International AIDS Conference; Jul. 22-27;Washington, DC.
Raffi, F. et al. (2013) "Once-daily dolutegravir versus twice-daily raltegravir in antiretroviral-naive adults with HIV-1 infection (Spring-2 study): 96 week results from a randomised, double-blind, non-inferiority trial" www.thelancet.com/infection13:927-935.
Raffi_Poster_DTG clinical data summary IAS Kuala Lumpur Jul. 2013 (Spring 2), 1 page.
Ragan, J. et al. (1995) "Studies of the Alkylation of Chiral, Non-Racemic, Tricyclic Pyrrolidinones," Heterocycles 41:57-70.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Remington et al. (2000): The Science and Practice of Pharmacy, 20th Edition (Philadelphia College of Pharmacy and Science.
Reviews in Antiviral Therapy Infectious Diseases, Abstract Book, 12th International Workshop on Clinical Pharmacology of HIV Therapy, Apr. 13-15, 2011, Miami, Florida, USA; [available on http:regist2.virology-education.com/abstractbook/2011_3.pdf].
Rhodes, M., et al., "Assessing a Theoretical Risk of Dolutegravir-Induced Developmental Immunotoxicity in Juvenile Rats,"Toxicological Sciences 130(1), 70-81 (2012).
Saag, M.S., (2006), "Emtricitabine, a new antiretroviral agent with activity against HIV and hepatitis B virus", Clin Infect Dis., 42:126-31.
Schenone et al. (1990) "Reaction of 2-Dimethylaminomethylene-1,3-diones with Dinucleophiles. VIII. Synthesis of Ethyl and Methyl 2,4-disubstituted 5-Pyrimidinecarboxylates" 27(2): 295-305.
SciFinder Journal (2013) "Bridged Oxazine Search" CAS Registry 248280-06-0. American Cancer Society: 1-3.
Song, I. et al. (2010) "Lack of Interaction Between the HIV Integrase Inhibitor S/GSK1349572 and Tenofovir in Healthy Subjects" JAIDS 55(3):365-367.
Song, I. et al. (2012) "Effect of Food on the Pharmacokinetics of the Integrase Inhibitor Dolutegravir" Antimicrob Agents and Chemother 56(3):1627-1629.
Song, I. et al. (2013) "Dolutegrvir Has No Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.
Song, I. et al. (2013) "Pharmacokinetics (PK) and Pk.sub.—Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy;Sep. 10-13; Denver, CO.
Soriano, V., et al. (2011) "Dolutegravir (GSKNiiV Integrase) Treatment (with 50mg Once & Twice Daily) of HIV Subjects with Raltegravir Resistance & 3-Class ART Resistance: viral suppression at Week 24 in the Viking Study" Presentation; EACS; Oct. 12-15; Belgrade, Serbia.
Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIVPathogenesis, Treatment and Prevention Jun. 30-Jul. 3; Kuala Lumpur, Malaysia.
Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.
Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.
Springthorpe et. al (2007) "From ATP to AZD61640: The Discovery of an Orally Active Reversible P2Y(12) Receptor Antagonist for the Prevention of Thrombosis." Biorganic & Medicinal Chemistry Letters, 17(21):6013-6018.
Stellbrink, H. et al. (2013) "Dolutegravir in antiretroviral-naive adults with HIV-1: 96-week results from a randomized dose-ranging study" AIDS 27:1771-1778.
Summa, V., et al. (2006) "4,5-Dihydroxypyrimidine Carboxamides and N-Alky1-5-hydroxypyrimidinone Carboxamides are Potent, Selective HIV Integrase Inhibitors with Good Pharmacokinetic Profiles in Preclinical Species" J. Med. Chem; 49:6646-6649.
Summary of Product Characteristics—Annex I, Leaflet, 62 pages—EU—Triumeq [downloaded Sep. 8, 2014].
Tao Y. et al. "Stereoselective synthesis of disubstituted 3(2H)—furanones via catalytic intramolecular C-H insertion reactions of [alpha]-diazo-[beta]-keto esters including asymmetric induction" Tetrahedron Letters, 35(39): 7626-7272.
Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans,LA.

(56) References Cited

OTHER PUBLICATIONS

Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.
Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.
Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page; retrieved byHaolun Jin.
Thomson Reuters Drug News "Results from phase III trials of dolutegravir presented," Fri Jul. 5, 2013, 1 page; retrieved by Haolun Jin.
Trinite, B. et al. (2013) "An HIV-1 Replication Pathway Utilizing Reverse Transcription Products That Fail to Integrate" Journal of Virology 87(23):12701-12720.
Tseng, A. et al. (2014) "Drug Interactions with Integrase Inhibitors" Pharm. D.
Van Lunzen, J. et al. (2012) "Once daily dolutegravir (S/GSK1349572) in combination therapy in antiretroviral-naive adults with HIV: planned interim 48 week results from Spring-1, a dose-ranging, randomised, phase 2b trial" Lancet Infectious Disease12(2):111-118.
Wai, J., et al. (2007) "Dihydroxypyridopyrazine-1,6-dione HIV-1 Integrase Inhibitors" Bioorganic & Medicinal Chemistry Letters; 17:5595-5599.
Walmsley, S. et al. (2012) "Dolutegravir (DTG; S/GSK1349572) + Abacavir/Lamivudine Once Daily Statistically Superior to Tenofovir/Emtricitabine/Efavirenz: 48-Week Results—Single (ING114467)" Presentation H-556b; 52nd Interscience Conference onAntimicrobial Agents and Chemotherapy; Sep. 9-12; San Francisco, CA.
Walmsley, S. et al. (2013) "Dolutegravir plus Abacavir-Lamivudine for the Treatment of HIV-1 Infection" N Engl J Med 369(19):1807-1818.
Wang, F. et al. (1999) "Modifications of norditerpenoid alkaloids. I. N-deethylation reactions" Abstract, Chinese Chemical Letters 10(5):375-378.
Wang, F. et al. (2005) "To seek an approach toward the chemical conversion of C19-diterpenoid alkaloids to taxoids" Tetrahedron 61(8):2149-2167.
Wang, H. et al. (2015) "An Efficient and Highly Diastereoselective Synthesis of GSK1265744, a Potent HIV Integrase Inhibitor" Org. Letters 17:564-567.
Wang, Y., et al., (2002) "Switch in asymmetric induction sense in cycloadditions using camphor-based nitroso dienop", Tetrahedron: Asymmetry 13:691-5.
Weller, S. et al. (2013) "Pharmacokinetics (PK) and Safety of Dolutegravir (DTG) in Subjects With Severe Renal Impairment and Healthy Controls" Poster A-1571; 53rd Interscience Conference on Antimicrobial Agents and Chemotherapy; Sep. 10-13; Denver, CO.
Weller, S., et al., (2013) "Bioequivalence of a Dolutegravir, Abacavir, and Lamivudine Fixed-Dose Combination Tablet and the Effect of Food", Poster A-1572; 53rd Interscience Conference on Antimicrobial Agents and Chemotherapy; Sep. 10-13, 2013; Denver, CO.
Wensing, A. et al. (2014) "Special Contribution 2014 Update of the Drug Resistance Mutations in HIV-1" IAS-USA Topics in Antiviral Medicine 22(3):642-650.
Wolkowicz, U. et al. (2014) Structural Basis of Mos1 Transposase Inhibition by the Anti-retroviral Drug Raltegravir ACS Chem. Biol. 9:743-751.
Wu Y.Q. et al. (1993) "Preparation of the pure diastereomeric forms of S-(5'-deoxy-5'-adenosyl)-1-ammonio-4-methyl sulfonio-2 cyclopentene and their evaluation as irreversible inhibitors of S-adenosylmethionine decarboxylase from *Escherichia coli*" Bioorganic & Medicinal Chemistry, 1(5)349-360.
Wu, B. et al. (2008) "Enantioselective Desymmetrization of meso-Aziridines with TMSN.sub.3 and TMSCN Catalyzed by Discrete Yttrium Complexes" Supporting Information, Angew. Chem. Int. Ed., 64pgs.
Yoshifumi et al. (2015) "Dioxanone-Fused Dienes Enable Highly Endo-Selective Intramolecular Diels-Alder Reactions" Organic Letters, 17(11): 2756-2759; 2758: Scheme 7, compounds 10a and 10b.
Zhang, X. et al. (2008) "Rapid analysis of a Chinese herbal prescription by liquid chromatography-time-of-flight tandem mass spectrometry" Abstract, Journal of Chromatography A 1206(2:140-146).
Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.
Office Action dated Feb. 15, 2017 for the Canadian Application No. 2,893,843.

SUBSTITUTED 2,3,4,5,7,9,13,13A-OCTAHYDRO-1,5-METHANOPYRIDO[1',2':4,5]PYRAZINO[1,2-A][1,3]DIAZEPINES AND METHODS FOR TREATING VIRAL INFECTIONS

CROSS-REFERENCE TO RELATED APPLICATIONS

This patent application is a Continuation of U.S. patent application Ser. No. 15/349,934, filed Nov. 11, 2016, which is a Continuation of U.S. patent application Ser. No. 14/815,504, filed Jul. 31, 2015, which is a Continuation of U.S. patent application Ser. No. 14/133,858, filed Dec. 19, 2013, which claims the benefit under 35 U.S.C. § 119(e) of U.S. Provisional Patent Application No. 61/845,803 filed Jul. 12, 2013, and U.S. Provisional Patent Application No. 61/788,397, filed Mar. 15, 2013, and U.S. Provisional Patent Application No. 61/745,375, filed Dec. 21, 2012. The foregoing applications are incorporated herein by reference in their entireties.

BACKGROUND

Field

Compounds, compositions, and methods for the treatment of human immunodeficiency virus (HIV) infection are disclosed. In particular, novel polycyclic carbamoylpyridone compounds and methods for their preparation and use as therapeutic or prophylactic agents are disclosed.

Description of the Related Art

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N. Engl. J Med.* (1998) 338:853-860; Richman, D. D. *Nature* (2001) 410:995-1001).

Pregnane X receptor (PXR) is a nuclear receptor that is one of the key regulators of enzymes involved in metabolism and elimination of small molecules from the body. Activation of PXR is known to up-regulate or induce the production of metabolic enzymes such as cytochrome P450 3A4 (CYP3A4) as well as enzymes involved in transport such as OATP2 in the liver and intestine (*Endocrine Reviews* (2002) 23(5):687-702). When one drug causes the up-regulation of these and other enzymes by activation of PXR, this can reduce the absorption and/or exposure of a co-administered drug that is susceptible to the up-regulated enzymes. To minimize the risk of this type of drug-drug interaction, it is desirable to minimize PXR activation. Further, it is known that PXR is activated by many different classes of molecules (*Endocrine Reviews* (2002) 23(5):687-702). Thus for drugs that will be co-administered with other drugs, it is important to test for and minimize PXR activation.

Transporters have been identified as playing a role in the pharmacokinetic, safety and efficacy profile or drugs, and certain drug-drug interactions are mediated by transporters. See, Giacomini K M, et al. ""Membrane transporters in drug development," *Nat. Rev Drug Discov.* 9: 215-236, 2010; Zhang L, et al. "Transporter-Mediated Drug-Drug Interactions," *Clin. Pharm. Ther.* 89(4):481-484 (2011). One transporter, the organic cation transporter 2 (OCT2; SLC22A2), is a member of the solute carrier (SLC) super-family of transporters and is primarily localized on the basolateral membrane of the renal proximal tubule. OCT2, in concert with apical expressed multidrug and toxin extrusion (MATE) transporters 1 and 2-K, is believed to form the major cationic secretion pathway in the kidney and has been shown to transport endogenous compounds including creatinine and xenobiotics including metformin. Inhibition of OCT2 can thus lead to increased levels of serum creatinine and the potential for increased levels of other OCT2 substrates. It is important as well to test and reduce OCT2 inhibition of drugs.

A goal of antiretroviral therapy is to achieve viral suppression in the HIV infected patient. Treatment guidelines published by the United States Department of Health and Human Services provide that achievement of viral suppression requires the use of combination therapies, i.e., several drugs from at least two or more drug classes. (Panel on Antiretroviral Guidelines for Adults and Adolescents. Guidelines for the use of antiretroviral agents in HIV-1-infected adults and adolescents. Department of Health and Human Services. Available at http://aidsinfo.nih.gov/ContentFiles/AdultandAdolescentGL.pdf. Section accessed Mar. 14, 2013.) In addition, decisions regarding the treatment of HIV infected patients are complicated when the patient requires treatment for other medical conditions (Id. at E-12). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

Accordingly, there is a need for new agents that inhibit the replication of HIV and that minimize PXR activation when co-administered with other drugs.

BRIEF SUMMARY

The present invention is directed to novel polycyclic carbamoylpyridone compounds, having antiviral activity, including stereoisomers and pharmaceutically acceptable salts thereof, and the use of such compounds in the treatment of HIV infections. The compounds of the invention may be used to inhibit the activity of HIV integrase and may be used to reduce HIV replication.

In one embodiment of the present invention, compounds having the following Formula (I) are provided:

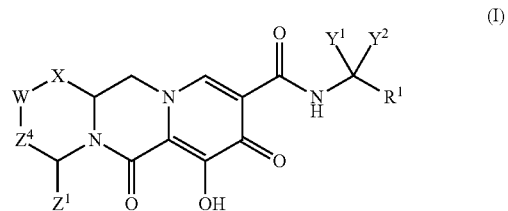

or a stereoisomer or pharmaceutically acceptable salt thereof,
wherein:
X is —O— or —NZ³— or —CHZ³—;
W is —CHZ²—;
Z¹, Z² and Z³ are each, independently, hydrogen or $C_{1-3}$alkyl, or wherein Z¹ and Z² or Z¹ and Z³, taken together, form -L- wherein L is —C(R$^a$)$_2$—, —C(R$^a$)$_2$C(R$^a$)$_2$—, —C($R^a$)$_2$C($R^a$)$_2$C($R^a$)$_2$—, or —C($R^a$)$_2$C($R^a$)$_2$C($R^a$)$_2$C($R^a$)$_2$—, wherein at least one of $Z^1$ and $Z^2$ or $Z^1$ and $Z^3$, taken together, form -L-;

$Z^4$ is a bond, —CH$_2$—, or —CH$_2$CH$_2$—;

$Y^1$ and $Y^2$ are each, independently, hydrogen, $C_{1-3}$alkyl or $C_{1-3}$haloalkyl;

$R^1$ is phenyl substituted with one to three halogens; and each $R^a$ is, independently, hydrogen, halo, hydroxyl or $C_{1-4}$alkyl.

In another embodiment of the present invention, compounds having the following Formula (I) are provided:

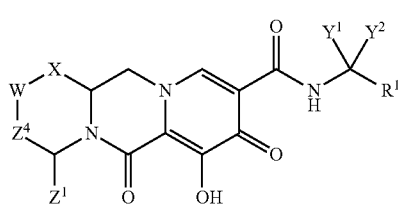

(I)

or a stereoisomer or pharmaceutically acceptable salt thereof,
wherein:

X is —O— or —N$Z^3$— or —CH$Z^3$—;

W is —O— or —N$Z^2$— or —CH$Z^2$—;

$Z^1$, $Z^2$ and $Z^3$ are each, independently, hydrogen or $C_{1-3}$alkyl, or wherein $Z^1$ and $Z^2$ or $Z^1$ and $Z^3$, taken together, form -L- wherein L is —C($R^a$)$_2$—, —C($R^a$)$_2$C($R^a$)$_2$—, —C($R^a$)$_2$C($R^a$)$_2$C($R^a$)$_2$—, —C($R^a$)$_2$C($R^a$)$_2$C($R^a$)$_2$C($R^a$)$_2$—, —C($R^a$)$_2$OC($R^a$)$_2$—, —C($R^a$)$_2$NR$^a$C($R^a$)$_2$—, —C($R^a$)$_2$SC($R^a$)$_2$—, —C($R^a$)$_2$S(O)C($R^a$)$_2$—, —C($R^a$)$_2$SO$_2$C($R^a$)$_2$—, —C($R^a$)$_2$OC($R^a$)$_2$C($R^a$)$_2$—, —C($R^a$)$_2$C($R^a$)$_2$OC($R^a$)$_2$—, —C($R^a$)$_2$NR$^a$C($R^a$)$_2$C($R^a$)$_2$—, —C($R^a$)$_2$C($R^a$)$_2$NR$^a$C($R^a$)$_2$—, —C($R^a$)$_2$SC($R^a$)$_2$C($R^a$)$_2$—, —C($R^a$)$_2$C($R^a$)$_2$SC($R^a$)$_2$—, —C($R^a$)$_2$S(O)C($R^a$)$_2$C($R^a$)$_2$—, —C($R^a$)$_2$C($R^a$)$_2$S(O)C($R^a$)$_2$—, —C($R^a$)$_2$SO$_2$C($R^a$)$_2$C($R^a$)$_2$—, —C($R^a$)$_2$C($R^a$)$_2$SO$_2$C($R^a$)$_2$—, —C($R^a$)$_2$SO$_2$NR$^a$C($R^a$)$_2$— or —C($R^a$)$_2$NR$^a$SO$_2$C($R^a$)$_2$—;

$Z^4$ is a bond or —CH$_2$—, —CH$_2$CH$_2$—, —CH$_2$CH$_2$CH$_2$—, —CH$_2$OCH$_2$—, —CH$_2$NR$^a$CH$_2$—, —CH$_2$SCH$_2$—, —CH$_2$S(O)CH$_2$— or —CH$_2$SO$_2$CH$_2$—;

$Y^1$ and $Y^2$ are each, independently, hydrogen, $C_{1-3}$alkyl or $C_{1-3}$haloalkyl, or $Y^1$ and $Y^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more $R^a$;

$R^1$ is optionally substituted aryl or optionally substituted heteroaryl; and each $R^a$ is, independently, hydrogen, halo, hydroxyl or $C_{1-4}$alkyl, or wherein two $R^a$ groups, together with the carbon atom to which they are attached, form =O, and wherein at least one of: (i) $Z^1$ and $Z^2$ or $Z^1$ and $Z^3$, taken together, form -L-; or (ii) $Y^1$ and $Y^2$, together with the carbon atom to which they are attached, form a carbocyclic ring having from 3 to 6 ring atoms or a heterocyclic ring having from 3 to 6 ring atoms.

In another embodiment, a pharmaceutical composition is provided comprising a compound having Formula (I), or a stereoisomer or pharmaceutically acceptable salt thereof, and a pharmaceutically acceptable carrier, diluent or excipient.

The invention also provides the use of a pharmaceutical composition as described hereinabove for the treatment of an HIV infection in a human being having or at risk of having the infection.

In another embodiment, a method of using a compound having Formula (I) in therapy is provided. In particular, a method of treating the proliferation of the HIV virus, treating AIDS, or delaying the onset of AIDS or ARC symptoms in a mammal (e.g., a human) is provided, comprising administering to the mammal a compound having Formula (I), or a stereoisomer or pharmaceutically acceptable salt thereof, and a pharmaceutically acceptable carrier, diluent or excipient.

In another embodiment, use of a compound of Formula (I) as described herein, or a pharmaceutically acceptable salt thereof, for the treatment of an HIV infection in a human being having or at risk of having the infection is disclosed.

In another embodiment, the use of a compound of Formula (I) as described herein, or a pharmaceutically acceptable salt thereof, for the manufacture of a medicament for the treatment of an HIV infection in a human being having or at risk of having the infection is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula (I) according to this invention or a pharmaceutically acceptable salt thereof.

In still another embodiment, a method of inhibiting the replication of HIV is disclosed. The method comprises exposing the virus to an effective amount of the compound of Formula (I), or a salt thereof, under conditions where replication of HIV is inhibited.

In another embodiment, the use of a compound of Formula (I) to inhibit the activity of the HIV integrase enzyme is disclosed.

In another embodiment, the use of a compound of Formula (I), or a salt thereof, to inhibit the replication of HIV is disclosed.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless the context requires otherwise, reference throughout this specification to "a compound of Formula (I)" or "compounds of Formula (I)" refers to all embodiments of Formula (I), including, for example, compounds of Formulas (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as well as the specific compounds disclosed herein.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_A$ where $R_A$ is an alkyl radical as defined above containing one to twelve carbon atoms. Unless stated otherwise specifically in the specification, an alkoxy group may be optionally substituted.

"Alkylamino" refers to a radical of the formula —$NHR_A$ or —$NR_AR_A$ where each $R_A$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_A$ where $R_A$ is an alkyl radical as defined above containing one to twelve carbon atoms. Unless stated otherwise specifically in the specification, a thioalkyl group may be optionally substituted.

"Aryl" refers to a monocylic hydrocarbon ring system radical comprising hydrogen and 6 to 18 carbon atoms. Aryl radicals include, but are not limited to, aryl radicals derived from benzene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_B$—$R_C$ where $R_B$ is an alkylene chain as defined above and $R_C$ is one or more aryl radicals as defined above, for example, benzyl. Unless stated otherwise specifically in the specification, an aralkyl group may be optionally substituted.

"Cycloalkyl" or "carbocyclic ring" refers to a stable non-aromatic monocyclic hydrocarbon radical consisting solely of carbon and hydrogen atoms, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Unless otherwise stated specifically in the specification, a cycloalkyl group may be optionally substituted.

"Cycloalkylalkyl" refers to a radical of the formula —$R_BR_D$ where $R_B$ is an alkylene chain as defined above and $R_D$ is a cycloalkyl radical as defined above. Unless stated otherwise specifically in the specification, a cycloalkylalkyl group may be optionally substituted.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. In the embodiments disclosed herein, the heterocyclyl radical is a monocyclic ring system; and the heterocyclyl radical may be partially or fully saturated. Examples of such heterocyclyl radicals include, but are not limited to, dioxolanyl, thienyl, [1,3]dithianyl, imidazolinyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group may be optionally substituted.

"Heterocyclylalkyl" refers to a radical of the formula —$R_BR_E$ where $R_B$ is an alkylene chain as defined above and $R_E$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered monocyclic ring system radical comprising hydrogen atoms, one to thirteen carbon atoms, one to six heteroatoms selected from the group consisting of nitrogen, oxygen and sulfur. Examples include, but are not limited to, azepinyl, furanyl, furanonyl, isothiazolyl, imidazolyl, isoxazolyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, pyrazolyl, pyridinyl, pyrazinyl, pyrimidinyl, pyridazinyl, thiazolyl, thiadiazolyl, triazolyl, tetrazolyl, triazinyl, thiophenyl, and thienyl. Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_BR_F$ where $R_B$ is an alkylene chain as defined above and $R_F$ is a heteroaryl radical as defined above. Unless stated otherwise specifically in the specification, a heteroarylalkyl group may be optionally substituted. The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_GR_H$, —$NR_GC(=O)R_H$, —$NR_GC(=O)$ $NR_GR_H$, —$NR_GC(=O)OR_H$, —$NR_GC(=NR_g)NR_GR_H$, —$NR_GSO_2R_H$, —$OC(=O)NR_GR_H$, —$OR_G$, —$SR_G$, —$SOR_G$, —$SO_2R_G$, —$OSO_2R_G$, —$SO_2OR_G$, =$NSO_2R_G$, and —$SO_2NR_GR_H$. "Substituted also means any of the above groups in which one or more hydrogen atoms are replaced with —$C(=O)R_G$, —$C(=O)OR_G$, —$C(=O)$ $NR_GR_H$, —$CH_2SO_2R_G$, —$CH_2SO_2NR_GR_H$. In the foregoing, $R_G$ and $R_H$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TB-DPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

The invention disclosed herein is also meant to encompass all pharmaceutically acceptable compounds of Formula (I) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

These radiolabeled compounds could be useful to help determine or measure the effectiveness of the compounds, by characterizing, for example, the site or mode of action, or binding affinity to pharmacologically important site of action. Certain isotopically-labeled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-naphthalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of Formula (I) or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

A "prodrug" refers to a compound that is chemically designed to efficiently liberate the parent drug after overcoming biological barriers to oral delivery. In certain embodiments, the present invention includes prodrugs of the compounds of Formula (I).

Compounds

As noted above, in one embodiment of the present invention, compounds having antiviral activity are provided, the compounds having the following Formula (I):

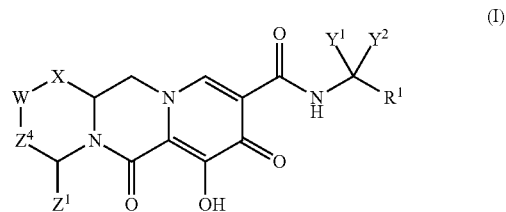

or a stereoisomer or pharmaceutically acceptable salt thereof, wherein:

X is —O— or —NZ$^3$— or —CHZ$^3$—;

W is —CHZ$^2$—;

Z$^1$, Z$^2$ and Z$^3$ are each, independently, hydrogen or C$_{1-3}$alkyl, or wherein Z$^1$ and Z$^2$ or Z$^1$ and Z$^3$, taken together, form -L- wherein L is —C(R$^a$)$_2$—, —C(R$^a$)$_2$C(R$^a$)$_2$—, —C(R$^a$)$_2$C(R$^a$)$_2$C(R$^a$)$_2$—, or —C(R$^a$)$_2$C(R$^a$)$_2$C(R$^a$)$_2$C(R$^a$)$_2$—, wherein at least one of Z$^1$ and Z$^2$ or Z$^1$ and Z$^3$, taken together, form -L-;

Z$^4$ is a bond, —CH$_2$—, or —CH$_2$CH$_2$—;

Y$^1$ and Y$^2$ are each, independently, hydrogen, C$_{1-3}$alkyl or C$_{1-3}$haloalkyl;

R$^1$ is phenyl substituted with one to three halogens; and each R$^a$ is, independently, hydrogen, halo, hydroxyl or C$_{1-4}$alkyl.

In another embodiment, compounds are provided having the following Formula (II-A):

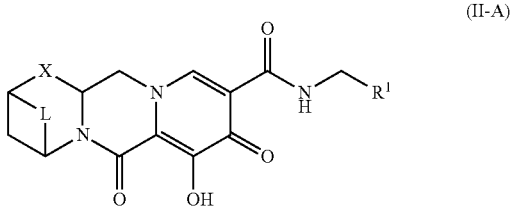

(II-A)

In another embodiment, compounds are provided having the following Formula (II-B):

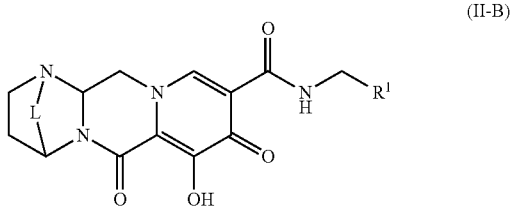

(II-B)

In another embodiment, compounds are provided having the following Formula (II-C):

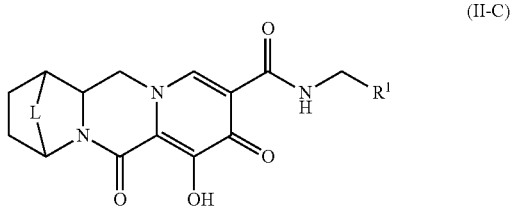

(II-C)

In another embodiment, L is —C(R$^a$)$_2$—. In a further embodiment, L is —C(R$^a$)$_2$C(R$^a$)$_2$—. In still a further embodiment, L is —C(R$^a$)$_2$C(R$^a$)$_2$C(R$^a$)$_2$—. In still a further embodiment, each R$^a$ is hydrogen. In still a further embodiment, one R$^a$ is methyl and each remaining R$^a$ is hydrogen. In still a further embodiment, one R$^a$ is halogen and each remaining R$^a$ is hydrogen. In still a further embodiment, two R$^a$ are halogen and each remaining R$^a$ is hydrogen. In still a further embodiment, one R$^a$ is halogen and each remaining R$^a$ is hydrogen.

In another embodiment, X is —O—. In another embodiment, X is —NZ$^3$—. In another embodiment, X is —NH—. 16. In another embodiment, X is —CHZ$^3$— and Z$^1$ and Z$^3$, taken together, form -L-. In a further embodiment, Z$^2$ is hydrogen. In another embodiment, X is —CH$_2$—.

In another embodiment, Z$^4$ is a bond or —CH$_2$—. In another embodiment, Z$^4$ is —CH$_2$—. In another embodiment, Z$^4$ is a bond.

In another embodiment, Y$^1$ and Y$^2$ are each independently hydrogen, methyl or trifluoromethyl.

In another embodiment, R$^1$ is substituted with one halogen. In a further embodiment, R$^1$ is 4-fluorophenyl or 2-fluorophenyl.

In another embodiment, R$^1$ is substituted with two halogens. In a further embodiment, R$^1$ is 2,4-difluorophenyl, 2,3-difluorophenyl, 2,6-difluorophenyl, 3-fluoro-4-chlorophenyl, 3,4-difluorophenyl, 2-fluoro-4-chlorophenyl, or 3,5-difluorophenyl. In still a further embodiment, R$^1$ is 2,4-difluorophenyl.

In another embodiment, R$^1$ is substituted with three halogens. In a further embodiment, R$^1$ is 2,4,6-trifluorophenyl or 2,3,4-trifluorophenyl. In still a further embodiment, R$^1$ is 2,4,6-trifluorophenyl.

In one embodiment, a pharmaceutical composition is provided comprising a compound of any one of the Formulas (I), (II-A), (II-B), or (II-C), as noted above, or a stereoisomer or pharmaceutically acceptable salt thereof, and a pharmaceutically acceptable carrier, diluent or excipient.

Another embodiment is provided comprising a method of treating an HIV infection in a human having or at risk of having the infection by administering to the human a therapeutically effective amount of a compound of any one of the Formulas (I), (II-A), (II-B), or (II-C), as noted above, or a pharmaceutical composition thereof. Another embodiment is provided comprising a method of treating or preventing an HIV infection in a human having or at risk of having the infection by administering to the human a therapeutically effective amount of a compound of any one of the Formulas (I), (II-A), (II-B), or (II-C), as noted above, or a pharmaceutical composition thereof.

In another embodiment, the use of a compound of any one of the Formulas (I), (II-A), (II-B), or (II-C), as noted above, or a pharmaceutical composition thereof, for the treatment of an HIV infection in a human having or at risk of having the infection is provided. In another embodiment, the use of a compound of any one of the Formulas (I), (II-A), (II-B), or (II-C), as noted above, or a pharmaceutical composition thereof, for the treatment or prevention of an HIV infection in a human having or at risk of having the infection is provided.

In another embodiment, the use in medical therapy of a compound of any one of the Formulas (I), (II-A), (II-B), or (II-C), as noted above, or a pharmaceutical composition thereof, is provided.

In another embodiment, the use of a compound of any one of the Formulas (I), (II-A), (II-B), or (II-C), as noted above, or a pharmaceutical composition thereof, for use in the therapeutic treatment of an HIV infection is provided. In another embodiment, the use of a compound of any one of the Formulas (I), (II-A), (II-B), or (II-C), as noted above, or a pharmaceutical composition thereof, for use in the prophylactic or therapeutic treatment of an HIV infection is provided.

As further noted above, in another embodiment of the present invention, compounds having antiviral activity are provided, the compounds having the following Formula (I):

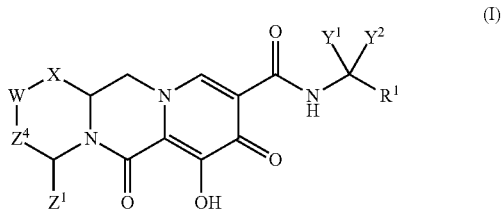

(I)

or a stereoisomer or pharmaceutically acceptable salt thereof,
wherein:
X is —O— or —NZ$^3$— or —CHZ$^3$—;
W is —O— or —NZ$^2$— or —CHZ$^2$—;
Z$^1$, Z$^2$ and Z$^3$ are each, independently, hydrogen, C$_{1-3}$alkyl or C$_{1-3}$haloalkyl, or wherein Z$^1$ and Z$^2$ or Z$^1$ and Z$^3$, taken together, form -L- wherein L is —C(R$^a$)$_2$—, —C(R$^a$)$_2$C(R$^a$)$_2$—, —C(R$^a$)$_2$C(R$^a$)$_2$C(R$^a$)$_2$—, —C(R$^a$)$_2$C(R$^a$)$_2$C(R$^a$)$_2$C(R$^a$)$_2$—, —C(R$^a$)$_2$OC(R$^a$)$_2$—, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, —C(R$^a$)$_2$SO$_2$C(R$^a$)$_2$—, —C(R$^a$)$_2$OC(R$^a$)$_2$C(R$^a$)$_2$—, —C(R$^a$)$_2$C(R$^a$)$_2$OC(R$^a$)$_2$—, —C(R$^a$)$_2$NR$^a$C(R$^a$)$_2$C(R$^a$)$_2$—, —C(R$^a$)$_2$C(R$^a$)$_2$NR$^a$C(R$^a$)$_2$—, —C(R$^a$)$_2$SC(R$^a$)$_2$C(R$^a$)$_2$—, —C(R$^a$)$_2$C(R$^a$)$_2$SC(R$^a$)$_2$—, —C(R$^a$)$_2$S(O)C(R$^a$)$_2$C(R$^a$)$_2$—, —C(R$^a$)$_2$C(R$^a$)$_2$S(O)C(R$^a$)$_2$—, —C(R$^a$)$_2$SO$_2$C(R$^a$)$_2$C(R$^a$)$_2$—, —C(R$^a$)$_2$SO$_2$C(R$^a$)$_2$—, —C(R$^a$)$_2$SO$_2$NR$^a$C(R$^a$)$_2$— or —C(R$^a$)$_2$NR$^a$SO$_2$C(R$^a$)$_2$—;

$Z^4$ is a bond or —CH$_2$—, —CH$_2$CH$_2$—, —CH$_2$CH$_2$CH$_2$—, —CH$_2$OCH$_2$—, —CH$_2$NR$^a$CH$_2$—, —CH$_2$SCH$_2$—, —CH$_2$S(O)CH$_2$— or —CH$_2$SO$_2$CH$_2$—;

$Y^1$ and $Y^2$ are each, independently, hydrogen or $C_{1-3}$alkyl, or $Y^1$ and $Y^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more R$^a$;

$R^1$ is optionally substituted aryl or optionally substituted heteroaryl; and each R$^a$ is, independently, hydrogen, halo, hydroxyl or $C_{1-4}$alkyl, or wherein two R$^a$ groups, together with the carbon atom to which they are attached, form =O, and wherein at least one of: (i) $Z^1$ and $Z^2$ or $Z^1$ and $Z^3$, taken together, form -L-; or (ii) $Y^1$ and $Y^2$, together with the carbon atom to which they are attached, form a carbocyclic ring having from 3 to 6 ring atoms or a heterocyclic ring having from 3 to 6 ring atoms.

In another embodiment, W is —CHZ$^2$—.

In another embodiment, $Z^1$ and $Z^2$ or $Z^1$ and $Z^3$, taken together, form -L-.

In another embodiment, compounds are provided having one of the following Formulas (II-A), (II-B), or (II-C):

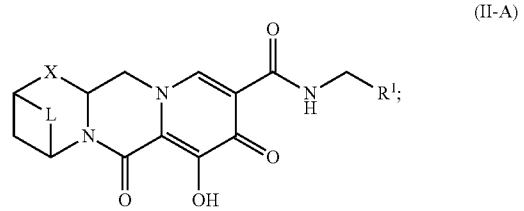

(II-A)

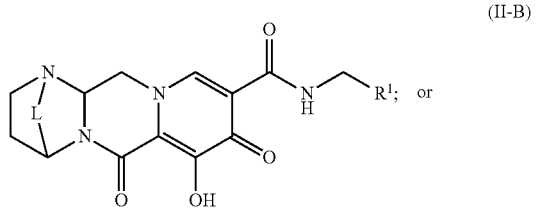

(II-B)

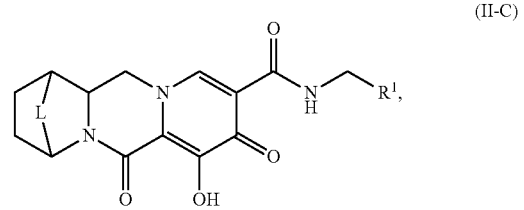

(II-C)

wherein L is —C(R$^a$)$_2$—, —C(R$^a$)$_2$C(R$^a$)$_2$—, —C(R$^a$)$_2$C(R$^a$)$_2$C(R$^a$)$_2$—, —C(R$^a$)$_2$C(R$^a$)$_2$C(R$^a$)$_2$C(R$^a$)$_2$—, —C(R$^a$)$_2$OC(R$^a$)$_2$—, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, —C(R$^a$)$_2$SO$_2$C(R$^a$)$_2$—, —C(R$^a$)$_2$OC(R$^a$)$_2$C(R$^a$)$_2$—, —C(R$^a$)$_2$C(R$^a$)$_2$OC(R$^a$)$_2$—, —C(R$^a$)$_2$NR$^a$C(R$^a$)$_2$C(R$^a$)$_2$—, —C(R$^a$)$_2$C(R$^a$)$_2$NR$^a$C(R$^a$)$_2$—, —C(R$^a$)$_2$SC(R$^a$)$_2$C(R$^a$)$_2$—, —C(R$^a$)$_2$C(R$^a$)$_2$SC(R$^a$)$_2$—, —C(R$^a$)$_2$S(O)C(R$^a$)$_2$C(R$^a$)$_2$—, —C(R$^a$)$_2$C(R$^a$)$_2$S(O)C(R$^a$)$_2$—, —C(R$^a$)$_2$SO$_2$C(R$^a$)$_2$C(R$^a$)$_2$—, —C(R$^a$)$_2$SO$_2$C(R$^a$)$_2$—, —C(R$^a$)$_2$SO$_2$NR$^a$C(R$^a$)$_2$— or —C(R$^a$)$_2$NR$^a$SO$_2$C(R$^a$)$_2$—.

In another embodiment, $Y^1$ and $Y^2$, together with the carbon atom to which they are attached, form a carbocyclic ring having from 3 to 6 ring atoms or a heterocyclic ring having from 3 to 6 ring atoms.

In another embodiment, compounds are provided having one of the following Formulas (III-A), (III-B), (III-C) or (III-D):

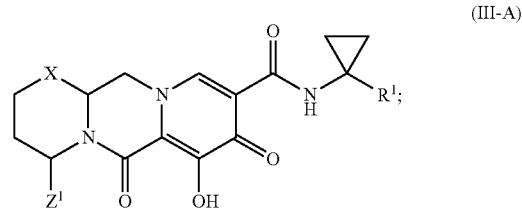

(III-A)

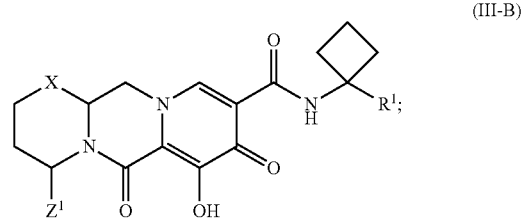

(III-B)

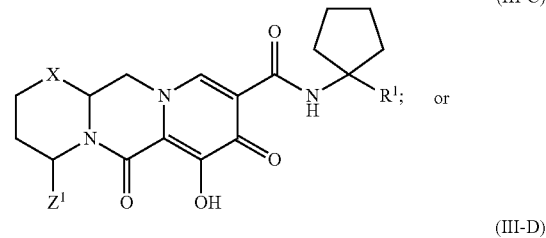

(III-C) or

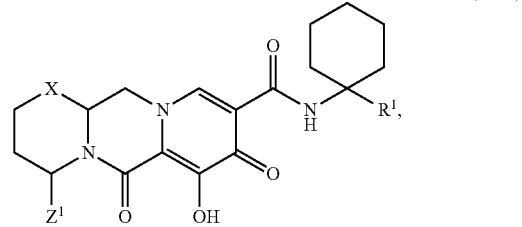

(III-D)

wherein $Z^1$ and $Z^3$ are each, independently, hydrogen or $C_{1-3}$alkyl.

In another embodiment, compounds are provided having one of the following Formulas (III-E), (III-F), (III-G) or (III-H):

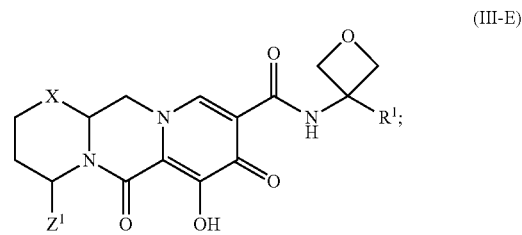

(III-E)

(III-F)
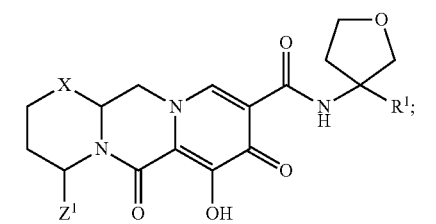

(III-G)
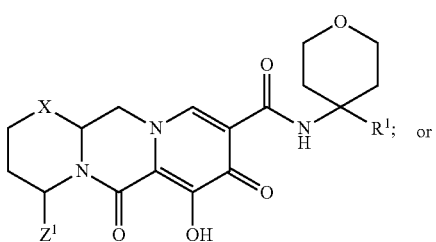  or (III-H)
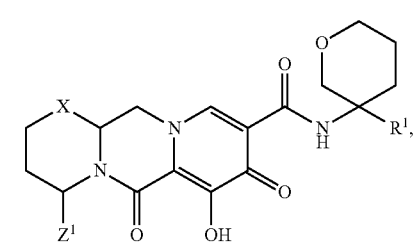

wherein $Z^1$ and $Z^3$ are each, independently, hydrogen or $C_{1-3}$alkyl.

In another embodiment, both (i) $Z^1$ and $Z^2$ or $Z^1$ and $Z^3$, taken together, form -L-, and (ii) $Y^1$ and $Y^2$, together with the carbon atom to which they are attached, form a carbocyclic ring having from 3 to 6 ring atoms or a heterocyclic ring having from 3 to 6 ring atoms.

In another embodiment, compounds are provided having one of the following Formulas (IV-AA), (IV-AB), (IV-AC), (IV-AD), (IV-AE), (IV-AF), (IV-AG) or (IV-AH):

(IV-AA)
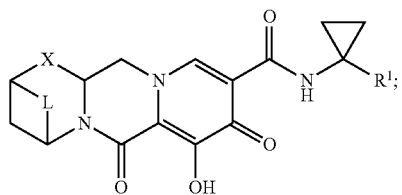

(IV-AB)
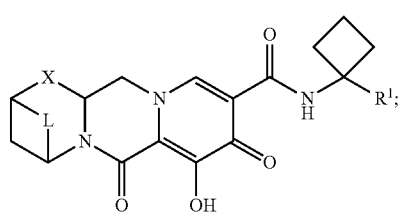

(IV-AC)
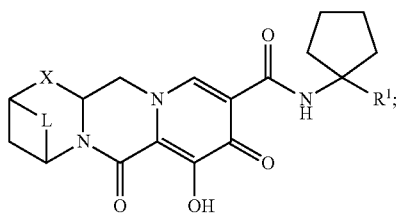

(IV-AD)
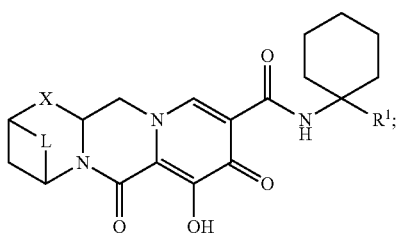

(IV-AE)
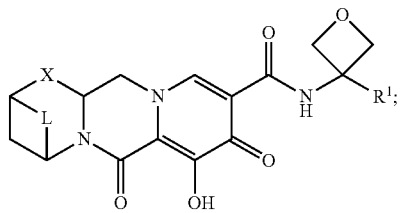

(IV-AF)
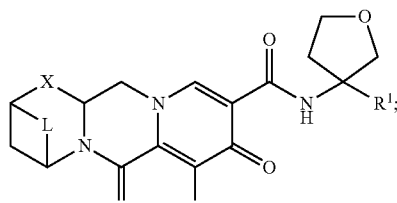

(IV-AG)
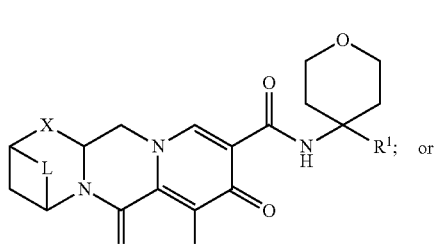  or (IV-AH)
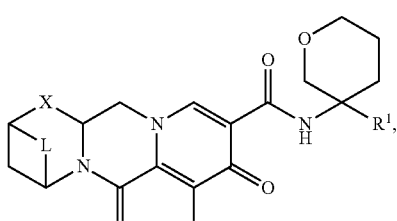

wherein L is —C(R$^a$)$_2$—, —C(R$^a$)$_2$C(R$^a$)$_2$—, —C(R$^a$)$_2$C(R$^a$)$_2$C(R$^a$)$_2$—, —C(R$^a$)$_2$C(R$^a$)$_2$C(R$^a$)$_2$C(R$^a$)$_2$—, —C(R$^a$)$_2$OC(R$^a$)$_2$—, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, —C(R$^a$)$_2$SO$_2$C(R$^a$)$_2$—, —C(R$^a$)$_2$OC(R$^a$)$_2$C(R$^a$)$_2$—, —C(R$^a$)$_2$C(R$^a$)$_2$OC(R$^a$)$_2$—, —C(R$^a$)$_2$NR$^a$C(R$^a$)$_2$C(R$^a$)$_2$—, —C(R$^a$)$_2$C(R$^a$)$_2$NR$^a$C(R$^a$)$_2$—, —C(R$^a$)$_2$SC(R$^a$)$_2$C(R$^a$)$_2$—, —C(R$^a$)$_2$C(R$^a$)$_2$SC(R$^a$)$_2$—, —C(R$^a$)$_2$S(O)C(R$^a$)$_2$C(R$^a$)$_2$—, —C(R$^a$)$_2$C(R$^a$)$_2$S(O)C $(R^a)_2$—, —$C(R^a)_2SO_2C(R^a)_2C(R^a)_2$—, —$C(R^a)_2C(R^a)_2$ $SO_2C(R^a)_2$—, —$C(R^a)_2SO_2NR^aC(R^a)_2$— or —$C(R^a)_2$ $NR^aSO_2C(R^a)_2$—.

In another embodiment, compounds are provided having one of the following Formulas (IV-BA), (IV-BB), (IV-BC), (IV-BD), (IV-BE), (IV-BF), (IV-BG) or (IV-BH):

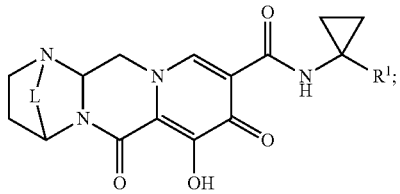

(IV-BA)

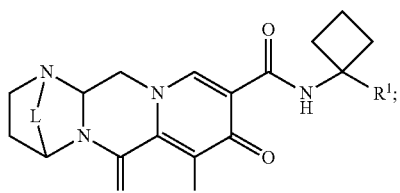

(IV-BB)

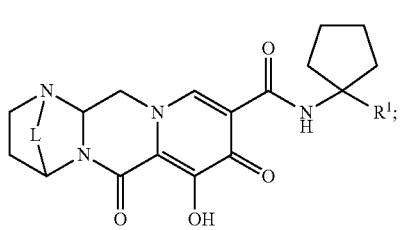

(IV-BC)

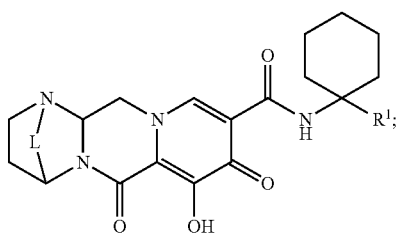

(IV-BD)

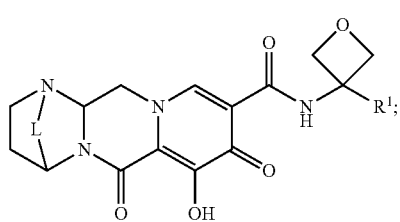

(IV-BE)

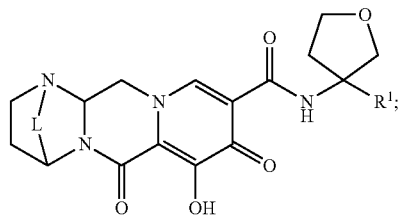

(IV-BF)

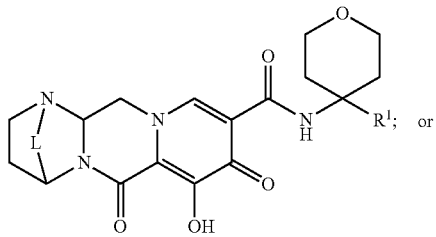

(IV-BG)

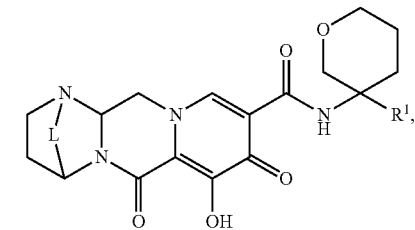

(IV-BH)

wherein L is —$C(R^a)_2$—, —$C(R^a)_2C(R^a)_2$—, —$C(R^a)_2C(R^a)_2C(R^a)_2$—, —$C(R^a)_2C(R^a)_2C(R^a)_2C(R^a)_2$—, —$C(R^a)_2OC(R^a)_2$—, —$C(R^a)_2NR^aC(R^a)_2$—, —$C(R^a)_2SC(R^a)_2$—, —$C(R^a)_2S(O)C(R^a)_2$—, —$C(R^a)_2SO_2C(R^a)_2$—, —$C(R^a)_2OC(R^a)_2C(R^a)_2$—, —$C(R^a)_2C(R^a)_2OC(R^a)_2$—, —$C(R^a)_2NR^aC(R^a)_2C(R^a)_2$—, —$C(R^a)_2C(R^a)_2NR^aC(R^a)_2$—, —$C(R^a)_2SC(R^a)_2C(R^a)_2$—, —$C(R^a)_2C(R^a)_2SC(R^a)_2$—, —$C(R^a)_2S(O)C(R^a)_2C(R^a)_2$—, —$C(R^a)_2C(R^a)_2S(O)C(R^a)_2$—, —$C(R^a)_2SO_2C(R^a)_2C(R^a)_2$—, —$C(R^a)_2C(R^a)_2SO_2C(R^a)_2$—, —$C(R^a)_2SO_2NR^aC(R^a)_2$— or —$C(R^a)_2NR^aSO_2C(R^a)_2$—.

In another embodiment, L is —$C(R^a)_2$—, —$C(R^a)_2C(R^a)_2$—, —$C(R^a)_2C(R^a)_2C(R^a)_2$—, or —$C(R^a)_2C(R^a)_2C(R^a)_2C(R^a)_2$—. In a further embodiment, L is —$C(R^a)_2$—. In still a further embodiment, L is —$C(R^a)_2C(R^a)_2$—. In still a further embodiment, L is —$C(R^a)_2C(R^a)_2C(R^a)_2$—. In still a further embodiment, each $R^a$ is hydrogen. In still a further embodiment, one $R^a$ is methyl and each remaining $R^a$ is hydrogen. In still a further embodiment, one $R^a$ is halogen and each remaining $R^a$ is hydrogen. In still a further embodiment, two $R^a$ are halogen and each remaining $R^a$ is hydrogen. In still a further embodiment, one $R^a$ is halogen and each remaining $R^a$ is hydrogen.

In another embodiment, L is —$C(R^a)_2OC(R^a)_2$—, —$C(R^a)_2NR^aC(R^a)_2$—, —$C(R^a)_2SC(R^a)_2$—, —$C(R^a)_2S(O)C(R^a)_2$—, or —$C(R^a)_2SO_2C(R^a)_2$—. In a further embodiment, L is —$C(R^a)_2OC(R^a)_2$—. In still a further embodiment, each $R^a$ is hydrogen. In still a further embodiment, one $R^a$ is methyl and each remaining $R^a$ is hydrogen. In still a further embodiment, one $R^a$ is halogen and each remaining $R^a$ is hydrogen. In still a further embodiment, two $R^a$ are halogen and each remaining $R^a$ is hydrogen. In still a further embodiment, one $R^a$ is halogen and each remaining $R^a$ is hydrogen.

In another embodiment, X is —O—. In a further embodiment, $Z^2$ is hydrogen. In another embodiment, X is —$NZ^3$—. In another embodiment, X is —NH—. In another embodiment, X is —$CHZ^3$—. In another embodiment, X is —$CH_2$—.

In another embodiment, $Z^4$ is a bond or —$CH_2$—. In another embodiment, $Z^4$ is —$CH_2$—. In another embodiment, $Z^4$ is a bond.

In another embodiment, $Y^1$ and $Y^2$ are each independently hydrogen, methyl or trifluoromethyl.

In another embodiment, R¹ is substituted with one halogen. In a further embodiment, R¹ is 4-fluorophenyl or 2-fluorophenyl.

In another embodiment, R¹ is phenyl. In another embodiment, R¹ is pyridinyl.

In another embodiment, R¹ is substituted with at least one halogen.

In another embodiment, R¹ is substituted with one halogen. In a further embodiment, R¹ is 4-fluorophenyl or 2-fluorophenyl.

In another embodiment, R¹ is substituted with two halogens. In a further embodiment, R¹ is 2,4-difluorophenyl, 2,3-difluorophenyl, 2,6-difluorophenyl, 3-fluoro-4-chlorophenyl, 3,4-difluorophenyl, 2-fluoro-4-chlorophenyl, or 3,5-difluorophenyl. In still a further embodiment, R¹ is 2,4-difluorophenyl.

In another embodiment, R¹ is substituted with three halogens. In a further embodiment, R¹ is 2,4,6-trifluorophenyl or 2,3,4-trifluorophenyl. In still a further embodiment, R¹ is 2,4,6-trifluorophenyl.

In another embodiment, R¹ is 3-trifluoromethyl-4-fluorophenyl or 2-cyclopropoxy-4-fluorophenyl.

In one embodiment, a pharmaceutical composition is provided comprising a compound of any one of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a stereoisomer or pharmaceutically acceptable salt thereof, and a pharmaceutically acceptable carrier, diluent or excipient.

Another embodiment is provided comprising a method of treating an HIV infection in a human having or at risk of having the infection by administering to the human a therapeutically effective amount of a compound of any one of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof. Another embodiment is provided comprising a method of treating or preventing an HIV infection in a human having or at risk of having the infection by administering to the human a therapeutically effective amount of a compound of any one of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof.

In another embodiment, the use of a compound of any one of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof for the treatment of an HIV infection in a human having or at risk of having the infection. In another embodiment, the use of a compound of any one of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof for the treatment or prevention of an HIV infection in a human having or at risk of having the infection.

In another embodiment, the use in medical therapy of a compound of any one of the Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof, is provided.

In another embodiment, the use of a compound of any one of the Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof, for use in the therapeutic treatment of an HIV infection is provided. In another embodiment, the use of a compound of any one of the Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as noted above, or a pharmaceutical composition thereof, for use in the prophylactic or therapeutic treatment of an HIV infection is provided.

It is understood that any embodiment of the compounds of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as set forth above, and any specific substituent set forth herein for a $R^1$, $R^a$, X, W, $Y^1$, $Y^2$, L, $Z^1$, $Z^2$, $Z^3$, or $Z^4$ group in the compounds of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), as set forth above, may be independently combined with other embodiments and/or substituents of compounds of Formulas (I), (II-A), (II-B), (II-C), (III-A), (III-B), (III-C), (III-D), (III-E), (III-F), (III-G), (III-H), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), to form embodiments of the inventions not specifically set forth above. In addition, in the event that a list of substitutents is listed for any particular $R^1$, $R^a$, X, W, $Y^1$, $Y^2$, L, $Z^1$, $Z^2$, $Z^3$, or $Z^4$ in a particular embodiment and/or claim, it is understood that each individual substituent may be deleted from the particular embodiment and/or claim and that the remaining list of substituents will be considered to be within the scope of the invention.

As one of skill in the art will appreciate, compounds of Formulas (I), (II-A), (II-B), (II-C), (IV-AA), (IV-AB), (IV-AC), (IV-AD), (IV-AE), (IV-AF), (IV-AG), (IV-AH), (IV-BA), (IV-BB), (IV-BC), (IV-BD), (IV-BE), (IV-BF), (IV-BG), and (IV-BH), wherein $Z^1$ and $Z^2$ or $Z^1$ and $Z^3$, taken together, form -L- may be shown in several different ways. For example, the Compound 3 of Example 3 may be shown as:

3

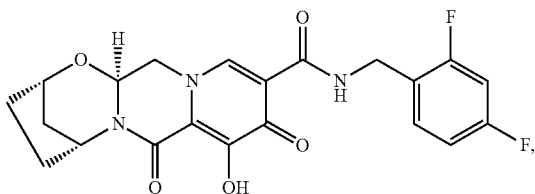

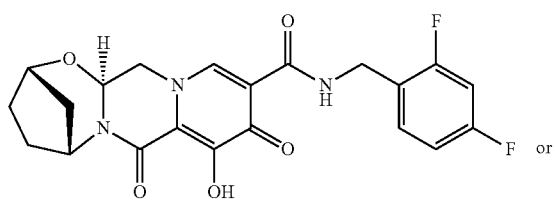

3

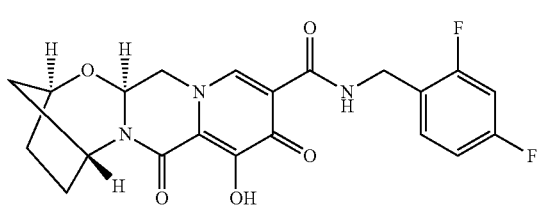

3

Pharmaceutical Compositions

For the purposes of administration, in certain embodiments, the compounds described herein are administered as a raw chemical or are formulated as pharmaceutical compositions. Pharmaceutical compositions disclosed herein include a compound of Formula (I) and one or more of: a pharmaceutically acceptable carrier, diluent or excipient. The compound of Formula (I) is present in the composition in an amount which is effective to treat a particular disease or condition of interest. The activity of compounds of Formula (I) can be determined by one skilled in the art, for example, as described in the Examples below. Appropriate concentrations and dosages can be readily determined by one skilled in the art. In certain embodiments, a compound of Formula (I) is present in the pharmaceutical composition in an amount from about 25 mg to about 500 mg. In certain embodiments, a compound of Formula (I) is present in the pharmaceutical composition in an amount of about 100 mg to about 300 mg. In certain embodiments, a compound of Formula (I) is present in the pharmaceutical composition in an amount of about 25 mg, 50 mg, 100 mg, 200 mg, 300 mg, 400 mg or about 500 mg.

Administration of the compounds of the invention, or their pharmaceutically acceptable salts, in pure form or in an appropriate pharmaceutical composition, is carried out via any of the accepted modes of administration of agents for serving similar utilities. The pharmaceutical compositions of the invention are prepared by combining a compound of the invention with an appropriate pharmaceutically acceptable carrier, diluent or excipient, and in specific embodiments are formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral, sublingual, buccal, rectal, vaginal, and intranasal. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings described herein.

The pharmaceutical compositions disclosed herein are prepared by methodologies well known in the pharmaceutical art. For example, in certain embodiments, a pharmaceutical composition intended to be administered by injection is prepared by combining a compound of the invention with sterile, distilled water so as to form a solution. In some embodiments, a surfactant is added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Combination Therapy

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents.

In one embodiment, pharmaceutical compositions comprising a compound disclosed herein, or a pharmaceutically acceptable salt thereof, in combination with one or more additional therapeutic agents, and a pharmaceutically acceptable carrier, diluent or excipient are provided.

In one embodiment, combination pharmaceutical agents comprising a compound disclosed herein, or a pharmaceutically acceptable salt thereof, in combination with one or more additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof. In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A:

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDXO10 (ipilimumab), PBS 119, ALG 889, and PA-1050040 (PA-040), and combinations thereof In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

The following Examples illustrate various methods of making compounds of this invention, i.e., compound of Formula (I):

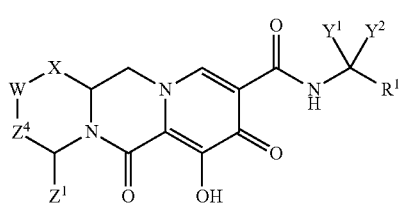

wherein $R^1$, X, W, $Y^1$, $Y^2$, $Z^1$, $Z^2$, or $Z^4$ are as defined above. It is understood that one skilled in the art may be able to make these compounds by similar methods or by combining other methods known to one skilled in the art. It is also understood that one skilled in the art would be able to make, in a similar manner as described below, other compounds of Formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

General Synthetic Schemes

Schemes 1-3 are provided as further embodiments of the invention and illustrate general methods which were used to prepare compounds having Formula (I) and which can be used to prepare additional compound having Formula (I).

Scheme 1

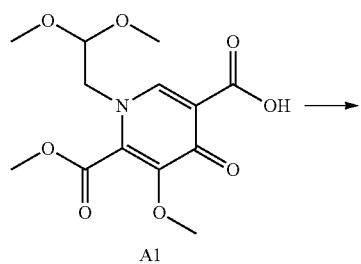

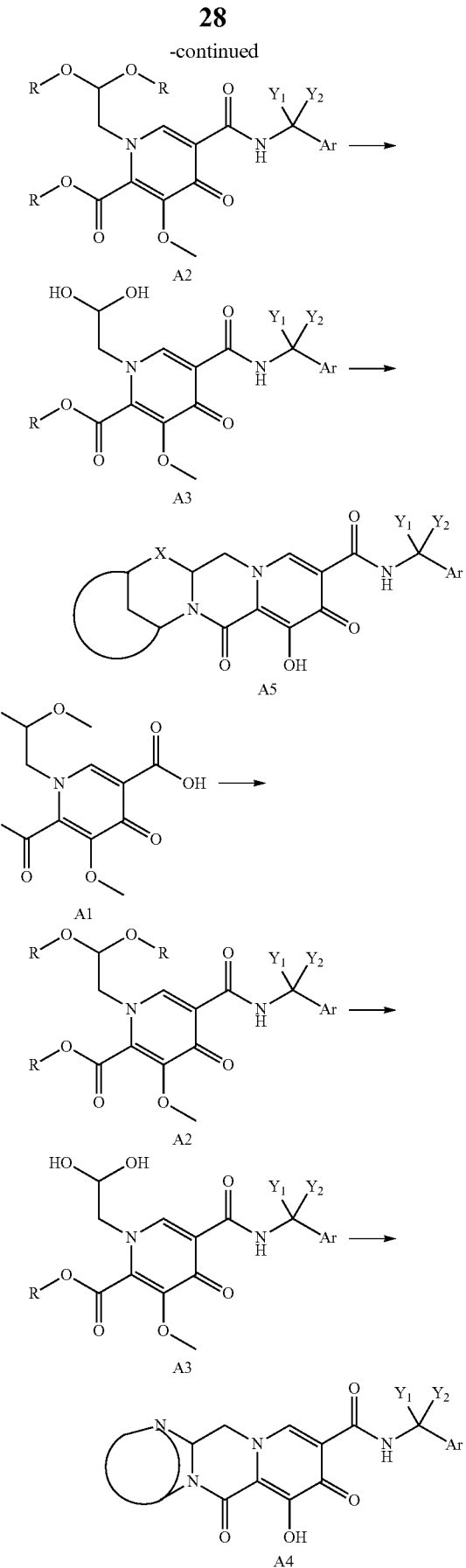

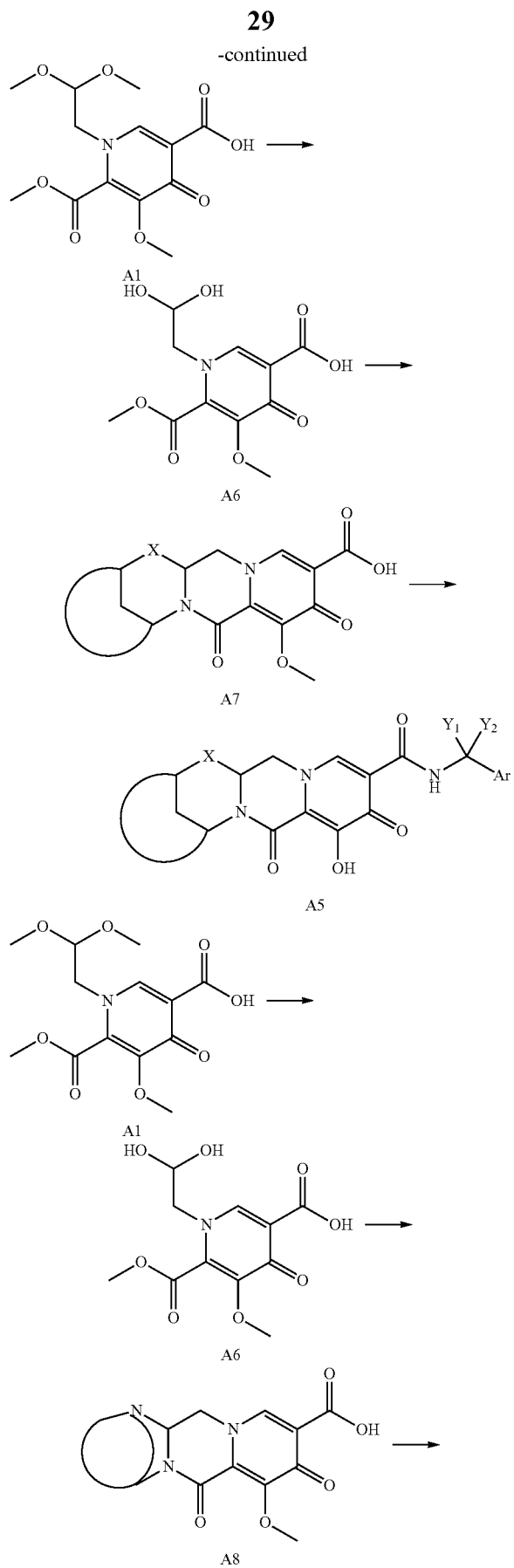

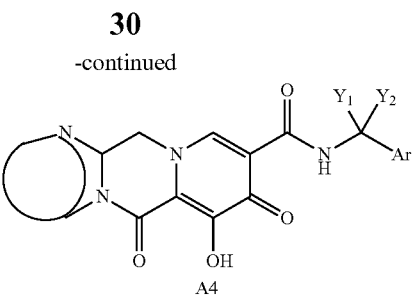

A1 can be converted to amide A2 with an appropriate amine and a coupling reagent such as HATU or EDCI. A2 can be converted to A3 with a strong acid such as methanesulfonic acid. A3 can be converted to either A5 or A4 by heating with an appropriate cyclic diamine or cyclic aminoalcohol followed by methyl deprotection with a reagent such as magnesium bromide.

Alternatively, A1 can be converted to A6 by treatment with a strong acid such as methanesulfonic acid. A6 can be condensed with an appropriate cyclic diamine or cyclic aminoalcohol followed by methyl deprotection with a reagent such as magnesium bromide to form either A7 or A8 respectively. A7 or A8 can be converted into amides A5 and A4 by treatment with an appropriate amine and a coupling reagent such as HATU or EDCI followed by methyl deprotection with a reagent such as magnesium bromide.

Scheme 2

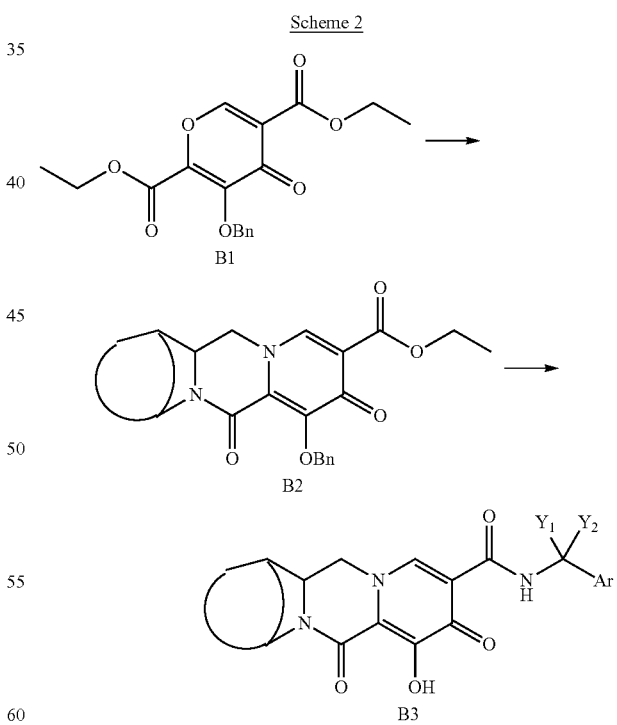

B1 (as described in WO2012/018065) is condensed with diamine under reflux condition to give B2. B2 is hydrolyzed and coupled with an amine by an amide-forming method to afford product B3 upon removal of a benzyl protecting group.

Representative Compounds

Example 1

Preparation of Compound 1

N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

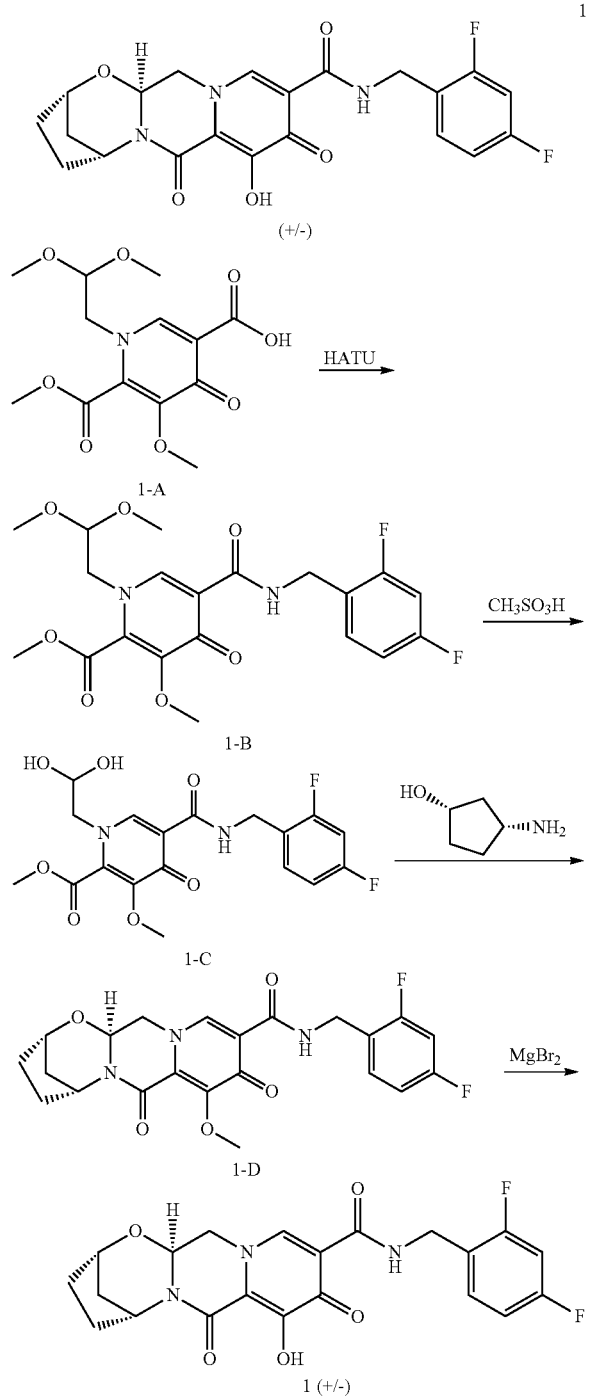

Step 1

1-(2,2-dimethoxyethyl)-5-methoxy-6-(methoxycarbonyl)-4-oxo-1,4-dihydropyridine-3-carboxylic acid (1-A, 0.300 g, 0.95 mmol), prepared as described in WO2011/119566 A1, was evaporated once from dry toluene, suspended in acetonitrile (4 mL) and treated with N,N-diisopropylethylamine (DIPEA) (0.329 mL, 1.90 mmol), 2,4-difluorobenzylamine (0.125 mL, 1.05 mmol) and HATU (0.433 g, 1.14 mmol). The reaction mixture was stirred for 10 minutes and concentrated. The residue was purified by flash chromatography on silica gel (10 to 60% ethyl acetate:dichloromethane) to afford the compound methyl 5-(2,4-difluorobenzylcarbamoyl)-1-(2,2-dimethoxyethyl)-3-methoxy-4-oxo-1,4-dihydropyridine-2-carboxylate, 1-B. $^1$H-NMR (400 MHz, DMSO-d6) δ 10.28 (t, J=6.0 Hz, 1H), 8.46 (s, 1H), 7.42 (dd, J=15.4, 8.6 Hz, 1H), 7.24 (m, 1H), 7.06 (m, 1H), 4.52 (m, 3H), 4.22 (d, J=4.4 Hz, 2H), 3.92 (s, 3H), 3.80 (s, 3H), 3.29 (d, 6H). LCMS-ESI$^+$ (m/z): [M+H]$^+$ calculated for $C_{20}H_{23}F_2N_2O_7$: 441.15; found: 441.2.

Step 2

Methyl 5-(2,4-difluorobenzylcarbamoyl)-1-(2,2-dimethoxyethyl)-3-methoxy-4-oxo-1,4-dihydropyridine-2-carboxylate (1-B, 0.106 g, 0.24 mmol) in acetonitrile (0.9 mL) and acetic acid (0.1 mL) was treated with methanesulfonic acid (0.005 mL, 0.072 mmol), sealed with a yellow cap, and heated to 70° C. After 16 hours, the mixture was cooled to afford a crude solution of methyl 5-(2,4-difluorobenzylcarbamoyl)-1-(2,2-dihydroxyethyl)-3-methoxy-4-oxo-1,4-dihydropyridine-2-carboxylate, 1-C. LCMS-ESI$^+$ (m/z): [M+H]$^+$ calculated for $C_{18}H_{19}F_2N_2O_7$: 413.12; found: 413.1.

Steps 3 and 4

Methyl 5-(2,4-difluorobenzylcarbamoyl)-1-(2,2-dihydroxyethyl)-3-methoxy-4-oxo-1,4-dihydropyridine-2-carboxylate (1-C, 0.65 mL of the crude mixture from the previous step, 0.17 mmol) was treated with acetonitrile (0.65 mL) and cis-3-aminocyclpentanol (0.06 mL). The reaction mixture was sealed and heated to 90° C. After 30 minutes, the reaction mixture was cooled and magnesium bromide (0.063 g, 0.34 mmol) was added. The mixture was resealed and heated to 50° C. After 10 minutes, the reaction mixture was partitioned between dichloromethane and hydrochloric acid (0.2 M aq). The organic layer was removed and the aqueous layer extracted again with dichlormethane. The combined organic layers were dried over sodium sulfate, filtered and concentrated. Prep-HPLC purification (30-70% acetonitrile:water, 0.1% TFA) afforded Compound 1 as a racemic mixture. $^1$H-NMR (400 MHz, DMSO-d6) δ 12.45 (br s, 1H), 10.35 (t, J=5.8 Hz, 1H), 8.45 (s, 1H), 7.37 (dd, J=15.4, 8.6 Hz, 1H), 7.23 (dt, J=2.5, 9.9 Hz, 1H), 7.05 (dt, J=2.2, 8.7 Hz, 1H), 5.43 (dd, J=9.6, 4.0 Hz, 1H), 5.09 (br s, 1H), 4.68 (dd, J=13.2, 4.0 Hz, 1H), 4.59 (br s, 1H), 4.53 (m, 2H), 4.02 (dd, J=12.6, 9.4 Hz, 1H), 1.93 (br s, 4H), 1.83 (d, J=12.0 Hz), 1.57 (dt, J=12.2, 3.2 Hz). LCMS-ESI$^+$ (m/z): [M+H]$^+$ calculated for $C_{21}H_{20}F_2N_3O_5$: 432.14; found: 432.2.

Examples 2 and 3

Preparation of Compounds 2 and 3

(2R,5S,13aR)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide (2) and (2S,5R,13aS)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide (3)

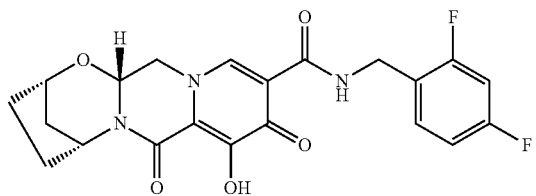

Compound 1 (16 mg) was separated by chiral HPLC using Chiralpak AS-H with 100% ethanol as eluent to afford Compounds 2 and 3 in enantiomerically enriched form. For Compound 2: LCMS-ESI+ (m/z): [M+H]+ calculated for $C_{21}H_{20}F_2N_3O_5$: 432.14; found: 432.2, Chiral HPLC retention time=4.50 minutes (Chiralpak AS-H, 150×4.6 mm, 1 mL/min EtOH). For Compound 3: LCMS-ESI+ (m/z): [M+H]+ calculated for $C_{21}H_{20}F_2N_3O_5$: 432.14; found: 432.2, Chiral HPLC retention time=6.84 minutes (Chiralpak AS-H, 150×4.6 mm, 1 mL/min EtOH). $^1$H-NMR (400 MHz, DMSO-d6) δ 12.45 (br s, 1H), 10.35 (t, J=5.8 Hz, 1H), 8.44 (s, 1H), 7.37 (dd, J=15.2, 8.4 Hz, 1H), 7.23 (m, 1H), 7.05 (dt, J=1.8 Hz, 8.7 Hz, 1H), 5.44 (dd, J=9.6, 4.0 Hz), 5.09 (br s, 1H), 4.68 (dd, J=12.8, 4.0 Hz, 1H), 4.59 (br s, 1H), 4.53 (m, 2H), 4.02 (dd, J=12.6, 9.4 Hz, 1H), 1.93 (br s, 4H), 1.83 (d, J=12.4 Hz, 1H), 1.57 (m, 1H).

Alternatively, Compound 3 was prepared as follows:

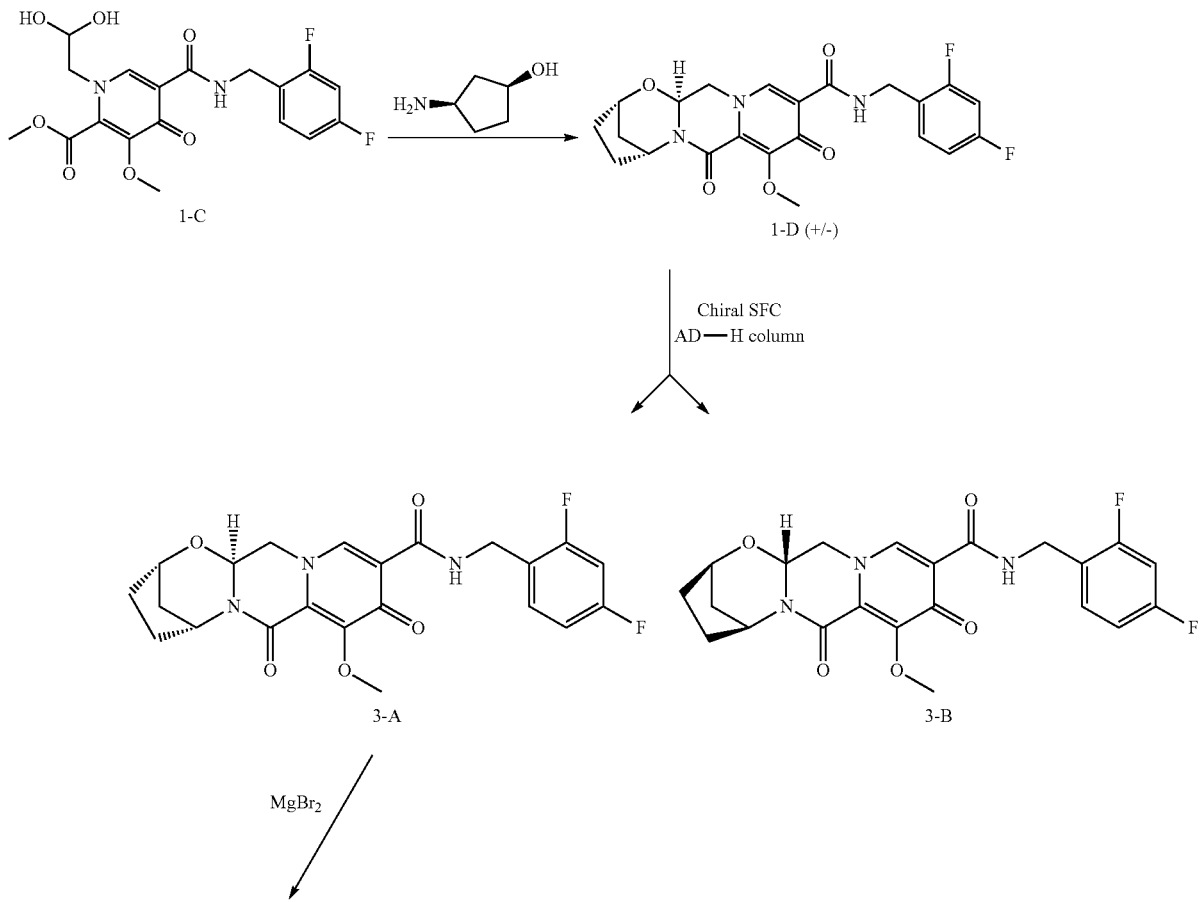

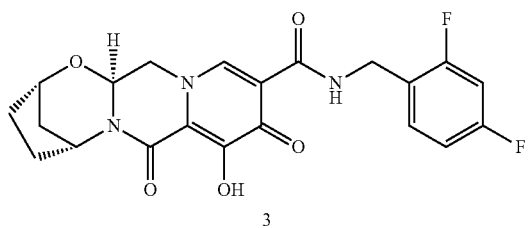

3

Methyl 5-(2,4-difluorobenzylcarbamoyl)-1-(2,2-dihydroxyethyl)-3-methoxy-4-oxo-1,4-dihydropyridine-2-carboxylate (1-C, 1.2 mmol in 5 mL of 9:1 acetonitrile:acetic acid containing 0.026 mL methanesulfonic acid) was treated with acetonitrile (5.0 mL) and cis-3-aminocyclpentanol (0.24 g, 2.4 mmol). The reaction mixture was sealed and heated to 90° C. After 30 minutes, the reaction mixture was cooled, treated with potassium carbonate (0.332 g, 2.4 mmol), sealed and reheated to 90° C. After 15 minutes, the mixture was cooled and partitioned between dichlormethane and hydrochloric acid (0.2 M aqueous). The organic layer was removed and the aqueous solution was extracted again with dichloromethane. The combined organic layers were dried over sodium sulfate (anhydrous), filtered and concentrated. The residue was purified by flash chromatography (0-8% ethanol (containing 11% saturated aqueous ammonium hydroxide) in dichloromethane) to afford Intermediate 1-D. LCMS-ESI$^+$ (m/z): [M+H]$^+$ calculated for $C_{22}H_{22}F_2N_3O_5$: 446.15; found: 446.2.

Intermediate 1-D (270 mg) was separated by chiral SFC on a 50 mm Chiralpak AD-H column using 50% (1:1 methanol:acetonitrile) in supercritical carbon dioxide as eluent to afford Intermediates 3-A (first eluting peak) and 3-B (second eluting peak) in enantioenriched form. For 3-A: LCMS-ESI$^+$ (m/z): [M+H]$^+$ calculated for $C_{22}H_{22}F_2N_3O_5$: 446.15; found: 446.2. For 3-B: LCMS-ESI$^+$ (m/z): [M+H]$^+$ calculated for $C_{22}H_{22}F_2N_3O_5$: 446.15; found: 446.2.

Intermediate 3-A (0.110 g, 0.247 mmol) in acetonitrile (5 mL) was treated portion wise with magnesium bromide (0.091 g, 0.494 mmol), sealed and heated to 50° C. After 10 minutes the mixture was cooled and partitioned between dichloromethane and hydrochloric acid (0.2 M aqueous). The organic layer was separated and the aqueous extracted again with dichloromethane. The combined organic layers were dried over sodium sulfate, filtered and concentrated. Preparative HPLC purification (30-70% acetonitrile:water, 0.1% TFA) afforded Compound 3 in enantioenriched form. Chiral HPLC retention time=6.51 minutes (Chiralpak AS-H, 150×4.6 mm, 1 mL/min EtOH). LCMS-ESI$^+$ (m/z): [M+H]$^+$ calculated for $C_{21}H_{20}F_2N_3O_5$: 432.14; found: 432.2. $^1$H-NMR (400 MHz, DMSO-d6) δ 12.45 (br s, 1H), 10.35 (t, J=5.8 Hz, 1H), 8.44 (s, 1H), 7.37 (dd, J=15.2, 8.4 Hz, 1H), 7.23 (m, 1H), 7.05 (dt, J=1.8 Hz, 8.7 Hz, 1H), 5.44 (dd, J=9.6, 4.0 Hz, 1H), 5.09 (br s, 1H), 4.68 (dd, J=12.8, 4.0 Hz, 1H), 4.59 (br s, 1H), 4.53 (m, 2H), 4.02 (dd, J=12.6, 9.4 Hz, 1H), 1.93 (br s, 4H), 1.83 (d, J=12.4 Hz, 1H), 1.57 (m, 1H).

Example 4

Preparation of Compound 4

(1S,4R)—N-(2,4-difluorobenzyl)-7-hydroxy-6,8-dioxo-3,4,6,8,12,12a-hexahydro-2H-1,4-methanopyrido[1',2':4,5]pyrazino[1,2-a]pyrimidine-9-carboxamide

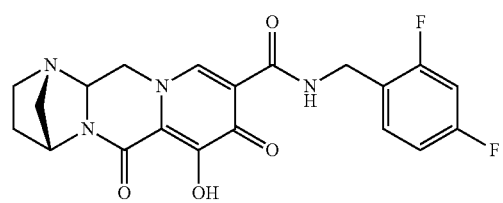

4

Methyl 5-(2,4-difluorobenzylcarbamoyl)-1-(2,2-dihydroxyethyl)-3-methoxy-4-oxo-1,4-dihydropyridine-2-carboxylate (1-C, 0.12 mmol in 0.53 mL of 9:1 acetonitrile: acetic acid containing 0.002 mL methanesulfonic acid) was treated with acetonitrile then (R)-pyrrolidin-3-amine (0.032 mL, 0.36 mmol). The reaction mixture was capped and heated to 90° C. for 5.5 hours. After cooling, the mixture was partitioned between dichloromethane and sodium bicarbonate (1M aqueous). The organic layer was separated and the aqueous was extracted again with ethyl acetate. The combined organic layers were dried over sodium sulfate (anhydrous), filtered and concentrated. The residue was dissolved in acetonitrile (1 mL), treated with magnesium bromide (0.022 g, 0.12 mmol), capped and heated to 50° C. for 10 minutes. After cooling the mixture was partitioned between dichloromethane and ammonium chloride (sat). The organic layer was separated and the aqueous was extracted again with dichloromethane. The aqueous layer was adjusted to pH=1 with HCl (aq) and extracted again with dichloromethane. The aqueous solution was adjusted to pH=3 with NaOH (aq) and extracted again with dichloromethane. The combined organic layers were dried over sodium sulfate, filtered, and concentrated. Preparative HPLC purification (10-55% acetonitrile:water, 0.1% TFA) afforded Compound 4. $^1$H-NMR (400 MHz, CD$_3$OD-d4) δ 8.42 (s, 1H), 7.42, (q, J=7.7 Hz, 1H), 6.99-6.90 (m, 2H), 5.07 (br s, 1H), 4.73 (br d, J=10.8 Hz, 1H), 4.62 (s, 2H), 4.51 (br d, J=12.8 Hz, 1H), 4.07 (t, J=11.8 Hz, 1H), 3.4-3.0 (m, 3H), 2.76 (br d, J=8.8 Hz, 1H), 2.15-2.0 (m, 1H), 1.9-1.8 (m, 1H). LCMS-ESI$^+$ (m/z): [M+H]$^+$ calculated for $C_{20}H_{19}F_2N_4O_4$: 417.14; found: 417.2.

Example 5

Preparation of Compound 5

(4R,12aS)—N-(1-(2,4-difluorophenyl)cyclopropyl)-7-hydroxy-4-methyl-6,8-dioxo-3,4,6,8,12,12a-hexahydro-2H-[1,3]oxazino[3,2-d]pyrido[1,2-a]pyrazine-9-carboxamide

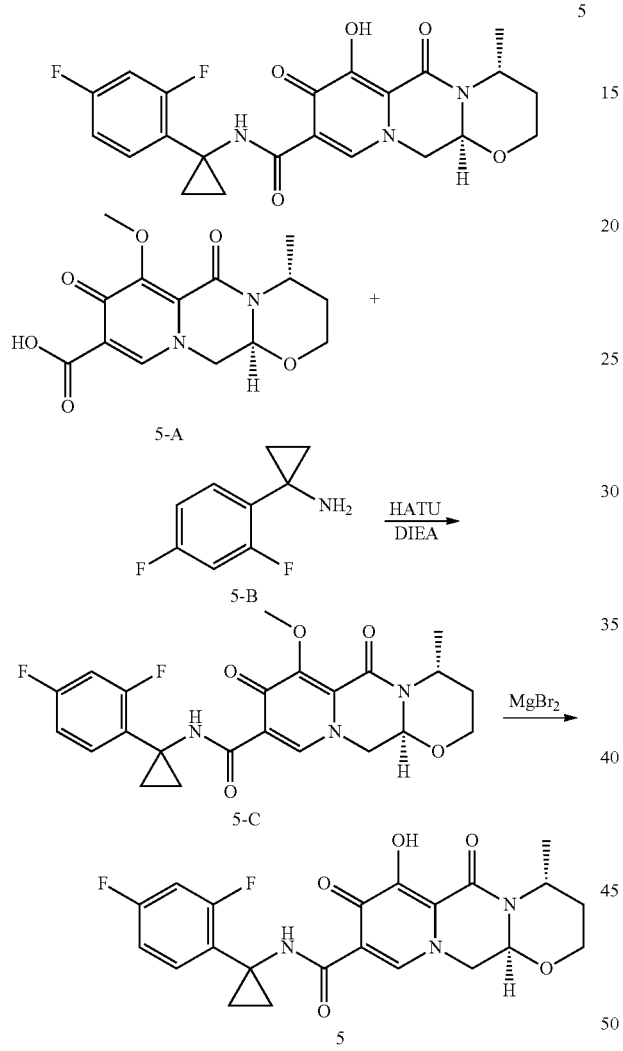

Step 1

(4R,12aS)-7-methoxy-4-methyl-6,8-dioxo-3,4,6,8,12,12a-hexahydro-2H-[1,3]oxazino[3,2-d]pyrido[1,2-a]pyrazine-9-carboxylic acid (Intermediate 5-A) was prepared in an analogous manner to (3S,11aR)-6-methoxy-3-methyl-5,7-dioxo-2,3,5,7,11,11a-hexahydrooxazolo[3,2-d]pyrido[1,2-a]pyrazine-8-carboxylic acid as described in WO2011/119566, substituting (R)-3-aminobutan-1-ol for (S)-2-aminopropan-1-ol. WO2011/119566 is incorporated herein by reference in its entirety. A suspension of Intermediate 5-A (24.8 mg, 0.080 mmol), 1-(2,4-difluorophenyl)cyclopropanamine HCl salt (5-B, 21.9 mg, 0.107 mmol), and HATU (48 mg, 0.126 mmol) in CH$_2$Cl$_2$ (2 mL) was stirred at ambient temperature as N,N-diisopropylethylamine (DIPEA) (0.1 mL, 0.574 mmol) was added. After 30 minutes, the reaction mixture was diluted with ethyl acetate before washing with 10% aqueous citric acid solution (×1) and saturated aqueous NaHCO$_3$ solution (×1). After the aqueous fractions were extracted with ethyl acetate (×1), the organic fractions were combined, dried (MgSO$_4$), and concentrated. The residue was purified by combiflash (12 g column) using hexanes, ethyl acetate, and 200% methanol in ethyl acetate to obtain (4R,12aS)—N-(1-(2,4-difluorophenyl)cyclopropyl)-7-methoxy-4-methyl-6,8-dioxo-3,4,6,8,12,12a-hexahydro-2H-[1,3]oxazino[3,2-d]pyrido[1,2-a]pyrazine-9-carboxamide, Intermediate 5-C. LCMS-ESI$^+$ (m/z): [M+H]$^+$ calculated for C$_{23}$H$_{24}$F$_2$N$_3$O$_5$: 460.17; found 460.2.

Step 2

A suspension of Intermediate 5-C (39 mg, 0.080 mmol) and magnesium bromide (42 mg, 0.2282 mmol) in acetonitrile (2 mL) was stirred at 50° C. After 1 hour, the reaction mixture was stirred at 0° C. bath when 1 N HCl (2 mL) was added. After the resulting mixture was diluted with water (~20 mL), the product was extracted with dichloromethane (×3) and the combined extracts were dried (MgSO$_4$) and concentrated. The residue was purified by preparative HPLC to obtain (4R,12aS)—N-(1-(2,4-difluorophenyl)cyclopropyl)-7-hydroxy-4-methyl-6,8-dioxo-3,4,6,8,12,12a-hexahydro-2H-[1,3]oxazino[3,2-d]pyrido[1,2-a]pyrazine-9-carboxamide, compound 5, as TFA salt. $^1$H-NMR (400 MHz, CDCl$_3$) δ 10.72 (br s, 1H), 8.37 (s, 1H), 7.57 (d, J=7.9 Hz, 1H), 6.71-6.81 (m, 2H), 5.23 (dd, J=5.6 and 4.4 Hz, 1H), 4.98 (br quint, J=~6.5 Hz, 1H), 4.26 (dd, J=13.6 and 4.4 Hz, 1H), 4.12 (dd, J=13.6 and 5.6 Hz, 1H), 4.00-4.06 (m, 2H), 2.16-2.25 (m, 1H), 1.55 (br dd, J=13.8 and 1.8 Hz, 1H), 1.40 (d, J=6.8 Hz, 3H), 1.22-1.31 (m, 4H). $^{19}$F NMR (376.1 MHz, CDCl$_3$) δ −76.38 (s, 3F), −111.69~−111.645 (m, 2F). LCMS-ESI$^+$ (m/z): [M+H]$^+$ calculated for C$_{22}$H$_{22}$F$_2$N$_3$O$_5$: 446.15; found: 446.2.

Example 6

Preparation of Compound 6

(1R,4S)—N-(2,4-difluorobenzyl)-7-hydroxy-6,8-dioxo-3,4,6,8,12,12a-hexahydro-2H-1,4-methanopyrido[1',2':4,5]pyrazino[1,2-a]pyrimidine-9-carboxamide Methyl 5-(2,4-difluorobenzylcarbamoyl)-1-(2,2-dihydroxyethyl)-3-methoxy-4-oxo-1,4-dihydropyridine-2-carboxylate (1-C, 0.100 g, 0.243 mmol), (S)-pyrrolidin-3-amine (0.043 mL, 0.485 mmol) and potassium carbonate (0.067 g, 0.485 mmol) were suspended in acetonitrile (1.9 mL) and acetic acid (0.1 mL) and heated to 90° C. for 1.5 hours. After cooling, the mixture was treated with magnesium bromide (0.090 g) and heated to 50° C. for 30 minutes. After cooling, the mixture partitioned between dichloromethane and 0.2 M HCl. The organic layer was separated and the aqueous was extracted again with dichloromethane.

The combined organic layers were dried over sodium sulfate (anhydrous), filtered and concentrated. Preparative HPLC purification (25-50% acetonitrile:water, 0.1% TFA) afforded Compound 6. $^1$H-NMR (400 MHz, DMSO-d$_6$) δ 10.33 (t, J=6.0 Hz, 1H), 8.44 (s, 1H), 7.48-7.32 (m, 1H), 7.31-7.15 (m, 1H), 7.14-6.97 (m, 1H), 4.86 (d, J=2.9 Hz, 1H), 4.62-4.54 (m, 1H), 4.52 (d, J=5.9 Hz, 1H), 4.01 (d, J=13.0 Hz, 1H), 2.99-2.76 (m, 3H), 1.96-1.81 (m, 1H), 1.71-1.53 (m, 1H). LCMS-ESI$^+$ (m/z): [M+H]$^+$ calculated for C$_{20}$H$_{19}$F$_2$N$_4$O$_4$: 417.14; found: 417.2.

Example 7

Preparation of Compound 7

(2S,6R)—N-(2,4-difluorobenzyl)-9-hydroxy-8,10-dioxo-3,4,5,6,8,10,14,14a-octahydro-2H-2,6-methanopyrido[1',2':4,5]pyrazino[2,1-b][1,3]oxazocine-11-carboxamide

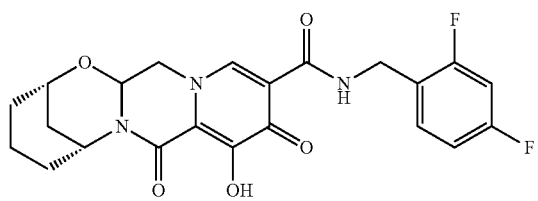

Methyl 5-(2,4-difluorobenzylcarbamoyl)-1-(2,2-dihydroxyethyl)-3-methoxy-4-oxo-1,4-dihydropyridine-2-carboxylate (1-C, 0.050 g, 0.121 mmol), (1S,3R)-3-aminocyclohexanol (0.028 g, 0.243 mmol) and potassium carbonate (0.034 g, 0.243 mmol) were suspended in acetonitrile (0.95 mL) and heated to 90° C. for 0.5 hour. After cooling, acetic acid (0.050 mL) was added and the mixture was reheated to 90° C. for 2 h. After cooling the mixture was treated with magnesium bromide (0.044 g) and heated to 50° C. for 1 hour. After cooling, a second portion of magnesium bromide (0.044 g) was added and the mixture was reheated to 50° C. for 15 minutes. After cooling, the mixture partitioned between dichloromethane and 0.2 M HCl. The organic layer was separated and the aqueous was extracted again with dichloromethane. The combined organic layers were dried over sodium sulfate (anhydrous), filtered and concentrated. Preparative HPLC purification (40-80% acetonitrile:water, 0.1% TFA) afforded Compound 7. $^1$H-NMR (400 MHz, DMSO-d$_6$) δ 12.40 (s, 1H), 10.36 (t, J=6.1 Hz, 1H), 8.45 (s, 1H), 7.48-7.29 (m, 1H), 7.31-7.13 (m, 1H), 7.13-6.97 (m, 1H), 5.56 (dd, J=10.0, 4.1 Hz, 1H), 4.70 (dd, J=12.7, 4.1 Hz, 1H), 4.52 (d, J=5.5 Hz, 2H), 4.40-4.29 (m, 2H), 4.06 (dd, J=12.5, 10.2 Hz, 1H), 2.46-2.36 (m, 1H), 1.98-1.63 (m, 4H), 1.57-1.30 (m, 3H). LCMS-ESI$^+$ (m/z): [M+H]$^+$ calculated for C$_{22}$H$_{22}$F$_2$N$_3$O$_5$: 446.15; found: 446.2.

Example 8

Preparation of Compound 8

(2R,6S)—N-(2,4-difluorobenzyl)-9-hydroxy-8,10-dioxo-3,4,5,6,8,10,14,14a-octahydro-2H-2,6-methanopyrido[1',2':4,5]pyrazino[2,1-b][1,3]oxazocine-11-carboxamide

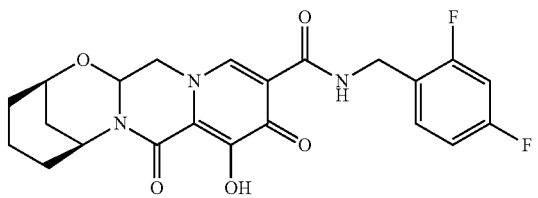

Compound 8 was prepared in a similar manner to compound 7 using (1R,3S)-3-aminocyclohexanol in place of (1S,3R)-3-aminocyclohexanol. $^1$H-NMR (400 MHz, DMSO-d$_6$) δ 12.40 (s, 1H), 10.36 (t, J=6.1 Hz, 1H), 8.45 (s, 1H), 7.48-7.30 (m, 1H), 7.23 (td, J=10.6, 2.7 Hz, 1H), 7.05 (td, J=8.3, 2.3 Hz, 1H), 5.56 (dd, J=10.1, 4.1 Hz, 1H), 4.70 (dd, J=12.8, 3.9 Hz, 1H), 4.52 (d, J=5.6 Hz, 2H), 4.39-4.27 (m, 2H), 4.06 (dd, J=12.6, 10.0 Hz, 1H), 2.47-2.35 (m, 1H), 2.00-1.64 (m, 4H), 1.58-1.30 (m, 3H). LCMS-ESI$^+$ (m/z): [M+H]$^+$ calculated for C$_{22}$H$_{22}$F$_2$N$_3$O$_5$: 446.15; found: 446.2.

Examples 9 and 10

Preparation of Compounds 9 and 10

(2S,5R,13aS)—N—((R)-1-(4-fluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide 9 and (2R,5S,13aR)—N—((R)-1-(4-fluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide 10

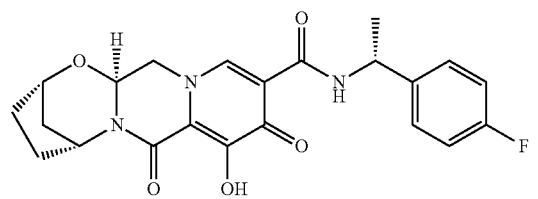

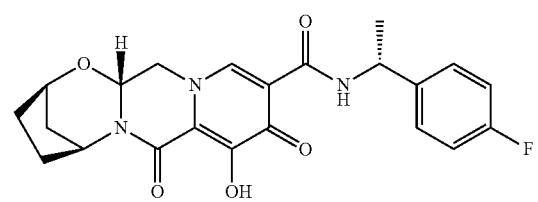

-continued

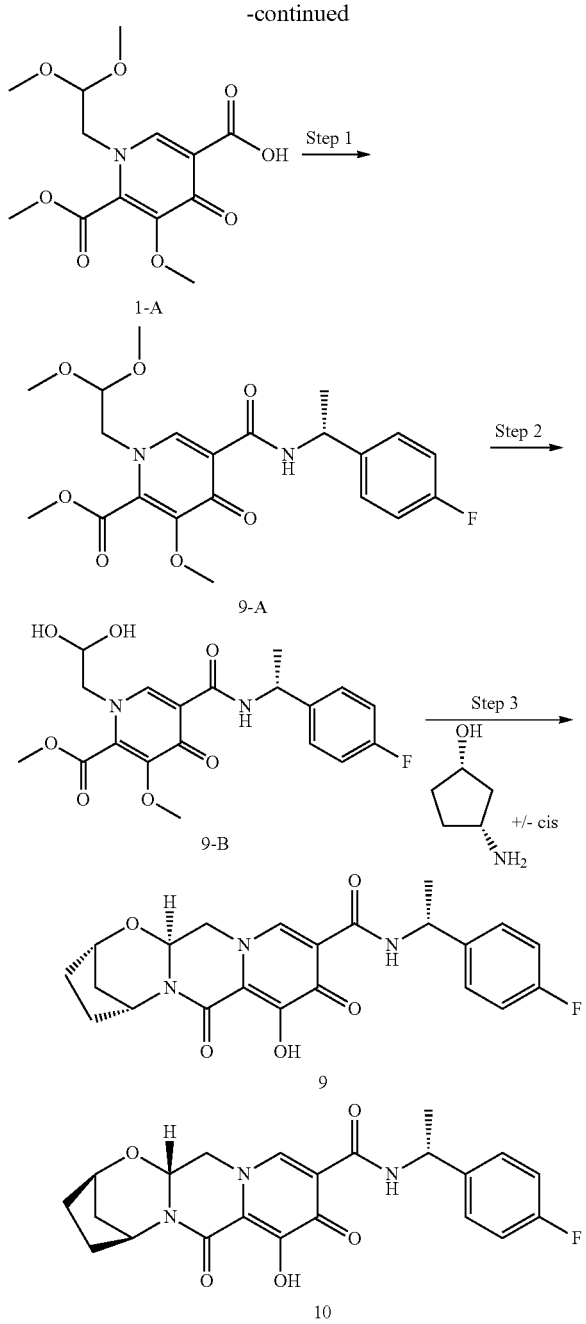

Step 1

1-(2,2-dimethoxyethyl)-5-methoxy-6-(methoxycarbonyl)-4-oxo-1,4-dihydropyridine-3-carboxylic acid (1-A, 0.500 g, 1.59 mmol), was suspended in acetonitrile (6 mL) and treated with N,N-diisopropylethylamine (DIPEA) (0.550 mL, 3.17 mmol), (R)-1-(4-fluorophenyl)ethanamine (0.242 mg, 1.74 mmol) and HATU (0.661 g, 1.74 mmol). The reaction mixture was stirred for 2 hours and partitioned between ethyl acetate and water. The organic layer was separated and washed with HCl (10% aq), sodium bicarbonate (1M aq), dried over sodium sulfate, filtered and concentrated to afford crude (R)-methyl 1-(2,2-dimethoxyethyl)-5-(1-(4-fluorophenyl)ethylcarbamoyl)-3-methoxy-4-oxo-1,4-dihydropyridine-2-carboxylate which was used without purification in the next step: LCMS-ESI+ (m/z): [M+H]+ calculated for $C_{21}H_{26}FN_2O_7$: 437.17; found: 437.1.

Step 2

(R)-methyl 1-(2,2-dimethoxyethyl)-5-(1-(4-fluorophenyl)ethylcarbamoyl)-3-methoxy-4-oxo-1,4-dihydropyridine-2-carboxylate was suspended in acetonitrile (5.7 mL) and acetic acid (0.6 mL) and treated with methane sulfonic acid (0.031 mL, 0.477 mmol). The mixture was capped and heated to 75° C. After 7 h, the mixture was cooled and used without purification in the next step: LCMS-ESI+ (m/z): [M+H]+ calculated for $C_{19}H_{22}FN_2O_7$: 409.14; found: 409.0.

Step 3

(R)-methyl 1-(2,2-dihydroxyethyl)-5-(1-(4-fluorophenyl)ethylcarbamoyl)-3-methoxy-4-oxo-1,4-dihydropyridine-2-carboxylate (3.6 mL of the crude mixture from Step 2, 0.8 mmol) was diluted with acetonitrile (3.6 mL) and treated with cis-3-aminocyclpentanol, HCl salt (0.219 g, 1.6 mmol) and potassium carbonate (0.276 g, 2.0 mmol). The mixture was capped and heated to 90° C. After 20 minutes, the reaction mixture was cooled and partitioned between dichloromethane and HCl (0.2 M aq). The layers were separated and the aqueous layer was extracted again with dichloromethane. The combined organic layers were treated with a small amount of acetonitrile, dried over sodium sulfate, filtered and concentrated.

The residue was suspended in acetonitrile (4 mL) and treated with magnesium bromide (0.177 g). The mixture was capped and heated to 50° C. After 10 minutes, the reaction mixture was cooled and partitioned between dichloromethane and HCl (0.2 M aq). The layers were separated and the aqueous layer was extracted again with dichlormethane. The combined organic layers were dried over sodium sulfate, filtered and concentrated. The residue was purified by flash chromatography on silica gel (0-8% ethanol:DCM) to afford a diastereomeric mixture of desired 9 and 10.

The mixture was separated by chiral HPLC using Chiralpak AD-H with 100% ethanol as eluent to afford Compounds 9 and 10 in enantiomerically enriched form:

For Compound 9: LCMS-ESI+ (m/z): [M+H]+ calculated for $C_{22}H_{23}FN_3O_5$: 428.16; found: 428.1. Chiral HPLC retention time=10.177 minutes (Chiralpak AD-H, 150×4.6 mm, 1 mL/min EtOH). $^1$H-NMR (400 MHz, DMSO-d$_6$) δ 12.45 (s, 1H), 10.45 (d, J=7.7 Hz, 1H), 8.40 (s, 1H), 7.37 (dd, J=8.6, 5.6 Hz, 2H), 7.15 (t, J=8.9 Hz, 2H), 5.44 (dd, J=9.5, 4.2 Hz, 1H), 5.17-5.04 (m, 2H), 4.73-4.62 (m, 1H), 4.59 (s, 1H), 4.00 (dd, J=12.7, 9.5 Hz, 1H), 1.93 (s, 4H), 1.83 (d, J=11.8 Hz, 1H), 1.56 (dt, J=12.1, 3.4 Hz, 1H), 1.44 (d, J=6.9 Hz, 3H).

For Compound 10: LCMS-ESI+ (m/z): [M+H]+ calculated for $C_{22}H_{23}FN_3O_5$: 428.16; found: 428.1. Chiral HPLC retention time=14.061 minutes (Chiralpak AD-H, 150×4.6 mm, 1 mL/min EtOH). $^1$H-NMR (400 MHz, DMSO-d$_6$) δ 12.44 (s, 1H), 10.46 (d, J=7.8 Hz, 1H), 8.41 (s, 1H), 7.37 (dd, J=8.6, 5.6 Hz, 2H), 7.15 (t, J=8.9 Hz, 2H), 5.42 (dd, J=9.6, 4.1 Hz, 1H), 5.18-5.02 (m, 2H), 4.67 (dd, J=12.8, 4.2 Hz, 1H), 4.59 (s, 1H), 4.02 (dd, J=12.7, 9.6 Hz, 1H), 1.93 (s, 4H), 1.83 (d, J=12.0 Hz, 1H), 1.57 (dt, J=13.0, 3.5 Hz, 1H), 1.44 (d, J=6.9 Hz, 3H).

Example 11

Preparation of Compound 11

(2S,5R,13aS)—N—((R)-1-(2,4-difluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

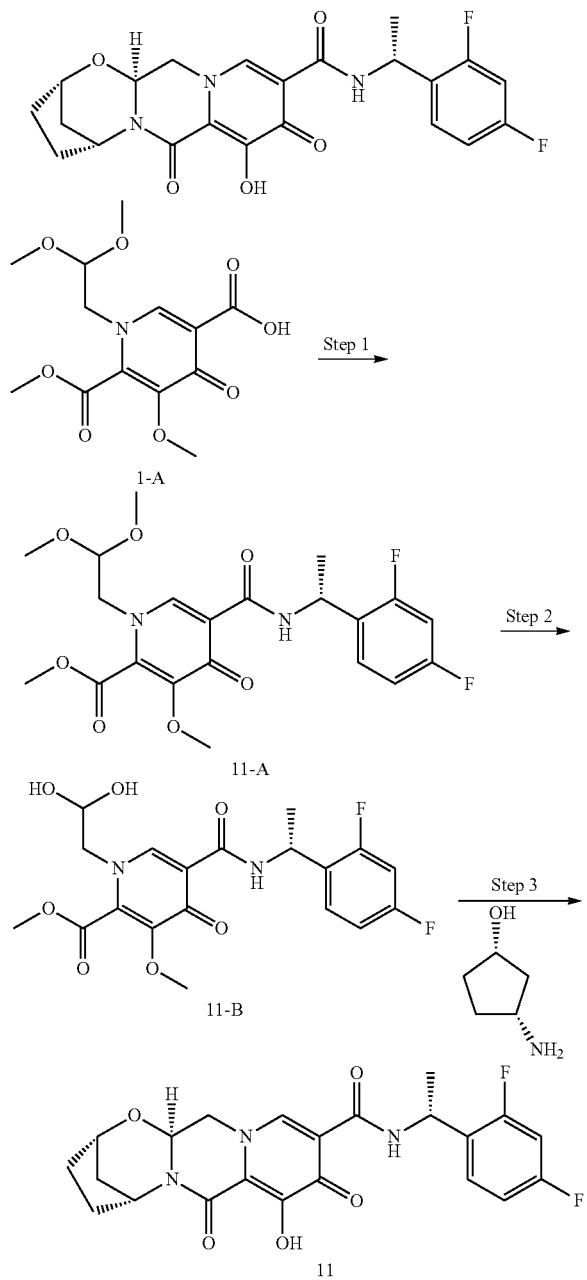

Step 1

1-(2,2-dimethoxyethyl)-5-methoxy-6-(methoxycarbonyl)-4-oxo-1,4-dihydropyridine-3-carboxylic acid (1-A, 0.315 g, 1.00 mmol), was suspended in acetonitrile (4 mL) and treated with N,N-diisopropylethylamine (DIPEA) (0.348 mL, 2.00 mmol), (R)-1-(2,4-difluorophenyl)ethanamine HCl salt (0.213 mg, 1.10 mmol) and HATU (0.418 g, 1.10 mmol). The reaction mixture was stirred for 1 hour and partitioned between dichloromethane and HCl (10% aq). The organic layer was separated and washed sodium bicarbonate (1M aq), dried over sodium sulfate, filtered and concentrated to afford crude (R)-methyl 5-(1-(2,4-difluorophenyl)ethylcarbamoyl)-1-(2,2-dimethoxyethyl)-3-methoxy-4-oxo-1,4-dihydropyridine-2-carboxylate which was used without purification in the next step. LCMS-ESI$^+$ (m/z): [M+H]$^+$ calculated for $C_{21}H_{25}F_2N_2O_7$: 455.16; found: 455.1.

Step 2

(R)-methyl 5-(1-(2,4-difluorophenyl)ethylcarbamoyl)-1-(2,2-dimethoxyethyl)-3-methoxy-4-oxo-1,4-dihydropyridine-2-carboxylate was suspended in acetonitrile (3.6 mL) and acetic acid (0.4 mL) and treated with methane sulfonic acid (0.020 mL). The mixture was capped and heated to 75° C. After 16 hours, the crude mixture was cooled and used without purification in the next step. LCMS-ESI$^+$ (m/z): [M+H]$^+$ calculated for $C_{19}H_{21}F_2N_2O_7$: 427.13; found: 427.1.

Step 3

(R)-methyl 5-(1-(2,4-difluorophenyl)ethylcarbamoyl)-1-(2,2-dihydroxyethyl)-3-methoxy-4-oxo-1,4-dihydropyridine-2-carboxylate (half of the crude mixture from Step 2, approx 0.5 mmol) was diluted with acetonitrile (2.5 mL) and treated with (1S,3R)-3-aminocyclopentanol (0.110 g, 1.09 mmol) and potassium carbonate (0.069 g, 0.50 mmol). The mixture was capped and heated to 90° C. After 15 minutes, the reaction mixture was cooled and magnesium bromide (0.184 g) was added. The reaction mixture was heated to 50° C. After 10 minutes, the mixture was cooled and treated with an additional portion of magnesium bromide (0.184 g). The reaction mixture was reheated to 50° C. and stirred for 10 minutes. After cooling, the mixture was partitioned between dichloromethane and HCl (0.2 M aq). The layers were separated and the aqueous layer was extracted again with dichloromethane. The combined organic layers were dried over sodium sulfate, filtered and concentrated. Preparative HPLC purification (30-60% acetonitrile:water, 0.1% TFA) afforded desired Compound 11. LCMS-ESI$^+$ (m/z): [M+H]$^+$ calculated for $C_{22}H_{22}F_2N_3O_5$: 446.15; found: 446.1. $^1$H-NMR (400 MHz, DMSO-d) δ 12.46 (s, 1H), 10.53 (d, J=7.5 Hz, 1H), 8.38 (s, 1H), 7.39 (q, J=8.5 Hz, 1H), 7.29-7.12 (m, 1H), 7.13-6.93 (m, 1H), 5.44 (dd, J=9.8, 4.2 Hz, 1H), 5.28 (p, J=7.3, 6.8 Hz, 1H), 5.09 (s, 1H), 4.66 (dd, J=13.2, 4.3 Hz, 1H), 4.59 (s, 1H), 3.99 (dd, J=13.1, 9.6 Hz, 1H), 1.93 (s, 4H), 1.83 (d, J=12.4 Hz, 1H), 1.56 (dt, J=12.5, 2.9 Hz, 1H), 1.45 (d, J=6.9 Hz, 3H).

Example 12

Preparation of Compound 12

(2R,5S,13aR)—N—((R)-1-(2,4-difluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

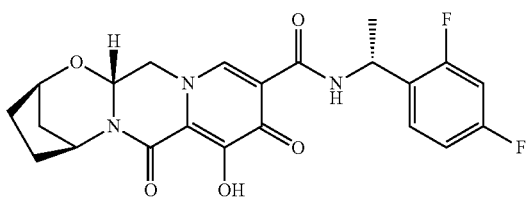

12

Compound 12 was prepared in a similar manner to compound 11 using (1R,3S)-3-aminocyclopentanol in place of (1S,3R)-3-aminocyclopentanol. $^1$H-NMR (400 MHz, DMSO-d$_6$) δ 12.43 (s, 1H), 10.52 (d, J=8.2 Hz, 1H), 8.38 (s, 1H), 7.39 (q, J=8.4 Hz, 1H), 7.28-7.12 (m, 1H), 7.11-6.97 (m, 1H), 5.41 (dd, J=10.0, 4.0 Hz, 1H), 5.35-5.20 (m, 1H), 5.08 (s, 1H), 4.65 (dd, J=13.1, 3.8 Hz, 1H), 4.58 (s, 1H), 4.01 (dd, J=12.8, 9.5 Hz, 1H), 1.92 (s, 4H), 1.83 (d, J=11.5 Hz, 1H), 1.61-1.51 (m, 1H), 1.44 (d, J=6.9 Hz, 3H). LCMS-ESI$^+$ (m/z): [M+H]$^+$ calculated for C$_{22}$H$_{22}$F$_2$N$_3$O$_5$: 446.15; found: 446.1.

Example 13

Preparation of Compound 13

(2S,5R,13aS)—N—((S)-1-(2,4-difluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

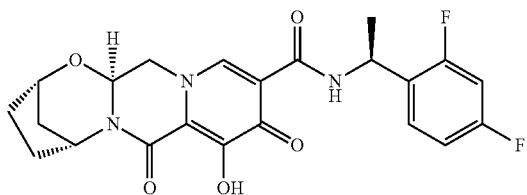

13

Compound 13 was prepared in a similar manner to compound 11 using (S)-1-(2,4-difluorophenyl)ethanamine in place of (R)-1-(2,4-difluorophenyl)ethanamine, and using only a single portion of magnesium bromide (0.184 g). $^1$H-NMR (400 MHz, DMSO-d$_6$) δ 12.44 (s, 1H), 10.53 (d, J=7.8 Hz, 1H), 8.39 (s, 1H), 7.39 (q, J=8.5 Hz, 1H), 7.32-7.14 (m, 1H), 7.05 (t, J=9.1 Hz, 1H), 5.42 (dd, J=9.5, 4.2 Hz, 1H), 5.29 (p, J=6.9 Hz, 1H), 5.09 (s, 1H), 4.65 (dd, J=12.9, 4.3 Hz, 1H), 4.59 (s, 1H), 4.02 (dd, J=12.6, 9.8 Hz, 1H), 1.92 (s, 4H), 1.83 (d, J=12.1 Hz, 1H), 1.61-1.52 (m, 1H), 1.44 (d, J=6.9 Hz, 3H). LCMS-ESI$^+$ (m/z): [M+H]$^+$ calculated for C$_{22}$H$_{22}$F$_2$N$_3$O$_5$: 446.15; found: 446.2.

Example 14

Preparation of Compound 14

(2R,5S,13aR)—N—((S)-1-(2,4-difluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

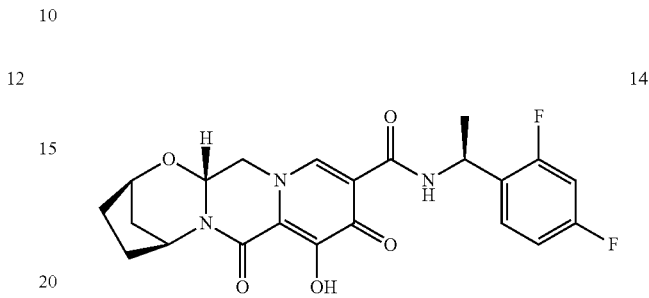

14

Compound 14 was prepared in a similar manner to compound 11 using (S)-1-(2,4-difluorophenyl)ethanamine in place of (R)-1-(2,4-difluorophenyl)ethanamine and using (1R,3S)-3-aminocyclopentanol in place of (1S,3R)-3-aminocyclopentanol. $^1$H-NMR (400 MHz, DMSO-d$_6$) δ 12.46 (s, 1H), 10.53 (d, J=7.6 Hz, 1H), 8.38 (s, 1H), 7.39 (q, J=8.6 Hz, 1H), 7.28-7.14 (m, 1H), 7.05 (t, J=8.5 Hz, 1H), 5.44 (dd, J=9.8, 3.8 Hz, 1H), 5.28 (p, J=8.0 Hz, 1H), 5.09 (s, 1H), 4.66 (dd, J=12.9, 4.0 Hz, 1H), 4.59 (s, 1H), 3.99 (dd, J=12.5, 9.6 Hz, 1H), 1.93 (s, 4H), 1.83 (d, J=12.6 Hz, 1H), 1.56 (dt, J=13.0, 3.3 Hz, 1H), 1.45 (d, J=6.9 Hz, 3H). LCMS-ESI$^+$ (m/z): [M+H]$^+$ calculated for C$_{22}$H$_{22}$F$_2$N$_3$O$_5$: 446.15; found: 446.1.

Example 15

Preparation of Compound 15

(2S,5R,13aS)—N-(4-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

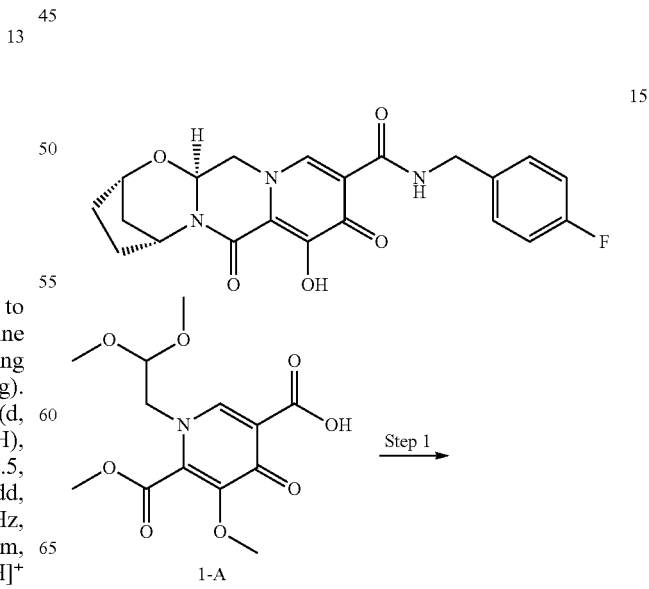

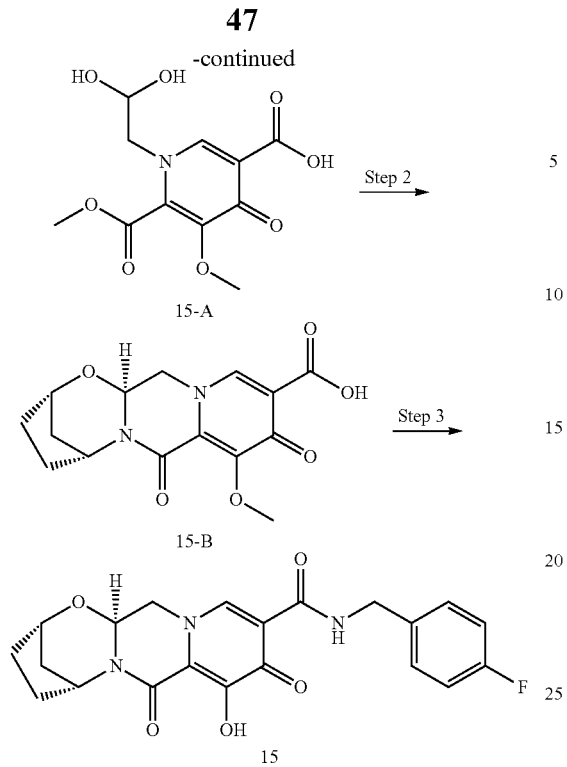

Step 1
1-(2,2-dimethoxyethyl)-5-methoxy-6-(methoxycarbonyl)-4-oxo-1,4-dihydropyridine-3-carboxylic acid (1-A, 3.15 g, 10.0 mmol), suspended in acetonitrile (36 mL) and acetic acid (4 mL) was treated with methane sulfonic acid (0.195 mL). The mixture heated to 75° C. After 7 hours, the crude mixture was cooled and stored in a −10° C. for three days. The crude mixture was reheated to 75° C. for 2 hours, cooled used without purification in the next step. LCMS-ESI⁺ (m/z): [M+H]⁺ calculated for $C_{19}H_{21}F_2N_2O_7$: 288.07; found: 288.1.

Step 2
Crude 1-(2,2-dihydroxyethyl)-5-methoxy-6-(methoxycarbonyl)-4-oxo-1,4-dihydropyridine-3-carboxylic acid (16.8 mL of crude mixture from Step 1, approx 4 mmol) was combined with (1S,3R)-3-aminocyclopentanol (0.809 g, 8 mmol), diluted with acetonitrile (16.8 mL), and treated with potassium carbonate (0.553 g, 4 mmol). The reaction mixture was heated to 85° C., stirred for 15 minutes, cooled to ambient temperature and stirred an additional 16 hours. HCl (50 mL, 0.2M aq) was added and the clear yellow solution was extracted three times with dichloromethane. The combined organics were dried over sodium sulfate, filtered and concentrated to a yellow solid. This crude material was precipitated from dichloromethane/hexanes to afford desired intermediate 15-B as a light beige powder. ¹H-NMR (400 MHz, DMSO-d₆) δ 8.72 (s, 1H), 5.42 (dd, J=9.6, 4.1 Hz, 1H), 5.09 (s, 1H), 4.72 (dd, J=13.0, 3.7 Hz, 1H), 4.57 (s, 1H), 4.09 (dd, J=12.5, 9.6 Hz, 1H), 3.83 (s, 3H), 1.92 (s, 3H), 1.78 (m, 2H), 1.62-1.47 (m, 1H). LCMS-ESI⁺ (m/z): [M+H]⁺ calculated for $C_{15}H_{17}N_2O_6$: 321.11; found: 321.2.

Step 3
Intermediate 15-B (0.040 g, 0.125 mmol) and (4-fluorophenyl)methanamine (0.017 g, 0.137 mmol) were suspended in acetonitrile (1 mL) and treated with N,N-diisopropylethylamine (DIPEA) (0.033 mL, 0.187 mmol) and HATU (0.052 g, 0.137 mmol). After stirring for 30 minutes, the reaction mixture was treated with magnesium bromide (0.046 g, 0.25 mmol) and heated to 50° C. After 10 minutes, the reaction mixture was cooled and treated with HCl (2 mL, 10% aq). After a few minutes, the precipitate was filtered and washed with HCl (10% aq) and water. Preparative HPLC purification of the precipitate (20-65% acetonitrile: water, 0.1% TFA) afforded desired Compound 15. ¹H-NMR (400 MHz, DMSO-d₆) δ 12.44 (s, 1H), 10.36 (t, J=6.0 Hz, 1H), 8.46 (s, 1H), 7.37-7.28 (m, 2H), 7.19-7.09 (m, 2H), 5.43 (dd, J=9.6, 4.0 Hz, 1H), 5.08 (s, 1H), 4.68 (dd, J=12.8, 4.1 Hz, 1H), 4.59 (s, 1H), 4.58-4.42 (m, 3H), 4.02 (dd, J=12.7, 9.6 Hz, 1H), 1.92 (s, 5H), 1.83 (d, J=12.2 Hz, 1H), 1.56 (dt, J=12.0, 3.4 Hz, 1H). LCMS-ESI⁺ (m/z): [M+H]⁺ calculated for $C_{21}H_{21}FN_3O_5$: 414.15; found: 414.2.

Example 16

Preparation of Compound 16

(2S,5R,13aS)—N-(2,3-difluorobenzyl)-8-hydroxy-7,9-dioxo-2,3,4,5,7,9,13,13a-octahydro-2,5-methanopyrido[1′,2′:4,5]pyrazino[2,1-b][1,3]oxazepine-10-carboxamide

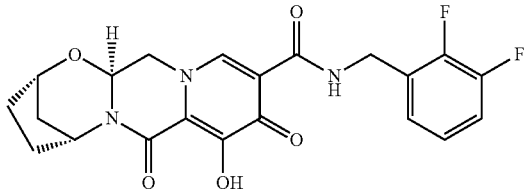

Compound 16 was prepared in a similar manner to compound 15 using (2,3-difluorophenyl)methanamine in place of (4-fluorophenyl)methanamine. ¹H-NMR (400 MHz, DMSO-d₆) δ 12.46 (s, 1H), 10.41 (t, J=6.1 Hz, 1H), 8.45 (s, 1H), 7.43-7.25 (m, 1H), 7.25-7.05 (m, 2H), 5.44 (dd, J=9.5, 3.9 Hz, 1H), 5.09 (s, 1H), 4.68 (dd, J=12.8, 4.0 Hz, 1H), 4.65-4.53 (m, 3H), 4.02 (dd, J=12.7, 9.8 Hz, 1H), 3.56 (s, 1H), 1.93 (s, 4H), 1.83 (d, J=11.9 Hz, 1H), 1.57 (dt, J=11.5, 3.0 Hz, 1H). LCMS-ESI⁺ (m/z): [M+H]⁺ calculated for $C_{21}H_{20}F_2N_3O_5$: 432.14; found: 432.2.

Example 17

Preparation of Compound 17

(2S,5R,13aS)—N-(4-chloro-2-fluorobenzyl)-8-hydroxy-7,9-dioxo-2,3,4,5,7,9,13,13a-octahydro-2,5-methanopyrido[1′,2′:4,5]pyrazino[2,1-b][1,3]oxazepine-10-carboxamide

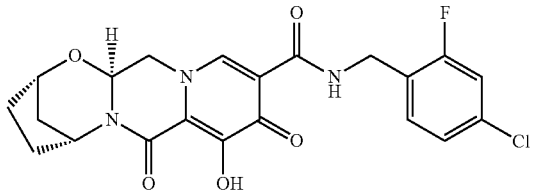

Compound 17 was prepared in a similar manner to compound 15 using (4-chloro-2-fluorophenyl)methanamine in place of (4-fluorophenyl)methanamine. $^1$H-NMR (400 MHz, DMSO-d$_6$) δ 12.46 (s, 1H), 10.45-10.29 (m, 1H), 8.44 (s, 1H), 7.42 (dd, J=10.0, 2.0 Hz, 1H), 7.33 (t, J=8.1 Hz, 1H), 7.26 (dd, J=8.4, 1.8 Hz, 1H), 5.50-5.38 (m, 1H), 5.09 (s, 1H), 4.68 (dd, J=13.0, 4.0 Hz, 1H), 4.59 (s, 1H), 4.54 (m, 2H), 4.02 (dd, J=12.8, 9.7 Hz, 1H), 1.93 (s, 4H), 1.83 (d, J=12.0 Hz, 1H), 1.57 (dt, J=11.9, 3.4 Hz, 1H). LCMS-ESI$^+$ (m/z): [M+H]$^+$ calculated for C$_{21}$H$_{20}$ClFN$_3$O$_5$: 448.11; found: 448.2.

Example 18

Preparation of Compound 18

(2S,5R,13aS)—N-(3,4-difluorobenzyl)-8-hydroxy-7,9-dioxo-2,3,4,5,7,9,13,13a-octahydro-2,5-methano-pyrido[1',2':4,5]pyrazino[2,1-b][1,3]oxazepine-10-carboxamide

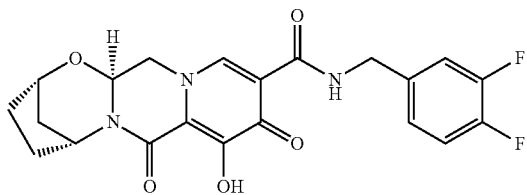

18

Compound 18 was prepared in a similar manner to compound 15 using (3,4-difluorophenyl)methanamine in place of (4-fluorophenyl)methanamine. $^1$H-NMR (400 MHz, DMSO-d$_6$) δ 12.46 (s, 1H), 10.51-10.27 (m, 1H), 8.46 (s, 1H), 7.50-7.23 (m, 2H), 7.23-7.03 (m, 1H), 5.44 (dd, J=9.5, 3.6 Hz, 1H), 5.09 (s, 1H), 4.75-4.63 (m, 1H), 4.60 (s, 1H), 4.57-4.44 (m, 2H), 4.02 (dd, J=12.6, 9.8 Hz, 1H), 1.93 (s, 4H), 1.83 (d, J=12.0 Hz, 1H), 1.57 (dt, J=12.0, 3.4 Hz, 1H). LCMS-ESI$^+$ (m/z): [M+H]$^+$ calculated for C$_{21}$H$_{20}$F$_2$N$_3$O$_5$: 432.14; found: 432.2.

Example 19

Preparation of Compound 19

(1R,5S)—N-(2,4-difluorobenzyl)-8-hydroxy-7,9-dioxo-2,3,4,5,7,9,13,13a-octahydro-1,5-methano-pyrido[1',2':4,5]pyrazino[1,2-a][1,3]diazepine-10-carboxamide

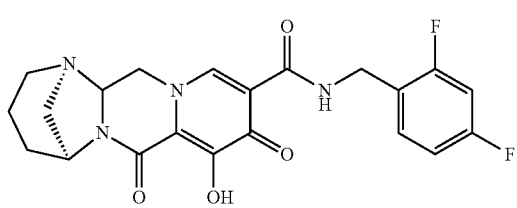

19

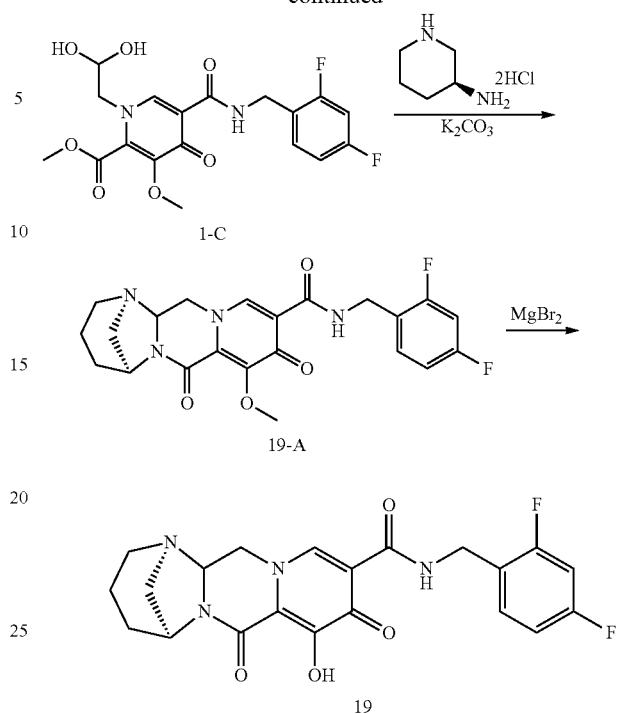

Steps 1 and 2

Methyl 5-(2,4-difluorobenzylcarbamoyl)-1-(2,2-dihydroxyethyl)-3-methoxy-4-oxo-1,4-dihydropyridine-2-carboxylate (1-C, 97.5 mg, 0.236 mmol) was treated with acetonitrile (1.9 mL), acetic acid (0.1 mL), potassium carbonate (145 mg, 1.05 mmol), and (S)-piperidin-3-amine dihydrochloride (82 mg, 0.472 mmol). The reaction mixture was sealed and heated to 90° C. After 60 minutes, the reaction mixture was cooled partitioned between brine and dichloromethane. The aqueous phase was thrice extracted into dichloromethane and the combined organic phases were combined, dried over MgSO4, filtered, concentrated. The crude product was dissolved into acetonitrile (2 mL) and magnesium bromide (89.1 mg, 0.48 mmol) was added. The mixture was resealed and heated to 50° C. After 90 minutes, the reaction mixture was quenched with ~5 mL of 0.2M HCl(aq), the pH adjusted to ~10, diluted with brine, and thrice extracted into DCM. HPLC purification (Acetonitrile: water, 0.1% TFA) afforded Compound 19. $^1$H-NMR (400 MHz, Chloroform-d) δ 10.43 (t, J=5.9 Hz, 1H), 8.43 (s, 1H), 7.39-7.30 (m, 1H), 6.81 (q, J=8.1 Hz, 2H), 4.89 (dd, J=11.6, 3.8 Hz, 1H), 4.69 (s, 1H), 4.64 (d, J=5.8 Hz, 2H), 4.26 (dd, J=12.6, 3.8 Hz, 1H), 3.91 (t, J=12.1 Hz, 1H), 3.20-3.10 (m, 2H), 3.06 (s, 2H), 2.14-2.02 (m, 1H), 1.96-1.81 (m, 2H), 1.81-1.70 (m, 1H). LCMS-ESI$^+$ (m/z): [M+H]$^+$ calculated for C$_{21}$H$_{20}$F$_2$N$_4$O$_4$: 431.15; found: 431.2.

Example 20

Preparation of Compound 20

(1S,5R)—N-(2,4-difluorobenzyl)-8-hydroxy-7,9-dioxo-2,3,4,5,7,9,13,13a-octahydro-1,5-methanopyrido[1',2':4,5]pyrazino[1,2-a][1,3]diazepine-10-carboxamide

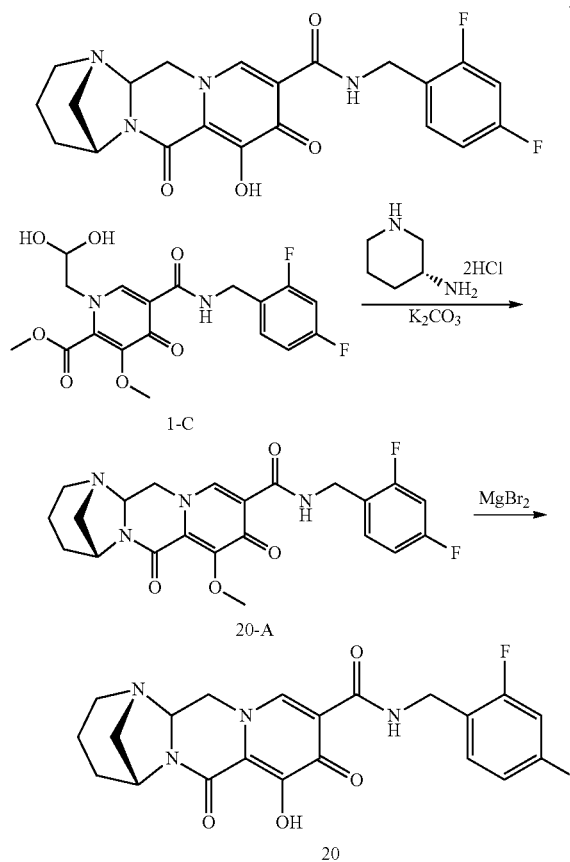

Steps 1 and 2

Methyl 5-(2,4-difluorobenzylcarbamoyl)-1-(2,2-dihydroxyethyl)-3-methoxy-4-oxo-1,4-dihydropyridine-2-carboxylate (1-C, 103.3 mg, 0.25 mmol) was treated with acetonitrile (1.9 mL), acetic acid (0.1 mL), potassium carbonate (159.8 mg, 1.16 mmol), and (R)-piperidin-3-amine dihydrochloride (90 mg, 0.52 mmol). The reaction mixture was sealed and heated to 90° C. After 40 minutes, the reaction mixture was cooled partitioned between brine and dichloromethane. The aqueous phase was thrice extracted into dichloromethane and the combined organic phases were combined, dried over MgSO$_4$, filtered, concentrated. The crude product was dissolved into acetonitrile (2 mL) and magnesium bromide (96.5 mg, 0.52 mmol) was added. The mixture was resealed and heated to 50° C. After 80 minutes, the reaction mixture was quenched with ~5 mL of 0.2M HCl (aq), the pH adjusted to ~10, diluted with brine, and thrice extracted into DCM. HPLC purification (Acetonitrile:water, 0.1% TFA) afforded Compound 20. $^1$H-NMR (400 MHz, DMSO-d$_6$) δ 10.35 (t, J=6.0 Hz, 1H), 8.48 (s, 1H), 7.45-7.33 (m, 1H), 7.29-7.18 (m, 1H), 7.05 (td, J=8.5, 2.4 Hz, 1H), 5.06 (dd, J=11.4, 3.5 Hz, 1H), 4.56-4.47 (m, 3H), 4.44 (s, 1H), 4.05 (t, J=11.8 Hz, 1H), 3.07-2.89 (m, 4H), 1.85-1.73 (m, 3H), 1.54-1.46 (m, 1H). LCMS-ESI$^+$ (m/z): [M+H]$^+$ calculated for C$_{21}$H$_{20}$F$_2$N$_4$O$_4$: 431.15; found: 431.2.

Example 21

Preparation of Compound 21

(2S,5R,13aS)—N—((S)-1-(4-fluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

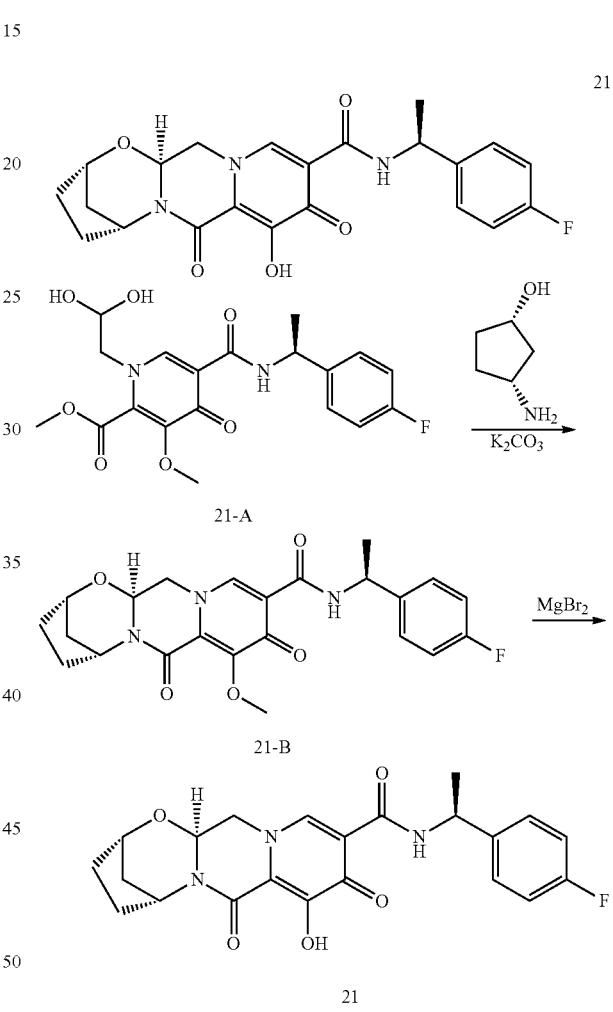

Steps 1 and 2

(S)-Methyl 1-(2,2-dihydroxyethyl)-5-(1-(4-fluorophenyl)ethylcarbamoyl)-3-methoxy-4-oxo-1,4-dihydropyridine-2-carboxylate (21-A, 1 mL, 0.23 M solution in 19:1 acetonitrile:acetic acid, prepared as per (R)-methyl 1-(2,2-dihydroxyethyl)-5-(1-(4-fluorophenyl)ethylcarbamoyl)-3-methoxy-4-oxo-1,4-dihydropyridine-2-carboxylate 9-A from Example 9 using (S)-1-(4-fluorophenyl)ethanamine in place of (R)-1-(4-fluorophenyl)ethanamine) was treated with (1S,3R)-3-aminocyclopentanol (62 mg, 0.61 mmol) and potassium carbonate (34 mg, 0.25 mmol). The reaction mixture was sealed and heated to 90° C. After 60 minutes, the reaction mixture was cooled partitioned between brine and dichloromethane. The aqueous phase was thrice extracted into dichloromethane and the combined organic phases were combined, dried over MgSO$_4$, filtered, and concentrated. The crude product was dissolved into acetonitrile (2 mL) and magnesium bromide (74 mg, 0.4 mmol) was added. The mixture was resealed and heated to 50° C. After 100 minutes, the reaction mixture was quenched with 0.2M HCl (aq), diluted with brine, and thrice extracted into DCM. HPLC purification (acetonitrile:water, 0.1% TFA) afforded Compound 21. $^1$H-NMR (400 MHz, DMSO-d$_6$) δ 12.42 (br s, 1H), 10.45 (d, J=7.9 Hz, 1H), 8.40 (s, 1H), 7.36 (dd, J=8.6, 5.5 Hz, 2H), 7.14 (t, J=8.9 Hz, 2H), 5.42 (dd, J=9.6, 4.2 Hz, 1H), 5.15-5.04 (m, 2H), 4.72-4.55 (m, 2H), 4.02 (dd, J=12.7, 9.7 Hz, 1H), 1.97-1.89 (m, 4H), 1.82 (d, J=12.2 Hz, 1H), 1.56 (dt, J=11.9, 3.3 Hz, 1H), 1.43 (d, J=6.9 Hz, 3H). LCMS-ESI$^+$ (m/z): [M+H]$^+$ calculated for C$_{22}$H$_{22}$FN$_3$O$_5$: 428.16; found: 428.1.

Example 22

Preparation of Compound 22

(2R,5S,13aR)—N—((S)-1-(4-fluorophenyl)ethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

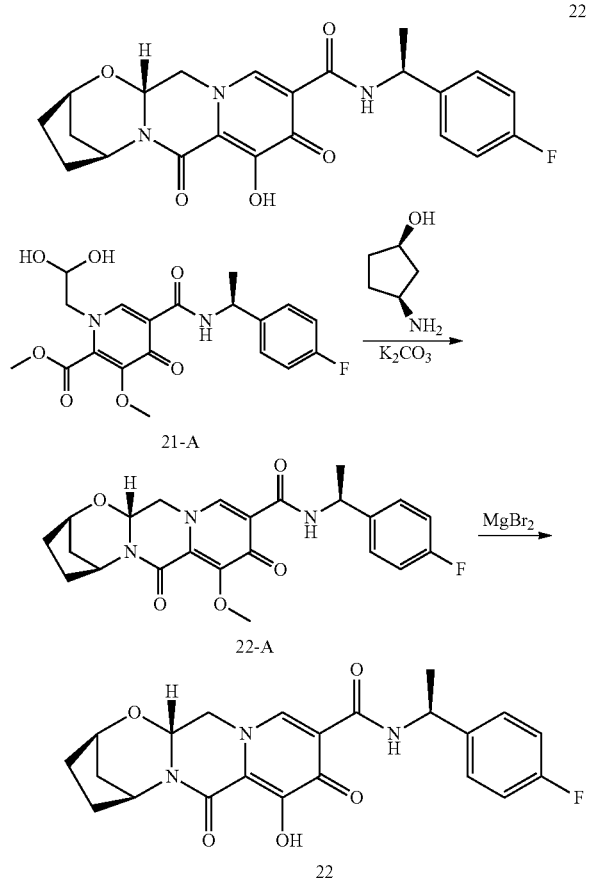

Steps 1 and 2

(S)-methyl 1-(2,2-dihydroxyethyl)-5-(1-(4-fluorophenyl) ethylcarbamoyl)-3-methoxy-4-oxo-1,4-dihydropyridine-2-carboxylate (21-A, 1 mL, 0.23 M solution in 19:1 acetonitrile:acetic acid) was treated with (1R,3S)-3-aminocyclopentanol (52 mg, 0.51 mmol) and potassium carbonate (31 mg, 0.22 mmol). The reaction mixture was sealed and heated to 90° C. After 60 minutes, the reaction mixture was cooled partitioned between brine and dichloromethane. The aqueous phase was thrice extracted into dichloromethane and the combined organic phases were combined, dried over MgSO$_4$, filtered, and concentrated. The crude product was dissolved into acetonitrile (2 mL) and magnesium bromide (91 mg, 0.49 mmol) was added. The mixture was resealed and heated to 50° C. After 100 minutes, the reaction mixture was quenched with 0.2M HCl(aq), diluted with brine, and thrice extracted into DCM. HPLC purification (acetonitrile:water, 0.1% TFA) afforded Compound 22. $^1$H-NMR (400 MHz, DMSO-d$_6$) δ 12.44 (br s, 1H), 10.45 (d, J=7.7 Hz, 1H), 8.39 (s, 1H), 7.36 (dd, J=8.5, 5.6 Hz, 2H), 7.14 (t, J=8.9 Hz, 2H), 5.43 (dd, J=9.6, 4.0 Hz, 1H), 5.15-5.06 (m, 2H), 4.66 (dd, J=12.8, 3.9 Hz, 1H), 4.58 (s, 1H), 3.99 (dd, J=12.6, 9.5 Hz, 1H), 1.93 (s, 4H), 1.82 (d, J=12.0 Hz, 1H), 1.56 (dt, J=12.0, 3.0 Hz, 1H), 1.44 (d, J=6.9 Hz, 3H). LCMS-ESI$^+$ (m/z): [M+H]$^+$ calculated for C$_{22}$H$_{22}$FN$_3$O$_5$: 428.16; found: 428.1.

Example 23

Preparation of Compound 23

(2S,5R,13aS)—N-(2-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

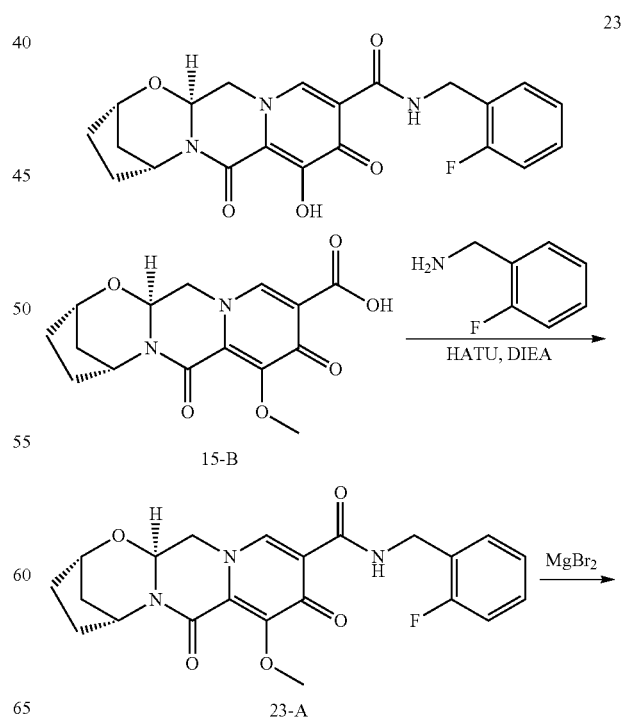

-continued

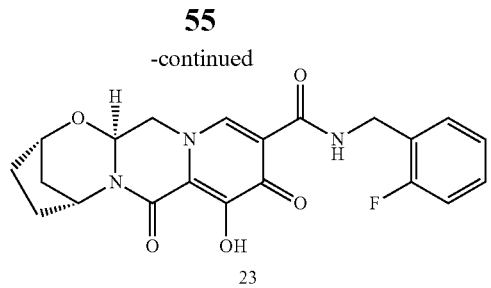

23

-continued

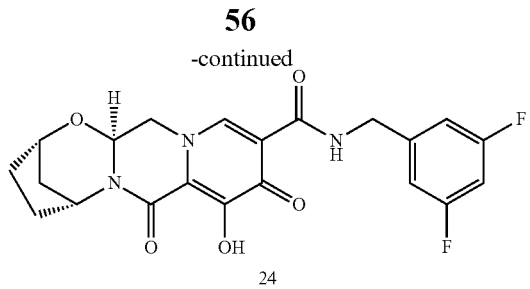

24

Steps 1 and 2

15-B (41 mg, 0.13 mmol) was treated with acetonitrile (1 mL), (2-fluorophenyl)methanamine (17 mg, 0.14 mmol), HATU (67 mg, 0.18 mmol), and N,N-diisopropylethylamine (DIPEA) (24 mg, 0.19 mmol). The reaction mixture was stirred at room temperature for one hour and magnesium bromide (47 mg, 0.26 mmol) was added. The mixture was sealed and heated to 50° C. After 60 minutes, the reaction mixture was quenched with 0.2M HCl (aq), diluted with brine, and thrice extracted into DCM. HPLC purification (Acetonitrile:water, 0.1% TFA) afforded Compound 23. $^1$H-NMR (400 MHz, Chloroform-d) δ 10.42 (s, 1H), 8.34 (s, 1H), 7.36 (t, J=7.9 Hz, 1H), 7.24-7.17 (m, 1H), 7.12-6.97 (m, 2H), 5.40-5.32 (m, 1H), 5.29 (t, J=3.5 Hz, 1H), 4.67 (s, 3H), 4.28-4.20 (m, 1H), 4.06-3.95 (m, 1H), 2.20-1.96 (m, 4H), 1.95-1.84 (m, 1H), 1.59 (dt, J=12.4, 3.3 Hz, 1H). LCMS-ESI$^+$ (m/z): [M+H]$^+$ calculated for $C_{21}H_{20}FN_3O_5$: 414.15; found: 414.2.

Example 24

Preparation of Compound 24

(2S,5R,13aS)—N-(3,5-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide Steps 1 and 2

15-B (44 mg, 0.14 mmol) was treated with acetonitrile (1 mL), (3,5-difluorophenyl)methanamine (32 mg, 0.23 mmol), HATU (54 mg, 0.14 mmol), and N,N-diisopropylethylamine (37 mg, 0.29 mmol). The reaction mixture was stirred at room temperature for one hour and magnesium bromide (57 mg, 0.31 mmol) was added. The mixture was sealed and heated to 50° C. After 60 minutes, the reaction mixture was quenched with 0.2M HCl (aq), diluted with brine, and thrice extracted into DCM HPLC purification (Acetonitrile:water, 0.1% TFA) afforded Compound 24. $^1$H-NMR (400 MHz, Chloroform-d) δ 10.39 (s, 1H), 8.42 (s, 1H), 6.82 (d, J=7.9 Hz, 2H), 6.65 (t, J=8.8 Hz, 1H), 5.38 (d, J=7.7 Hz, 1H), 5.28 (s, 1H), 4.78-4.41 (m, 3H), 4.32 (d, J=12.1 Hz, 1H), 4.02 (t, J=10.9 Hz, 1H), 2.30-1.97 (m, 4H), 1.97-1.81 (m, 1H), 1.59 (d, J=12.3 Hz, 1H). LCMS-ESI$^+$ (m/z): [M+H]$^+$ calculated for $C_{21}H_{19}F_2N_3O_5$: 432.14; found: 432.2.

Example 25

Preparation of Compound 25

(2S,5R,13aS)—N-(4-fluoro-3-(trifluoromethyl)benzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

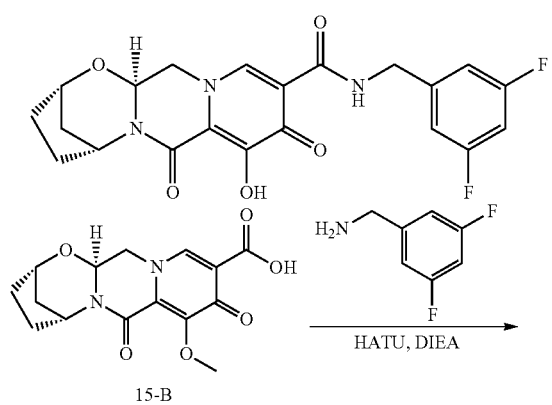

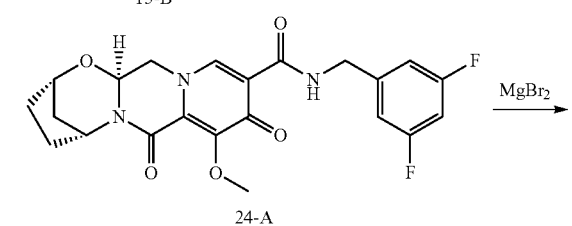

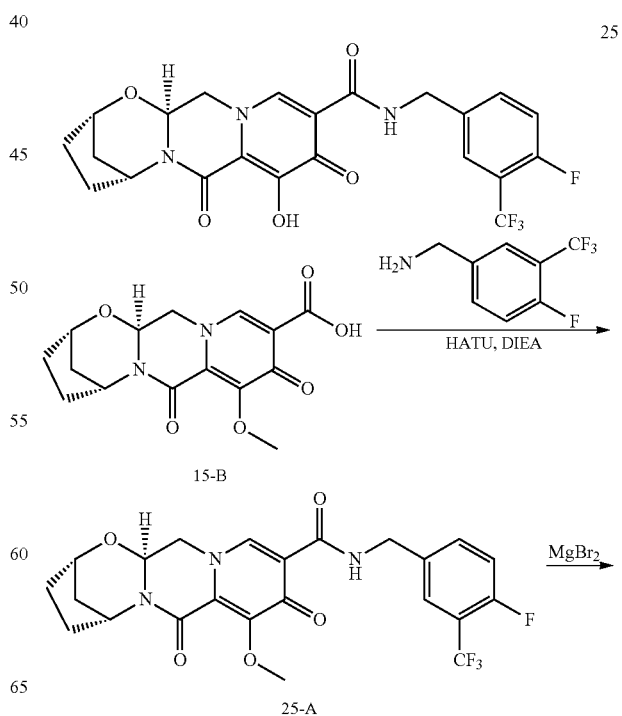

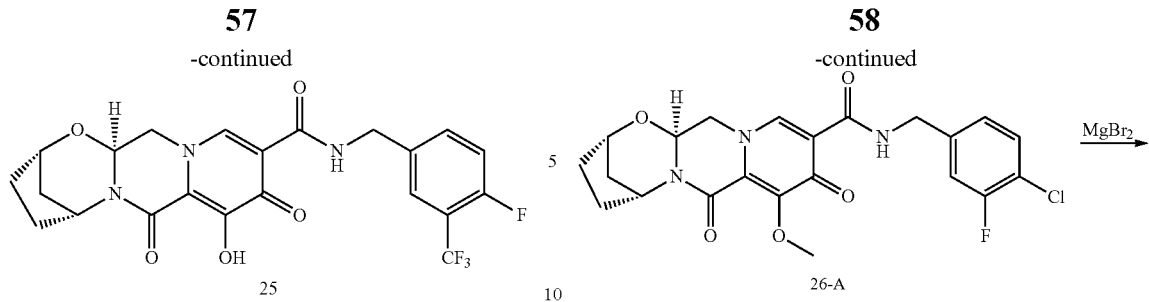

Steps 1 and 2

15-B (43 mg, 0.13 mmol) was treated with acetonitrile (1 mL), (4-fluoro-3-(trifluoromethyl)phenyl)methanamine (29 mg, 0.15 mmol), HATU (62 mg, 0.16 mmol), and N,N-diisopropylethylamine (26 mg, 0.20 mmol). The reaction mixture was stirred at room temperature for one hour and magnesium bromide (62 mg, 0.34 mmol) was added. The mixture was sealed and heated to 50° C. After 60 minutes, the reaction mixture was quenched with 0.2M HCl(aq), diluted with brine, and thrice extracted into DCM. HPLC purification (Acetonitrile:water, 0.1% TFA) afforded Compound 25. $^1$H-NMR (400 MHz, Chloroform-d) δ 10.44 (s, 1H), 8.29 (s, 1H), 7.56-7.38 (m, 2H), 7.06 (t, J=9.2 Hz, 1H), 5.30 (dd, J=9.3, 3.5 Hz, 1H), 5.21 (s, 1H), 4.65-4.45 (m, 3H), 4.21 (dd, J=12.8, 3.4 Hz, 1H), 3.95 (dd, J=12.4, 9.7 Hz, 1H), 2.11-1.89 (m, 4H), 1.89-1.74 (m, 1H), 1.53 (dt, J=12.4, 3.2 Hz, 1H). LCMS-ESI$^+$ (m/z): [M+H]$^+$ calculated for $C_{22}H_{19}F_4N_3O_5$: 482.14; found: 482.2.

Example 26

Preparation of Compound 26

(2S,5R,13aS)—N-(4-chloro-3-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

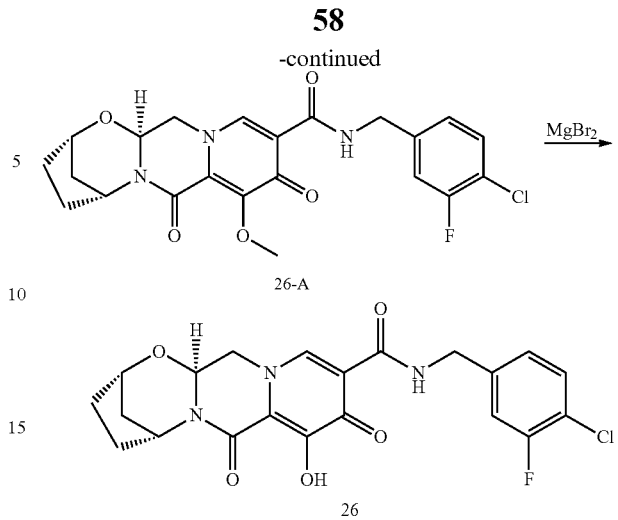

Steps 1 and 2

15-B (41 mg, 0.13 mmol) was treated with acetonitrile (1 mL), (4-chloro-3-fluorophenyl)methanamine (40 mg, 0.25 mmol), HATU (60 mg, 0.16 mmol), and N,N-diisopropylethylamine (28 mg, 0.22 mmol). The reaction mixture was stirred at room temperature for one hour and magnesium bromide (48 mg, 0.26 mmol) was added. The mixture was sealed and heated to 50° C. After 60 minutes, the reaction mixture was quenched with 0.2M HCl (aq), diluted with brine, and thrice extracted into DCM. HPLC purification (Acetonitrile:water, 0.1% TFA) afforded Compound 26. $^1$H-NMR (400 MHz, Chloroform-d) δ 10.41 (s, 1H), 8.30 (s, 1H), 7.24 (t, J=6.1 Hz, 1H), 7.13-6.90 (m, 2H), 5.30 (dd, J=9.1, 3.2 Hz, 1H), 5.22 (s, 1H), 4.61 (s, 1H), 4.51 (s, 2H), 4.20 (d, J=9.4 Hz, 1H), 3.95 (d, J=12.0 Hz, 1H), 2.11-1.90 (m, 4H), 1.90-1.76 (m, 1H), 1.53 (d, J=12.2 Hz, 1H). LCMS-ESI$^+$ (m/z): [M+H]$^+$ calculated for $C_{21}H_{19}ClFN_3O_5$: 448.11; found: 448.2.

Example 27

Preparation of Compound 27

(2S,5R)—N-(1-(2,4-difluorophenyl)cyclopropyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

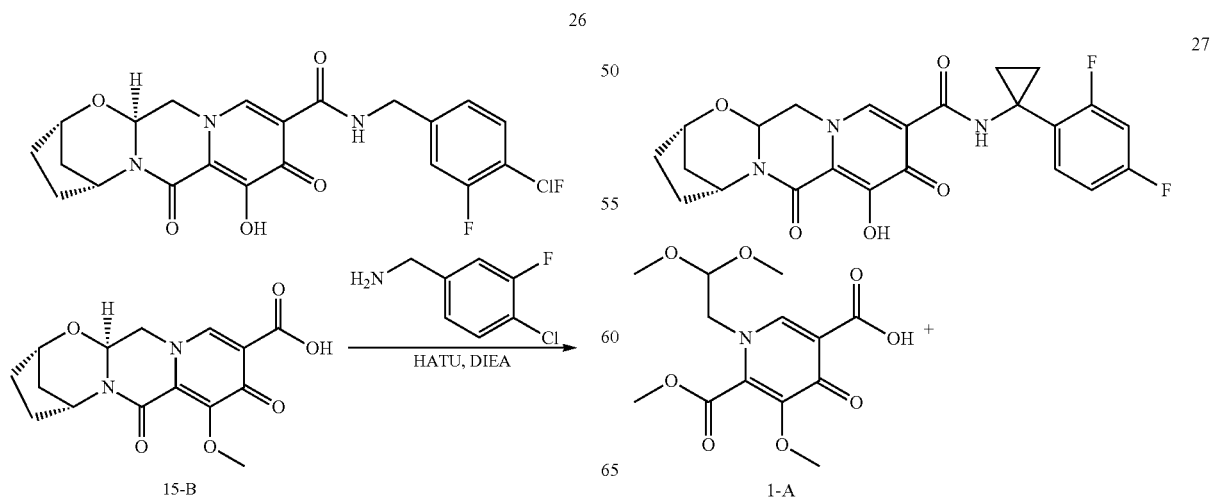

-continued

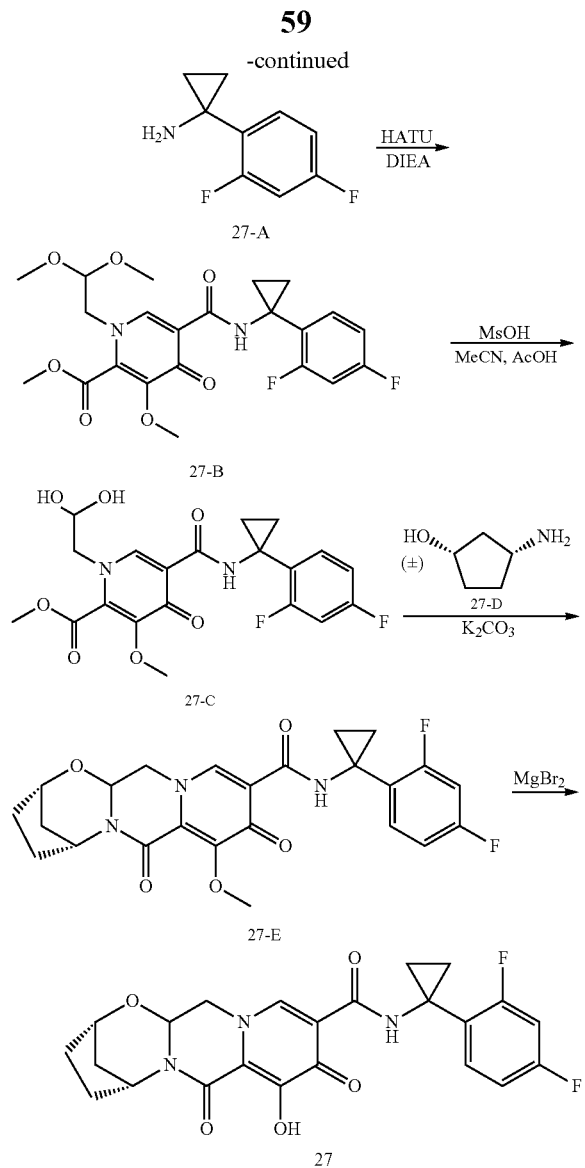

Step 1

A suspension of the compound 1-A (1.004 g, 3.19 mmol), the amine 27-A (688 mg, 3.35 mmol), and HATU (1.453 g 3.82 mmol) in $CH_2Cl_2$ (20 mL) was stirred in 0° C. bath as N,N-diisopropylethylamine (DIEA) (2 mL, 11.48 mmol) was added. After 1 hour at 0° C., the reaction mixture was concentrated to a syrup, diluted with ethyl acetate, and washed with water (×2). After the aqueous fractions were extracted with ethyl acetate (×1), the organic fractions were combined, dried ($Na_2SO_4$), and concentrated. The residue was purified by CombiFlash (120 g column) using hexanes-ethyl acetate as eluents. The major peak was combined and concentrated to afford 1.082 g (73%) of the product 27-B. After the minor peak was combined and concentrated, the concentrated residue was dissolved in $CH_2Cl_2$ and some insoluble materials were filtered. The filtrate was concentrated to get 361 mg (24%) of the additional product 27-B. LCMS-ESI$^+$ (m/z): [M+H]$^+$ calculated for $C_{22}H_{25}F_2N_2O_7$: 467.16; found: 467.1.

Step 2 and 3

Compound 27-B (81 mg, 0.174 mmol) was dissolved in a mixture (1 mL) of acetonitrile (22 mL), AcOH (2 mL), and methanesulfonic acid (0.14 mL, 2.16 mmol) at room temperature and the resulting solution was stirred at 65° C. for 20 hours.

After the resulting solution was cooled to room temperature, the aminoalcohol 27-D (50 mg, racemic, 0.363 mmol), $K_2CO_3$ (50 mg, 0.362 mmol), and acetonitrile (2 mL) were added to the solution. The resulting mixture was stirred at 65° C. bath for 1 hour. After the reaction mixture was cooled to room temperature, it was acidified with 1 N HCl (~2 mL), diluted with water (~8 mL), and extracted with $CH_2Cl_2$ (×3). Combined extracts were dried ($Na_2SO_4$), concentrated, and purified by CombiFlash to obtain 67 mg (82%) of compound 27-E. $^1$H-NMR (400 MHz, CDCl$_3$) δ 10.53 (s, 1H), 8.25 (s, 1H), 7.60 (td, J=8.5, 6.5 Hz, 1H), 6.85-6.57 (m, 2H), 5.33 (br, 1H), 5.26 (dd, J=9.6, 3.9 Hz, 1H), 4.60 (t, J=3.0 Hz, 1H), 4.18-4.06 (m, 1H), 4.01 (s, 3H), 3.92 (dd, J=12.7, 9.6 Hz, 1H), 2.11-1.91 (m, 4H), 1.88-1.71 (m, 1H), 1.60-1.49 (m, 1H), 1.31-1.10 (m, 4H). $^{19}$F-NMR (376.1 MHz, CDCl$_3$) δ -111.80 (q, J=8.8 Hz, 1F), -112.05 (p, J=7.9 Hz, 1F). LCMS-ESI$^+$ (m/z): [M+H]$^+$ calculated for $C_{24}H_{24}F_2N_3O_5$: 472.17; found: 472.1.

Step 4

A mixture of compound 27-E (67 mg, 0.142 mmol) and MgBr$_2$ (66 mg, 0.358 mmol) in MeCN (3 mL) was stirred at 50° C. for 30 minutes and cooled to 0° C. before treating with 1 N HCl (3 mL). After the mixture was diluted with water (~30 mL), the product was extracted with $CH_2Cl_2$ (×3), and the combined extracts were dried ($Na_2SO_4$) and concentrated. The product was purified by preparative HPLC and freeze-dried to obtain product 27 as a 1:1 mixture with trifluoroacetic acid. $^1$H-NMR (400 MHz, CDCl$_3$) δ 10.70 (s, 1H), 8.35 (s, 1H), 7.57 (q, J=8.2 Hz, 1H), 6.91-6.56 (m, 2H), 5.31 (dt, J=14.3, 4.0 Hz, 2H), 4.68 (s, 1H), 4.22 (dd, J=13.2, 3.9 Hz, 1H), 3.99 (dd, J=12.8, 9.3 Hz, 1H), 2.28-1.96 (m, 5H), 1.88 (ddt, J=12.1, 8.6, 3.7 Hz, 1H), 1.71-1.49 (m, 1H), 1.38-1.11 (m, 4H). $^{19}$F-NMR (376.1 MHz, CDCl$_3$) δ -76.37 (s, 3F), -111.6~-111.75 (m, 2F). LCMS-ESI$^+$ (m/z): [M+H]$^+$ calculated for $C_{23}H_{22}F_2N_3O_5$: 458.15; found: 458.1.

Example 28

Preparation of Compound 28

(2S,6R)—N-(1-(2,4-difluorophenyl)cyclopropyl)-9-hydroxy-8,10-dioxo-3,4,5,6,8,10,14,14a-octahydro-2H-2,6-methanopyrido[1',2':4,5]pyrazino[2,1-b][1,3]oxazocine-11-carboxamide

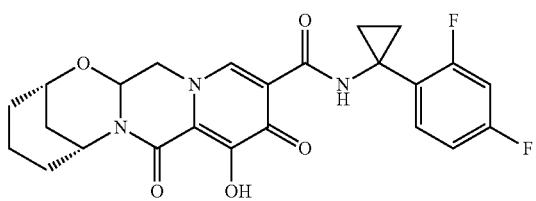

-continued

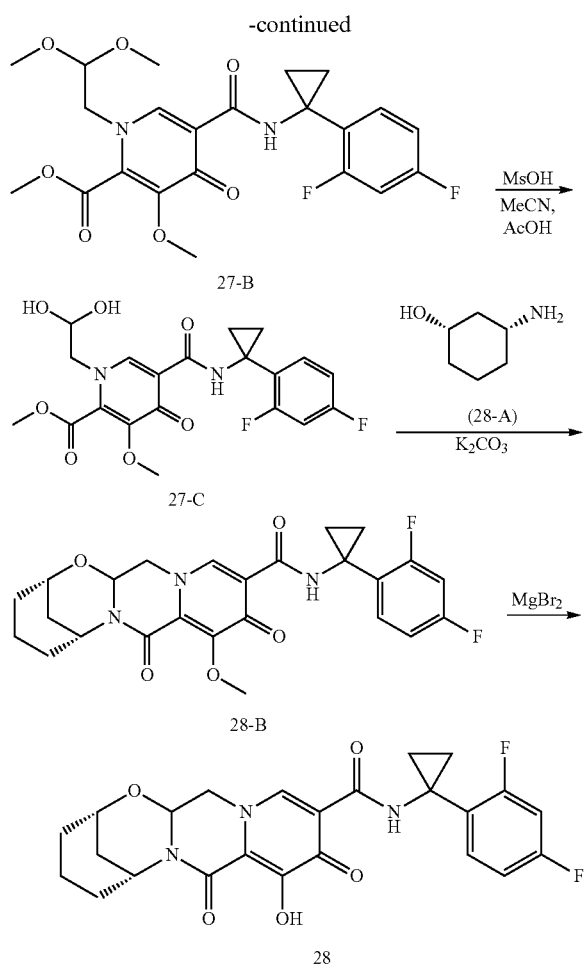

−112.01 (p, J=7.9 Hz, 1F). LCMS-ESI⁺ (m/z): [M+H]⁺ calculated for $C_{25}H_{26}F_2N_3O_5$: 486.18; found: 486.2.

Step 3

Compound 28-B (18 mg, 0.037 mmol) was treated with MgBr₂ as described in step 4 in the synthesis of compound 27-E to obtain compound 28. ¹H-NMR (400 MHz, CDCl₃) δ 10.66 (s, 1H), 8.29 (s, 1H), 7.59 (td, J=8.5, 6.6 Hz, 1H), 6.89-6.60 (m, 2H), 5.51 (dd, J=9.9, 4.0 Hz, 1H), 4.55 (s, 1H), 4.48 (t, J=4.2 Hz, 1H), 4.21 (dd, J=12.9, 4.1 Hz, 1H), 3.99 (dd, J=12.8, 9.8 Hz, 1H), 2.56-2.35 (m, 1H), 2.14 (dd, J=16.1, 5.9 Hz, 1H), 1.96-1.74 (m, 3H), 1.66-1.37 (m, 3H), 1.28 (d, J=4.4 Hz, 2H), 1.26-1.19 (m, 2H). ¹⁹F-NMR (376.1 MHz, CDCl₃) δ −76.41 (s, 3F, −111.79 (m, 2F). LCMS-ESI⁺ (m/z): [M+H]⁺ calculated for $C_{24}H_{23}F_2N_3O_5$: 472.17; found: 472.1.

Example 29

Preparation of Compound 29

(2R,6S)—N-(1-(2,4-difluorophenyl)cyclopropyl)-9-hydroxy-8,10-dioxo-3,4,5,6,8,10,14,14a-octahydro-2H-2,6-methanopyrido[1',2':4,5]pyrazino[2,1-b][1,3]oxazocine-11-carboxamide

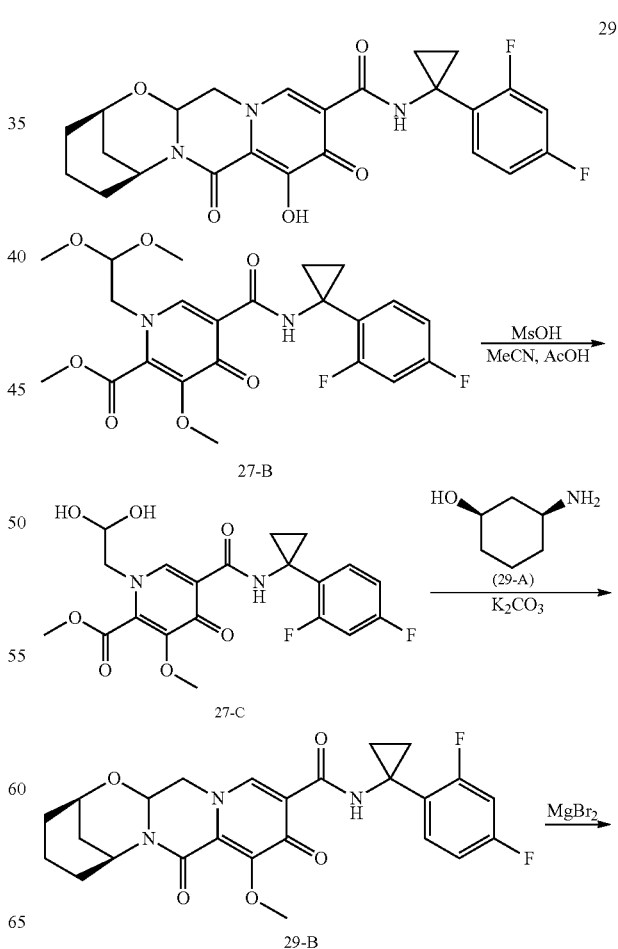

Step 1 and 2

Compound 27-B (87 mg, 0.187 mmol) was dissolved in a mixture (2 mL) of acetonitrile (22 mL), AcOH (2 mL), and methanesulfonic acid (0.14 mL, 2.16 mmol) at room temperature and the resulting solution was stirred at 65° C. for 20 hours.

After the resulting solution was cooled to room temperature, the aminoalcohol 28-A (44 mg, racemic, 0.382 mmol) and acetonitrile (2 mL) were added to the solution. After the resulting mixture was stirred at 65° C. bath for 30 minutes, K₂CO₃ (41 mg, 0.297 mmol) was added and the mixture was stirred at 65° C. for 21 hours. The reaction mixture was cooled to room temperature, it was acidified with 1 N HCl (~2 mL), diluted with water (~8 mL), and extracted with CH₂Cl₂ (×3). Combined extracts were dried (Na₂SO₄), concentrated, and purified by preparative HPLC and the fraction containing the product was freeze-dried. After the residue was dissolved in ethyl acetate, the solution was washed with saturated NaHCO₃ (×1), dried (Na₂SO₄), and concentrated to obtain 18 mg (20%) of compound 28-B as a 1:1 mixture with trifluoroacetic acid. ¹H-NMR (400 MHz, CDCl₃) δ 10.54 (s, 1H), 8.26 (s, 1H), 7.63 (td, J=8.6, 6.6 Hz, 1H), 6.76 (dddd, J=21.9, 11.2, 8.7, 2.3 Hz, 2H), 5.39 (dd, J=9.6, 3.7 Hz, 1H), 4.53-4.36 (m, 2H), 4.09 (dd, J=12.8, 3.7 Hz, 1H), 4.03 (s, 3H), 3.99 (dd, J=12.7, 9.7 Hz, 1H), 2.41-2.20 (m, 2H), 1.84 (dtd, J=19.7, 9.3, 8.8, 4.4 Hz, 2H), 1.74 (dd, J=14.6, 2.5 Hz, 1H), 1.62-1.35 (m, 2H), 1.34-1.14 (m, 5H). ¹⁹F-NMR (376.1 MHz, CDCl₃) δ −111.75 (q, J=8.9 Hz, 1F), -continued

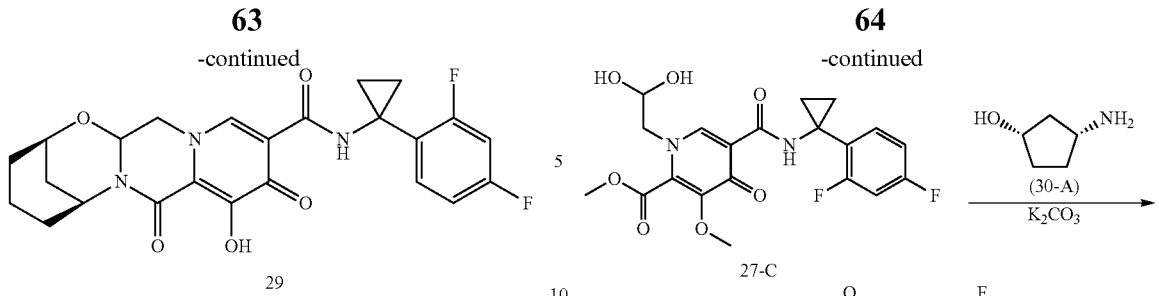

Step 1 and 2

Compound 29-B (13 mg, 14%) was prepared from compound 27-B (87 mg, 0.187 mmol) and the aminoalcohol 29-A (45 mg, 0.391 mmol) in a manner similar to that described in step 1 of the synthesis of compound 28-B. $^1$H-NMR (400 MHz, CDCl$_3$) δ 10.54 (s, 1H), 8.26 (s, 1H), 7.63 (td, J=8.6, 6.6 Hz, 1H), 6.76 (dddd, J=21.9, 11.2, 8.7, 2.3 Hz, 2H), 5.39 (dd, J=9.6, 3.7 Hz, 1H), 4.53-4.36 (m, 2H), 4.09 (dd, J=12.8, 3.7 Hz, 1H), 4.03 (s, 3H), 3.99 (dd, J=12.7, 9.7 Hz, 1H), 2.41-2.20 (m, 2H), 1.84 (dtd, J=19.7, 9.3, 8.8, 4.4 Hz, 2H), 1.74 (dd, J=14.6, 2.5 Hz, 1H), 1.62-1.35 (m, 2H), 1.34-1.14 (m, 5H). $^{19}$F-NMR (376.1 MHz, CDCl$_3$) δ -111.75 (q, J=8.9 Hz, 1F), -112.01 (p, J=7.9 Hz, 1F). LCMS-ESI$^+$ (m/z): [M+H]$^+$ calculated for C$_{25}$H$_{26}$F$_2$N$_3$O$_5$: 486.18; found: 486.2.

Step 3

Compound 29 was prepared from compound 29-B in a manner similar to that described in step 2 of the synthesis of compound 16. $^1$H-NMR (400 MHz, CDCl$_3$) δ 10.66 (s, 1H), 8.29 (s, 1H), 7.59 (td, J=8.5, 6.6 Hz, 1H), 6.89-6.60 (m, 2H), 5.51 (dd, J=9.9, 4.0 Hz, 1H), 4.55 (s, 1H), 4.48 (t, J=4.2 Hz, 1H), 4.21 (dd, J=12.9, 4.1 Hz, 1H), 3.99 (dd, J=12.8, 9.8 Hz, 1H), 2.56-2.35 (m, 1H), 2.14 (dd, J=16.1, 5.9 Hz, 1H), 1.96-1.74 (m, 3H), 1.66-1.37 (m, 3H), 1.28 (d, J=4.4 Hz, 2H), 1.26-1.19 (m, 2H). $^{19}$F-NMR (376.1 MHz, CDCl$_3$) δ -76.41 (s, 3F, -111.79 (m, 2F). LCMS-ESI$^+$ (m/z): [M+H]$^+$ calculated for C$_{24}$H$_{23}$F$_2$N$_3$O$_5$: 472.17; found: 472.1.

Example 30

Preparation of Compound 30

(2S,5R,13aS)—N-(1-(2,4-difluorophenyl)cyclopropyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

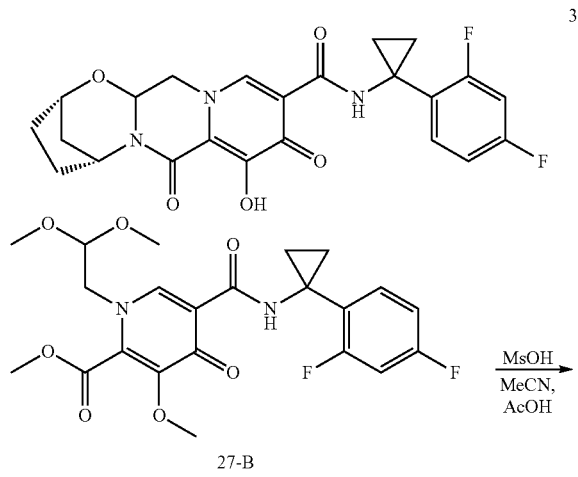

Step 1 and 2

Compound 27-B (150 mg, 0.322 mmol) was dissolved in acetonitrile (2 mL), AcOH (0.2 mL), and methanesulfonic acid (0.007 mL, 0.108 mmol) at room temperature and the resulting solution was stirred at 65° C. for 20 hours. After the resulting solution was cooled to room temperature, the aminoalcohol 30-A (72.1 mg, chiral, 0.713 mmol), K$_2$CO$_3$ (89.4 mg, 0.647 mmol), and acetonitrile (2 mL) were added to the solution. The resulting mixture was stirred at 65° C. bath for 0.5 hour. After the reaction mixture was cooled to room temperature, it was acidified with 1 N HCl (~3 mL), diluted with water (~12 mL), and extracted with CH$_2$Cl$_2$ (×3). Combined extracts were dried (Na$_2$SO$_4$), concentrated, and purified by CombiFlash to obtain 128 mg (84%) of compound 30-B. $^1$H-NMR (400 MHz, CDCl$_3$) δ 10.52 (s, 1H), 8.24 (s, 1H), 7.61 (td, J=8.6, 6.6 Hz, 1H), 6.85-6.65 (m, 2H), 5.33 (t, J=4.1 Hz, 1H), 5.25 (dd, J=9.5, 3.9 Hz, 1H), 4.61 (d, J=3.4 Hz, 1H), 4.18-4.08 (m, 1H), 4.02 (s, 3H), 3.99-3.87 (m, 1H), 2.12-1.91 (m, 4H), 1.85-1.69 (m, 1H), 1.55 (ddd, J=12.3, 4.1, 2.8 Hz, 1H), 1.31-1.14 (m, 4H). $^{19}$F-NMR (376.1 MHz, CDCl$_3$) δ -111.79 (q, J=8.8 Hz, 1F), -112.05 (p, J=7.9 Hz, 1F). LCMS-ESI$^+$ (m/z): [M+H]$^+$ calculated for C$_{24}$H$_{24}$F$_2$N$_3$O$_5$: 472.17; found: 472.2.

Step 3

A mixture of compound 30-B (128 mg, 0.272 mmol) and MgBr$_2$ (130 mg, 0.706 mmol) in MeCN (5 mL) was stirred at 50° C. for 30 minutes and cooled to 0° C. before treating with 1 N HCl (4 mL). After the mixture was diluted with water, the product was extracted with CH$_2$Cl$_2$ (×3), and the combined extracts were dried (Na$_2$SO$_4$) and concentrated. The product was purified by CombiFlash to obtain product 30. $^1$H-NMR (400 MHz, CDCl$_3$) δ 12.27 (s, 1H), 10.52 (s, 1H), 8.16 (s, 1H), 7.61 (td, J=8.6, 6.6 Hz, 1H), 6.96-6.54 (m, 2H), 5.36-5.23 (m, 2H), 4.66 (t, J=3.1 Hz, 1H), 4.18-4.06 (m, 1H), 3.94 (dd, J=12.8, 9.4 Hz, 1H), 2.20-1.95 (m, 4H), 1.89 (td, J=11.4, 9.8, 6.7 Hz, 1H), 1.70-1.54 (m, 1H), 1.32-1.15 (m, 4H). $^{19}$F-NMR (376.1 MHz, CDCl$_3$)

δ −111.87 (q, J=8.9 Hz, 1F), −112.21 (p, J=7.9 Hz, 1F). LCMS-ESI+ (m/z): [M+H]+ calculated for C23H22F2N3O5: 458.15; found: 458.2.

Example 31

Preparation of Compound 31

(2R,5S)—N-(1-(2,4-difluorophenyl)cyclopropyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

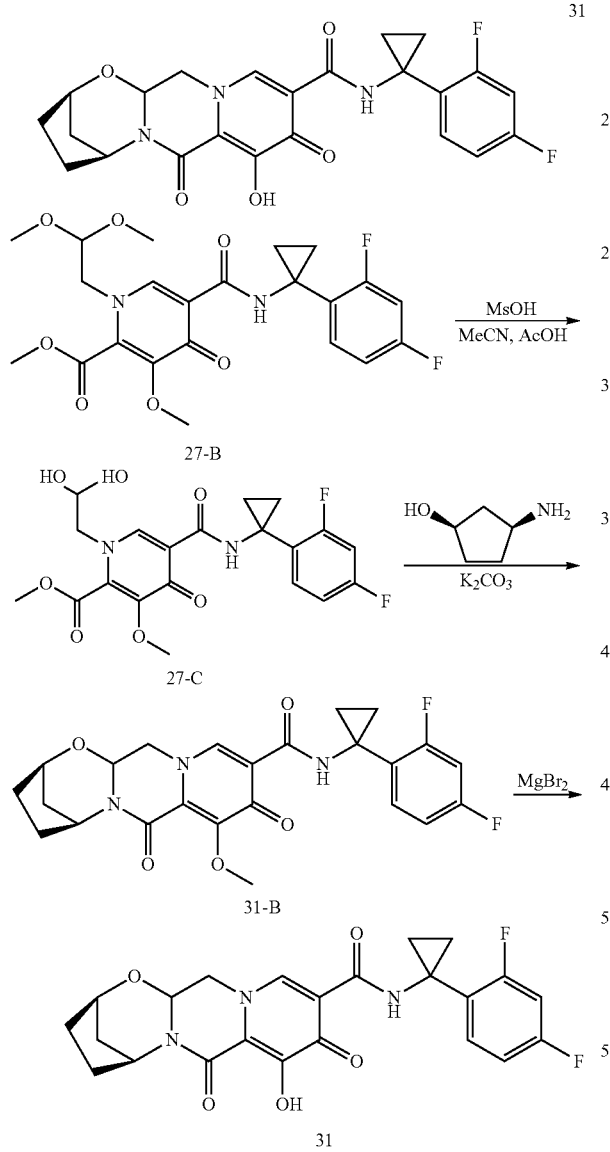

Step 1 and 2

Compound 31-B (123 mg, 81%) was prepared from compound 27-B (150 mg, 0.322 mmol) and the aminoalcohol 31-A (70.3 mg, 0.695 mmol) in a manner similar to that described in step 1 and 2 of the synthesis of compound 30-B. 1H-NMR (400 MHz, CDCl3) δ 10.52 (s, 1H), 8.24 (s, 1H), 7.62 (td, J=8.6, 6.6 Hz, 1H), 6.91-6.63 (m, 2H), 5.33 (t, J=4.1 Hz, 1H), 5.25 (dd, J=9.5, 3.9 Hz, 1H), 4.61 (d, J=3.4 Hz, 1H), 4.14-4.07 (m, 1H), 4.03 (s, 3H), 3.93 (dd, J=12.7, 9.5 Hz, 1H), 2.12-1.91 (m, 4H), 1.85-1.69 (m, 1H), 1.55 (ddd, J=12.3, 4.1, 2.8 Hz, 1H), 1.31-1.14 (m, 4H). 19F-NMR (376.1 MHz, CDCl3) δ −111.79 (q, J=9.2, 8.7 Hz, 1F), −112.03 (h, J=8.1, 7.5 Hz, 1F). LCMS-ESI+ (m/z): [M+H]+ calculated for C24H24F2N3O5: 472.17; found: 472.1.

Step 3

Compound 31 was prepared from compound 31-B in a manner similar to that described in step 3 of the synthesis of compound 30. 1H-NMR (400 MHz, CDCl3) δ 12.26 (s, 1H), 10.49 (s, 1H), 8.13 (s, 1H), 7.58 (td, J=8.6, 6.5 Hz, 1H), 6.90-6.56 (m, 2H), 5.32 (dd, J=9.4, 4.1 Hz, 1H), 5.27-5.22 (m, 1H), 4.64 (t, J=3.1 Hz, 1H), 4.11 (dd, J=12.8, 4.0 Hz, 1H), 4.01-3.79 (m, 1H), 2.28-1.95 (m, 4H), 1.95-1.80 (m, 1H), 1.71 (m, 1H), 1.56 (m, 1H), 1.42-1.08 (m, 4H). 19F-NMR (376.1 MHz, CDCl3) δ −111.95 (q, J=8.9 Hz, 1F), −112.22 (p, J=7.9 Hz, 1F). LCMS-ESI+ (m/z): [M+H]+ calculated for C23H22F2N3O5: 458.15; found: 458.1.

Example 32

Preparation of Compound 32

(2S,5R)—N-(1-(2,4-difluorophenyl)cyclobutyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

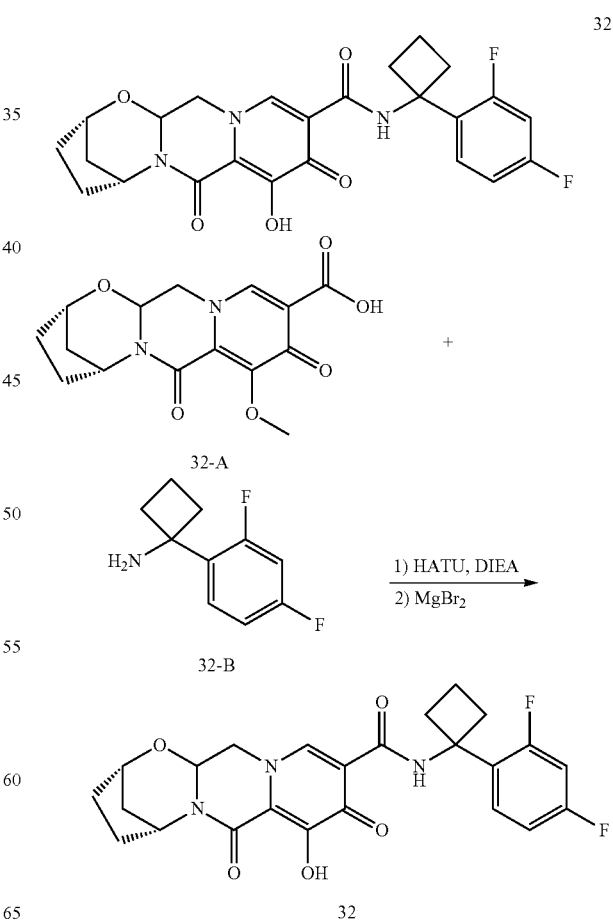

A solution of compound 32-A (22.2 mg, 0.069 mmol), compound 32-B (18.7 mg, 0.102 mmol), and HATU (43 mg, 0.113 mmol) in CH$_2$Cl$_2$ (2 mL) was stirred at room temperature as N,N-diisopropylethylamine (DIPEA) (0.075 mL, 0.431 mmol) was added. After 30 minutes, the reaction mixture was diluted with ethyl acetate and washed with water (×2). After the aqueous fractions were extracted with EA (×1), the organic fractions were combined, dried, concentrated, and dried in vacuum.

A mixture of the above crude product and MgBr$_2$ (35 mg, 0.190 mmol) in MeCN (2 mL) was stirred at 50° C. bath for 1 hour and cooled to 0° C. before being treated with 1 N HCl (~1 mL). The resulting solution was diluted with water, and extracted with CH$_2$Cl$_2$ (×3). The combined extracts were dried (Na$_2$SO$_4$), and concentrated. The product was purified by preparative HPLC and freeze-dried to obtain compound 32. $^1$H-NMR (400 MHz, CDCl$_3$) δ 10.87 (s, 1H), ~9.3 (br, 1H), 8.35 (s, 1H), 7.50 (td, J=8.7, 6.3 Hz, 1H), 6.89-6.78 (m, 1H), 6.72 (ddd, J=11.2, 8.9, 2.6 Hz, 1H), 5.48-5.12 (m, 2H), 4.72-4.60 (m, 1H), 4.22 (dd, J=13.0, 4.1 Hz, 1H), 3.98 (dd, J=12.9, 9.4 Hz, 1H), 2.68 (m, 4H), 2.33-1.98 (m, 6H), 1.90 (m, 2H), 1.60 (ddd, J=12.4, 4.1, 2.7 Hz, 1H). $^{19}$F-NMR (376.1 MHz, CD$_3$CN) δ −76.39 (s, 3F), −110.50 (q, J=9.2 Hz, 1F), −112.65 (p, J=7.8 Hz, 1F). LCMS-ESI$^+$ (m/z): [M+H]$^+$ calculated for C$_{24}$H$_{24}$F$_2$N$_3$O$_5$: 472.17; found: 472.0.

Example 33

Preparation of Compound 33

(2S,5R)—N-(1-(2,4-difluorophenyl)cyclopentyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

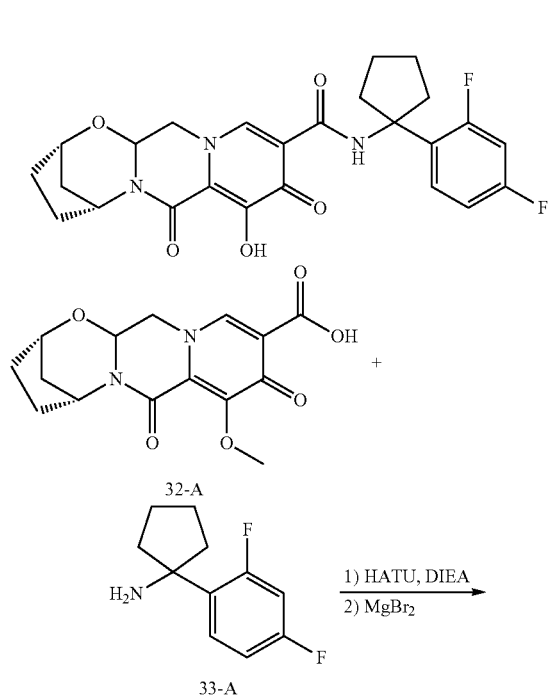

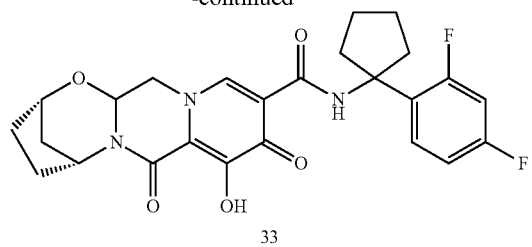

Compound 33 was obtained from compound 32-A and compound 33-A as described in the synthesis of compound 32. $^1$H-NMR (400 MHz, CDCl$_3$) δ 10.70 (s, 1H), ~9.5 (br, 1H), 8.41 (s, 1H), 7.43 (td, J=8.9, 6.4 Hz, 1H), 6.85-6.76 (m, 1H), 6.72 (ddd, J=11.5, 8.8, 2.6 Hz, 1H), 5.48-5.18 (m, 2H), 4.68 (t, J=3.2 Hz, 1H), 4.26 (dd, J=13.0, 4.1 Hz, 1H), 4.00 (dd, J=13.0, 9.4 Hz, 1H), 2.72-2.45 (m, 2H), 2.22-1.96 (m, 6H), 1.96-1.75 (m, 5H), 1.60 (ddd, J=12.5, 4.1, 2.7 Hz, 1H). $^{19}$F-NMR (376.1 MHz, CD$_3$CN) δ −76.41 (s, 3F), −107.86 (q, J=9.4 Hz, 1F), −113.13 (p, J=8.0 Hz, 1F). LCMS-ESI$^+$ (m/z): [M+H]$^+$ calculated for C$_{25}$H$_{26}$F$_2$N$_3$O$_5$: 486.18; found: 485.9.

Example 34

Preparation of Compound 34

(2S,5R)—N-(1-(2,4-difluorophenyl)cyclohexyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

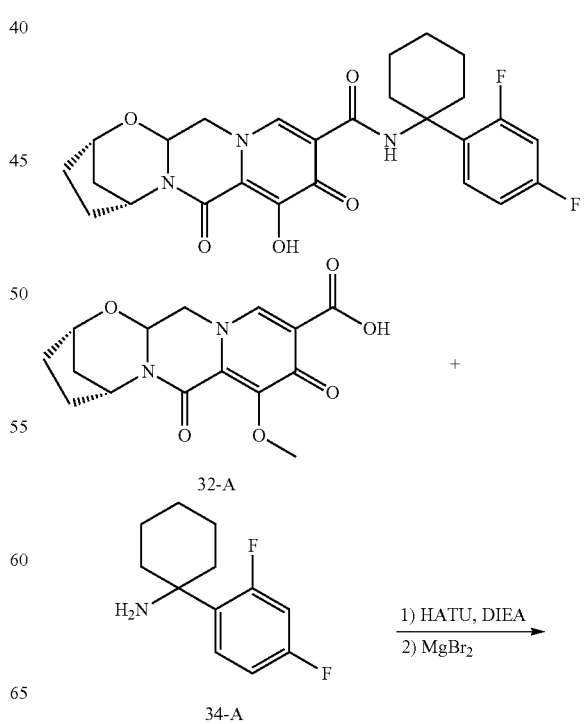

-continued

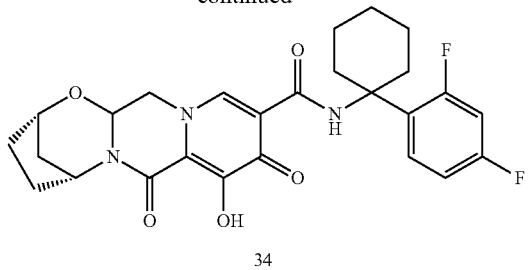

34

Compound 34 was obtained from compound 32-A and compound 34-A as described in the synthesis of compound 32. ¹H-NMR (400 MHz, CDCl₃) δ 10.83 (s, 1H), ~9.6 (br, 1H), 8.44 (s, 1H), 7.37 (td, J=9.0, 6.4 Hz, 1H), 6.97-6.76 (m, 1H), 6.69 (ddd, J=11.9, 8.8, 2.7 Hz, 1H), 5.48-5.18 (m, 2H), 4.68 (t, J=3.0 Hz, 1H), 4.28 (dd, J=13.1, 4.1 Hz, 1H), 4.03 (dd, J=13.0, 9.4 Hz, 1H), 2.60 (d, J=13.1 Hz, 2H), 2.29-1.96 (m, 4H), 1.95-1.77 (m, 4H), 1.77-1.65 (m, 4H), 1.61 (ddd, J=12.5, 4.1, 2.7 Hz, 1H), 1.30 (br, 1H). ¹⁹F-NMR (376.1 MHz, CD₃CN) δ −76.41 (s, 3F), −107.86 (q, J=9.4 Hz, 1F), −113.13 (p, J=8.0 Hz, 1F). LCMS-ESI⁺ (m/z): [M+H]⁺ calculated for $C_{26}H_{28}F_2N_3O_5$: 500.20; found: 500.0.

Example 35

Preparation of Compound 35

(2S,5R)—N-(4-(2,4-difluorophenyl)tetrahydro-2H-pyran-4-yl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

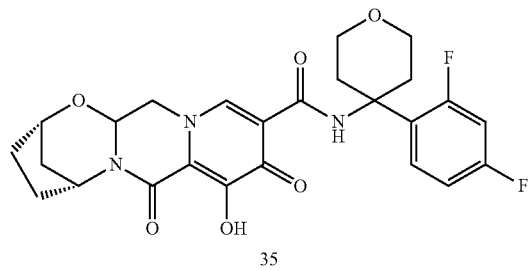

35

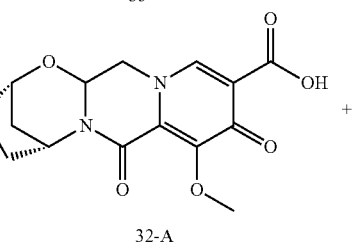

32-A

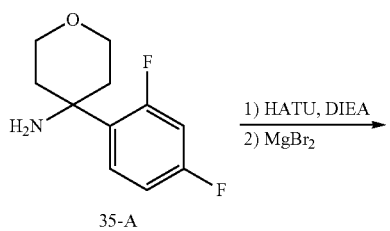

35-A

1) HATU, DIEA
2) MgBr₂ →

-continued

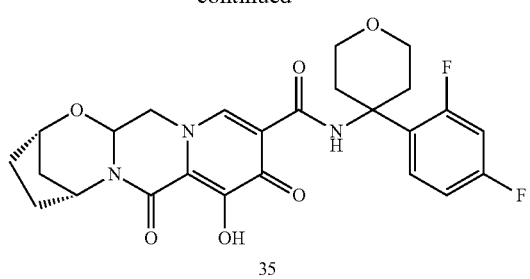

35

Compound 35 was obtained from compound 32-A and compound 35-A as described in the synthesis of compound 32. ¹H-NMR (400 MHz, CDCl₃) δ 10.95 (s, 1H), 8.33 (s, 1H), ~7.6 (br, 1H), 7.38 (td, J=9.0, 6.3 Hz, 1H), 6.85 (td, J=8.4, 2.6 Hz, 1H), 6.73 (ddd, J=11.7, 8.6, 2.6 Hz, 1H), 5.32 (dt, J=14.4, 4.0 Hz, 2H), 4.68 (t, J=3.1 Hz, 1H), 4.24 (dd, J=13.0, 3.9 Hz, 1H), 4.11-3.81 (m, 5H), 2.60 (d, J=13.7 Hz, 2H), 2.33-2.17 (m, 2H), 2.18-1.97 (m, 4H), 1.87 (m, 1H), 1.61 (dt, J=12.5, 3.3 Hz, 1H). ¹⁹F-NMR (376.1 MHz, CD₃CN) δ −76.40 (s, 3F), −108.78 (q, J=10.3, 9.8 Hz, 1F), −112.63 (p, J=8.0 Hz, 1F). LCMS-ESI⁺ (m/z): [M+H]⁺ calculated for $C_{25}H_{26}F_2N_3O_6$: 502.18; found: 502.0.

Example 36

Preparation of Compound 36

(2S,5R)—N—((S)-1-(2,4-difluorophenyl)-2,2,2-trifluoroethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

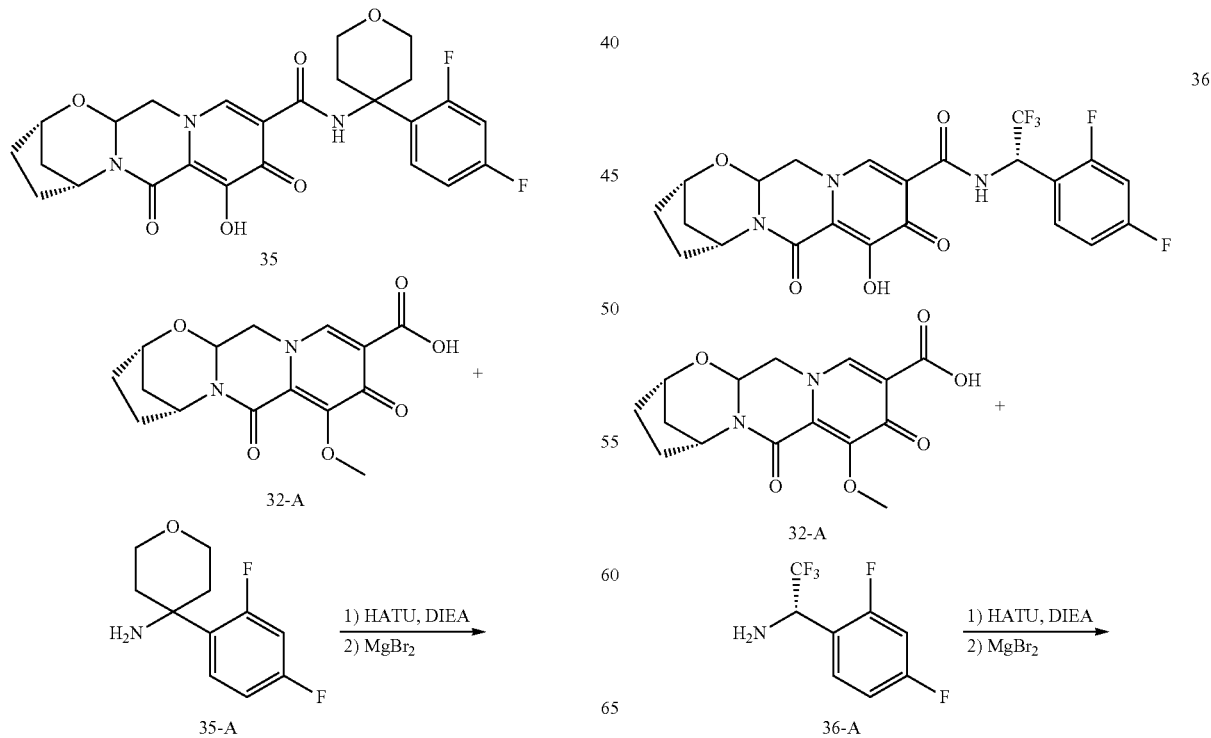

-continued

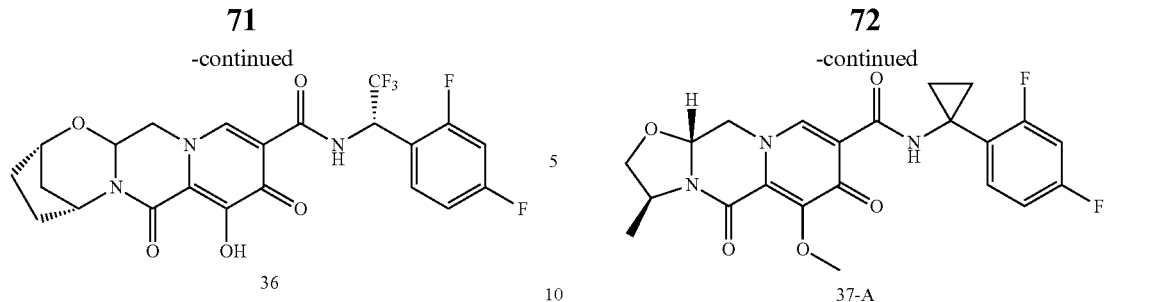

Compound 36 was obtained from compound 32-A and compound 36-A as described in the synthesis of compound 32. $^1$H-NMR (400 MHz, CDCl$_3$) δ 11.31 (d, J=9.4 Hz, 1H), 8.41 (s, 1H), 7.65-7.44 (m, 1H), 6.95 (ddd, J=9.6, 5.6, 2.0 Hz, 1H), 6.92-6.79 (m, 1H), 6.15 (h, J=7.4 Hz, 1H), ~6 (br, 1H), 5.41 (dd, J=9.5, 4.0 Hz, 1H), 5.31 (t, J=4.0 Hz, 1H), 4.70 (s, 1H), 4.34 (dd, J=12.8, 3.9 Hz, 1H), 4.05 (dd, J=12.9, 9.4 Hz, 1H), 2.26-1.99 (m, 4H), 1.99-1.87 (m, 1H), 1.62 (dt, J=12.6, 3.4 Hz, 1H). $^{19}$F-NMR (376.1 MHz, CDCl$_3$) δ −75.23 (t, J=6.9 Hz, 3F), −76.33 (s, 3F), −108.31 (m, 1F), −112.30 (p, J=8.0 Hz, 1F). LCMS-ESI$^+$ (m/z): [M+H]$^+$ calculated for C$_{22}$H$_{19}$F$_5$N$_3$O$_5$: 500.12; found: 500.1.

Example 37

Preparation of Compound 37

(3S,11aR)—N-(1-(2,4-difluorophenyl)cyclopropyl)-6-hydroxy-3-methyl-5,7-dioxo-2,3,5,7,11,11a-hexahydrooxazolo[3,2-a]pyrido[1,2-d]pyrazine-8-carboxamide

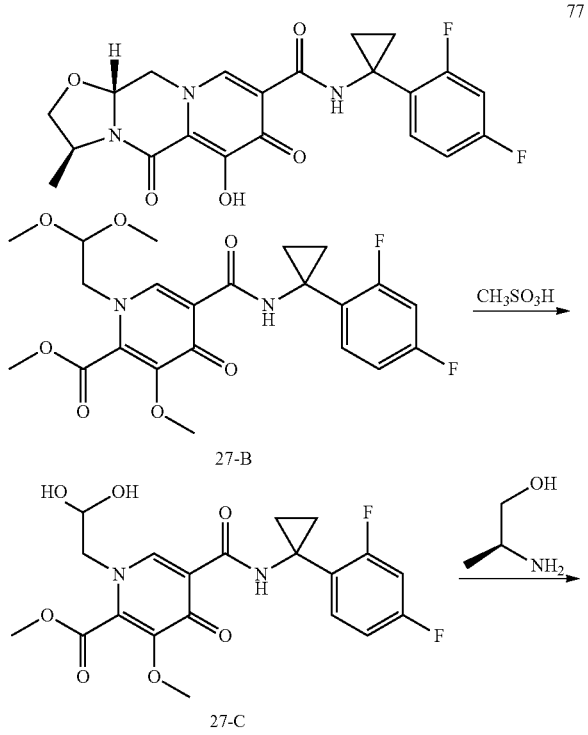

Step 1

Methyl 5-(1-(2,4-difluorophenyl)cyclopropylcarbamoyl)-1-(2,2-dimethoxyethyl)-3-methoxy-4-oxo-1,4-dihydropyridine-2-carboxylate (27-B, 0.150 g, 0.32 mmol) in acetonitrile (1.5 mL) and acetic acid (0.2 mL) was treated with methanesulfonic acid (0.05 mL), sealed with a yellow cap, and heated to 70° C. After 16 hours, the mixture was cooled to afford a crude solution of methyl 5-(1-(2,4-difluorophenyl)cyclopropylcarbamoyl)-1-(2,2-dihydroxyethyl)-3-methoxy-4-oxo-1,4-dihydropyridine-2-carboxylate 27-C. LCMS-ESI$^+$ (m/z): [M+H]$^+$ calculated for C$_{18}$H$_{19}$F$_2$N$_2$O$_7$: 439; found: 439.

Steps 2 and 3

Methyl 5-(1-(2,4-difluorophenyl)cyclopropylcarbamoyl)-1-(2,2-dihydroxyethyl)-3-methoxy-4-oxo-1,4-dihydropyridine-2-carboxylate (27-C, 0.32 mmol, the crude mixture from the previous step) was dissolved in acetonitrile (1.5 mL) and acetic acid (0.2 mL). (S)-2-aminopropan-1-ol (0.048 g, 0.64 mmol) and K$_2$CO$_3$ (0.088 g, 0.64 mmol) were added to the reaction mixture. The reaction mixture was sealed and heated to 70° C. After 3 hours, the reaction mixture was cooled and magnesium bromide (0.081 g, 0.44 mmol) was added. The mixture was resealed and heated to 50° C. After 10 minutes, the reaction mixture was cooled to 0° C. and 1 N hydrochloric acid (0.5 mL) was added in. Then the reaction mixture was diluted with MeOH (2 mL). After filtration, the crude was purified by Prep-HPLC (30-70% acetonitrile:water, 0.1% TFA) to afford Compound 37 as a TFA salt. $^1$H-NMR (400 MHz, Methanol-d$_4$) δ 8.31 (s, 1H), 7.62 (td, J=9.2, 8.7, 6.5 Hz, 1H), 7.02-6.78 (m, 2H), 5.53-5.20 (m, 1H), 4.68 (dd, J=12.3, 4.2 Hz, 1H), 4.40 (dq, J=19.1, 6.7 Hz, 2H), 3.98 (dd, J=12.2, 10.0 Hz, 1H), 3.71 (dd, J=8.3, 6.3 Hz, 1H), 1.41 (d, J=6.1 Hz, 3H), 1.22 (s, 4H). $^{19}$F-NMR (376 MHz, Methanol-d$_4$) δ −113.66~−113.95 (m, 1F), −113.94~−114.29 (m, 1F). LCMS-ESI$^+$ (m/z): [M+H]$^+$ calculated for C$_{21}$H$_{20}$F$_2$N$_3$O$_5$: 432; found: 432.

Example 38

Preparation of Compound 38

(1S,4R,12aR)—N-(2,4-difluorobenzyl)-7-hydroxy-6,8-dioxo-1,2,3,4,6,8,12,12a-octahydro-1,4-methano-dipyrido[1,2-a:1',2'-d]pyrazine-9-carboxamide

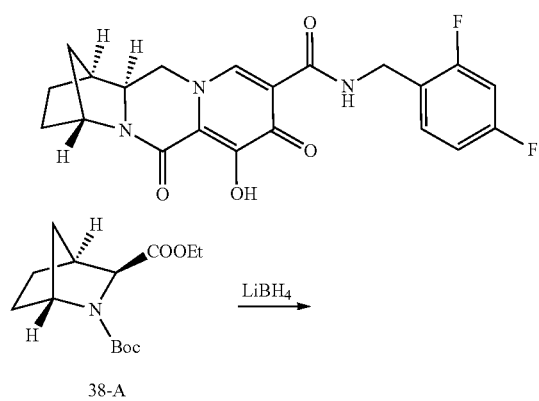

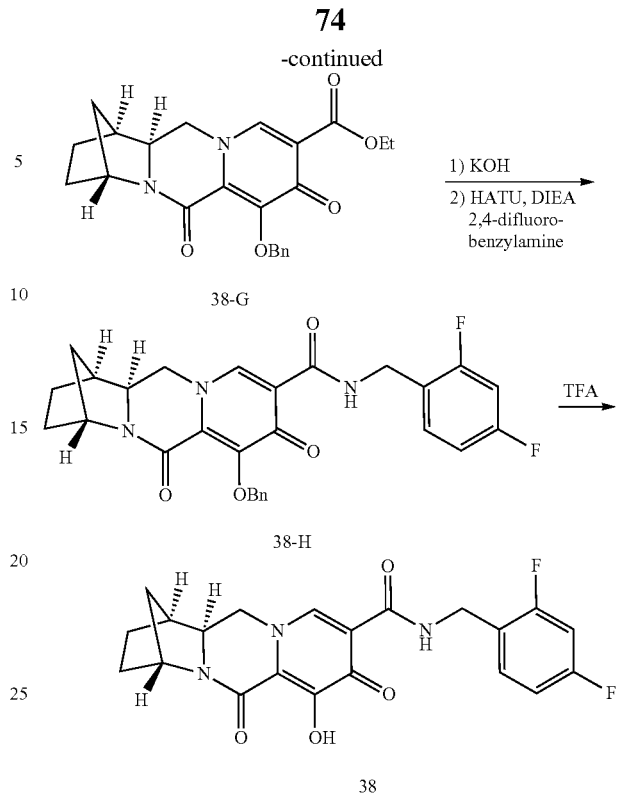

Step 1

A solution of compound 38-A (1562 mg, 5.799 mmol) (see Example 41b in WO 97/05139) in THF (10 mL) was stirred at −78° C. as 2.0 M LiBH₄ in THF (3.2 mL) was added and the resulting mixture was stirred at room temperature. After 3 hours, additional 2.0 M LiBH₄ in THF (3.2 mL) was added and the solution was stirred at room temperature for 17.5 hours. After the reaction mixture was diluted with ethyl acetate and added water slowly, two phases were separated, and the separated aqueous fraction was extracted with ethyl acetate (×1). Two organic fractions were washed with water (×1), combined, dried (Na₂SO₄), and concentrated. The residue was purified by CombiFlash (40 g column) using hexanes-ethyl acetate as eluents to afford compound 38-B. ¹H-NMR (400 MHz, Chloroform-d) δ 4.11 (s, 1H), 3.65-3.52 (m, 2H), 3.45 (m, 1H), 2.32 (d, J=4.1 Hz, 1H), 2.20 (s, 1H), 1.75-1.64 (m, 2H), 1.61 (m, 2H), 1.49-1.41 (m, 1H), 1.47 (s, 9H), 1.28-1.23 (d, J=10 Hz, 1H). LCMS-ESI⁺ (m/z): [M+H]⁺ calculated for $C_{12}H_{22}NO_3$: 228.16; found: 227.7.

Step 2

A solution of compound 38-B (589 mg, 2.591 mmol) and NEt₃ (0.47 mL, 3.369 mmol) in CH₂Cl₂ (6 mL) was stirred at 0° C. as MsCl (0.22 mL, 2.842 mmol) was added. After 1 hour at room temperature, the mixture was diluted with ethyl acetate and washed with water (×2). The aqueous fractions were extracted with ethyl acetate (×1), and the organic fractions were combined, dried (Na₂SO₄), and concentrated. The residue was purified by Combi Flash (40 g column) using hexanes-ethyl acetate as eluents to afford compound 38-C. ¹H-NMR (400 MHz, Chloroform-d) δ 4.39-4.28 (m, 1H), 4.16 (s, 0.4H), 4.06 (s, 0.6H), 3.98 (dd, J=10.0, 8.7 Hz, 0.6H), 3.86 (t, J=9.6 Hz, 0.4H), 3.51 (dd, J=9.3, 3.7 Hz, 0.6H), 3.43 (dd, J=9.3, 3.6 Hz, 0.4H), 3.02 (s, 3H), 2.59 (m, 1H), 1.82-1.58 (m, 4H), 1.51-1.44 (m, 9H), 1.41 (d, J=14.8 Hz, 1H), 1.31 (s, 0.6H), 1.29 (s, 0.4H).

Step 3

To a solution of compound 38-C (769 mg, 2.518 mmol) in DMF (5 mL) was added sodium azide (819 mg, 12.6 mmol). The reaction mixture was stirred at 50° C. for 15 hours, at 80° C. for 5 hours, and at 100° C. for 19 hours. The reaction mixture was diluted with 5% LiCl solution and the product was extracted with ethyl acetate (×2). After the organic fractions were washed with water (×1), the two organic fractions were combined, dried (Na$_2$SO$_4$), and concentrated. The residue was purified by CombiFlash (40 g column) using hexanes-ethyl acetate as eluents to afford compound 38-D. $^1$H-NMR (400 MHz, Chloroform-d) δ 4.16 (s, 0.4H), 4.06 (s, 0.6H), 3.61 (dd, J=12.2, 3.6 Hz, 0.6H), 3.51 (dd, J=12.1, 3.2 Hz, 0.4H), 3.38 (dd, J=9.4, 3.4 Hz, 0.6H), 3.26 (dd, J=9.8, 3.3 Hz, 0.4H), 3.06 (dd, J=12.2, 9.4 Hz, 0.6H), 3.01-2.92 (m, 0.4H), 2.48 (d, J=5.2 Hz, 1H), 1.82-1.57 (m, 4H), 1.46 (d, J=3.0 Hz, 9H), 1.42 (m, 1H), 1.28 (m, 0.6H), 1.27-1.23 (m, 0.4H).

Step 4

To a solution of compound 38-D (507 mg, 2.009 mmol) in ethyl acetate (10 mL) and EtOH (10 mL) was added 10% Pd/C (52 mg). The reaction mixture was stirred under H$_2$ atmosphere for 1.5 hours. The mixture was filtered through celite and the filtrate was concentrated to afford crude compound 38-E. LCMS-ESI$^+$ (m/z): [M+H]$^+$ calculated for C$_{12}$H$_{23}$N$_2$O$_2$: 227.18; found: 226.8.

Step 5

The mixture of crude compound 38-E (206 mg, 0.910 mmol), compound 38-F (330 mg, 0.953 mmol), and NaHCO$_3$ (154 mg, 1.833 mmol) in water (3 mL) and EtOH (3 mL) was stirred at room temperature for 20 hours. After the reaction mixture was diluted with water and extracted with ethyl acetate (×2), the extracts were washed with water (×1), combined, dried (Na$_2$SO$_4$), and concentrated to afford the crude pyridine product.

The crude residue (388 mg) was dissolved in CH$_2$Cl$_2$ (4 mL) and 4 N HCl in dioxane (4 mL). After 1.5 hours, additional 4 N HCl in dioxane (4 mL) was added and stirred for 1 hour at room temperature. The mixture was concentrated to dryness, coevaporated with toluene (×1) and dried in vacuum for 30 minutes.

The crude residue and 1,8-diazabicycloundec-7-ene (DBU) (1.06 mL, 7.088 mmol) in toluene (10 mL) was stirred at 110° C. bath. After 30 minutes, the mixture was concentrated and the residue was purified by CombiFlash (40 g column) using ethyl acetate-20% MeOH/ethyl acetate as eluents to obtain compound 38-G. $^1$H-NMR (400 MHz, Chloroform-d) δ 8.03 (s, 1H), 7.68-7.58 (m, 2H), 7.36-7.27 (m, 3H), 5.53 (d, J=9.9 Hz, 1H), 5.11 (d, J=9.9 Hz, 1H), 4.93 (s, 1H), 4.43-4.30 (m, 2H), 3.89 (dd, J=12.2, 3.3 Hz, 1H), 3.73 (t, J=12.0 Hz, 1H), 3.59 (dd, J=11.9, 3.3 Hz, 1H), 2.53 (d, J=2.8 Hz, 1H), 1.87-1.67 (m, 4H), 1.55 (d, J=10.0 Hz, 1H), 1.51-1.45 (m, 1H), 1.38 (t, J=7.1 Hz, 3H). LCMS-ESI$^+$ (m/z): [M+H]$^+$ calculated for C$_{23}$H$_{25}$N$_2$O$_5$: 409.18; found: 409.2.

Step 6

The mixture of compound 38-G (232 mg, 0.568 mmol) in THF (3 mL) and MeOH (3 mL) was stirred at room temperature as 1 N KOH (3 mL) was added. After 1 hour, the reaction mixture was neutralized with 1 N HCl (~3.1 mL), concentrated, and the residue was concentrated with toluene (×3). After the residue was dried in vacuum for 30 minutes, a suspension of the crude residue, 2,4-difluorobenzylamine (86 mg, 0.601 mmol), and HATU (266 mg, 0.700 mmol) were in CH$_2$Cl$_2$ (4 mL) and DMF (4 mL) was stirred at 0° C. as N,N-diisopropylethylamine (DIPEA) (0.7 mL, 4.019 mmol) was added. After 45 minutes, additional 2,4-difluorobenzylamine (86 mg, 0.559 mmol), HATU (266 mg, 0.700 mmol), and N,N-diisopropylethylamine (DIPEA) (0.7 mL, 4.019 mmol) were added at room temperature. After 1.25 hours, the mixture was concentrated to remove most of CH$_2$Cl$_2$, diluted with ethyl acetate, and washed with 5% LiCl (×2). After the aqueous fractions were extracted with ethyl acetate (×1), the organic fractions were combined, dried (Na2SO4), and concentrated. The residue was purified by Combiflash (40 g column) using ethyl acetate –20% MeOH/ethyl acetate as eluents to afford compound 38-H. $^1$H-NMR (400 MHz, Chloroform-d) δ 10.48 (t, J=6.0 Hz, 1H), 8.33 (s, 1H), 7.62-7.51 (m, 2H), 7.40-7.27 (m, 4H), 6.87-6.75 (m, 2H), 5.39 (d, J=10.0 Hz, 1H), 5.15 (d, J=10.0 Hz, 1H), 4.92 (s, 1H), 4.68-4.53 (m, 2H), 3.97 (dd, J=12.5, 3.4 Hz, 1H), 3.77 (t, J=12.2 Hz, 1H), 3.55 (dd, J=12.1, 3.3 Hz, 1H), 2.53 (d, J=3.1 Hz, 1H), 1.88-1.62 (m, 4H), 1.59-1.42 (m, 2H). $^{19}$F-NMR (376 MHz, Chloroform-d) δ –112.17 (q, J=7.6 Hz, 1F), –114.79 (q, J=8.6 Hz, 1F). LCMS-ESI$^+$ (m/z): [M+H]$^+$ calculated for C28H26F2N3O4: 506.19; found: 506.2.

Step 7

Compound 38-H (240 mg, 0.475 mmol) was dissolved in TFA (3 mL) at room temperature for 30 minutes, and the solution was concentrated. The residue was purified by CombiFlash (40 g column) using CH$_2$Cl$_2$-20% MeOH in CH$_2$Cl$_2$ as eluents. After the collected product fractions were concentrated, the residue was triturated in MeCN (~2 mL) at 0° C. for 15 minutes, and the solids were filtered and washed with MeCN. The collected solids were dried in vacuum to afford compound 38.

The filtrate was concentrated, and the residue was dissolved in MeCN (~1 mL) and water (~1 mL) by heating. The solution was slowly cooled to room temperature and then in ice bath for 15 minutes. The solids were filtered and washed with MeCN, and dried in vacuum to afford additional compound 38. $^1$H-NMR (400 MHz, Chloroform-d) δ 11.68 (s, 1H), 10.42 (s, 1H), 8.27 (s, 1H), 7.41-7.31 (m, 1H), 6.86-6.73 (m, 2H), 4.90 (d, J=2.5 Hz, 1H), 4.71-4.53 (m, 2H), 4.07 (d, J=10.6 Hz, 1H), 3.90-3.67 (m, 2H), 2.68 (s, 1H), 2.01 (s, 1H), 1.97-1.80 (m, 3H), 1.80-1.62 (m, 2H). $^{19}$F-NMR (376 MHz, Chloroform-d) δ –112.28 (m, 1F), –114.74 (m, 1F). LCMS-ESI$^+$ (m/z): [M+H]$^+$ calculated for C$_{21}$H$_{19}$F$_2$N$_3$O$_4$: 416.14; found: 416.3.

Examples 39 and 40
Preparation of Compounds 39 and 40
(2R,3S,5R,13aS)—N-(2,4-difluorobenzyl)-8-hydroxy-3-methyl-7,9-dioxo-2,3,4,5,7,9,13,13a-octahydro-2,5-methanopyrido[1',2':4,5]pyrazino[2,1-b][1,3]oxazepine-10-carboxamide 39 and (2S,3R,5S,13aR)—N-(2,4-difluorobenzyl)-8-hydroxy-3-methyl-7,9-dioxo-2,3,4,5,7,9,13,13a-octahydro-2,5-methanopyrido[1',2':4,5]pyrazino[2,1-b][1,3]oxazepine-10-carboxamide 40
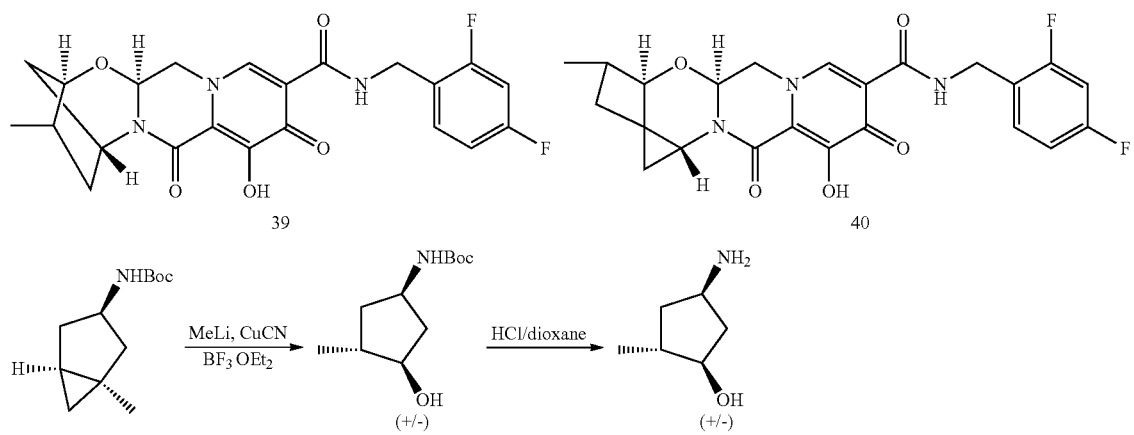
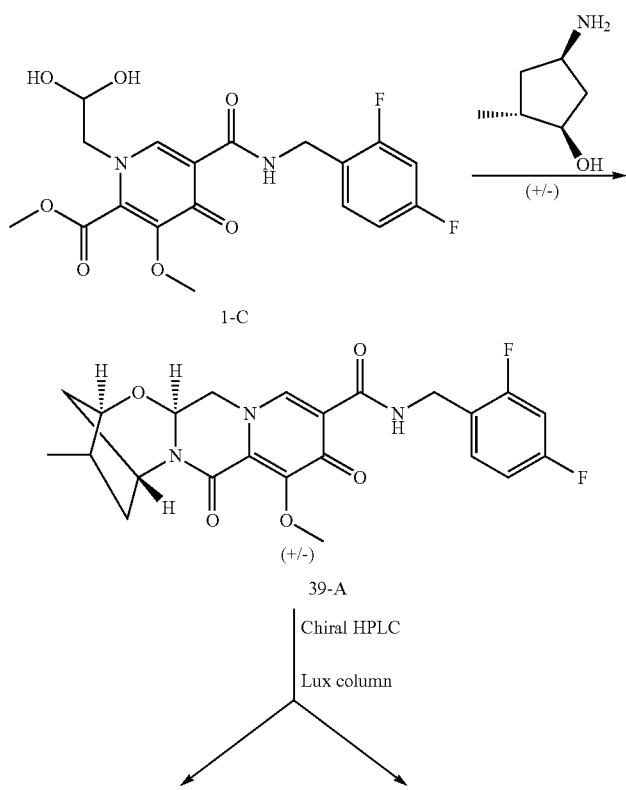

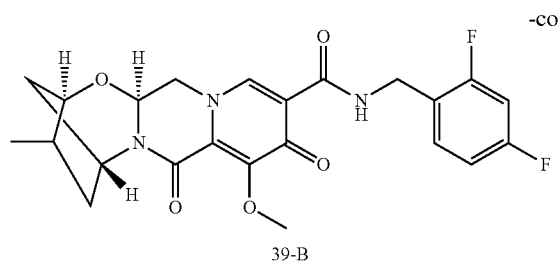

39-B

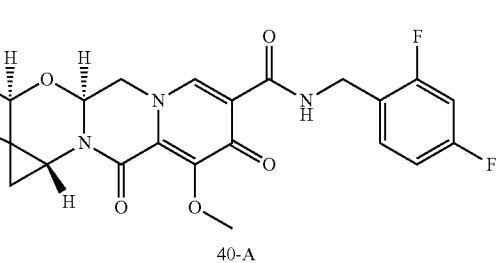

40-A

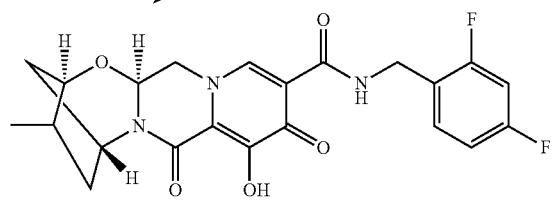

39

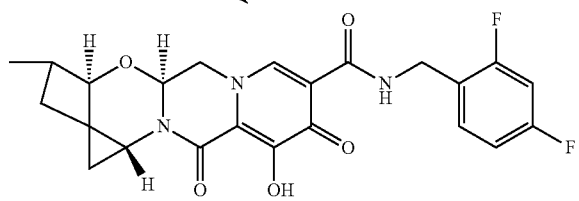

40

Step 1

Cuprous cyanide (290 mg, 3.27 mmol) was suspended in 3.3 mL THF and cooled to −78° C. A 1.6M solution of MeLi (4.1 mL, 6.56 mmol) in diethyl ether was added dropwise, the reaction solution was allowed to warm to room temperature over the course of 2 hours, and recooled to −78° C. Tert-butyl (1R,3R,5S)-6-oxabicyclo[3.1.0]hexan-3-ylcarbamate (330 mg, 1.66 mmol) was added dropwise in 3.3 mL THF, followed by boron trifluoride diethyl etherate (0.25 mL, 1.99 mmol), allowed to warm to −30° C. over 30 minutes, and stirred between −35° C. and −25° C. for one hour. The reaction solution was then warmed to room temperature and quenched with a mixture of saturated $NH_3$(aq)/$NH_4$(aq), extracted to EtOAc, washed with brine, dried over MgSO4, filtered, concentrated, and purified by SGC (0-10% EtOH/DCM) to afford racemic tert-butyl (1S,3S,4S)-3-hydroxy-4-methylcyclopentylcarbamate.

$^1$H-NMR (400 MHz, Chloroform-d) δ 5.16 (s, 1H), 3.98 (s, 1H), 3.74 (q, J=4.3 Hz, 1H), 3.65 (q, J=7.0 Hz, 1H), 2.23 (dt, J=14.0, 7.0 Hz, 1H), 1.98 (dt, J=13.3, 7.0 Hz, 1H), 1.89-1.79 (m, 1H), 1.58-1.44 (m, 1H), 1.38 (s, 9H), 1.18 (t, J=7.0 Hz, 1H), 0.91 (d, J=7.0 Hz, 3H).

Step 2

3 mL HCl/dioxane (4M, 12 mmol) was added to a solution of racemic tert-butyl (1S,3S,4S)-3-hydroxy-4-methylcyclopentylcarbamate (182 mg, 0.85 mmol) in 3 mL dioxane. The reaction mixture was stirred at room temperature for 2 hours, concentrated and twice chased with toluene to afford racemic (1S,2S,4S)-4-amino-2-methylcyclopentanol.

Step 3

Methyl 5-(2,4-difluorobenzylcarbamoyl)-1-(2,2-dihydroxyethyl)-3-methoxy-4-oxo-1,4-dihydropyridine-2-carboxylate (1-C, 310 mg, 0.75 mmol), racemic (1S,2S,4S)-4-amino-2-methylcyclopentanol (115 mg, 0.76 mmol), and potassium carbonate (232 mg, 1.68 mmol) were taken up in 3.8 mL acetonitrile/0.2 mL acetic acid and stirred at 90° C. for 2 hours, after which the reaction mixture was partitioned between DCM and brine, the aqueous phase extracted to DCM, combined organic phases dried over $MgSO_4$, filtered, concentrated, and purified by SGC (0-10% EtOH/DCM) to afford intermediate 39-A.

Step 4

Intermediate 39-A (190 mg) was separated by chiral Prep-HPLC on a Lux Cellulose-2 column using 9:1 ACN:MeOH as eluent to afford Intermediates 39-B (first eluting peak) and 40-A (second eluting peak) in enantioenriched form. For intermediate 39-B: (absolute stereochemistry confirmed by XRay crystallography), Chiral HPLC retention time=3.98 minutes (Lux Cellulose-2 IC, 150×4.6 mm, 2 mL/min 9:1 ACN:MeOH). For intermediate 40-A: (absolute stereochemistry confirmed by XRay crystallography), Chiral HPLC retention time=6.35 minutes (Lux Cellulose-2 IC, 150×4.6 mm, 2 mL/min 9:1 ACN:MeOH).

Step 5a

Magnesium bromide (68 mg, 0.37 mmol) was added to a solution of intermediate 39-B (83 mg, 0.18 mmol) in 2 mL acetonitrile. The reaction mixture was stirred at 50° C. for 1 hour, acidified with 10% aqueous HCl, partitioned between the aqueous and dichloromethane, and the aqueous phase extracted to dichloromethane. The combined organic phases were dried over MgSO4, filtered, concentrated, and purified by silica gel chromatography (0-10% EtOH/DCM) to afford compound 39. $^1$H-NMR (400 MHz, Chloroform-d) δ 12.32 (s, 1H), 10.36 (s, 1H), 8.29 (s, 1H), 7.44-7.33 (m, 1H), 6.88-6.76 (m, 2H), 5.37 (dd, J=9.5, 4.1 Hz, 1H), 5.28 (t, J=5.3 Hz, 1H), 4.63 (d, J=5.9 Hz, 2H), 4.23 (d, J=23.0 Hz, 2H), 3.99 (dd, J=12.7, 9.5 Hz, 1H), 3.72 (q, J=7.0 Hz, 1H), 2.51 (dq, J=13.7, 6.8, 6.1 Hz, 1H), 2.15 (ddd, J=14.7, 8.3, 2.3 Hz, 1H), 1.94 (d, J=12.7 Hz, 1H), 1.77 (ddd, J=12.7, 4.0, 2.9 Hz, 1H), 1.61 (dt, J=14.6, 5.2 Hz, 2H), 1.24 (t, J=7.0 Hz, 1H), 1.09 (d, J=7.2 Hz, 3H). LCMS-ESI$^+$ (m/z): [M+H]$^+$ calculated for $C_{22}H_{22}F_2N_3O_5$: 446.15; found: 446.2.

Step 5b

Magnesium bromide (59 mg, 0.32 mmol) was added to a solution of intermediate 40-A (70 mg, 0.15 mmol) in 2 mL acetonitrile. The reaction mixture was stirred at 50° C. for 1 hour, acidified with 10% aqueous HCl, partitioned between the aqueous and dichloromethane, and the aqueous phase extracted to dichloromethane. The combined organic phases were dried over $MgSO_4$, filtered, concentrated, and purified by silica gel chromatography (0-10% EtOH/DCM) to afford compound 40. $^1$H-NMR (400 MHz, Chloroform-d) δ 12.32 (s, 1H), 10.36 (s, 1H), 8.29 (s, 1H), 7.44-7.33 (m, 1H), 6.88-6.76 (m, 2H), 5.37 (dd, J=9.5, 4.1 Hz, 1H), 5.28 (t, J=5.3 Hz, 1H), 4.63 (d, J=5.9 Hz, 2H), 4.23 (d, J=23.0 Hz, 2H), 3.99 (dd, J=12.7, 9.5 Hz, 1H), 3.72 (q, J=7.0 Hz, 1H), 2.51 (dq, J=13.7, 6.8, 6.1 Hz, 1H), 2.15 (ddd, J=14.7, 8.3, 2.3 Hz, 1H), 1.94 (d, J=12.7 Hz, 1H), 1.77 (ddd, J=12.7, 4.0, 2.9 Hz, 1H), 1.61 (dt, J=14.6, 5.2 Hz, 2H), 1.24 (t, J=7.0 Hz, 1H), 1.09 (d, J=7.2 Hz, 3H). LCMS-ESI$^+$ (m/z): [M+H]$^+$ calculated for $C_{22}H_{22}F_2N_3O_5$: 446.15; found: 446.2.

Example 41

Preparation of Compound 41

(1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

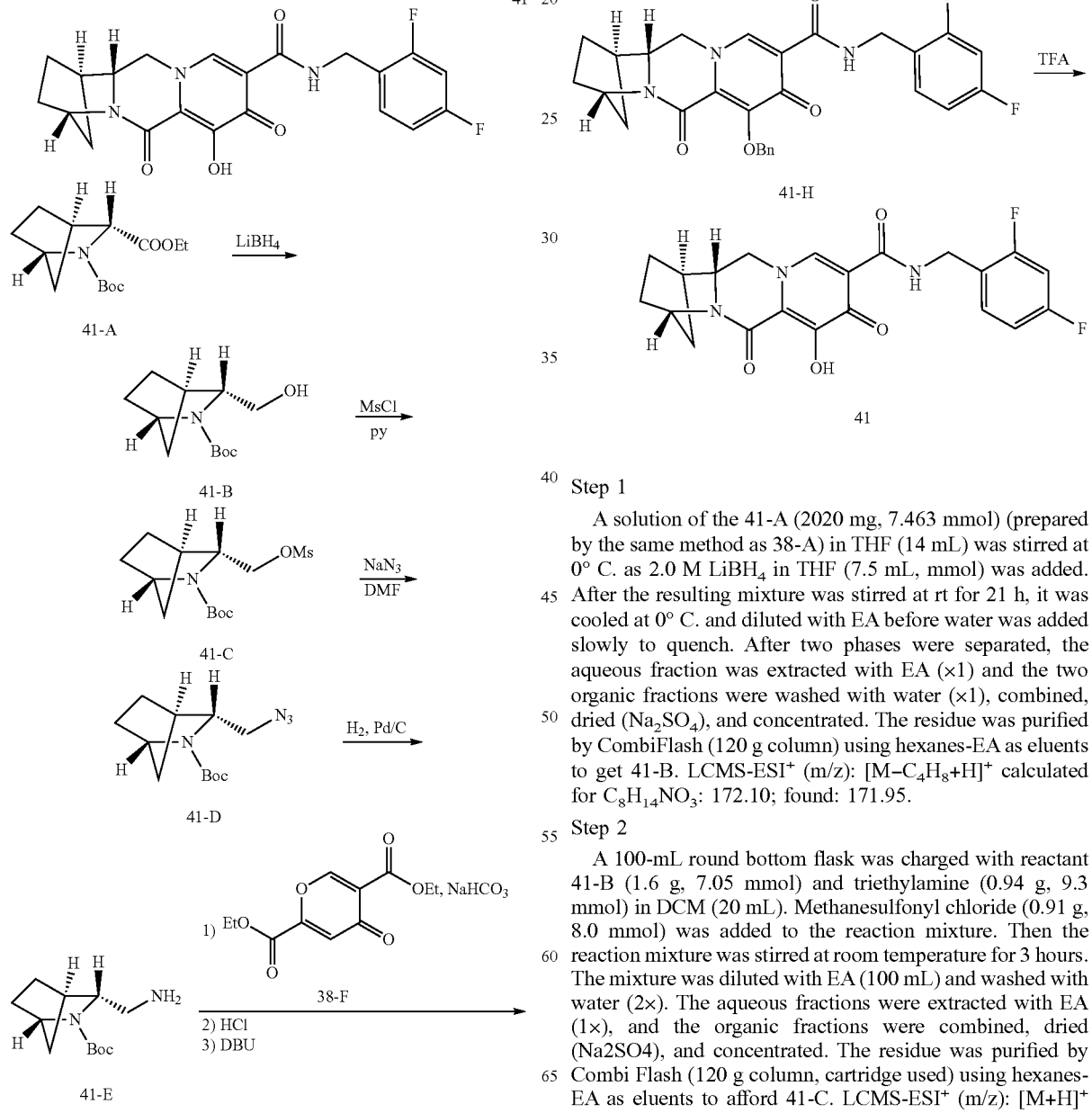

Step 1

A solution of the 41-A (2020 mg, 7.463 mmol) (prepared by the same method as 38-A) in THF (14 mL) was stirred at 0° C. as 2.0 M LiBH$_4$ in THF (7.5 mL, mmol) was added. After the resulting mixture was stirred at rt for 21 h, it was cooled at 0° C. and diluted with EA before water was added slowly to quench. After two phases were separated, the aqueous fraction was extracted with EA (×1) and the two organic fractions were washed with water (×1), combined, dried (Na$_2$SO$_4$), and concentrated. The residue was purified by CombiFlash (120 g column) using hexanes-EA as eluents to get 41-B. LCMS-ESI$^+$ (m/z): [M–C$_4$H$_8$+H]$^+$ calculated for $C_8H_{14}NO_3$: 172.10; found: 171.95.

Step 2

A 100-mL round bottom flask was charged with reactant 41-B (1.6 g, 7.05 mmol) and triethylamine (0.94 g, 9.3 mmol) in DCM (20 mL). Methanesulfonyl chloride (0.91 g, 8.0 mmol) was added to the reaction mixture. Then the reaction mixture was stirred at room temperature for 3 hours. The mixture was diluted with EA (100 mL) and washed with water (2×). The aqueous fractions were extracted with EA (1×), and the organic fractions were combined, dried (Na2SO4), and concentrated. The residue was purified by Combi Flash (120 g column, cartridge used) using hexanes-EA as eluents to afford 41-C. LCMS-ESI$^+$ (m/z): [M+H]$^+$ calculated for $C_{18}H_{19}F_2N_2O_7$: 306; found: 306.

Step 3

A 100-mL round bottom flask was charged with reactant 41-C (2.1 g, 6.9 mmol) and sodium azide (2.3 g, 34.5 mmol) in DMF (10 mL). Then the reaction mixture was stirred at 100° C. for overnight. The mixture was diluted with EA (100 mL) and washed with water (2×). The aqueous fractions were extracted with EA (1×), and the organic fractions were combined, dried (Na$_2$SO$_4$), and concentrated. The residue was purified by Combi Flash (120 g column, cartridge used) using hexanes-EA as eluents to afford 41-D. LCMS-ESI$^+$ (m/z): [M+H]$^+$ calculated for C$_{18}$H$_{19}$F$_2$N$_2$O$_7$: 253; found: 253.

Step 4

To a solution (purged with N$_2$) of reactant 41-D (1.3 g) in EA (20 mL) and EtOH (20 mL) was added Pd/C (130 mg). The mixture was stirred under H$_2$ for 3 hours. The mixture was filtered through celite and the filtrate was concentrated to afford compound 41-E. LCMS-ESI$^+$ (m/z): [M+H]$^+$ calculated for C$_{18}$H$_{19}$F$_2$N$_2$O$_7$: 227; found: 227.

Step 5

A 100-mL round bottom flask was charged with reactant 41-E (1.05 g, 4.62 mmol) and reactant 38-F (1.6 g, 4.62 mmol) in Ethanol (20 mL). Sodium bicarbonate (0.77 g, 9.2 mmol) in water (20 mL) was added to the reaction mixture. Then the reaction mixture was stirred at room temperature overnight. The mixture was diluted with EA (100 mL) and washed with water (2×). The aqueous fractions were extracted with EA (1×), and the organic fractions were combined, dried (Na2SO4), and concentrated. The crude product (2.4 g) was used for next step without further purification. LCMS-ESI$^+$ (m/z): [M+H]$^+$ calculated for C$_{18}$H$_{19}$F$_2$N$_2$O$_7$: 556; found: 556.

A 100-mL round bottom flask was charged with the crude product from the previous reaction in 4 N HCl/dioxane (24.7 mL). Then the reaction mixture was stirred at room temperature for 1 hour. After concentration, the intermediate (2.1 g) and DBU (3.27 g, 21.5 mmol) in toluene (30 mL) was heated to 110° C. with stirring for 1 hour. After concentration, the residue was purified by CombiFlash (120 g column) using hexanes-ethyl acetate as eluents to afford 41-F. LCMS-ESI$^+$ (m/z): [M+H]$^+$ calculated for C$_{18}$H$_{19}$F$_2$N$_2$O$_7$: 409; found: 409.

Step 6

A 100-mL round bottom flask was charged with reactant 41-F (0.5 g, 1.22 mmol) in THF (5 mL) and MeOH (5 mL). 1 N KOH (3.7 mL) was added to the reaction mixture. Then the reaction mixture was stirred at room temperature for 1 hour. The reaction mixture was acidified by adding 1 N HCl (3.7 mL), concentrated to remove most of organic solvents, and extracted with EtOAc (2×). The organic layers were combined, dried (Na$_2$SO$_4$), and concentrated to afford compound 41-G.

Step 7

A 100-mL round bottom flask was charged with reactant 41-G (0.14 g, 0.37 mmol), (2,4,6-trifluorophenyl)methanamine (0.12 g, 0.73 mmol), N,N-diisopropylethylamine (DIPEA) (0.24 g, 1.84 mmol) and HATU (0.28 g, 0.74 mmol) were dissolved in DCM (5 mL). The reaction mixture was stirred at room temperature for 2 hours. The mixture was diluted with EA (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford compound 41-H. LCMS-ESI$^+$ (m/z): [M+H]$^+$ calculated for C$_{18}$H$_{19}$F$_2$N$_2$O$_7$: 524.5; found: 524.5.

Step 8

A 50-mL round bottom flask was charged with reactant 41-H (0.13 g, 0.25 mmol) in TFA (2 mL). The reaction mixture was stirred at room temperature for 30 minutes. After concentration, the crude was purified by column chromatography on silica gel with EtOAc-MeOH to afford compound 41. $^1$H-NMR (400 MHz, Chloroform-d) δ 11.61 (s, 1H), 10.70-10.01 (m, 1H), 8.26 (s, 1H), 6.65 (t, J=8.1 Hz, 2H), 4.88 (s, 1H), 4.65 (dd, J=6.1, 2.4 Hz, 2H), 4.07 (d, J=10.9 Hz, 1H), 3.93-3.58 (m, 2H), 2.67 (d, J=3.1 Hz, 1H), 2.08-1.41 (m, 7H). $^{19}$F-NMR (376 MHz, Chloroform-d) δ −109.22 (d, J=11.6 Hz, 1F), −111.04~−112.79 (m, 2F). LCMS-ESI$^+$ (m/z): [M+H]$^+$ calculated for C$_{21}$H$_{20}$F$_2$N$_3$O$_5$: 434; found: 434.

Example 42

Preparation of Compound 42

(2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide

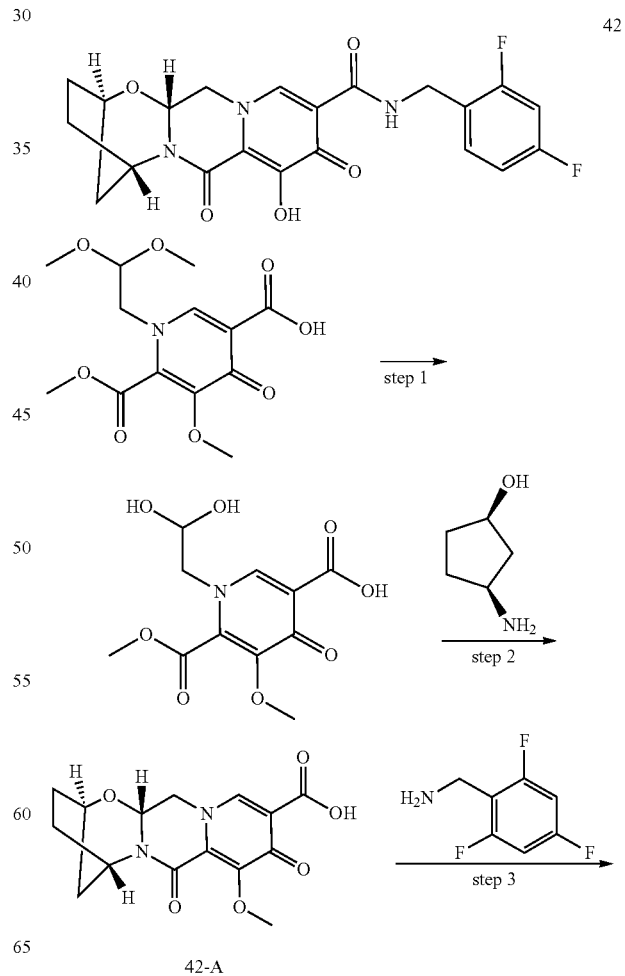

42-A

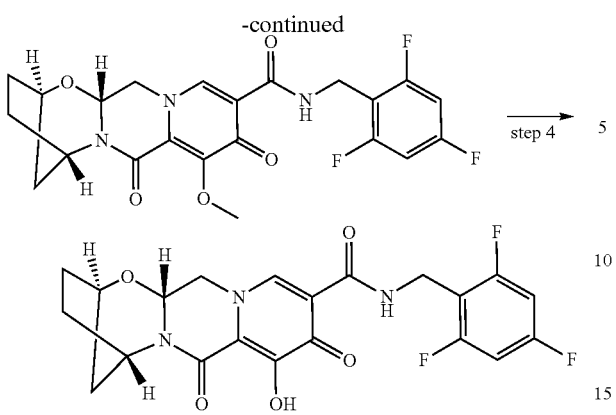

Step 1

1-(2,2-dimethoxyethyl)-5-methoxy-6-(methoxycarbonyl)-4-oxo-1,4-dihydropyridine-3-carboxylic acid (3.5 g, 10 mmol) in acetonitrile (36 mL) and acetic acid (4 mL) was treated with methanesulfonic acid (0.195 mL, 3 mmol) and placed in a 75 deg C. bath. The reaction mixture was stirred for 7 h, cooled and stored at −10° C. for 3 days and reheated to 75° C. for an additional 2 h. This material was cooled and carried on crude to the next step.

Step 2

Crude reaction mixture from step 1 (20 mL, 4.9 mmol) was transferred to a flask containing (1R,3S)-3-aminocyclopentanol (0.809 g, 8 mmol). The mixture was diluted with acetonitrile (16.8 mL), treated with potassium carbonate (0.553 g, 4 mmol) and heated to 85° C. After 2 h, the reaction mixture was cooled to ambient temperature and stirred overnight. 0.2M HCl (50 mL) was added, and the clear yellow solution was extracted with dichloromethane (2×150 mL). The combined organic layers were dried over sodium sulfate, filtered and concentrated to 1.49 g of a light orange solid. Recrystallization from dichlormethane:hexanes afforded the desired intermediate 42A: LCMS-ESI+ (m/z): [M+H]+ calculated for $C_{15}H_{17}N_2O_6$: 321.11; found: 321.3.

Step 3

Intermediate 42-A (0.225 g, 0.702 mmol) and (2,4,6-trifluorophenyl)methanamine (0.125 g, 0.773 mmol) were suspended in acetonitrile (4 mL) and treated with N,N-diisopropylethylamine (DIPEA) (0.183 mmol, 1.05 mmol). To this suspension was added (dimethylamino)-N,N-dimethyl(3H-[1,2,3]triazolo[4,5-b]pyridin-3-yloxy)methaniminium hexafluorophosphate (HATU, 0.294 g, 0.774 mmol). After 1.5 hours, the crude reaction mixture was taken on to the next step. LCMS-ESI+ (m/z): [M+H]+ calculated for $C_{22}H_{21}F_3N_3O_5$: 464.14; found: 464.2.

Step 4

To the crude reaction mixture of the previous step was added MgBr$_2$ (0.258 g, 1.40 mmol). The reaction mixture was stirred at 50° C. for 10 minutes, acidified with 10% aqueous HCl, and extract twice with dichloromethane. The combined organic phases were dried over MgSO$_4$, filtered, concentrated, and purified by silica gel chromatography (EtOH/dichlormethane) followed by HPLC (ACN/H$_2$O with 0.1% TFA modifier) to afford compound 42: $^1$H-NMR (400 MHz, DMSO-d$_6$) δ 12.43 (s, 1H), 10.34 (t, J=5.7 Hz, 1H), 8.42 (s, 1H), 7.19 (t, J=8.7 Hz, 2H), 5.43 (dd, J=9.5, 4.1 Hz, 1H), 5.08 (s, 1H), 4.66 (dd, J=12.9, 4.0 Hz, 1H), 4.59 (s, 1H), 4.56-4.45 (m, 2H), 4.01 (dd, J=12.7, 9.7 Hz, 1H), 1.93 (s, 4H), 1.83 (d, J=12.0 Hz, 1H), 1.56 (dt, J=12.0, 3.4 Hz, 1H). LCMS-ESI+ (m/z): [M+H]+ calculated for $C_{21}H_{19}F_3N_3O_5$: 450.13; found: 450.2.

Example 43

Preparation of Compound 43

(12aR)—N—((R)-1-(2,4-difluorophenyl)ethyl)-7-hydroxy-6,8-dioxo-1,2,3,4,6,8,12,12a-octahydro-1,4-methanodipyrido[1,2-a:1',2'-d]pyrazine-9-carboxamide

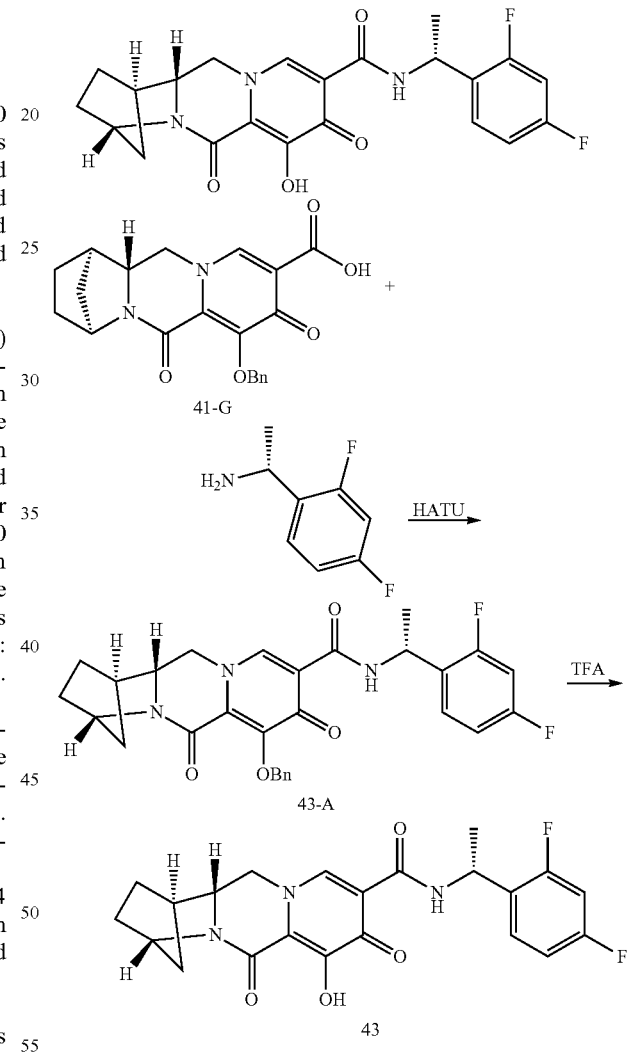

Step 1

A 100-mL round bottom flask was charged with reactant 41-G (0.14 g, 0.37 mmol), (R)-1-(2,4-difluorophenyl)ethanamine (0.12 g, 0.74 mmol), N,N-diisopropylethylamine (0.24 g, 1.84 mmol) and HATU (0.28 g, 0.74 mmol) and were dissolved in DCM (5 mL). The reaction mixture was stirred at room temperature for 2 hours. The mixture was diluted with EA (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford compound 43-A. LCMS-ESI⁺ (m/z): [M+H]⁺ calculated for $C_{18}H_{19}F_2N_2O_7$: 520; found: 520.

Steps 2

A 50-mL round bottom flask was charged with reactant 43-A (0.14 g, 0.27 mmol) in TFA (2 mL). The reaction mixture was stirred at room temperature for 30 minutes. After concentration, the crude was purified by column chromatography on silica gel with EtOAc-MeOH to afford compound 43. ¹H-NMR (400 MHz, Chloroform-d) δ 11.65 (s, 1H), 10.57 (s, 1H), 8.22 (s, 1H), 7.31 (m, 1H), 6.99-6.62 (m, 2H), 5.64-5.32 (m, 1H), 4.90 (d, J=2.7 Hz, 1H), 4.04 (d, J=11.5 Hz, 1H), 3.93-3.63 (m, 2H), 2.67 (s, 1H), 2.08-1.40 (m, 9H). ¹⁹F-NMR (376 MHz, Chloroform-d) δ –113.09 (m, 1F), –115.01 (m, 1F). LCMS-ESI⁺ (m/z): [M+H]⁺ calculated for $C_{21}H_{20}F_2N_3O_5$: 430; found: 430.

Example 44

Preparation of Compound 44

(13aS)-8-hydroxy-7,9-dioxo-N-(2,3,4-trifluorobenzyl)-2,3,4,5,7,9,13,13a-octahydro-2,5-methanopyrido[1',2':4,5]pyrazino[2,1-b][1,3]oxazepine-10-carboxamide

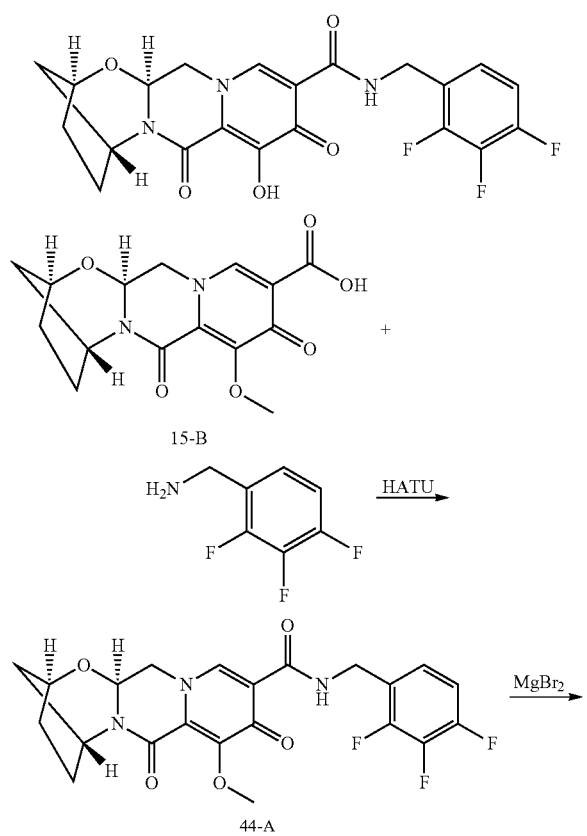

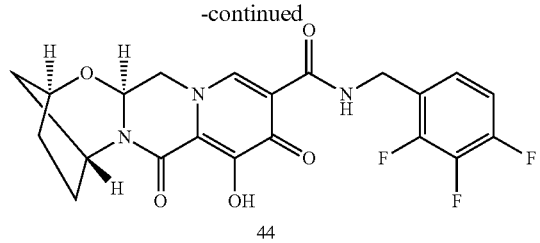

Step 1

Compound 15-B (40 mg, 0.12 mmol) was taken up in 1 mL acetonitrile and treated with 2,3,4-trifluorobenzylamine (29 mg, 0.18 mmol), HATU (53 mg, 0.14 mmol), N,N-diisopropylethylamine (DIPEA) (20 mg, 0.16 mmol), and stirred at room temperature for 2 hours, after which LCMS analysis revealed complete consumption of compound 15-B and formation of intermediate 44-A. The reaction mixture was carried onto the next step.

Step 2

To the crude reaction solution of the previous step was added MgBr₂ (63 mg, 0.34 mmol). The reaction mixture was stirred at 50° C. for one hour, acidified with 10% aqueous HCl, partitioned between the aqueous and dichloromethane, and the aqueous phase extracted to dichloromethane. The combined organic phases were dried over MgSO₄, filtered, concentrated, and purified by HPLC (ACN/H₂O with 0.1% TFA modifier) to compound 44. ¹H-NMR (400 MHz, DMSO-d₆) δ 12.45 (s, 1H), 10.38 (t, J=6.0 Hz, 1H), 8.43 (s, 1H), 7.27 (q, J=9.2 Hz, 1H), 7.16 (q, J=8.5 Hz, 1H), 5.42 (dd, J=9.5, 4.0 Hz, 1H), 5.08 (s, 1H), 4.76-4.47 (m, 4H), 4.01 (dd, J=12.8, 9.7 Hz, 1H), 1.92 (s, 4H), 1.82 (d, J=12.1 Hz, 1H), 1.55 (dt, J=12.2, 2.9 Hz, 1H). LCMS-ESI⁺ (m/z): [M+H]⁺ calculated for $C_{21}H_{19}F_3N_3O_5$: 450.13; found: 450.2.

Example 45

Preparation of Compound 45

(13aS)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide

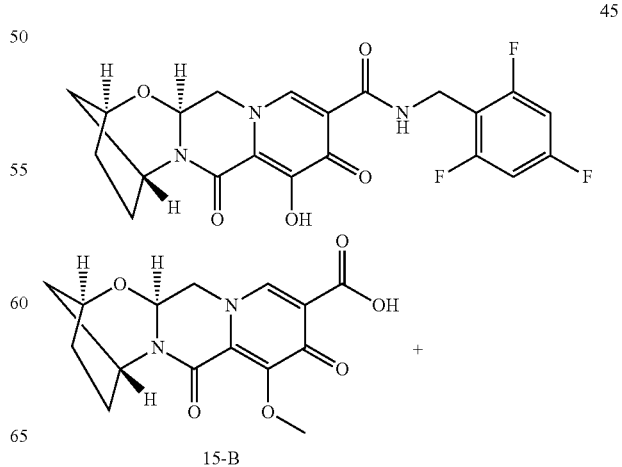

89

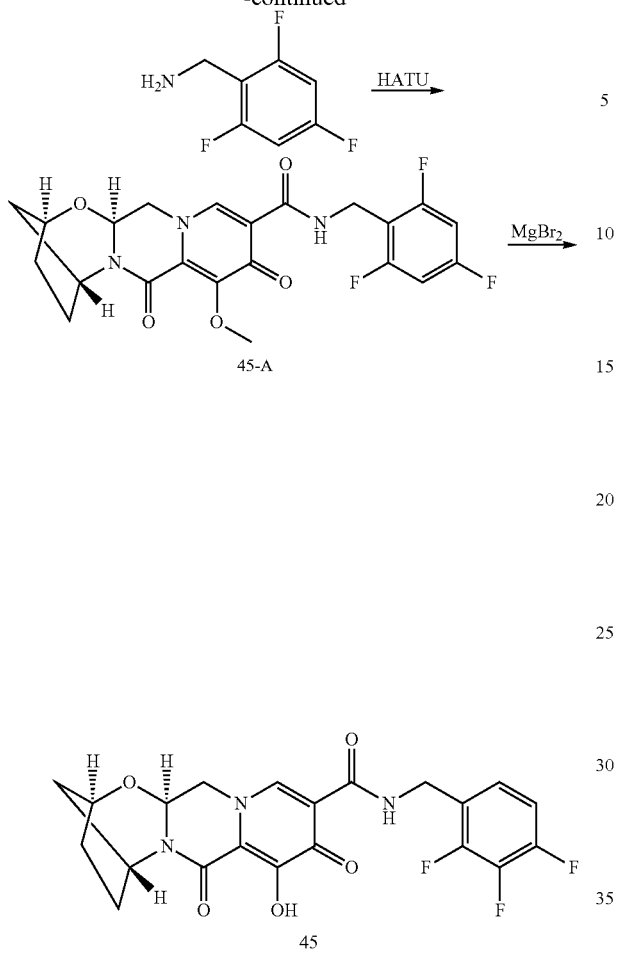

Step 1

Compound 15-B (38 mg, 0.12 mmol) was taken up in 1 mL acetonitrile and treated with 2,4,6-trifluorobenzylamine (34 mg, 0.21 mmol), HATU (50 mg, 0.13 mmol), N,N-diisopropylethylamine (DIPEA) (23 mg, 0.18 mmol), and stirred at room temperature for 2 hours, after which LCMS analysis revealed complete consumption of compound 15-B and formation of intermediate 45-A. The reaction mixture was carried onto the next step.

Step 2

To the crude reaction solution of the previous step was added MgBr$_2$ (55 mg, 0.30 mmol). The reaction mixture was stirred at 50° C. for one hour, acidified with 10% aqueous HCl, partitioned between the aqueous and dichloromethane, and the aqueous phase extracted with dichloromethane. The combined organic phases were dried over MgSO$_4$, filtered, concentrated, and purified by HPLC (ACN/H$_2$O with 0.1% TFA modifier) to afford compound 45. $^1$H-NMR (400 MHz, DMSO-d$_6$) δ 12.37 (s, 1H), 10.37-10.25 (m, 1H), 8.37 (s, 1H), 7.14 (t, J=8.7 Hz, 2H), 5.37 (dd, J=9.5, 4.0 Hz, 1H), 5.02 (s, 1H), 4.66-4.40 (m, 4H), 3.95 (dd, J=12.8, 9.6 Hz, 1H), 1.87 (s, 4H), 1.77 (d, J=11.9 Hz, 1H), 1.50 (dt, J=11.8, 3.2 Hz, 1H). LCMS-ESI$^+$ (m/z): [M+H]$^+$ calculated for C$_{21}$H$_{19}$F$_3$N$_3$O$_5$: 450.13; found: 450.2.

90

Example 46

Preparation of Compound 46

(13aS)—N-(2,6-difluorobenzyl)-8-hydroxy-7,9-di-oxo-2,3,4,5,7,9,13,13a-octahydro-2,5-methanopyrido[1',2':4,5]pyrazino[2,1-b][1,3]oxazepine-10-carbox-amide

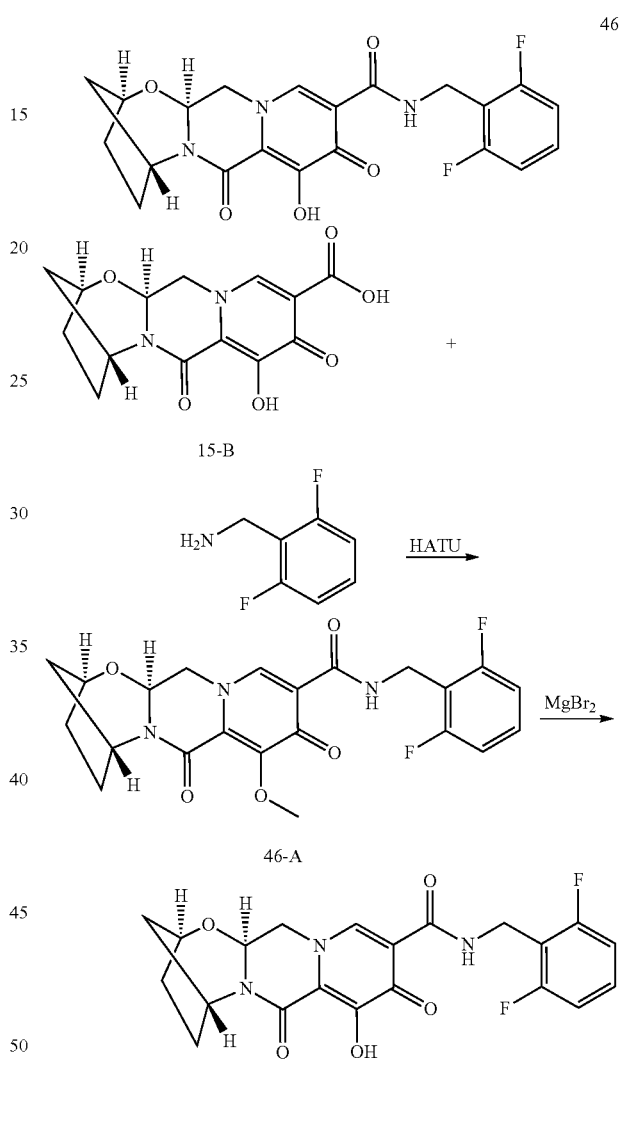

Step 1

Compound 15-B (38 mg, 0.12 mmol) was taken up in 1 mL acetonitrile and treated with 2,6-difluorobenzylamine (19 mg, 0.14 mmol), HATU (56 mg, 0.15 mmol), N,N-diisopropylethylamine (DIPEA) (20 mg, 0.15 mmol), and stirred at room temperature for 90 minutes, after which LCMS analysis revealed complete consumption of compound A and formation of intermediate 46-A. The reaction mixture was carried onto the next step.

Step 2

To the crude reaction solution of the previous step was added MgBr$_2$ (50 mg, 0.27 mmol). The reaction mixture was stirred at 50° C. for one hour, acidified with 10% aqueous HCl, partitioned between the aqueous and dichloromethane, and the aqueous phase extracted with dichloromethane. The combined organic phases were dried over MgSO$_4$, filtered, concentrated, and purified by HPLC (ACN/H$_2$O with 0.1% TFA modifier) to afford compound 46. $^1$H-NMR (400 MHz, DMSO-d$_6$) δ 12.37 (s, 1H), 10.33-10.26 (m, 1H), 8.37 (s, 1H), 7.39-7.29 (m, 1H), 7.05 (t, J=7.9 Hz, 2H), 5.37 (dd, J=9.5, 4.1 Hz, 1H), 5.02 (s, 1H), 4.66-4.45 (m, 4H), 3.95 (dd, J=12.7, 9.6 Hz, 1H), 1.87 (s, 4H), 1.77 (d, J=12.0 Hz, 1H), 1.50 (dt, J=12.2, 3.5 Hz, 1H). LCMS-ESI$^+$ (m/z): [M+H]$^+$ calculated for C$_{21}$H$_{20}$F$_2$N$_3$O$_5$: 432.14; found: 432.2.

Example 47

Preparation of Compound 47

(1R,4S,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

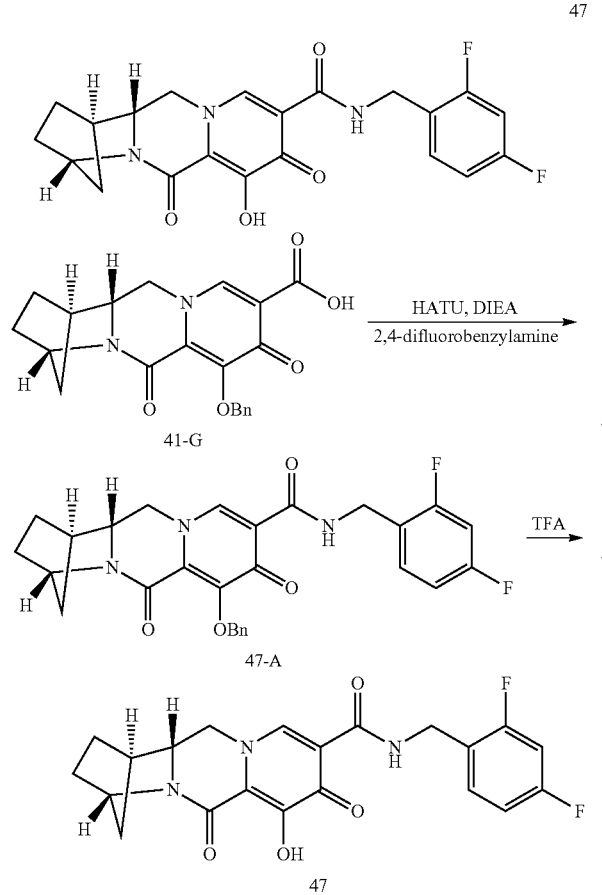

Step 1

The crude acid 41-G (0.45 g, 1.18 mmol), 2,4-difluobenzylamine (0.35 g, 2.44 mmol), N,N-diisopropylethylamine (DIPEA) (0.79 g, 6.11 mmol) and HATU (0.93 g, 2.44 mmol) were dissolved in DCM (10 mL). The reaction mixture was stirred at room temperature for 2 hours. The mixture was diluted with EA (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford compound 47-A. LCMS-ESI$^+$ (m/z): [M+H]$^+$ calculated for C$_{18}$H$_{19}$F$_2$N$_2$O$_7$: 506; found: 506.

Step 2

A 50-mL round bottom flask was charged with reactant 47-A (0.5 g, 0.99 mmol) in TFA (6 mL). The reaction mixture was stirred at room temperature for 30 minutes. After concentration, the crude was purified by column chromatography on silica gel with EtOAc-MeOH to afford compound 47. $^1$H NMR (400 MHz, Chloroform-d) δ 11.70 (s, 1H), 10.44 (s, 1H), 8.29 (s, 1H), 7.60-7.29 (m, 1H), 6.95-6.58 (m, 2H), 4.10 (s, 1H), 4.02-3.54 (m, 3H), 2.68 (d, J=3.1 Hz, 1H), 2.00-1.40 (m, 8H). $^{19}$F NMR (376 MHz, Chloroform-d) δ -112.31 (d, J=8.0 Hz, 1F), -114.77 (d, J=8.4 Hz, 1F). LCMS-ESI$^+$ (m/z): [M+H]$^+$ calculated for C$_{21}$H$_{20}$F$_2$N$_3$O$_5$: 416; found: 416.

Example 48

Preparation of Compound 48

(1S,4R,12aS)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

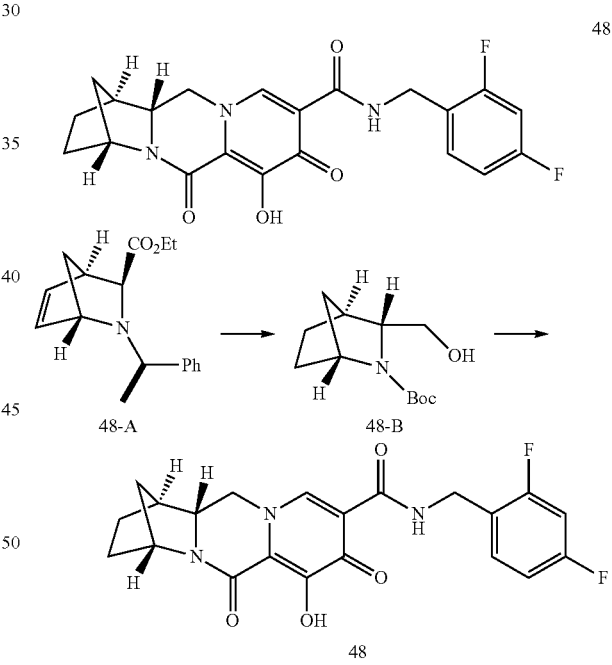

48-B was prepared analogously to 55-H in Example 55, substituting 48-A for 55-A. Compound 48 was prepared as described for compound 38 in Example 38, substituting 48-B for 38-B to afford compound 48. $^1$H-NMR (400 MHz, Chloroform-d) δ 11.79 (s, 1H), 10.44 (m, 1H), 8.33 (s, 1H), 7.42-7.31 (m, 1H), 6.86-6.74 (m, 2H), 4.74 (s, 1H), 4.63 (d, J=5.8 Hz, 2H), 4.19 (m, 1H), 4.07-4.03 (m, 2H), 2.83 (s, 1H), 1.92-1.68 (m, 6H). $^{19}$F NMR (376 MHz, Chloroform-d) δ -112.3 (m, 1F), -114.8 (m, 1F). LCMS-ESI$^+$ (m/z): [M+H]$^+$ calculated for C$_{21}$H$_{20}$F$_2$N$_3$O$_4$: 416.14; found: 416.07.

Example 49

Preparation of Compound 49

(2S,5R,13aS)-8-hydroxy-7,9-dioxo-N-((3-(trifluoromethyl)pyridin-2-yl)methyl)-2,3,4,5,7,9,13,13a-octahydro-2,5-methanopyrido[1',2':4,5]pyrazino[2,1-b][1,3]oxazepine-10-carboxamide

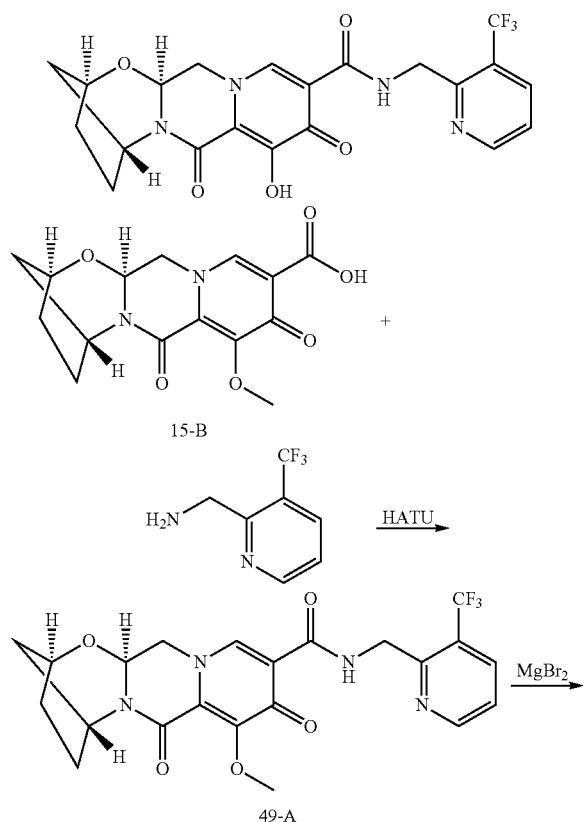

Step 1

Compound 15-B (44 mg, 0.14 mmol) was taken up in 1 mL acetonitrile and treated with (3-(trifluoromethyl)pyridin-2-yl)methanamine (38 mg, 0.18 mmol, HCl salt), HATU (69 mg, 0.18 mmol), N,N-diisopropylethylamine (DIPEA) (0.07 mL, 0.40 mmol), and stirred at room temperature for 1 hour, after which LCMS analysis revealed complete consumption of compound 15-B and formation of intermediate 49-A. The reaction mixture was carried onto the next step.

Step 2

To the crude reaction solution of the previous step was added MgBr$_2$ (51 mg, 0.28 mmol). The reaction mixture was stirred at 50° C. for 90 minutes, acidified with 10% aqueous HCl, partitioned between the aqueous and dichloromethane, and the aqueous phase extracted with dichloromethane. The combined organic phases were dried over MgSO$_4$, filtered, concentrated, and triturated by methanol followed by diethyl ether to afford compound 49. $^1$H-NMR (400 MHz, DMSO-d$_6$) δ 12.42 (s, 1H), 10.80-10.70 (m, 1H), 8.83 (d, J=5.0 Hz, 1H), 8.44 (s, 1H), 8.19 (d, J=8.6 Hz, 1H), 7.56 (dd, J=7.7, 5.2 Hz, 1H), 5.43 (dd, J=9.5, 4.0 Hz, 1H), 5.08 (s, 1H), 4.86-4.80 (m, 2H), 4.67 (dd, J=12.9, 4.0 Hz, 1H), 4.59 (s, 1H), 4.02 (dd, J=12.6, 9.8 Hz, 1H), 1.93 (s, 4H), 1.82 (d, J=12.1 Hz, 1H), 1.60-1.52 (m, 1H). LCMS-ESI$^+$ (m/z): [M+H]$^+$ calculated for C$_{21}$H$_{20}$F$_3$N$_4$O$_5$: 465.14; found: 465.2.

Examples 50 and 51

Preparation of Compounds 50 and 51

N-(2,4-difluorobenzyl)-9-hydroxy-8,10-dioxo-2,3,5,6,8,10,14,14a-octahydro-2,6-methanopyrido[1',2':4,5]pyrazino[2,1-b][1,6,3]dioxazocine-11-carboxamide 50 and 51

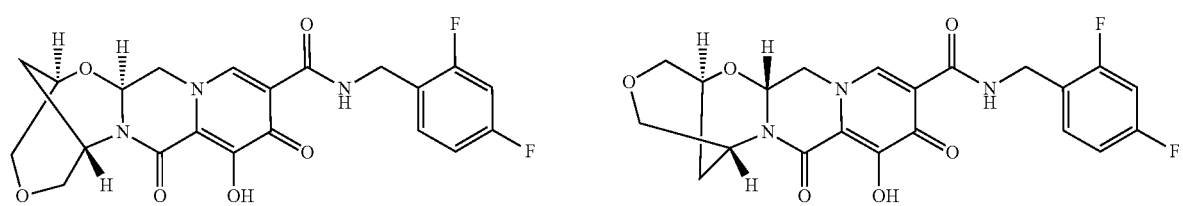

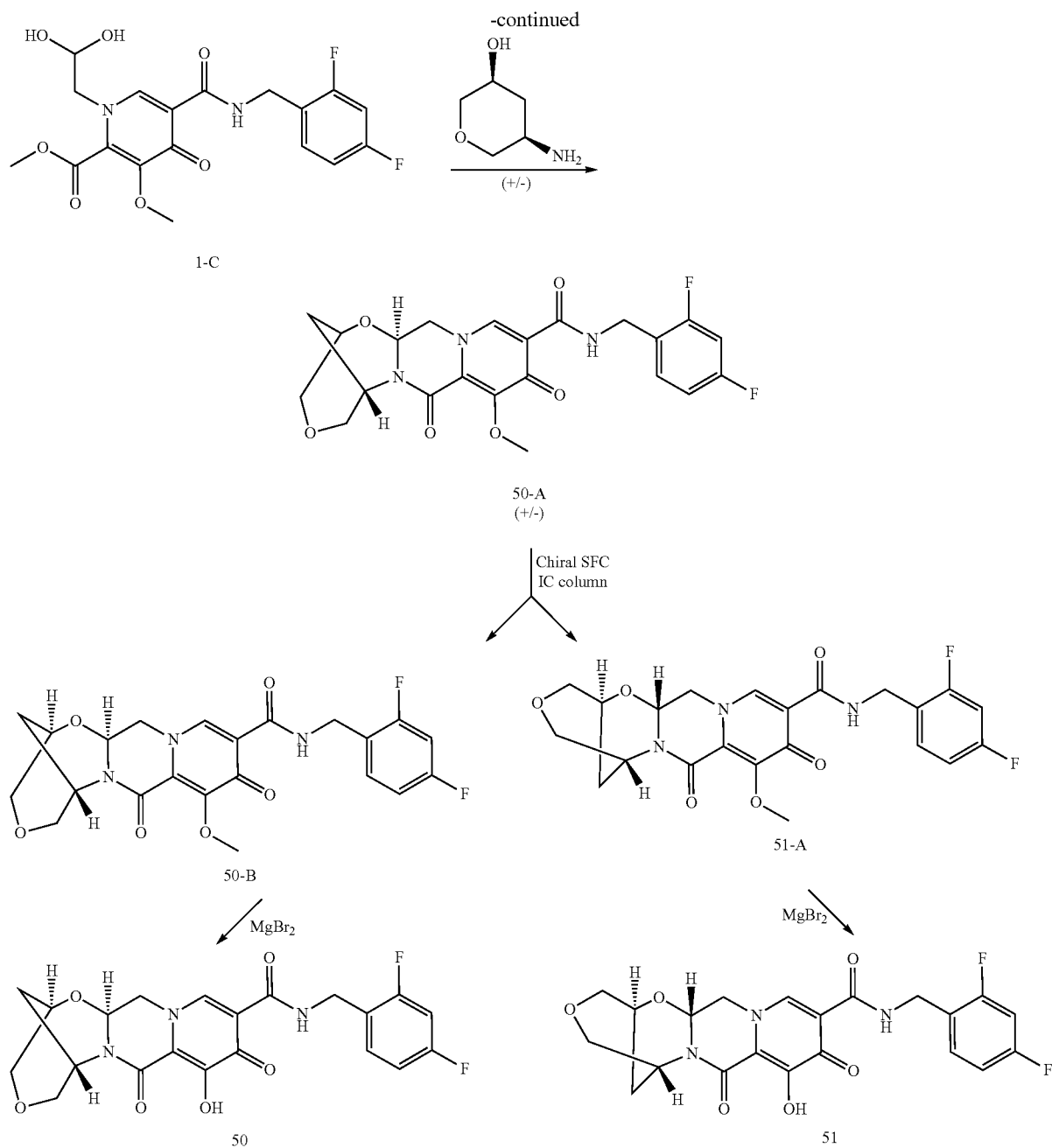

Step 1

Methyl 5-(2,4-difluorobenzylcarbamoyl)-1-(2,2-dihydroxyethyl)-3-methoxy-4-oxo-1,4-dihydropyridine-2-carboxylate (1-C, 392 mg, 0.95 mmol) (Example 87), racemic cis-5-aminotetrahydro-2H-pyran-3-ol (WO 2012/145569 Bennett, B. L. et al, filed Apr. 20, 2012) (112 mg, 0.95 mmol), and potassium carbonate (134 mg, 0.97 mmol) were taken up in 3.8 mL acetonitrile/0.2 mL acetic acid and stirred at 90° C. for 90 minutes, after which the reaction mixture was partitioned between DCM and brine, the aqueous phase extracted with DCM, combined organic phases dried over MgSO$_4$, filtered, concentrated, and purified by SGC (0-10% EtOH/DCM) to afford intermediate 50-A.

Step 2

Intermediate 50-A (40 mg) was separated by chiral SFC on a Chiralpak IC column using 10% DMF in supercritical carbon dioxide as eluent to afford Intermediates 50-B (first eluting peak) and 51-A (second eluting peak) in enantioenriched form. For intermediate 50-B: (absolute stereochemistry unknown), Chiral HPLC retention time=11.48 minutes (Chiralpak IC, 150×4.6 mm, 1 mL/min MeOH). For intermediate 51-A: (absolute stereochemistry unknown), Chiral HPLC retention time=14.35 minutes (Chiralpak IC, 150×4.6 mm, 1 mL/min MeOH).

Step 3a

Magnesium bromide (12 mg, 0.06 mmol) was added to a solution of intermediate 50-B (10.5 mg, 0.02 mmol, absolute stereochemistry unknown) in 1 mL acetonitrile. The reaction mixture was stirred at 50° C. for 1 hour, acidified with 10% aqueous HCl, partitioned between the aqueous and dichloromethane, and the aqueous phase extracted with dichloromethane. The combined organic phases were dried over MgSO₄, filtered, concentrated, and purified by HPLC (ACN/H₂O with 0.1% TFA modifier) to afford compound 50. ¹H-NMR (400 MHz, Chloroform-d) δ 10.47 (t, J=5.8 Hz, 1H), 8.42 (s, 1H), 7.35 (q, J=8.6, 8.2 Hz, 1H), 6.81 (q, J=8.7, 8.0 Hz, 2H), 6.41 (dd, J=10.0, 3.6 Hz, 1H), 4.79 (s, 1H), 4.65 (s, 2H), 4.36-4.26 (m, 2H), 4.20-4.08 (m, 2H), 3.98 (dd, J=12.4, 10.2 Hz, 1H), 3.88 (t, J=11.8 Hz, 2H), 2.27 (dt, J=13.3, 3.1 Hz, 1H), 2.15-2.06 (m, 1H). LCMS-ESI⁺ (m/z): [M+H]⁺ calculated for $C_{21}H_{20}F_2N_3O_6$: 448.40; found: 448.2.

Step 3b

Magnesium bromide (13 mg, 0.07 mmol) was added to a solution of intermediate 51-A (13.2 mg, 0.03 mmol, absolute stereochemistry unknown) in 1 mL acetonitrile. The reaction mixture was stirred at 50° C. for 1 hour, acidified with 10% aqueous HCl, partitioned between the aqueous and dichloromethane, and the aqueous phase extracted with dichloromethane. The combined organic phases were dried over MgSO₄, filtered, concentrated, and purified by HPLC (ACN/H₂O with 0.1% TFA modifier) to afford compound 51. ¹H-NMR (400 MHz, Chloroform-d) δ 10.47 (t, J=5.8 Hz, 1H), 8.42 (s, 1H), 7.35 (q, J=8.6, 8.2 Hz, 1H), 6.81 (q, J=8.7, 8.0 Hz, 2H), 6.41 (dd, J=10.0, 3.6 Hz, 1H), 4.79 (s, 1H), 4.65 (s, 2H), 4.36-4.26 (m, 2H), 4.20-4.08 (m, 2H), 3.98 (dd, J=12.4, 10.2 Hz, 1H), 3.88 (t, J=11.8 Hz, 2H), 2.27 (dt, J=13.3, 3.1 Hz, 1H), 2.15-2.06 (m, 1H). LCMS-ESI⁺ (m/z): [M+H]⁺ calculated for $C_{21}H_{20}F_2N_3O_6$: 448.40; found: 448.2.

Example 52

Preparation of Compound 52

(2S,5R,13aS)—N-(2-cyclopropoxy-4-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

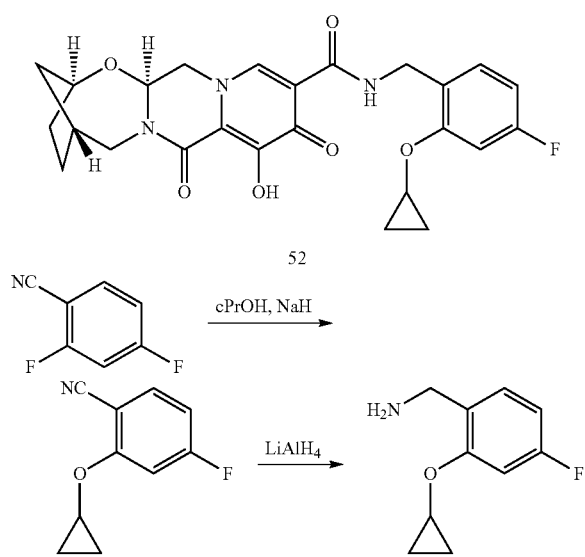

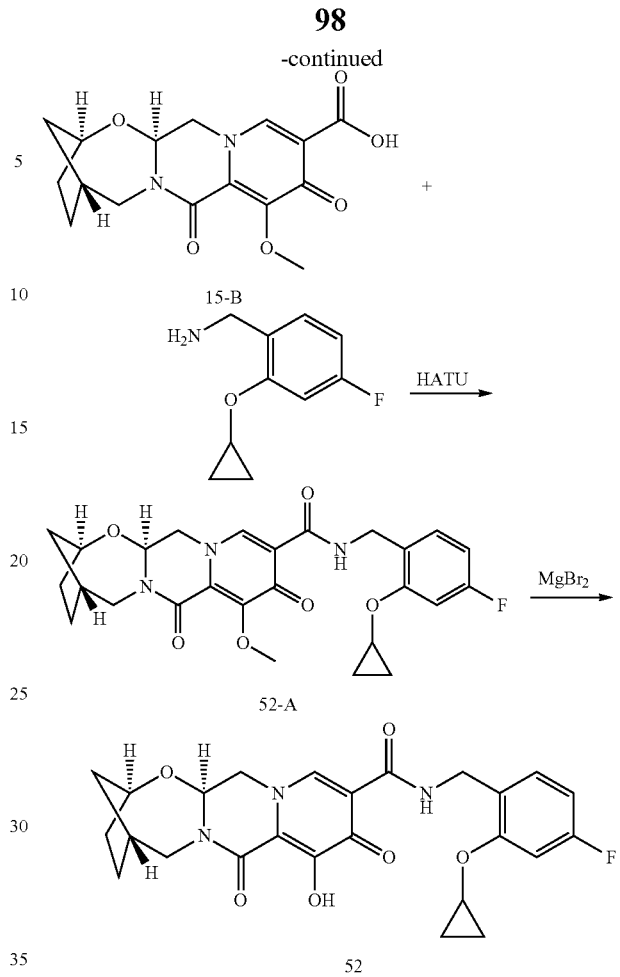

Step 1

A solution cyclopropanol (1.9 g, 29 mmol) in 20 mL dioxane was added dropwise to a 0° C. solution of Sodium hydride (60% dispersion in mineral oil, 1.04 g, 26 mmol) in 80 mL dioxane. The reaction mixture was allowed to warm to room temperature, 2,4-difluorobenzonitrile (3.48 g, 25 mmol) was added portionwise, and reaction temperature raised to 95° C. The reaction solution was cooled to room temperature after stirring for 18 hours, diluted with ethyl acetate, washed twice with water and twice with brine, dried over MgSO₄, filtered, and concentrated onto silica gel. Purification by silica gel chromatography (0-10% EtOAc/hexanes) afforded 2-cyclopropoxy-4-fluorobenzonitrile. ¹H-NMR (400 MHz, Chloroform-d) δ 7.52 (dd, J=8.6, 6.2 Hz, 1H), 7.05 (dd, J=10.5, 2.3 Hz, 1H), 6.73 (td, J=8.2, 2.3 Hz, 1H), 3.87-3.76 (m, 1H), 0.87 (m, 4H).

Step 2

To a 0° C. suspension of lithium aluminum hydride in THF (1M, 15 mL, mmol) was added 2-cyclopropoxy-4-fluorobenzonitrile in 14 mL diethyl ether dropwise. The reaction solution was stirred for 3 hours, gradually warming to room temperature, at which point it was recooled to 0° C., an additional 8 mL lithium aluminum hydride in THF (1M, 8 mmol) added, and stirred for an additional 90 minutes. The reaction was quenched by sequential addition of 0.9 mL water, 0.9 mL 15% NaOH$_{(aq)}$, and 2.7 mL water. The reaction was filtered through celite with diethyl ether rinses, dried over MgSO₄, and concentrated to afford 2-cyclopropoxy-4-fluorobenzylamine of sufficient purity to carry on as crude. ¹H-NMR (400 MHz, Chloroform-d) δ 7.17-7.08

(m, 1H), 6.96 (dd, J=10.9, 2.4 Hz, 1H), 6.61 (td. J=8.3, 2.5 Hz, 1H), 3.78-3.66 (m, 3H), 0.89-0.72 (m, 4H).

Step 3

Compound 15-B (46 mg, 0.14 mmol) was taken up in 1 mL acetonitrile and treated with 2-cyclopropoxy-4-fluorobenzylamine (32 mg, 0.18 mmol), HATU (62 mg, 0.16 mmol), N,N-diisopropylethylamine (DIPEA) (0.04 mL, 0.22 mmol), and stirred at room temperature for 2 hours, after which LCMS analysis revealed complete consumption of compound 15-B and formation of intermediate 52-A. The reaction mixture was carried onto the next step.

Step 4

To the crude reaction solution of the previous step was added MgBr$_2$ (56 mg, 0.30 mmol). The reaction mixture was stirred at 50° C. for 90 minutes, acidified with 10% aqueous HCl, partitioned between the aqueous and dichloromethane, and the aqueous phase extracted with dichloromethane. The combined organic phases were dried over MgSO$_4$, filtered, concentrated, and purified by HPLC (ACN/H$_2$O with 0.1% TFA modifier) to afford compound 52. $^1$H-NMR (400 MHz, DMSO-d$_6$) δ 12.44 (s, 1H), 10.21 (t, J=5.8 Hz, 1H), 8.41 (s, 1H), 7.22-7.15 (m, 1H), 7.12 (dd, J=11.2, 2.5 Hz, 1H), 6.72 (td, J=8.5, 2.5 Hz, 1H), 5.42 (dd, J=9.6, 4.1 Hz, 1H), 5.07 (s, 1H), 4.66 (dd, J=12.8, 4.1 Hz, 1H), 4.58 (s, 1H), 4.34 (dd, J=5.6, 2.4 Hz, 2H), 4.04-3.91 (m, 2H), 1.92 (s, 4H), 1.82 (d, J=11.9 Hz, 1H), 1.55 (dt, J=12.4, 3.5 Hz, 1H), 0.80 (q, J=6.3, 5.7 Hz, 2H), 0.72 (q, J=6.0, 4.9 Hz, 2H). LCMS-ESI$^+$ (m/z): [M+H]$^+$ calculated for C$_{24}$H$_{25}$FN$_3$O$_6$: 470.17; found: 470.1.

Example 53

Preparation of Compound 53

(2R,5S,13aR)—N-(2-cyclopropoxy-4-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

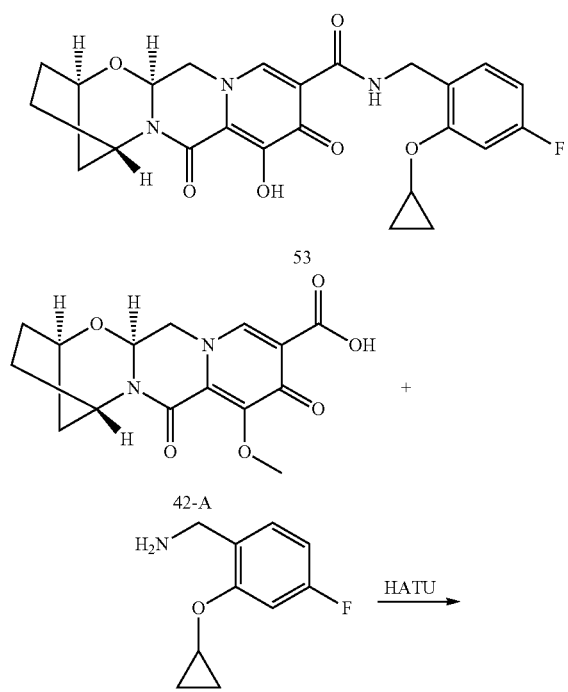

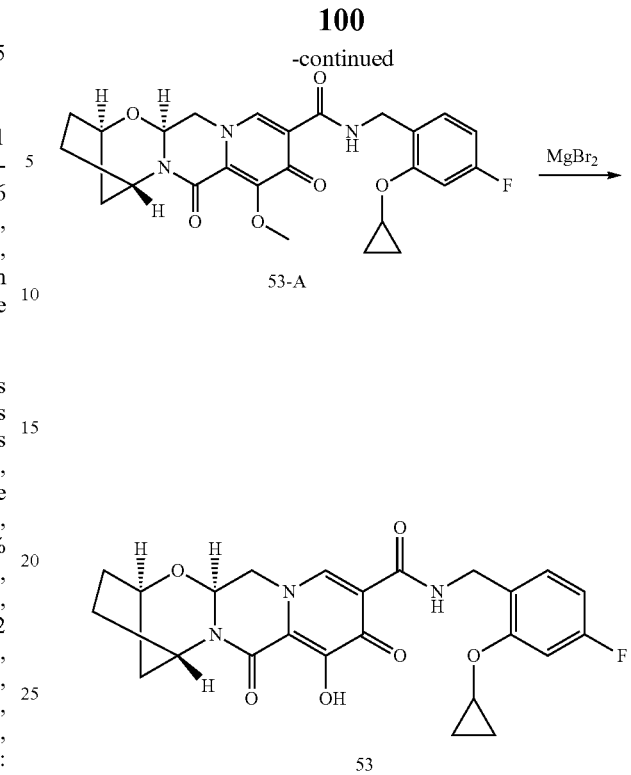

Step 1

Compound 42-A (46 mg, 0.14 mmol) was taken up in 1 mL acetonitrile and treated with 2-cyclopropoxy-4-fluorobenzylamine (33 mg, 0.18 mmol), HATU (61 mg, 0.16 mmol), N,N-diisopropylethylamine (DIPEA) (0.04 mL, 0.24 mmol), and stirred at room temperature for 2 hours, after which LCMS analysis revealed complete consumption of compound 42-A and formation of intermediate 53-A. The reaction mixture was carried onto the next step.

Step 2

To the crude reaction solution of the previous step was added MgBr$_2$ (55 mg, 0.30 mmol). The reaction mixture was stirred at 50° C. for 90 minutes, acidified with 10% aqueous HCl, partitioned between the aqueous and dichloromethane, and the aqueous phase extracted with dichloromethane. The combined organic phases were dried over MgSO$_4$, filtered, concentrated, and purified by HPLC (ACN/H$_2$O with 0.1% TFA modifier) to afford compound 53. $^1$H-NMR (400 MHz, DMSO-d$_6$) δ 12.44 (s, 1H), 10.21 (t, J=5.8 Hz, 1H), 8.41 (s, 1H), 7.22-7.15 (m, 1H), 7.12 (dd, J=11.2, 2.5 Hz, 1H), 6.72 (td, J=8.5, 2.5 Hz, 1H), 5.42 (dd, J=9.6, 4.1 Hz, 1H), 5.07 (s, 1H), 4.66 (dd, J=12.8, 4.1 Hz, 1H), 4.58 (s, 1H), 4.34 (dd, J=5.6, 2.4 Hz, 2H), 4.04-3.91 (m, 2H), 1.92 (s, 4H), 1.82 (d, J=11.9 Hz, 1H), 1.55 (dt, J=12.4, 3.5 Hz, 1H), 0.80 (q, J=6.3, 5.7 Hz, 2H), 0.72 (q, J=6.0, 4.9 Hz, 2H). LCMS-ESI$^+$ (m/z): [M+H]$^+$ calculated for C$_{24}$H$_{25}$FN$_3$O$_6$: 470.17; found: 470.1.

Example 54

Preparation of Compound 54

(2R,5S)—N—((S)-1-(2,4-difluorophenyl)-2,2,2-trifluoroethyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

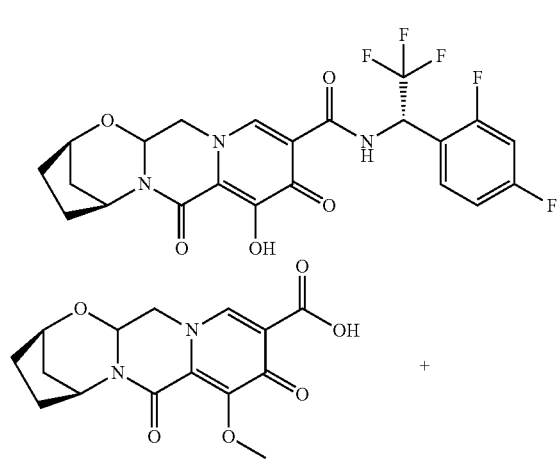

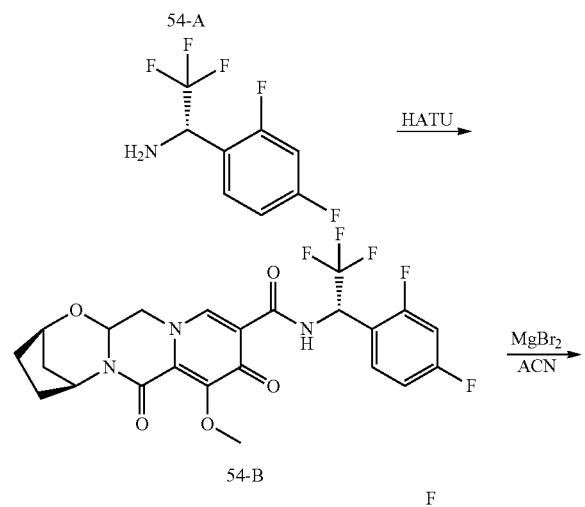

Step 1

A 50-mL round bottom flask was charged with reactant 54-A (0.02 g, 0.06 mmol), (S)-1-(2,4-difluorophenyl)-2,2,2-trifluoroethanamine (0.019 g, 0.09 mmol), N,N-diisopropylethylamine (DIPEA) (0.048 g, 0.38 mmol) and HATU (0.036 g, 0.09 mmol) in DCM (2 ml). The reaction mixture was stirred at room temperature for 1 hour. The reaction mixture was concentrated down, re-dissolved in EtOAc (50 mL), washed with saturated NaHCO₃ (2×), saturated NH₄Cl and dried over Na₂SO₄. After concentration, the crude was purified by column chromatography on silica gel with hexane-EtOAc to obtain 54-B. LCMS-ESI⁺ (m/z): [M+H]⁺ calculated for $C_{18}H_{19}F_2N_2O_7$: 514; found: 514.

Step 2

A 50-mL round bottom flask was charged with reactant 54-B (0.03 g, 0.058 mmol) and magnesium bromide (0.03 g, 0.15 mmol) in acetonitrile (2 mL). The reaction mixture was heated to 50° C. After 10 minutes, the reaction mixture was cooled to 0° C. and 1 N hydrochloric acid (0.5 mL) was added in. Then the reaction mixture was diluted with MeOH (2 mL). After filtration, the crude was purified by Pre-HPLC purification (30-70% acetonitrile:water, 0.1% TFA) afforded compound 54 as TFA salt. ¹H-NMR (400 MHz, Chloroform-d) δ 11.28 (d, J=9.4 Hz, 1H), 8.39 (s, 1H), 7.54 (q, J=7.8 Hz, 1H), 7.12-6.76 (m, 2H), 6.40-5.98 (m, 1H), 5.57-5.18 (m, 2H), 4.68 (s, 1H), 4.29 (dd, J=13.1, 4.0 Hz, 1H), 4.05 (dd, J=12.9, 9.3 Hz, 1H), 2.39-1.94 (m, 4H), 1.86 (t, J=10.5 Hz, 1H), 1.60 (dt, J=12.6, 3.4 Hz, 1H). ¹⁹F-NMR (376 MHz, Chloroform-d) δ −75.30 (t, J=6.8 Hz, 3F), −108.33 (dd, J=8.6, 6.3 Hz, 1F), −111.56−−113.23 (m, 1F). LCMS-ESI⁺ (m/z): [M+H]⁺ calculated for $C_{21}H_{20}F_2N_3O_5$: 500; found: 500.

Example 55

Preparation of Compound 55

(1R,4S,12aS)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

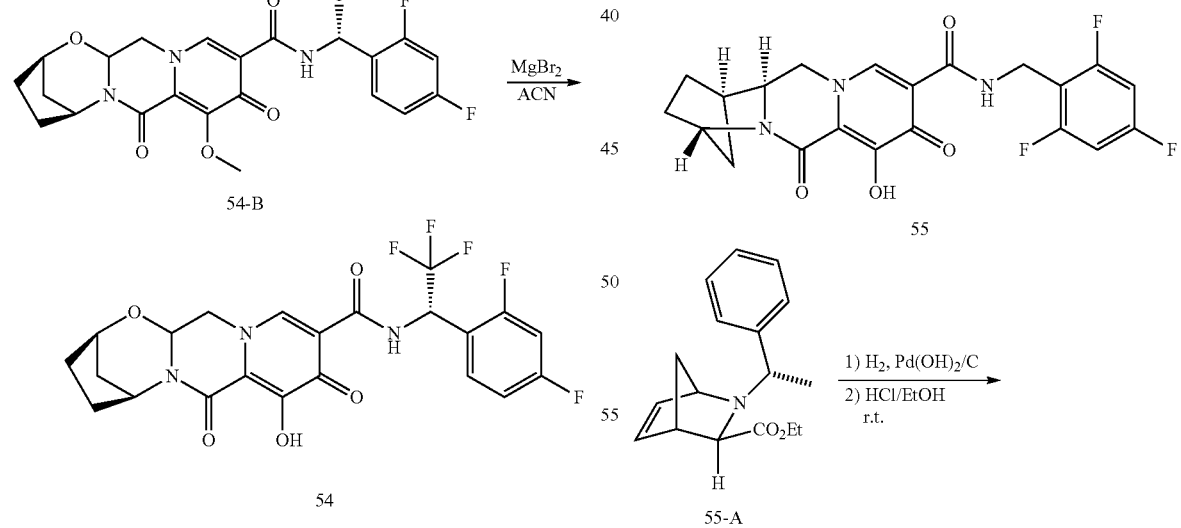

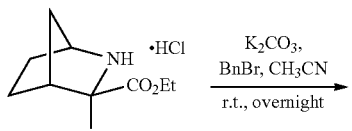

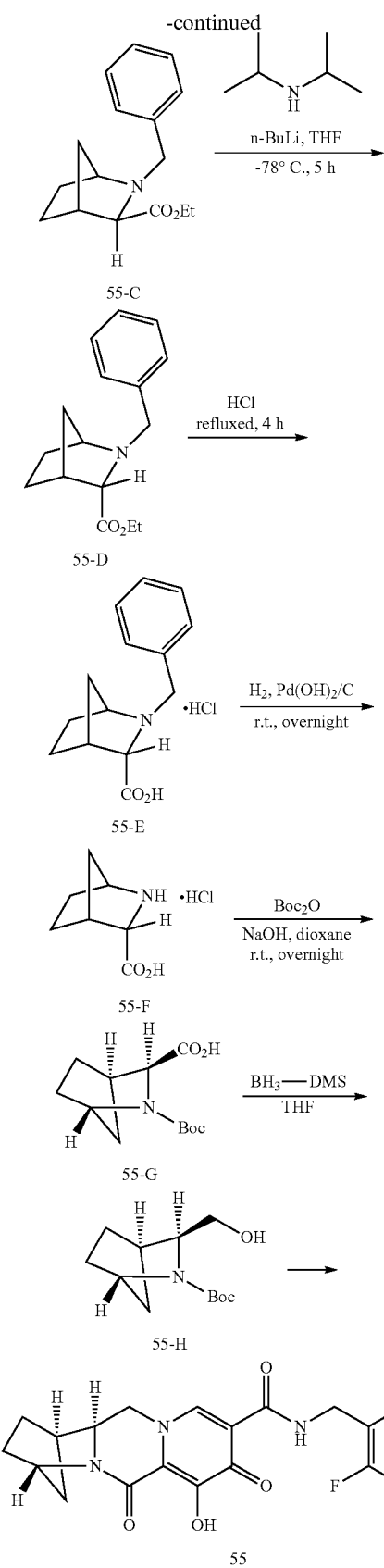

of H₂ was stirred at room temperature overnight. The reaction mixture was filtered and treated with HCl/EtOH (400 ml). The mixture was stirred at room temperature for 2 h. The reaction mixture was concentrated to give compound 55-B, which was used in next step without purification. LCMS-ESI⁺ (m/z): [M+H]⁺ calculated for $C_9H_{16}NO$: 170.1; found: 170.2.

Step 2

To a solution of compound 55-B (92.25 g, 0.45 mol) and $K_2CO_3$ (186.30 g, 1.35 mol) in $CH_3CN$ (1 L) was added benzyl bromide (76.50 g, 0.45 mol) at 0° C. The mixture was stirred at room temperature overnight. The reaction mixture was filtered, concentrated and the residue was purified by chromatography on silica gel to give compound 55-C.

Step 3

To a mixture of diisopropylamine (50 g, 0.50 mol) in THF (400 mL) was added n-BuLi (200 mL, 0.50 mol) at −78° C. at $N_2$ atmosphere. After 0.5 h, the reaction mixture was warmed to 20° C. and stirred for 0.5 h. The mixture was cooled to −78° C. and added a solution of compound 55-C (64.75 g, 0.25 mol) in THF (600 mL) under $N_2$ atmosphere. The mixture was stirred for 4 h and quenched with saturated $NH_4Cl$ solution. The mixture was extracted with EtOAc and the organic layer was washed with brine, dried over $Na_2SO_4$, filtered and concentrated. The residue was purified by chromatography on silica gel to give compound 55-D.

Step 4

A mixture of compound 55-D (129.50 g 0.50 mol) in 4N HCl (1.30 L) was refluxed for 4 h. the mixture was concentrated. The residue was purified by HPLC to give compound 55-E.

Step 5

To a mixture of compound 55-E (47 g, 176 mmol) and $Pd(OH)_2/C$ (9 g) in EtOH (400 mL) under an atmosphere of $H_2$ was stirred at room temperature overnight. The reaction mixture was concentrated to give compound 55-F, which was used in next step without purification. ¹H-NMR (400 MHz, $CDCl_3$) δ 4.22 (s, 1H), 4.06 (s, 1H), 2.98-2.95 (d, J=11.2 Hz, 1H), 1.96-1.93 (d, J=11.2 Hz, 1H), 1.86-1.82 (m, 2H), 1.76-1.74 (d, J=9.2 Hz, 2H), 1.49 (s, 1H). LCMS-ESI⁺ (m/z): [M+H]⁺ calculated for $C_7H_{12}NO_2$: 142.1; found: 142.1.

Step 6

To a mixture of compound 55-F (29.20 g, 165 mmol) and 2N NaOH solution (330 mL, 0.66 mol) in dioxane (120 mL) was added $Boc_2O$ (39.60 g, 181 mmol) at 0° C. The reaction mixture was stirred at room temperature overnight. The mixture was adjusted with 3N HCl to pH=5~6 and extracted with DCM. The organic layer was dried over $Na_2SO_4$, filtered and concentrated to give 55-G. ¹H-NMR (400 MHz, $CDCl_3$) δ 4.40 (s, 1H), 4.26 (s, 1H), 2.89 (s, 1H), 1.76-1.74 (s, 1H), 1.69-1.59 (m, 4H), 1.50 (s, 1H), 1.47 (s, 9H). LCMS-ESI⁺ (m/z): [M+Na]⁺ calculated for $C_{12}H_{19}NNaO_4$: 264.1; found: 264.1.

Step 7

To a mixture of compound 55-G (500 mg, 2.07 mmol) in THF (10 mL) chilled to 0° C. was added $BH_3$-DMS THF complex (2N in THF, 8.23 mmol, 4.1 mL) slowly. Gas evolution occurred. Internal temperature was monitored to ensure no major exotherm. Reaction was allowed to warm to r.t. overnight. Some starting material remained by LC/MS, additional 2 mL $BH_3$-DMS THF complex was added and the mixture was stirred for additional 3 hr then cooled reaction to 0° C. and slowly quenched with methanol (gas evolution occurs). Internal temperature monitored to ensure exotherm Step 1

A mixture of compound 55-A (40.60 g, 150 mmol) and $Pd(OH)_2/C$ (12 g) in EtOH (400 mL) under an atmosphere below 25° C. The mixture was concentrated then purified by silica gel chromotography (20-40% EtOAc/Hexanes) to afford 55-H.

Step 8

Compound 55 was prepared as described for Example 41, substituting 55-H for 41-B to afford compound 55. $^1$H-NMR (400 MHz, DMSO-d6) δ 11.81 (s, 1H), 10.40 (t, J=5.8 Hz, 1H), 8.39 (s, 1H), 7.19 (t, J=8.6 Hz, 2H), 4.59-4.48 (m, 4H), 4.16 (t, J=12.2 Hz, 1H), 4.03 (d, J=12.2 Hz, 1H), 2.69 (s, 1H), 1.75 (d, J=10.1 Hz, 1H), 1.69-1.55 (m, 5H). $^{19}$F NMR (376 MHz, DMSO-d6) δ −109.3 (m, 1F), −112.5 (m, 1F). LCMS-ESI$^+$ (m/z): [M+H]$^+$ calculated for $C_{21}H_{19}F_3N_3O_4$: 434.13; found: 434.32.

Example 56

Preparation of Compound 56

(1R,2S,4R,12aR)-2-fluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

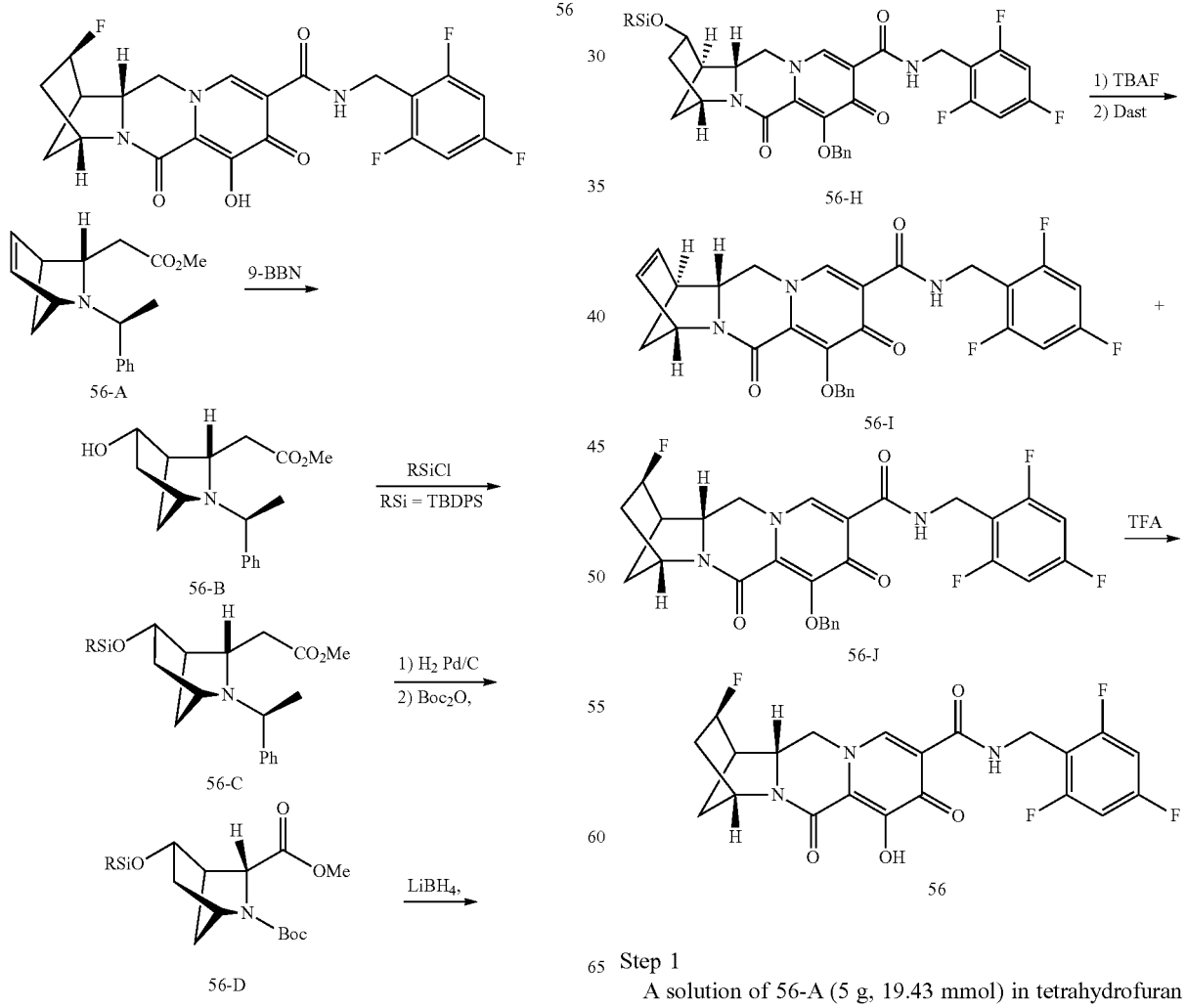

Step 1

A solution of 56-A (5 g, 19.43 mmol) in tetrahydrofuran (65 ml) was cooled in an ice bath as 0.5 M 9-borabicyclo

[3.3.1]nonane (48.58 ml) was added dropwise. The reaction mixture was warmed up to room temperature. After 18 hours, the reaction was cooled to 0° C. and a mixture of 2M sodium hydroxide (34 ml) and hydrogen peroxide (9.34 ml, 97.15 mmol) was added dropwise. After 2 hours at 0° C., the reaction was warmed up to room temperature and stirred for 1 hour. The mixture was diluted with EtOAc and washed with water. The aqueous fractions were extracted with EtOAc, and the organic fractions combined were dried ($Na_2SO_4$) and concentrated. The residue was purified by silica column chromatography (50-70% EtOAc/hexanes) to afford 56-B (3.05 g, 57%). LCMS-ESI$^+$ (m/z): [M+H]$^+$ calculated for $C_{16}H_{21}NO_3$: 275.34; found: 276.122.

Step 2

To a solution of 56-B (1.45 g, 5.27 mmol) in N,N-dimethylformamide (12 ml) was added tert-butylchlorodiphenylsilane (1.51 ml, 5.79 mmol) and imidazole (1.08 g, 15.8 mmol). After 18 hours, the mixture was diluted with water, extracted into EtOAc (2×), the organic fractions were combined, dried ($Na_2SO_4$), and concentrated. The residue was purified by silica column chromatography (10-20% EtOAc/hexanes) to afford 56-C (2.6 g, 96.1%). LCMS-ESI$^+$ (m/z): [M+H]$^+$ calculated for $C_{32}H_{39}NO_3Si$: 513.74; found: 514.625.

Step 3

To a solution of 56-C (3.27 g, 6.36 mmol) in EtOH (26 mL) and acetic acid (3 mL) was added 10% PdOH/C (0.52 g, 3.7 mmol) and the suspension was shaken in a Parr apparatus at 50 atm for 20 hours. After filtering through Celite, the cake was washed with EtOH, the filtrate was concentrated under vacuum. The residue was dissolved in ethanol (26 ml) and acetic acid (3 ml, 52.4 mmol), treated with 10% PdOH/C (0.52 g, 3.7 mmol) and shaken in a Parr apparatus at 50 atm for 20 hours. Filtered through Celite, the cake was washed with EtOH, the filtrate was concentrated under vacuum to dryness to afford the crude deprotected product (2.07 g, 79.4%). LCMS-ESI$^+$ (m/z): [M+H]$^+$ calculated for $C_{24}H_{31}NO_3Si$: 409.59; found: 410.485.

To the crude residue (2 g, 4.88 mmol) and di-tert-butyl dicarbonate 97% (2.14 g, 9.79 mmol) in THF (20 ml) was added N,N-diisopropylethylamine (DIPEA) (2.14 ml, 12.27 mmol). After 20 h, the reaction mixture was diluted with water, extracted into EtOAC (2×) and the two organic fractions were washed with water, combined, dried ($Na_2SO_4$), and concentrated. The residue was purified by silica column chromatography (10-20%. EtOAc/Hexanes) to afford 56-D (2.13 g, 86.14%). LCMS-ESI$^+$ (m/z): [M+H]$^+$ calculated for $C_{30}H_{41}NO_5Si$: 523.74; found: 523.922.

Step 4

A solution of 56-D (2.07 g, 4.06 mmol) in THF (20 ml) was stirred in an ice bath as 2.0 M $LiBH_4$ in THF (4.07 ml) was added and the resulting mixture was stirred at room temperature for 18 h. After, the reaction mixture was diluted with ethyl acetate and treated slowly with water. The two phases were separated, and the aqueous fraction was extracted again with ethyl acetate. The two organic fractions were washed with water, combined, dried ($Na_2SO_4$), and concentrated. The residue was purified by silica column chromatography (20-40% EOAc/hexanes) to afford 56-E (1.59 g, 81.3%). LCMS-ESI$^+$ (m/z): [M+H]$^+$ calculated for $C_{25}H_{39}NO_4Si$: 481.7; found: 482.337.

Step 5

A mixture of 56-E (1.58 g, 3.28 mmol), phthalimide (0.79 g, 5.38 mmol) and triphenylphosphine (1.93 g, 7.37 mmol) in THF (90 ml) was cooled in an ice bath. Diisopropyl azodicarboxylate, 95% (1.46 ml, 7.42 mmol) was added. The mixture was then warmed up to room temperature and stirred for 20 h. After, the reaction mixture was concentrated and the residue dissolved in ether, cooled in an ice bath and stirred for 1.5 h. The solids were filtered off and the filtrate was concentrated. The residue was purified by silica column chromatography (10-30% EtOAc/hexanes) to afford the protected amino compound (1.86 g, 92.8%).

A solution of the protected amino compound 56-F (1.85 g, 3.03 mmol) and hydrazine hydrate (0.6 ml, 12.39 mmol) in ethanol (19 ml) was stirred at 70° C. for 2 h. The reaction mixture was cooled in an ice bath, ether (10 ml) was added and the mixture was stirred for 30 min. The solid formed was filtered off and the filtrate was concentrated under vacuum to dryness.

Step 6

A mixture of crude amino compound 56-F (991 mg, 2.06 mmol), compound 38-F (Example 38) (714 mg, 2.06 mmol) and $NaHCO_3$ (347 mg, 4.12 mmol) in water (15 mL) and EtOH (15 mL) was stirred for 20 h. The reaction mixture was concentrated under vacuum and the residue was partitioned between water and EtOAc. The aqueous layer was re-extracted with EtOAc and the combined organic layers were dried ($Na_2SO_4$) and concentrated. The residue (1.5 g) was dissolved in $CH_2Cl_2$ (5 mL) and 4N HCl in dioxane (18.6 mL) was added. After 1.5 hours the mixture was concentrated to dryness, co-evaporated with toluene and dried in vacuo.

The crude residue (1.38 g) and DBU (1.4 ml, 9.38 mmol) in toluene (25 ml) was stirred at 110° C. After 35 minutes the mixture was concentrated and the residue was purified by silica column chromatography (5-15% MeOH/EtOAc) to afford 56-G (450 mg, 72.3%). LCMS-ESI$^+$ (m/z): [M+H]$^+$ calculated for $C_{39}H_{42}N_2O_6Si$: 662.85; found: 663.766.

Step 7

The mixture of 56-G (890 mg, 1.34 mmol) in MeOH (14 ml) and THF (14 ml) was stirred at room temperature as 1M KOH (7.09 ml) was added. After 30 min the reaction mixture was neutralized with 1N HCl, extracted into EtOAc (2×) and the combined organic extracts were dried ($Na_2SO_4$) and concentrated.

A suspension of the crude residue (850 mg), 2,4,6-trifluorobenzylamine (248 mg, 1.54 mmol) and HATU (662 mg, 1.74 mmol) in dichloromethane (5 ml) was stirred at room temperature as N,N-diisopropylethylamine (DIPEA) (1.63 ml, 9.37 mmol) was added. After 1 h, additional 2,4,6-difluorobenzylamine (32 mg, 0.2 mmol), HATU (153 mg, 0.4 mmol) and N,N-diisopropylethylamine (DIPEA) (0.12 ml, 0.67 mmol) were added. After 30 minutes the mixture was diluted with water, extracted into EtOAc (3×) the combined organic phases were dried ($Na_2SO_4$), concentrated and the residue was purified by silica column chromatography (50-75% EtOAc/hexanes) to afford 56-H (919 mg, 88.23%). LCMS-ESI$^+$ (m/z): [M+H]$^+$ calculated for $C_{44}H_{42}F_3N_3O_5Si$: 777.9; found: 778.409.

Step 8

A solution of 56-H (915 mg, 1.18 mmol) in THF (5 ml) was stirred in an ice bath as 1.0 M tetrabutylammonium fluoride in THF (1.18 ml) was added dropwise. The resulting mixture was stirred at room temperature for 30 min. The reaction mixture was concentrated under vacuum and the residue was diluted with EtOAc, washed with water, dried ($Na_2SO_4$), concentrated and the residue was purified by silica column chromatography (50-75% EtOAc/hexanes then 5% MeOH/EtOAc). The resulting material (248 mg, 0.46 mmol) was dissolved in dichloromethane (2 ml) cooled to −78° C. as diethylaminosulfur trifluoride (0.07 mL, 0.55 mmol) was added dropwise and the reaction was warmed to room temperature and stirred for 1 h. The reaction was cooled in an ice bath and quenched with saturated NaHCO₃, two phases were separated, and the separated aqueous fraction was extracted with CH₂Cl₂. The two organic fractions were combined dried (Na₂SO₄), and concentrated. The residue was purified by silica column chromatography (1% MeOH/EtOAc) to afford 56-J (75 mg) (LCMS-ESI⁺ (m/z): [M+H]⁺ calculated for $C_{28}H_{23}F_4N_3O_4$: 541.49; found: 542.320) and 56-I (30 mg) (LCMS-ESI⁺ (m/z): [M+H]⁺ calculated for $C_{28}H_{22}F_3N_3O_4$: 521.49; found: 522.05).

Step 9

Compound 56-J (75 mg, 139 mmol) was dissolved in TFA (1 mL), stirred at room temperature for 10 minutes, and the solution was concentrated. The residue was purified by reverse phase HPLC (Gemini, 15 to 43% ACN/H₂O+0.1% TFA) to afford compound 56. ¹H-NMR (400 MHz, DMSO-d6) δ 10.67 (s, 1H), 7.80 (s, 1H), 7.17 (t, J=8.6 Hz, 2H), 5.45-5.18 (m, 1H), 4.70-4.39 (m, 3H), 4.23 (d, J=11.5 Hz, 1H), 4.11-3.85 (m, 2H), 2.85 (dd, J=4.2, 2.0 Hz, 1H), 2.34-2.13 (m, 1H), 1.81 (s, 1H), 1.55-1.33 (m, 2H). ¹⁹F-NMR (376 MHz, DMSO-d₆) δ -74.20 (m), -106.95--116.45 (m), -190.65--194.54 (m).

Example 57

Preparation of Compound 57

(1R,4R,12aR)-2,2-difluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

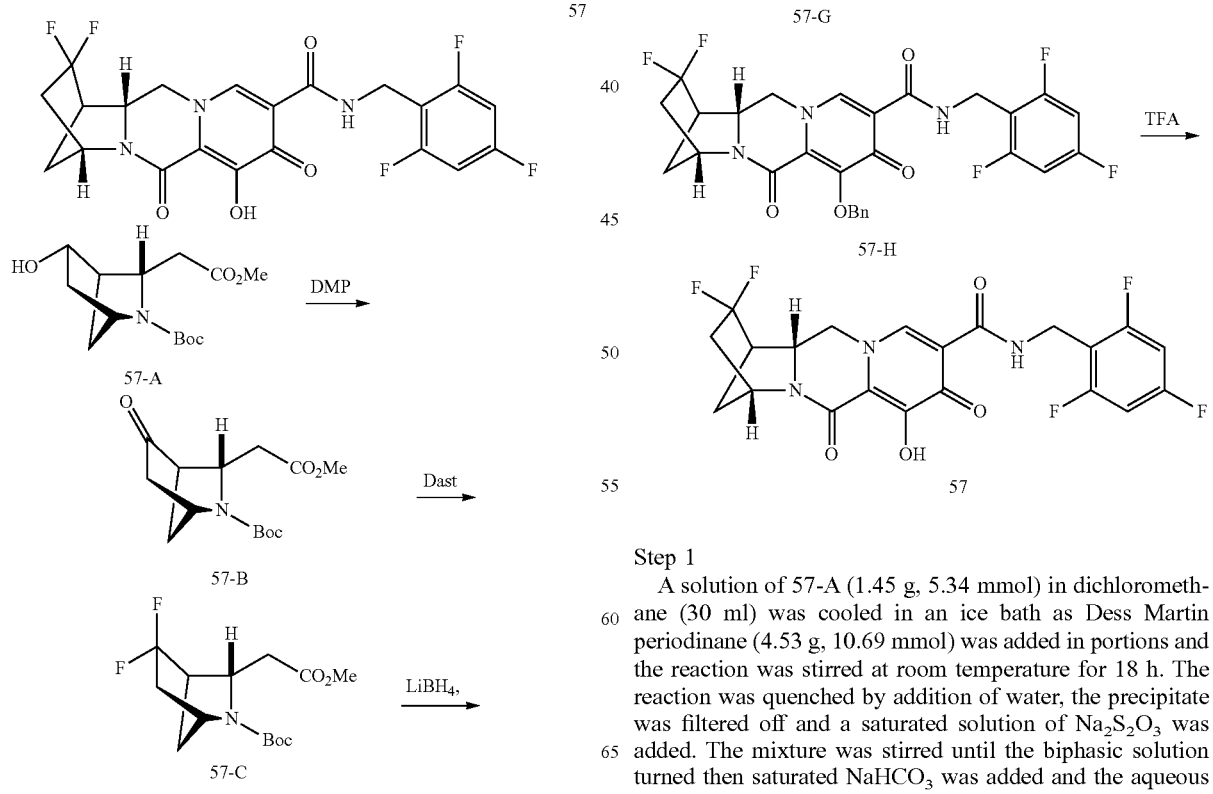

Step 1

A solution of 57-A (1.45 g, 5.34 mmol) in dichloromethane (30 ml) was cooled in an ice bath as Dess Martin periodinane (4.53 g, 10.69 mmol) was added in portions and the reaction was stirred at room temperature for 18 h. The reaction was quenched by addition of water, the precipitate was filtered off and a saturated solution of Na₂S₂O₃ was added. The mixture was stirred until the biphasic solution turned then saturated NaHCO₃ was added and the aqueous layer extracted with CH₂Cl₂. The combined organic fractions were dried (Na$_2$SO$_4$) and concentrated. The residue was purified by silica column chromatography (30-50% EtOAc/Hexanes) to afford 57-B (1.13 g, 78.2%). LCMS-ESI$^+$ (m/z): [M+H]$^+$ calculated for C$_{13}$H$_{19}$NO$_5$: 269.29; found: 269.722.

Step 2

A solution of 57-B (0.5 g, 1.86 mmol) in dichloromethane (10 ml) was cooled to −78° C. as diethylaminosulfur trifluoride (0.52 mL, 3.91 mmol) was added dropwise and the reaction was warmed to room temperature and stirred for 18 h. The reaction was cooled in an ice bath and quenched with saturated NaHCO$_3$, two phases were separated, and the separated aqueous fraction was extracted with CH$_2$Cl$_2$. The two organic fractions were combined, dried (Na$_2$SO$_4$) and concentrated. The residue was purified by silica column chromatography (20-50% EtOAc/hexanes) to afford 57-C (518 mg, 95.39%). $^1$H-NMR (400 MHz, Chloroform-d) δ 4.43 (s, 1H), 4.36-4.27 (m, 1H), 4.22 (s, 1H), 3.75 (s, 3H), 2.95 (t, J=8.1 Hz, 1H), 2.30-1.98 (m, 2H), 1.85-1.71 (m, 1H), 1.44 (m, 9H).

Step 3

A solution of 57-C (935 mg, 3.21 mmol) in THF (10 ml) was stirred in an ice bath as 2.0 M LiBH4 in THF (3.22 ml) was added and the resulting mixture was stirred at room temperature for 18 h. After, the reaction mixture was diluted with ethyl acetate and water was added slowly. The two phases were separated, and the separated aqueous fraction was extracted with ethyl acetate. The two organic fractions were washed with water, combined, dried (Na$_2$SO$_4$), and concentrated. The residue was purified by silica column chromatography (20-40% EtOAc/hexanes) to afford 57-D (724 mg, 85.67%). $^1$H-NMR (400 MHz, Chloroform-d) δ 4.30-3.48 (m, 5H), 2.75-2.56 (m, 1H), 2.24-1.90 (m, 3H), 1.86-1.65 (m, 1H), 1.47 (s, 9H).

Step 4

A mixture of 57-D (720 mg, 2.74 mmol), phthalimide (402 mg, 2.73 mmol) and triphenylphosphine (1.61 g, 6.15 mmol) in THF (45 ml) was cooled in an ice bath. Diisopropyl azodicarboxylate, 95% (1.22 ml, 6.19 mmol), was added. The mixture was then warmed up to room temperature and stirred for 20 h. After, the reaction mixture was concentrated and the residue dissolved in ether, cooled in an ice bath and stirred for 1.5 h. After the solids were filtered off, the filtrate was concentrated. The residue was purified by silica column chromatography (40-60% EtOAc/hexanes) to afford the phthalimide adduct (1.07 g, 99.7%). LCMS-ESI$^+$ (m/z): [M+H]$^+$ calculated for C$_{20}$H$_{22}$F$_2$N$_2$O$_4$: 392.4; found: 393.204.

A solution of the phthalimide adduct (1.07 g, 2.73 mmol) and hydrazine hydrate (0.54 mL, 11.15 mmol) in ethanol (10 ml) was stirred at 70° C. for 2 hours. The reaction mixture was cooled in an ice bath and ether (10 ml) was added. The mixture was stirred for 30 min. The solid formed was filtered off and the filtrate was concentrated under vacuum to dryness to afford crude 57-E.

Step 5

A mixture of crude 57-E (709 mg, 2.7 mmol) compound 38-F (Example 38) (936 mg, 2.7 mmol) and NaHCO$_3$ (454 mg, 5.41 mmol) in water (15 mL) and EtOH (15 mL) was stirred for 20 h. The reaction mixture was concentrated under vacuum and the residue was partitioned between water and EtOAc. The aqueous layer was re-extracted with EtOAc and the combined organic layers were dried (Na$_2$SO$_4$) and concentrated. The residue (1.5 g) was dissolved in CH$_2$Cl$_2$ (7 mL) and 4N HCl in dioxane (26.9 mL) was added. After 1.5 hours the mixture was concentrated to dryness, co-evaporated with toluene and dried in vacuum. The crude residue (1.3 g) and DBU (2 ml, 13.4 mmol) in toluene (25 ml) was stirred at 110° C. After 35 minutes the mixture was concentrated and the residue was purified by silica column chromatography (5-15% MeOH/EtOAc) to afford 57-F (426 mg, 36.17%). LCMS-ESI$^+$ (m/z): [M+H]$^+$ calculated for C$_{23}$H$_{22}$F$_2$N$_2$O$_5$: 444.43; found: 445.280.

Step 6

The mixture of compound 57-F (426 mg, 0.96 mmol) in MeOH (7 ml) and THF (7 ml) was stirred at room temperature as 1M KOH (5.06 ml) was added. After 30 minutes the reaction mixture was neutralized with 1N HCl, extracted into EtOAc (2×) and the combined organic extracts were dried (Na$_2$SO$_4$) and concentrated to crude 57-G.

Step 7

A suspension of the crude residue 57-G (189 mg), 2,4,6-trifluorobenzylamine (95 mg, 0.59 mmol) and HATU (276 mg, 0.73 mmol) in dichloromethane (3 ml) was stirred at room temperature as N,N-diisopropylethylamine (DIPEA) (0.59 ml, 3.4 mmol) was added. After 1 h the mixture was diluted with water, extracted into EtOAc (3×). The combined organic phases were dried (Na$_2$SO$_4$) and concentrated to 57-H. LCMS-ESI$^+$ (m/z): [M+H]$^+$ calculated for C$_{28}$H$_{22}$F$_5$N$_3$O$_4$: 559.48; found: 560.24.

Step 8

Compound 57-H (150 mg, 0.27 mmol) was dissolved in TFA (2 mL), stirred at room temperature for 10 min, and the solution was concentrated. The residue was purified by reverse phase HPLC (Gemini, 15 to 60% ACN/H$_2$O+0.1% TFA), to afford compound 57 (85 mg, 67.5%). LCMS-ESI$^+$ (m/z): [M+H]$^+$ calculated for C$_{21}$H$_{16}$F$_5$N$_3$O$_4$: 469.36; found: 470.229. $^1$H-NMR (400 MHz, DMSO-d$_6$) δ 10.41 (t, J=5.6 Hz, 1H), 8.20 (s, 1H), 7.12 (t, J=8.7 Hz, 2H), 4.79 (s, 1H), 4.48 (m, 3H), 4.10 (m, 2H), 3.02 (d, J=5.7 Hz, 1H), 2.33 (m, 1H), 2.22-1.97 (m, 2H), 1.85 (d, J=11.0 Hz, 1H), 1.21 (s, 1H). $^{19}$F NMR (376 MHz, DMSO-d) δ −69.88, −71.77, −74.09, −88.33 (dd, J=222.6, 23.8 Hz), −109.15-−109.60 (m), −110.04, −112.44 (t, J=7.6 Hz).

Example 58

Preparation of Compound 58

(1R,4R,12aR)—N-(3-chloro-2,4-difluorobenzyl)-2,2-difluoro-7-hydroxy-6,8-dioxo-1,2,3,4,6,8,12,12a-octahydro-1,4-methanodipyrido[1,2-a:1',2'-d]pyrazine-9-carboxamide

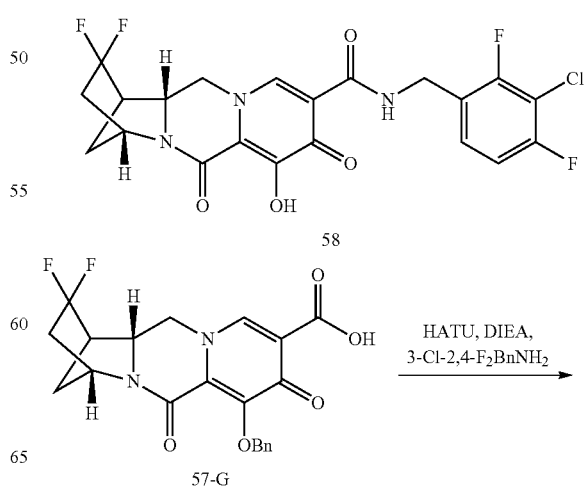

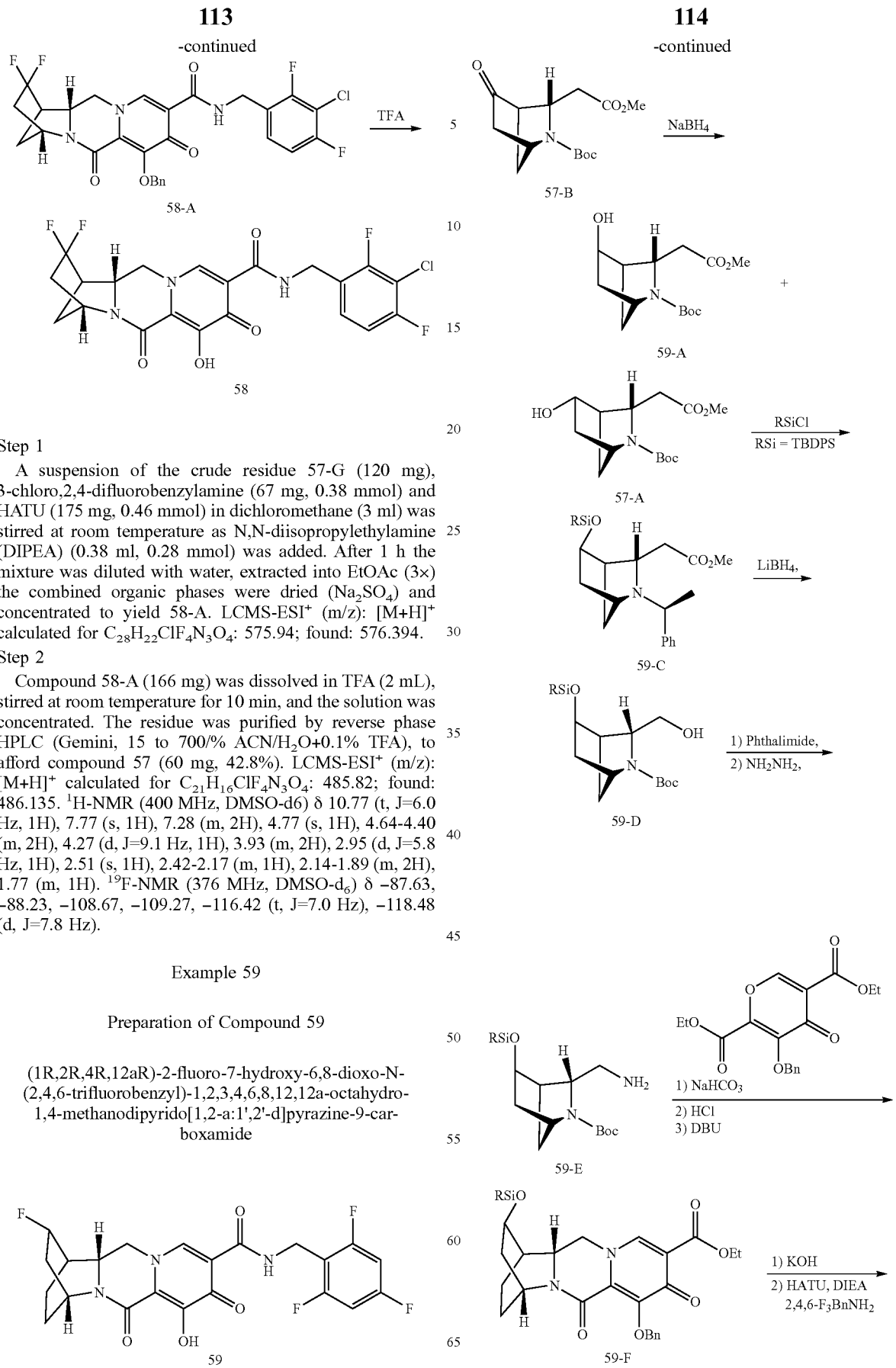

Step 1

A suspension of the crude residue 57-G (120 mg), 3-chloro,2,4-difluorobenzylamine (67 mg, 0.38 mmol) and HATU (175 mg, 0.46 mmol) in dichloromethane (3 ml) was stirred at room temperature as N,N-diisopropylethylamine (DIPEA) (0.38 ml, 0.28 mmol) was added. After 1 h the mixture was diluted with water, extracted into EtOAc (3×) the combined organic phases were dried (Na$_2$SO$_4$) and concentrated to yield 58-A. LCMS-ESI$^+$ (m/z): [M+H]$^+$ calculated for C$_{28}$H$_{22}$ClF$_4$N$_3$O$_4$: 575.94; found: 576.394.

Step 2

Compound 58-A (166 mg) was dissolved in TFA (2 mL), stirred at room temperature for 10 min, and the solution was concentrated. The residue was purified by reverse phase HPLC (Gemini, 15 to 700/% ACN/H$_2$O+0.1% TFA), to afford compound 57 (60 mg, 42.8%). LCMS-ESI$^+$ (m/z): [M+H]$^+$ calculated for C$_{21}$H$_{16}$ClF$_4$N$_3$O$_4$: 485.82; found: 486.135. $^1$H-NMR (400 MHz, DMSO-d6) δ 10.77 (t, J=6.0 Hz, 1H), 7.77 (s, 1H), 7.28 (m, 2H), 4.77 (s, 1H), 4.64-4.40 (m, 2H), 4.27 (d, J=9.1 Hz, 1H), 3.93 (m, 2H), 2.95 (d, J=5.8 Hz, 1H), 2.51 (s, 1H), 2.42-2.17 (m, 1H), 2.14-1.89 (m, 2H), 1.77 (m, 1H). $^{19}$F-NMR (376 MHz, DMSO-d$_6$) δ −87.63, −88.23, −108.67, −109.27, −116.42 (t, J=7.0 Hz), −118.48 (d, J=7.8 Hz).

Example 59

Preparation of Compound 59

(1R,2R,4R,12aR)-2-fluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

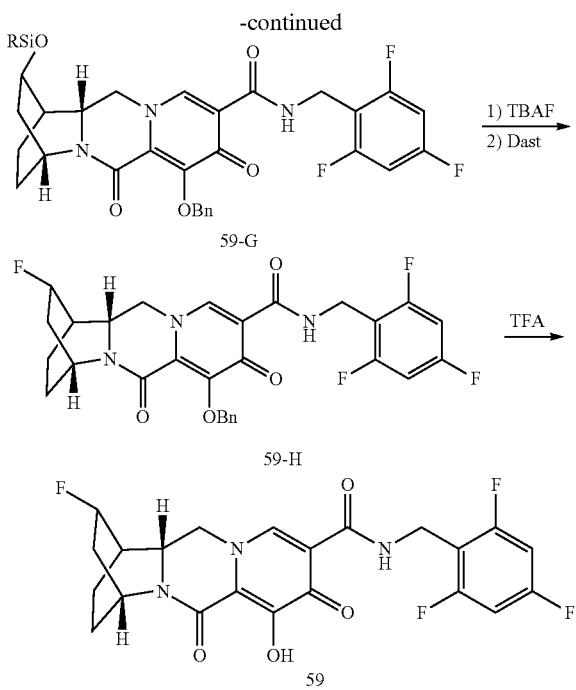

Step 1

A solution of 57-B (1.9 g, 7.06 mmol) in methanol (35 mL) was stirred at 0° C. as sodium borohydride (667 mg, 17.64 mmol) was added portionwise and the resulting mixture was stirred at room temperature for 30 min. The reaction mixture was cooled in an ice bath, quenched by addition of water and concentrated. The residue was partitioned between water and EtOAc. The aqueous layer was re-extracted with EtOAc and the combined organic layers were dried ($Na_2SO_4$) and concentrated. The residue was purified by silica column chromatography (30-60% EtOAc/hexanes) to afford 59-A (1.49 g). $^1$H-NMR (400 MHz, chloroform-d) δ 4.57 (s, 1H), 4.52-4.42 (m, 2H), 4.28 (s, 1H), 4.14 (s, 1H), 3.72 (d, J=2.1 Hz, 3H), 2.74 (s, 1H), 2.08-1.87 (m, 2H), 1.43 (d, J=23.1 Hz, 10H) and 57-A (96 mg): $^1$H-NMR (400 MHz, chloroform-d) δ 4.65-4.40 (m, 2H), 4.34-4.02 (m, 1H), 3.73 (d, J=2.3 Hz, 3H), 2.74 (t, J=5.3 Hz, 1H), 2.12-1.55 (m, 3H), 1.52-1.18 (m, 11H).

Step 2

To a solution of 59-A (686 mg, 2.53 mmol) in N,N-dimethylformamide (5 ml) was added tert-butylchlorodiphenylsilane (0.723 mL, 2.78 mmol) and imidazole (516 mg, 7.56 mmol). After 18 h, the mixture was diluted with water, extracted into EtOAc (2×), and the organic fractions were combined, dried ($Na_2SO_4$), and concentrated. The residue was purified by silica column chromatography (10-20%, EtOAc/hexanes) to afford 59-C. LCMS-ESI$^+$ (m/z): [M+H]$^+$ calculated for $C_{29}H_{39}NO_5Si$: 509.71; found: 510.793.

Step 3

A solution of 59-C (1.23 g, 2.41 mmol) in THF (13 ml) was stirred in an ice bath as 2.0 M LiBH$_4$ in THF (2.42 mL, 4.84 mmol)) was added and the resulting mixture was stirred at room temperature for 18 h. After the reaction mixture was diluted with ethyl acetate water was added slowly, two phases were separated, and the separated aqueous fraction was extracted with ethyl acetate. The two organic fractions were washed with water, combined, dried ($Na_2SO_4$), and concentrated. The residue was purified by silica column chromatography (20-40% EtOAc/hexanes) to afford 59-D. LCMS-ESI$^+$ (m/z): [M+H]$^+$ calculated for $C_{25}H_{39}NO_4Si$: 481.7; found: 482.741.

Step 4

A mixture of 59-D (963 mg, 2.0 mmol), phthalimide (482 mg, 3.28 mmol) and triphenylphosphine (1.18 g, 4.49 mmol) in THF (50 ml) was cooled in an ice bath. Diisopropyl azodicarboxylate, 95% (0.89 mL, 4.52 mmol) was added. The mixture was then warmed up to room temperature and stirred for 20 h. After, the reaction mixture was concentrated and the residue dissolved in ether, cooled in an ice bath and stirred for 1.5 h. After, the solids were filtered off and the filtrate was concentrated. The residue was purified by silica column chromatography (10-30% EtOAc/hexanes) to afford the phthalimide adduct. LCMS-ESI$^+$ (m/z): [M+H]$^+$ calculated for $C_{36}H_{42}N_2O_5Si$: 610.81; found: 611.935.

A solution of the phthalimide adduct (1.2 g, 1.97 mmol) and hydrazine hydrate (0.4 ml, 8.03 mmol) in ethanol (12 ml) was stirred at 70° C. for 2 h. The reaction mixture was cooled in an ice bath and ether (10 ml) was added, the mixture was stirred for 30 min. The solid formed was filtered off and the filtrate was concentrated under vacuum to dryness to afford 59-E. LCMS-ESI$^+$ (m/z): [M+H]$^+$ calculated for $C_{25}H_{40}N_2O_3Si$: 480.71; found: 481.356.

Step 5

A mixture of crude 59-E (770 mg, 1.60 mmol), compound 38-F (Example 38) (555 mg, 1.60 mmol) and NaHCO$_3$ (269 mg, 3.20 mmol) in water (12 mL) and EtOH (12 mL) was stirred for 20 h. The reaction mixture was concentrated under vacuum and the residue was partitioned between water and EtOAc. The aqueous layer was re-extracted with EtOAc and the combined organic layers were dried ($Na_2SO_4$) and concentrated.

The residue (1.29 g) was dissolved in $CH_2Cl_2$ (4 mL) and 4N HCl in dioxane (15.6 mL) was added. After 1.5 hours the mixture was concentrated to dryness, co-evaporated with toluene and dried in vacuum. LCMS-ESI$^+$ (m/z): [M+H]$^+$ calculated for $C_{41}H_{48}N_2O_7Si$: 708.91; found: 709.782.

The crude residue (1.09 mg) and DBU (1.17 ml, 7.8 mmol) in toluene (20 ml) was stirred at 110° C. After 35 min the mixture was concentrated and the residue was purified by silica column chromatography (5-15% MeOH/EtOAc) to afford 59-F. LCMS-ESI$^+$ (m/z): [M+H]$^+$ calculated for $C_{39}H_{42}N_2O_6Si$: 662.85; found: 663.677.

Step 6

A mixture of 59-F (680 mg, 1.03 mmol) in MeOH (10 ml) and THF (10 ml) was stirred at room temperature as 1M KOH (5.42 ml) was added. After 30 min the reaction mixture was neutralized with 1N HCl, extracted into EtOAc (2×) and the combined organic extracts were dried ($Na_2SO_4$) and concentrated. LCMS-ESI$^+$ (m/z): [M+H]$^+$ calculated for $C_{37}H_{38}N_2O_6Si$: 634.79; found: 635.466.

A suspension of the crude residue (650 mg), 2,4,6-trifluorobenzylamine (214 mg, 1.33 mmol) and HATU (623 mg, 1.64 mmol) in dichloromethane (6 ml) was stirred at room temperature as N,N-diisopropylethylamine (DIPEA) (1.34 ml, 7.68 mmol) was added. After 2 h, the mixture was diluted with water, extracted into EtOAc (3×) and the combined organic phases were dried ($Na_2SO_4$), concentrated and the residue was purified by silica column chromatography (50-75% EtOAc/hexanes) to afford 59-G. LCMS-ESI$^+$ (m/z): [M+H]$^+$ calculated for $C_{44}H_{42}F_3N_3O_5Si$: 777.9; found: 778.566.

Step 7

A solution of 59-G (648 mg, 0.83 mmol) in THF (10 ml) was stirred in an ice bath as 1.0 M tetrabutylammonium fluoride in THF (0.83 ml) was added dropwise and the resulting mixture was stirred at room temperature for 30 min. Additional 1.0 M tetrabutylammonium fluoride in THF (0.1 ml) was added dropwise. After 30 minutes, the reaction mixture was concentrated under vacuum and the residue was diluted with EtOAc, washed with water, dried (Na$_2$SO$_4$), concentrated and the residue was purified by silica column chromatography (5% MeOH/EtOAc). A solution of the residue (290 mg, 0.54 mmol) in dichloromethane (3 ml) was cooled to −78° C. as diethylaminosulfur trifluoride (0.09 mL, 0.65 mmol) was added dropwise and the reaction was warmed to room temperature and stirred for 2.5 h. The reaction was cooled in an ice bath, quenched with saturated NaHCO$_3$, two phases were separated, and the separated aqueous fraction was extracted with CH$_2$Cl$_2$. The two organic fractions were combined, dried (Na$_2$SO$_4$), and concentrated. The residue was purified by silica column chromatography (1% MeOH/EtOAc) to afford 59-H. LCMS-ESI$^+$ (m/z): [M+H]$^+$ calculated for C$_{28}$H$_{23}$F$_4$N$_3$O$_4$: 541.49; found: 542.320.

Step 8

Compound 59-H (103 mg, 0.19 mmol) was dissolved in TFA (1.4 mL) at room temperature for 15 min, and the solution was concentrated. The residue was suspended in DMF, filtered off, and the precipitated product was washed with water, dried under vacuum to afford compound 59. LCMS-ESI$^+$ (m/z): [M+H]$^+$ calculated for C$_{21}$H$_{17}$F$_4$N$_3$O$_4$: 451.37; found: 452.226. $^1$H-NMR (400 MHz, DMSO-d6) δ 11.53 (s, 1H), 10.35 (t, J=5.8 Hz, 1H), 8.34 (s, 1H), 7.18 (t, J=8.6 Hz, 2H), 5.15-4.88 (m, 1H), 4.73 (d, J=3.3 Hz, 1H), 4.49 (m, 3H), 4.04 (t, J=12.4 Hz, 1H), 3.65 (dd, J=12.4, 3.7 Hz, 1H), 2.95-2.76 (m, 1H), 2.26-2.03 (m, 1H), 1.96-1.64 (m, 3H). $^{19}$F-NMR (376 MHz, DMSO-d$_6$) δ −73.93, −74.74 (d, J=28.8 Hz), −109.31 (m), −112.51 (m), −165.65 (m).

Example 60

Preparation of Compound 60

(1R,4S,12aR)—N-(2,3-dichlorobenzyl)-7-hydroxy-6,8-dioxo-1,2,3,4,6,8,12,12a-octahydro-1,4-methanodipyrido[1,2-a:1',2'-d]pyrazine-9-carboxamide

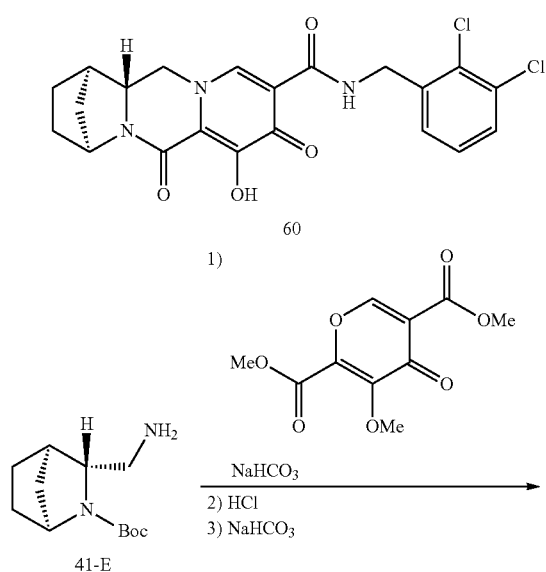

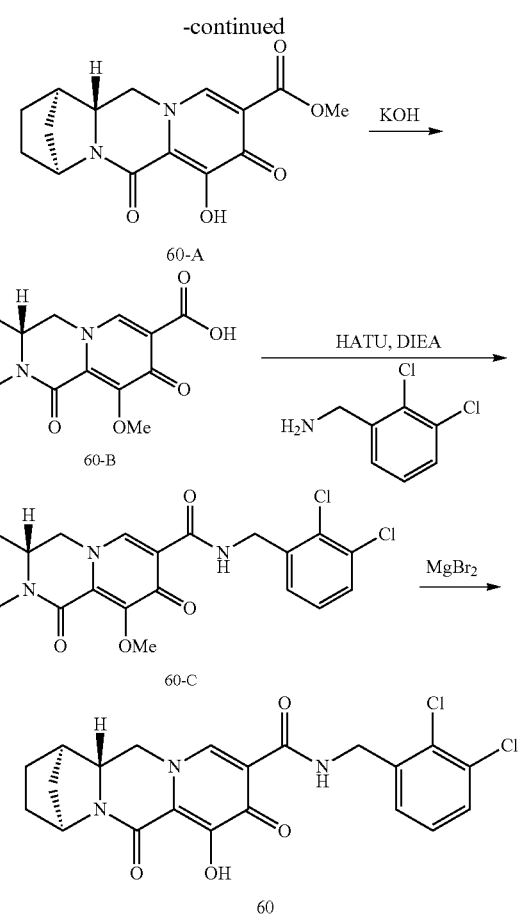

Step 1

To a solution of dimethyl 3-methoxy-4-oxo-4H-pyran-2,5-dicarboxylate (5.5 g, 23 mmol) in MeOH (100 mL) was added 41-E (Example 41) (5 g, 22 mmol) and sodium bicarbonate (3.6 g, 43 mmol). The solution was stirred at room temperature for 1.5 h. 4M HCl (in dioxane, 55 mL, 221 mmol) was added and the solution was heated to 50° C. for 2 h. The reaction was cooled to room temperature and concentrated in vacuo. The resulting oil was dissolved in sodium bicarbonate and washed with EtOAc. The aqueous layers were then extracted with CH$_2$Cl$_2$ (4×). The combined CH$_2$Cl$_2$ extractions were dried over Na$_2$SO$_4$ and concentrated to provide 60-A. LCMS-ESI (m/z): [M+H]$^+$ calculated for C$_{16}$H$_{19}$N$_2$O$_5$: 319.13; found: 319.20.

Step 2

To a suspension of 60-A (3.7 g, 11.6 mmol) in MeOH (12 mL) and THF (23 mL) was added aqueous KOH (2M, 15.7 mL, 31.4 mmol). The resulting solution was stirred at room temperature for 10 min. Volatiles were removed in vacuo, and the resulting aqueous layer was acidified with 1N HCl. The resulting white solid was filtered, washed with water, and dried in vacuo to provide 60-B. $^1$H-NMR (400 MHz, Chloroform-d) δ 8.36 (s, 1H), 5.01 (d, J=2.7 Hz, 1H), 4.12 (s, 4H), 3.90 (t, J=12.2 Hz, 1H), 3.78 (dd, J=12.1, 3.1 Hz, 1H), 2.69 (s, 1H), 1.95-1.71 (m, 4H), 1.70-1.54 (m, 2H). LCMS-ESI$^+$ (m/z): [M+H]$^+$ calculated for C$_{15}$H$_{17}$N$_2$O$_5$: 305.11; found: 305.15.

Step 3

To a solution of 60-B (0.10 g, 0.33 mmol) in CH$_2$Cl$_2$ (3.5 mL) was added (2,3-dichlorophenyl)methanamine (0.12 g, 0.70 mmol), HATU (0.25 g, 0.66 mmol), and N,N-diisopropylethylamine (DIPEA) (0.29 mL, 1.64 mmol). The resulting solution was stirred at room temperature until judged complete by LC/MS. The reaction mixture was diluted with $CH_2Cl_2$ and washed with 1N HCl. The aqueous layer was back-extracted with $CH_2Cl_2$, and the combined organic layers were dried over $Na_2SO_4$ and concentrated in vacuo. The crude material was dissolved in hot DMF and allowed to precipitate upon cooling. Filtration provided 60-C. LCMS-ESI$^+$ (m/z): [M+H]$^+$ calculated for $C_{22}H_{22}Cl_2N_3O_4$: 462.10; found: 462.14.

Step 4

To a slurry of 60-C (0.11 g, 0.24 mmol), in acetonitrile (4.5 mL), was added magnesium bromide (0.089 g, 0.48 mmol). The reaction mixture was heated to 45° C. for 2.5 h and then cooled to room temperature. The slurry was diluted with $CH_2Cl_2$ and washed with 1N HCl and brine. The aqueous layers were back-extracted with $CH_2Cl_2$ (2×) and the combined organic layers were dried over $Na_2SO_4$ and concentrated in vacuo. The crude solid was triturated with methanol and filtered to provide 60. $^1$H-NMR (400 MHz, DMSO-d6) δ 11.72 (s, 1H), 10.50 (t, 1H), 8.34 (s, 1H), 7.55 (dd, 1H), 7.40-7.24 (m, 2H), 4.67 (s, 1H), 4.61 (d, 2H), 4.45 (dd, 1H), 3.95 (t, 1H), 3.84-3.73 (m, 1H), 1.86-1.67 (m, 3H), 1.66-1.40 (m, 4H). LCMS-ESI$^+$ (m/z): [M+H]$^+$ calculated for $C_{21}H_{20}Cl_2N_3O_4$: 448.08; found: 448.18.

Example 61

Preparation of Compound 61

(1R,4S,12aS)—N-(3-chloro-2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

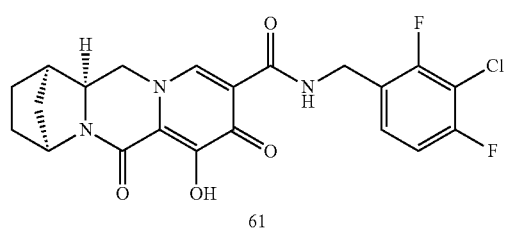

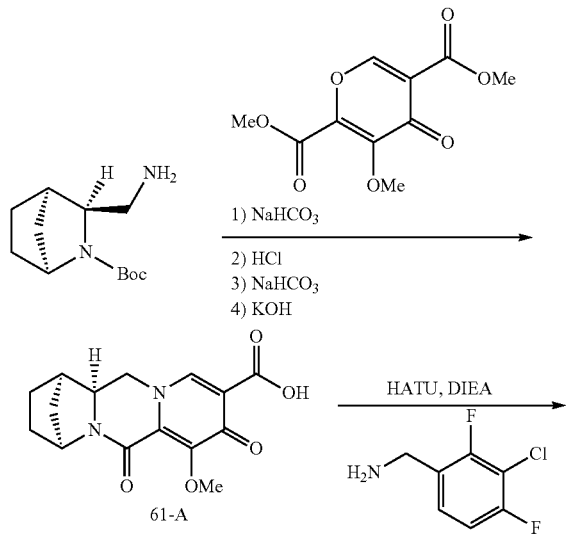

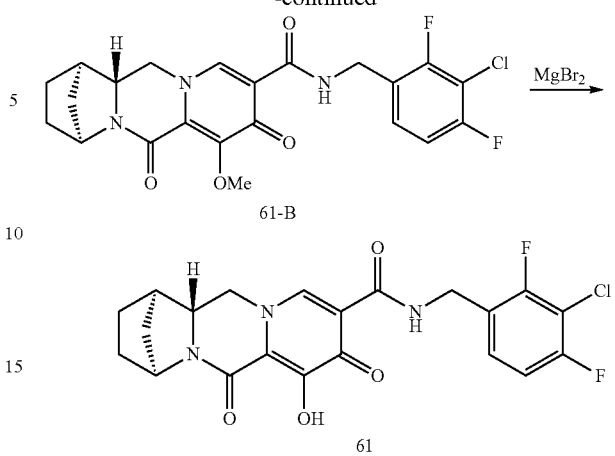

61 was prepared analogously to Example 60, substituting (1S,3S,4R)-tert-butyl 3-(aminomethyl)-2-azabicyclo[2.2.1]heptane-2-carboxylate (prepared in Example 55) for 41-E, and (3-chloro-2,4-difluorophenyl)methanamine for (2,3-dichlorophenyl)methanamine. $^1$H-NMR (400 MHz, DMSO-d6) δ 11.85 (s, 1H), 10.45 (t, 1H), 8.40 (s, 1H), 7.37 (td, 1H), 7.27 (td, 1H), 4.63-4.46 (m, 4H), 4.17 (t, 1H), 4.04 (dt, 1H), 1.76 (d, 1H), 1.73-1.54 (m, 5H). LCMS-ESI$^+$ (m/z): [M+H]$^+$ calculated for $C_{21}H_{19}ClF_2N_3O_4$: 450.10; found: 450.15.

Example 62

Preparation of Compound 62

'(2R,5S,13aR)—N-(4-fluoro-2-(trifluoromethyl)benzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

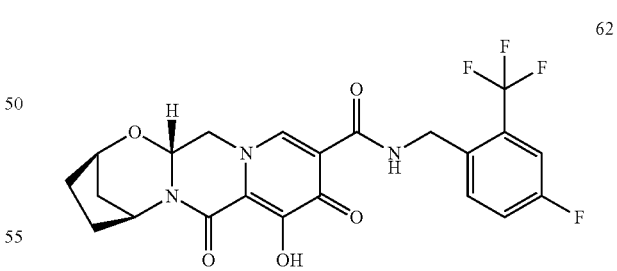

Compound 62 was prepared in a similar manner to compound 42 using (4-fluoro-2-(trifluoromethyl)phenyl)methanamine in place of (2,4,6-trifulorophenylphenyl)methanamine. $^1$H-NMR (400 MHz, Chloroform-d) δ 10.50 (s, 1H), 8.38 (s, 1H), 7.57 (dd, 1H), 7.36 (dd, 1H), 7.19 (td, 1H), 5.40-5.28 (m, 2H), 4.79 (t, 2H), 4.69 (s, 1H), 4.25 (dd, 1H), 4.03 (dd, 1H), 2.17-1.98 (m, 4H), 1.96-1.84 (m, 1H), 1.61 (dt, 1H). LCMS-ESI$^+$ (m/z): [M+H]$^+$ calculated for $C_{22}H_{20}F_4N_3O_5$: 482.13; found: 482.145.

Example 63

Preparation of Compound 63

(2R,5S,13aR)—N-(2-chloro-4-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

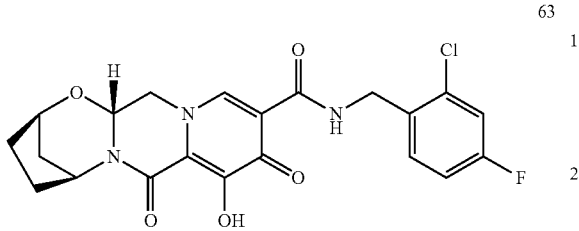

63

Compound 63 was prepared in a similar manner to compound 42 using (2-chloro-4-fluorophenyl)methanamine in place of (2,4,6-trifulorophenylphenyl)methanamine. $^1$H-NMR (400 MHz, Chloroform-d) δ 10.48 (s, 1H), 8.45 (s, 1H), 7.39 (dd, 1H), 7.12 (dd, 1H), 6.93 (td, 1H), 5.37 (d, 1H), 5.31 (t, 1H), 4.68 (s, 3H), 4.29 (d, 1H), 4.04 (t, 1H), 2.21-2.01 (m, 4H), 1.97-1.82 (m, 1H), 1.67-1.56 (m, 1H). LCMS-ESI$^+$ (m/z): [M+H]$^+$ calculated for $C_{21}H_{20}ClFN_3O_5$: 448.10; found: 448.143.

Example 64

Preparation of Compound 64

(2R,5S,13aR)-8-hydroxy-7,9-dioxo-N-(2,4,5-trifluorobenzyl)-2,3,4,5,7,9,13,13a-octahydro-2,5-methanopyrido[1',2':4,5]pyrazino[2,1-b][1,3]oxazepine-10-carboxamide

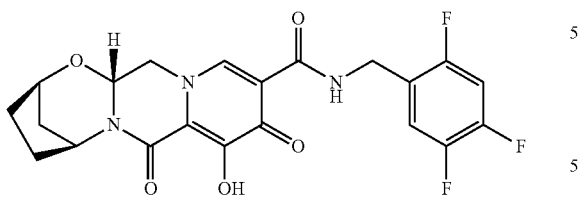

64

Compound 64 was prepared in a similar manner to compound 42 using (2,4,5-trifluorophenyl)methanamine in place of (2,4,6-trifulorophenylphenyl)methanamine. $^1$H-NMR (400 MHz, Chloroform-d) δ 10.42 (s, 1H), 8.42 (s, 1H), 7.19 (ddd, 1H), 6.91 (td, 1H), 5.38 (dd, 1H), 5.31 (t, 1H), 4.69 (s, 1H), 4.61 (d, 2H), 4.29 (dd, 1H), 4.05 (dd, 1H), 2.18-2.02 (m, 4H), 1.96-1.84 (m, 1H), 1.66-1.56 (m, 1H). LCMS-ESI$^+$ (m/z): [M+H]$^+$ calculated for $C_{21}H_{19}F_3N_3O_5$: 450.12; found: 450.119.

Example 65

Preparation of Compound 65

(2R,5S,13aR)—N-(5-chloro-2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

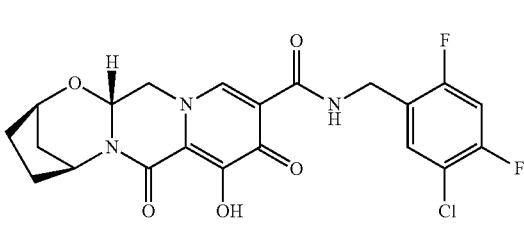

65

Compound 65 was prepared in a similar manner to compound 42 using (5-chloro-2,4-difluorophenyl)methanamine in place of (2,4,6-trifulorophenylphenyl)methanamine. $^1$H-NMR (400 MHz, Chloroform-d) δ 10.47 (t, 1H), 8.41 (s, 1H), 7.40 (dd, 1H), 6.90 (t, 1H), 5.37 (dd, 1H), 5.31 (t, 1H), 4.69 (s, 1H), 4.62 (d, 2H), 4.28 (d, 1H), 4.04 (dd, 1H), 2.17-2.02 (m, 4H), 1.94-1.86 (m, 1H), 1.61 (dt, 1H). LCMS-ESI$^+$ (m/z): [M+H]$^+$ calculated for $C_{21}H_{19}ClF_2N_3O_5$: 466.09; found: 466.107.

Example 66

Preparation of Compound 66

(1R,4S,12aR)—N-(3,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

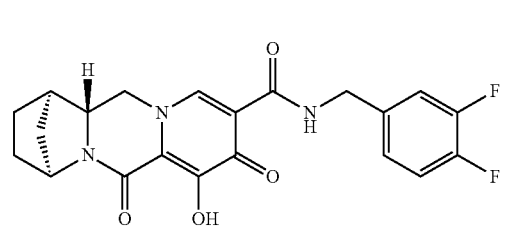

66

Compound 66 was prepared in a similar manner to compound 60 using (3,4-difluorophenyl)methanamine in place of (2,3-dichlorophenyl)methanamine. $^1$H-NMR (400 MHz, Chloroform-d) δ 10.59 (s, 1H), 7.24-7.16 (m, 2H), 7.14-7.04 (m, 2H), 4.91 (s, 1H), 4.58 (d, 3H), 3.94-3.82 (m, 1H), 3.79 (d, 1H), 1.99-1.81 (m, 4H), 1.76 (d, 1H), 1.70-1.60 (m, 3H). LCMS-ESI$^+$ (m/z): [M+H]$^+$ calculated for $C_{21}H_{20}F_2N_3O_4$: 416.13; found: 416.415.

Example 67

Preparation of Compound 67

(1R,4S,12aR)—N-(4-fluoro-2-(trifluoromethyl)benzyl)-7-hydroxy-6,8-dioxo-1,2,3,4,6,8,12,12a-octahydro-1,4-methanodipyrido[1,2-a:1',2'-d]pyrazine-9-carboxamide

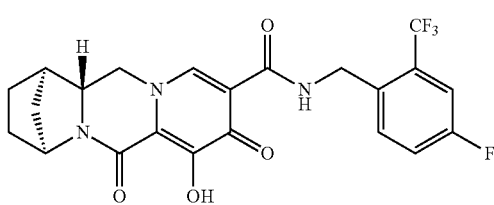

67

Compound 67 was prepared in a similar manner to compound 60 using (4-fluoro-2-(trifluoromethyl)phenyl)methanamine in place of (2,3-dichlorophenyl)methanamine. $^1$H-NMR (400 MHz, Chloroform-d) δ 11.72 (s, 1H), 10.55 (s, 1H), 8.29 (s, 1H), 7.61 (s, 1H), 7.36 (dd, 1H), 7.18 (td, 1H), 4.91 (s, 1H), 4.80 (d, 3H), 4.11 (s, 1H), 1.99-1.80 (m, 4H), 1.76 (d, 1H), 1.71-1.47 (m, 3H). LCMS-ESI$^+$ (m/z): [M+H]$^+$ calculated for $C_{22}H_{20}F_4N_3O_4$: 466.13; found: 466.297.

Example 68

Preparation of Compound 68

(1R,4S,12aR)—N-(2-chloro-4-fluorobenzyl)-7-hydroxy-6,8-dioxo-1,2,3,4,6,8,12,12a-octahydro-1,4-methanodipyrido[1,2-a:1',2'-d]pyrazine-9-carboxamide

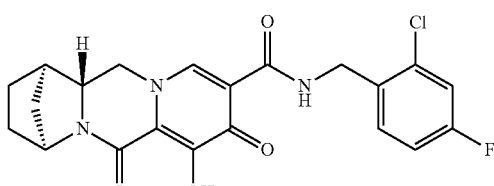

68

Compound 68 was prepared in a similar manner to compound 60 using (2-chloro-4-fluorophenyl)methanamine in place of (2,3-dichlorophenyl)methanamine. $^1$H-NMR (400 MHz, Chloroform-d) δ 11.68 (s, 1H), 10.52 (s, 1H), 8.27 (s, 1H), 7.44-7.37 (m, 1H), 7.11 (dd, 1H), 6.93 (td, 1H), 4.90 (s, 1H), 4.68 (d, 2H), 4.16-4.01 (m, 1H), 3.88-3.70 (m, 2H), 2.00-1.79 (m, 4H), 1.75 (d, 1H), 1.70-1.57 (m, 2H). LCMS-ESI$^+$ (m/z): [M+H]$^+$ calculated for $C_{21}H_{20}ClFN_3O_4$: 432.10; found: 432.214.

Example 69

Preparation of Compound 69

(1R,4S,12aR)—N-(3-chloro-2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

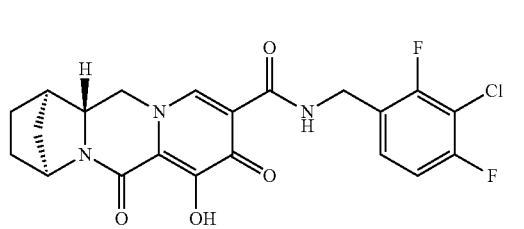

69

Compound 69 was prepared in a similar manner to compound 60 using (3-chloro-2,4-difluorophenyl)methanamine in place of (2,3-dichlorophenyl)methanamine. $^1$H-NMR (400 MHz, Chloroform-d) δ 11.71 (s, 1H), 10.48 (s, 1H), 8.26 (s, 1H), 7.27 (s, 1H), 6.92 (td, 1H), 4.90 (s, 1H), 4.66 (d, 2H), 4.08 (s, 1H), 3.91-3.69 (m, 2H), 2.01-1.79 (m, 3H), 1.75 (d, 1H), 1.71-1.44 (m, 2H). LCMS-ESI$^+$ (m/z): [M+H]$^+$ calculated for $C_{21}H_{19}ClF_2N_3O_4$: 450.10; found: 450.27.

Example 70

Preparation of Compound 70

(1R,4S,12aR)—N-(2-fluoro-3-methylbenzyl)-7-hydroxy-6,8-dioxo-1,2,3,4,6,8,12,12a-octahydro-1,4-methanodipyrido[1,2-a:1',2'-d]pyrazine-9-carboxamide

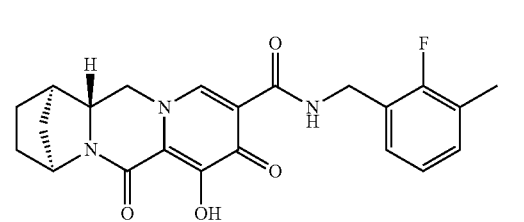

70

Compound 70 was prepared in a similar manner to compound 60 using (2-fluoro-3-methylphenyl)methanamine in place of (2,3-dichlorophenyl)methanamine. $^1$H-NMR (400 MHz, Chloroform-d) δ 11.62 (s, 1H), 10.39 (s, 1H), 8.30 (s, 1H), 7.19 (t, 1H), 7.07 (t, 1H), 6.96 (t, 1H), 4.89 (d, 1H), 4.67 (d, 2H), 4.08 (s, 1H), 3.88-3.67 (m, 2H), 2.26 (d, 3H), 1.97-1.79 (m, 3H), 1.78-1.39 (m, 3H). LCMS-ESI$^+$ (m/z): [M+H]$^+$ calculated for $C_{22}H_{23}FN_3O_4$: 412.16; found: 412.26.

Example 71

Preparation of Compound 71

(1R,4S,12aR)—N-(3,6-dichloro-2-fluorobenzyl)-7-hydroxy-6,8-dioxo-1,2,3,4,6,8,12,12a-octahydro-1,4-methanodipyrido[1,2-a:1',2'-d]pyrazine-9-carboxamide

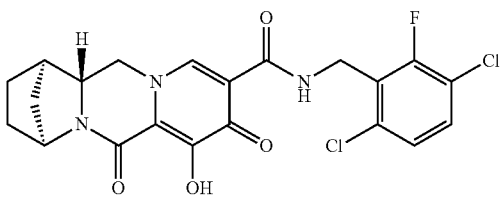

Compound 71 was prepared in a similar manner to compound 60 using (3,6-dichloro-2-fluorophenyl)methanamine in place of (2,3-dichlorophenyl)methanamine. $^1$H-NMR (400 MHz, Chloroform-d) δ 11.62 (s, 1H), 10.47 (t, 1H), 8.29 (s, 1H), 7.13 (dd, 1H), 4.88 (s, 1H), 4.85-4.73 (m, 2H), 4.09 (d, 1H), 3.88-3.68 (m, 2H), 1.99-1.53 (m, 8H). LCMS-ESI$^+$ (m/z): [M+H]$^+$ calculated for $C_{21}H_{19}Cl_2FN_3O_4$: 466.07; found: 466.257.

Example 72

Preparation of Compound 72

(1R,4S,12aR)—N-(3-chlorobenzyl)-7-hydroxy-6,8-dioxo-1,2,3,4,6,8,12,12a-octahydro-1,4-methanodipyrido[1,2-a:1',2'-d]pyrazine-9-carboxamide

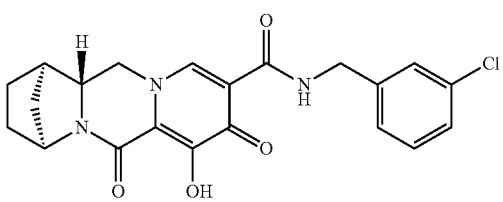

Compound 72 was prepared in a similar manner to compound 60 using (3-chlorophenyl)methanamine in place of (2,3-dichlorophenyl)methanamine. $^1$H-NMR (400 MHz, DMSO-d6) δ 11.75 (s, 1H), 10.44 (t, 1H), 8.38 (s, 1H), 7.42-7.22 (m, 4H), 4.68 (s, 1H), 4.54 (d, 2H), 4.48 (dd, 1H), 3.97 (t, 1H), 3.81 (dd, 1H), 2.58 (s, 1H), 1.87-1.69 (m, 3H), 1.68-1.51 (m, 2H), 1.46 (d, 1H). LCMS-ESI$^+$ (m/z): [M+H]$^+$ calculated for $C_{21}H_{21}ClN_3O_4$: 414.11; found: 414.21.

Example 73

Preparation of Compound 73

(1R,4S,12aR)—N-(3-chloro-2,6-difluorobenzyl)-7-hydroxy-6,8-dioxo-1,2,3,4,6,8,12,12a-octahydro-1,4-methanodipyrido[1,2-a:1',2'-d]pyrazine-9-carboxamide

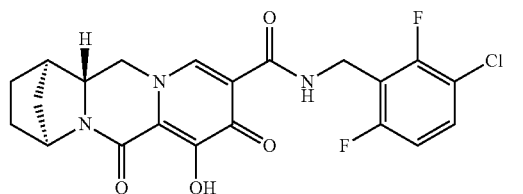

Compound 73 was prepared in a similar manner to compound 60 using (3-chloro-2,6-difluorophenyl)methanamine in place of (2,3-dichlorophenyl)methanamine. $^1$H-NMR (400 MHz, DMSO-d6) δ 11.71 (s, 1H), 10.46 (t, 1H), 8.34 (s, 1H), 7.60 (td, 1H), 7.19 (td, 1H), 4.67 (s, 1H), 4.62 (d, 2H), 4.44 (dd, 1H), 3.95 (t, 1H), 3.78 (dd, 1H), 2.57 (s, 1H), 1.86-1.68 (m, 3H), 1.67-1.49 (m, 2H), 1.45 (d, 1H). LCMS-ESI$^+$ (m/z): [M+H]$^+$ calculated for $C_{21}H_{19}ClF_2N_3O_4$: 450.10; found: 450.16.

Example 74

Preparation of Compound 74

(1R,4S,12aR)—N-(2-fluoro-3-(trifluoromethyl)benzyl)-7-hydroxy-6,8-dioxo-1,2,3,4,6,8,12,12a-octahydro-1,4-methanodipyrido[1,2-a:1',2'-d]pyrazine-9-carboxamide

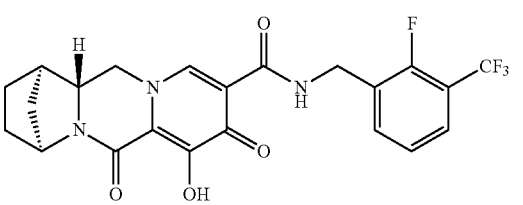

Compound 74 was prepared in a similar manner to compound 60 using (2-fluoro-3-(trifluoromethyl)phenyl)methanamine in place of (2,3-dichlorophenyl)methanamine. $^1$H-NMR (400 MHz, DMSO-d6) δ 11.76 (s, 1H), 10.48 (t, 1H), 8.36 (s, 1H), 7.68 (q, 2H), 7.38 (t, 1H), 4.68 (s, 1H), 4.65 (d, 2H), 4.47 (dd, 1H), 3.96 (t, 1H), 3.80 (dd, 1H), 2.57 (s, 1H), 1.88-1.69 (m, 3H), 1.67-1.50 (m, 2H), 1.45 (d, 1H). LCMS-ESI$^+$ (m/z): [M+H]$^+$ calculated for $C_{22}H_{20}F_4N_3O_4$: 466.13; found: 466.142.

Example 75

Preparation of Compound 75

(1R,4S,12aR)—N-(3-chloro-4-fluorobenzyl)-7-hydroxy-6,8-dioxo-1,2,3,4,6,8,12,12a-octahydro-1,4-methanodipyrido[1,2-a:1',2'-d]pyrazine-9-carboxamide

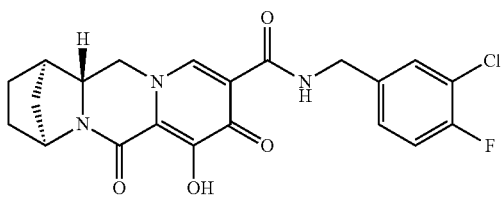

Compound 75 was prepared in a similar manner to compound 60 using (3-chloro-4-fluorophenyl)methanamine in place of (2,3-dichlorophenyl)methanamine. $^1$H-NMR (400 MHz, DMSO-d6) δ 11.75 (s, 1H), 10.43 (t, 1H), 8.38 (s, 1H), 7.51 (dd, 1H), 7.42-7.28 (m, 2H), 4.68 (s, 1H), 4.51 (d, 2H), 4.47 (dd, 1H), 3.97 (t, 1H), 3.80 (dd, 1H), 2.58 (s, 1H), 1.86-1.68 (m, 3H), 1.68-1.52 (m, 2H), 1.46 (d, 1H). LCMS-ESI$^+$ (m/z): [M+H]$^+$ calculated for $C_{21}H_{20}ClFN_3O_4$: 432.10; found: 432.159.

Example 76

Preparation of Compound 76

(1R,4S,12aR)—N-((3,5-difluoropyridin-2-yl)methyl)-7-hydroxy-6,8-dioxo-1,2,3,4,6,8,12,12a-octahydro-1,4-methanodipyrido[1,2-a:1',2'-d]pyrazine-9-carboxamide

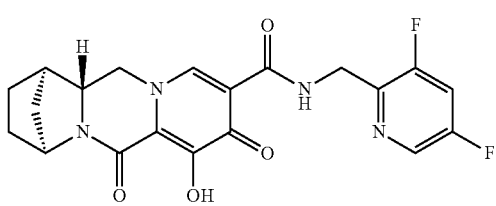

Compound 76 was prepared in a similar manner to compound 60 using (3,5-difluoropyridin-2-yl)methanamine in place of (2,3-dichlorophenyl)methanamine. $^1$H-NMR (400 MHz, Chloroform-d) δ 10.80 (s, 1H), 8.81 (s, 1H), 8.33 (d, 1H), 7.20 (td, 1H), 4.90 (s, 1H), 4.82 (s, 2H), 4.28 (d, 1H), 3.92-3.75 (m, 2H), 3.48 (s, 2H), 1.98-1.80 (m, 3H), 1.77 (d, 1H), 1.71-1.58 (m, 2H). LCMS-ESI$^+$ (m/z): [M+H]$^+$ calculated for $C_{20}H_{19}F_2N_4O_4$: 417.13; found: 417.189.

Example 77

Preparation of Compound 77

(1R,4S,12aR)-7-hydroxy-6,8-dioxo-N—((R)-1-(2,4,6-trifluorophenyl)ethyl)-1,2,3,4,6,8,12,12a-octahydro-1,4-methanodipyrido[1,2-a:1,2'-d]pyrazine-9-carboxamide

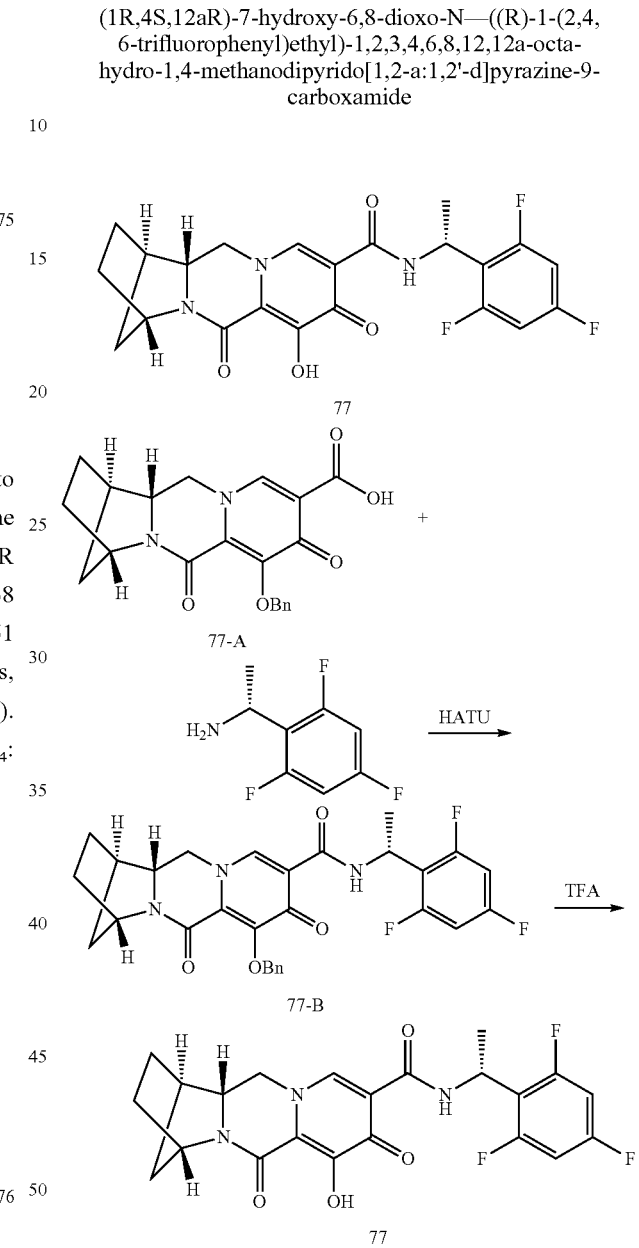

Step 1

A 50-mL round bottom flask was charged with 77-A (0.15 g, 0.39 mmol), (R)-1-(2,4,6-trifluorophenyl)ethanamine (0.14 g, 0.78 mmol), N,N-diisopropylethylamine (DIPEA) (0.25 g, 1.97 mmol) and HATU (0.29 g, 0.79 mmol) in DCM (10 ml). The reaction mixture was stirred at room temperature for 1 h. The reaction mixture was concentrated down, re-dissolved in EtOAc (50 mL), washed with saturated NaHCO$_3$ (2×), saturated NH$_4$Cl and dried over Na$_2$SO$_4$. After concentration, the crude was purified by column chromatography on silica gel with hexane-EtOAc to obtain 77-B as a white solid. LCMS-ESI$^+$ (m/z): [M+H]$^+$ found: 538.

Step 2

A 50-mL round bottom flask was charged with 77-B (0.20 g, 0.37 mmol) in TFA (2 mL). The reaction mixture was stirred at room temperature for 30 min. The solution was concentrated and the residue was purified by flash chromatography using EtOAc-20% MeOH in EtOAc as eluents to afford compound 77. $^1$H-NMR (400 MHz, Chloroform-d) δ 10.67 (d, J=8.2 Hz, 1H), 8.22 (s, 1H), 6.61 (t, J=8.4 Hz, 2H), 5.60 (dd, J=8.1, 6.9 Hz, 1H), 4.85 (s, 1H), 3.82 (t, J=12.2 Hz, 1H), 3.71 (dd, J=12.4, 3.4 Hz, 1H), 2.75-2.55 (m, 3H), 1.97-1.57 (m, 9H). $^{19}$F-NMR (376 MHz, Chloroform-d) δ −109.65−−111.29 (m), −111.76−−113.09 (m). LCMS-ESI$^+$ (m/z): [M+H]$^+$ found: 448.

Example 78

Preparation of Compound 78

(2R,13aR)-8-hydroxy-7,9-dioxo-N—((R)-1-(2,4,6-trifluorophenyl)ethyl)-2,3,4,5,7,9,13,13a-octahydro-2,5-methanopyrido[1',2':4,5]pyrazino[2,1-b][1,3]oxazepine-10-carboxamide

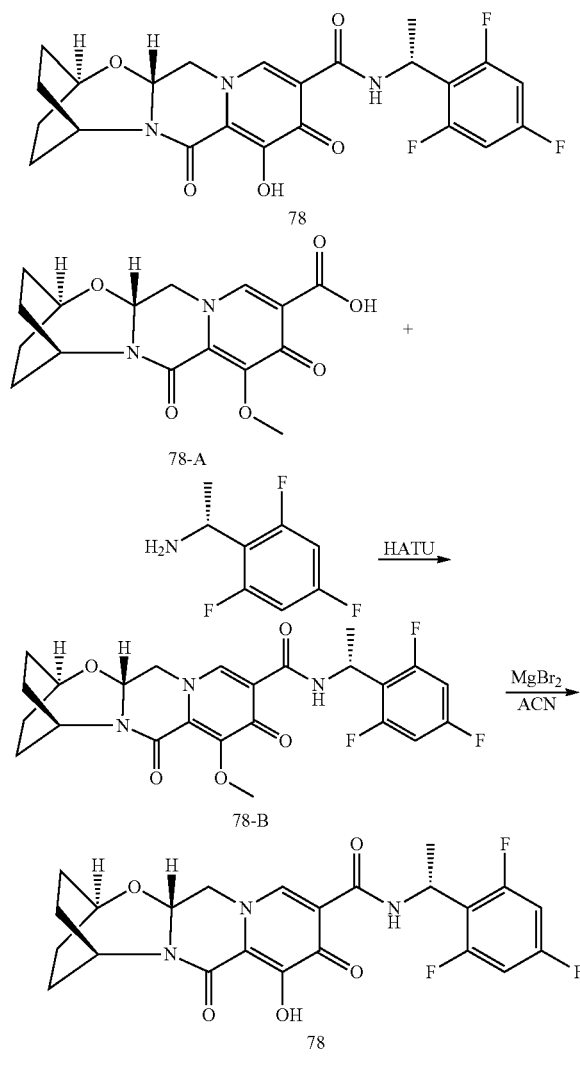

Step 1

A 50-mL round bottom flask was charged with 78-A (0.30 g, 0.94 mmol), (R)-1-(2,4,6-trifluorophenyl) ethanamine (0.39 g, 1.87 mmol), N,N-diisopropylethylamine (DIPEA) (0.61 g, 4.87 mmol) and HATU (0.71 g, 1.87 mmol) in DCM (10 ml). The reaction mixture was stirred at room temperature for 1 hour. The reaction mixture was concentrated down, re-dissolved in EtOAc (50 mL), washed with saturated NaHCO$_3$ (2×), saturated NH$_4$Cl and dried over Na$_2$SO$_4$. After concentration, the crude was purified by column chromatography on silica gel with hexane-EtOAc to obtain 78-B as a white solid. LCMS-ESI$^+$ (m/z): [M+H]$^+$; found: 478.

Step 2

A 50-mL round bottom flask was charged with 78-B (0.4 g, 0.84 mmol) and magnesium bromide (0.4 g, 2.2 mmol) in acetonitrile (5 mL). The reaction mixture was heated to 50° C. After 10 minutes, the reaction mixture was cooled to 0° C. and 1 N hydrochloric acid (4 mL) was added in. More water (~5 mL) was added and the solid was filtrated and washed with water and dried to afford compound 78. $^1$H-NMR (400 MHz, Chloroform-d) δ 12.30 (s, 1H), 10.59 (d, J=8.3 Hz, 1H), 8.21 (s, 1H), 6.60 (t, J=8.4 Hz, 2H), 5.59 (t, J=7.4 Hz, 1H), 5.37 (dd, J=9.4, 4.1 Hz, 1H), 5.31-5.09 (m, 1H), 4.64 (t, J=3.0 Hz, 1H), 4.20 (dd, J=12.9, 4.1 Hz, 2H), 3.96 (dd, J=12.8, 9.4 Hz, 2H), 2.21-1.85 (m, 4H), 1.71-1.43 (m, 3H). $^{19}$F-NMR (376 MHz, Chloroform-d) δ −110.37 (tt, J=8.7, 6.1 Hz), −112.19 (t, J=7.2 Hz). LCMS-ESI$^+$ (m/z): [M+H]$^+$ found: 464.

Example 79

Preparation of Compound 79

(1R,4S,12aR)-7-hydroxy-6,8-dioxo-N-(2,4,5-trifluorobenzyl)-1,2,3,4,6,8,12,12a-octahydro-1,4-methanodipyrido[1,2-a:1',2'-d]pyrazine-9-carboxamide

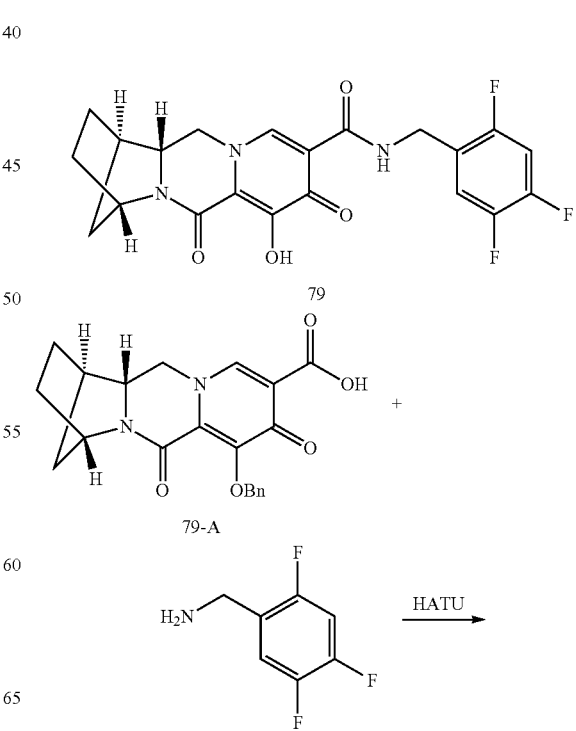

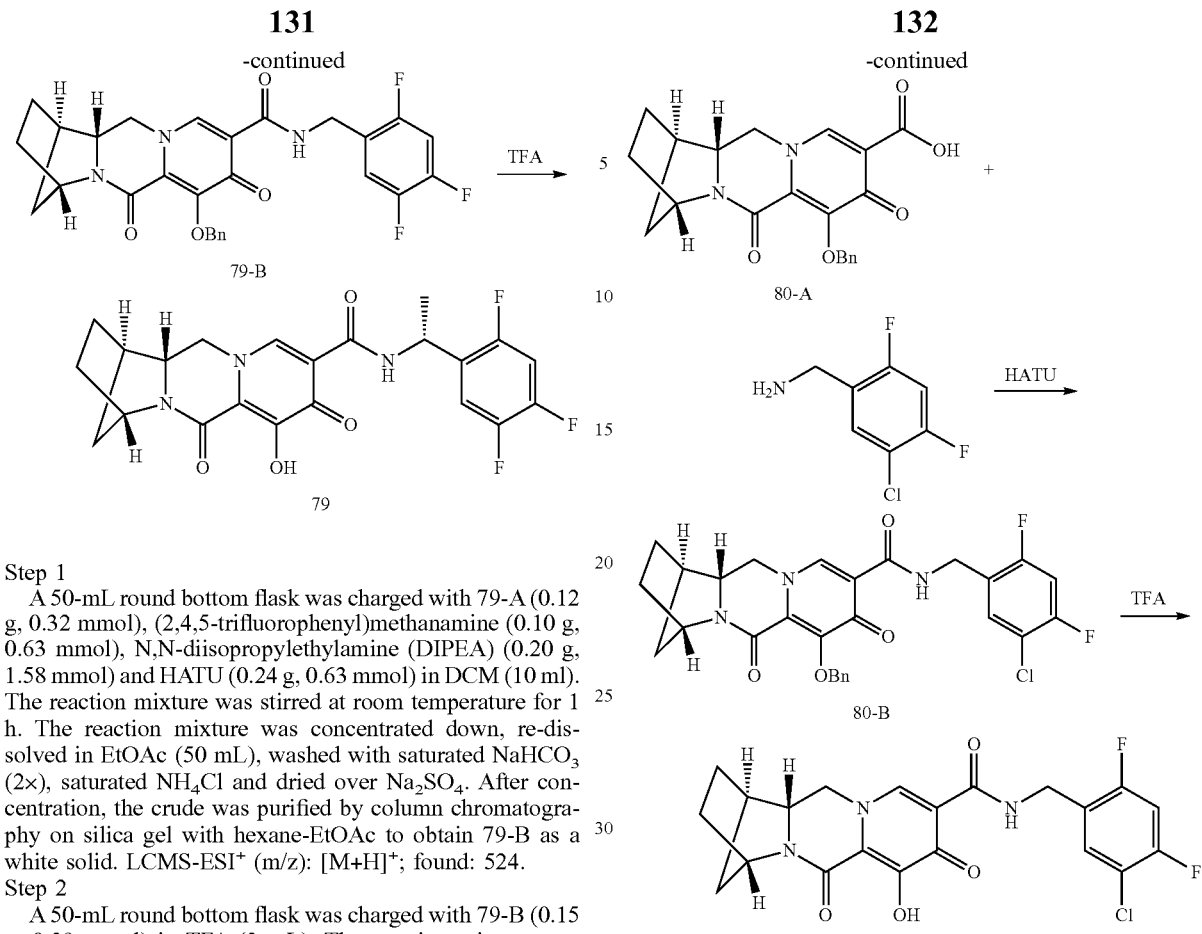

Step 1

A 50-mL round bottom flask was charged with 79-A (0.12 g, 0.32 mmol), (2,4,5-trifluorophenyl)methanamine (0.10 g, 0.63 mmol), N,N-diisopropylethylamine (DIPEA) (0.20 g, 1.58 mmol) and HATU (0.24 g, 0.63 mmol) in DCM (10 ml). The reaction mixture was stirred at room temperature for 1 h. The reaction mixture was concentrated down, re-dissolved in EtOAc (50 mL), washed with saturated NaHCO$_3$ (2×), saturated NH$_4$Cl and dried over Na$_2$SO$_4$. After concentration, the crude was purified by column chromatography on silica gel with hexane-EtOAc to obtain 79-B as a white solid. LCMS-ESI$^+$ (m/z): [M+H]$^+$; found: 524.

Step 2

A 50-mL round bottom flask was charged with 79-B (0.15 g, 0.29 mmol) in TFA (2 mL). The reaction mixture was stirred at room temperature for 30 min. The solution was concentrated and the residue was purified by flash chromatography using EtOAc-20% MeOH in EtOAc as eluents to afford compound 79. $^1$H-NMR (400 MHz, Chloroform-d) δ 11.70 (s, 1H), 10.65-10.18 (m, 1H), 8.27 (s, 1H), 7.26 (m, 1H), 6.90 (td, J=9.7, 6.4 Hz, 1H), 4.89 (s, 1H), 4.60 (d, J=6.0 Hz, 2H), 4.09 (dd, J=11.4, 2.6 Hz, 1H), 3.96-3.66 (m, 2H), 2.68 (s, 1H), 2.15-1.43 (m, 6H). $^{19}$F-NMR (376 MHz, Chloroform-d) δ 120.53--120.85 (m), −134.68--136.79 (m), −142.26--144.11 (m). LCMS-ESI$^+$ (m/z): [M+H]$^+$ found: 434.

Example 80

Preparation of Compound 80

(1R,4S,12aR)—N-(5-chloro-2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide

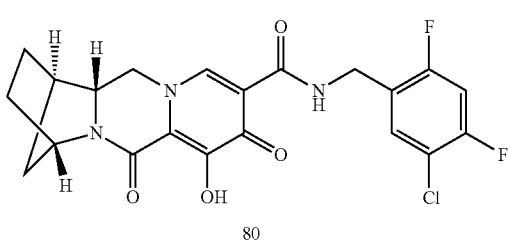

Step 1

A 50-mL round bottom flask was charged with 80-A (0.12 g, 0.32 mmol), (5-chloro-2,4-difluorophenyl)methanamine (0.11 g, 0.63 mmol), N,N-diisopropylethylamine (DIPEA) (0.20 g, 1.58 mmol) and HATU (0.24 g, 0.63 mmol) in DCM (10 ml). The reaction mixture was stirred at room temperature for 1 h. The reaction mixture was concentrated down, re-dissolved in EtOAc (50 mL), washed with saturated NaHCO$_3$ (2×), saturated NH$_4$Cl and dried over Na$_2$SO$_4$. After concentration, the crude was purified by column chromatography on silica gel with hexane-EtOAc to obtain 80-B as a white solid. LCMS-ESI$^+$ (m/z): [M+H]$^+$; found: 541.

Step 2

A 50-mL round bottom flask was charged with 80-B (0.14 g, 0.26 mmol) in TFA (2 mL). The reaction mixture was stirred at room temperature for 30 minutes. The solution was concentrated and the residue was purified by flash chromatography using EtOAc-20% MeOH in EtOAc as eluents to afford compound 80. $^1$H-NMR (400 MHz, Chloroform-d) δ 10.46 (s, 1H), 8.27 (s, 1H), 7.40 (t, J=7.8 Hz, 1H), 6.89 (t, J=9.1 Hz, 1H), 4.90 (s, 1H), 4.78-4.48 (m, 2H), 4.08 (dd, J=11.3, 2.5 Hz, 1H), 3.95-3.63 (m, 2H), 2.68 (s, 1H), 2.22-1.51 (m, 7H). $^{19}$F-NMR (376 MHz, Chloroform-d) δ −113.37 (q, J=8.1 Hz), −116.37 (q, J=8.0 Hz). LCMS-ESI$^+$ (m/z): [M+H]$^+$ found: 451.

Example 81

Preparation of Compound 81

(1R,3S,4S,12aS)-3-fluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

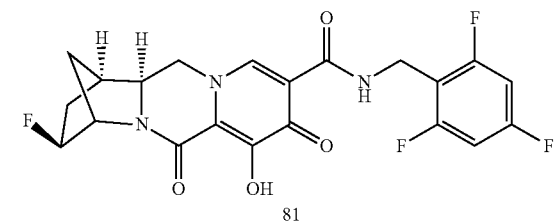

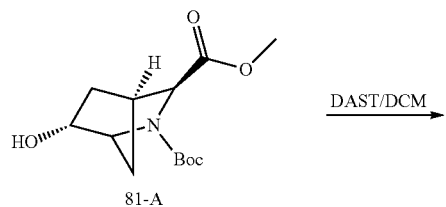

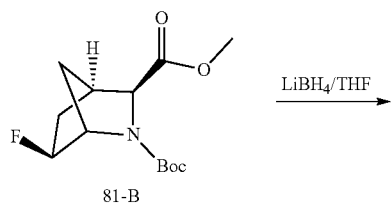

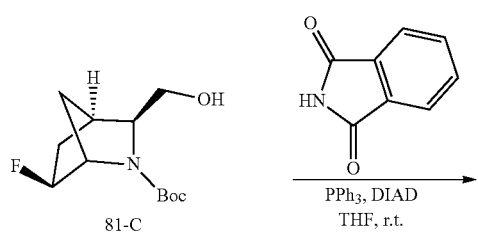

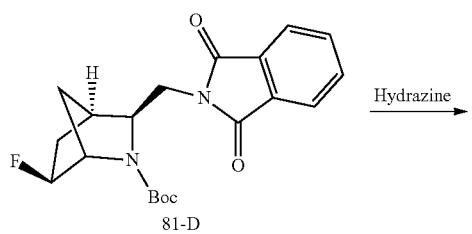

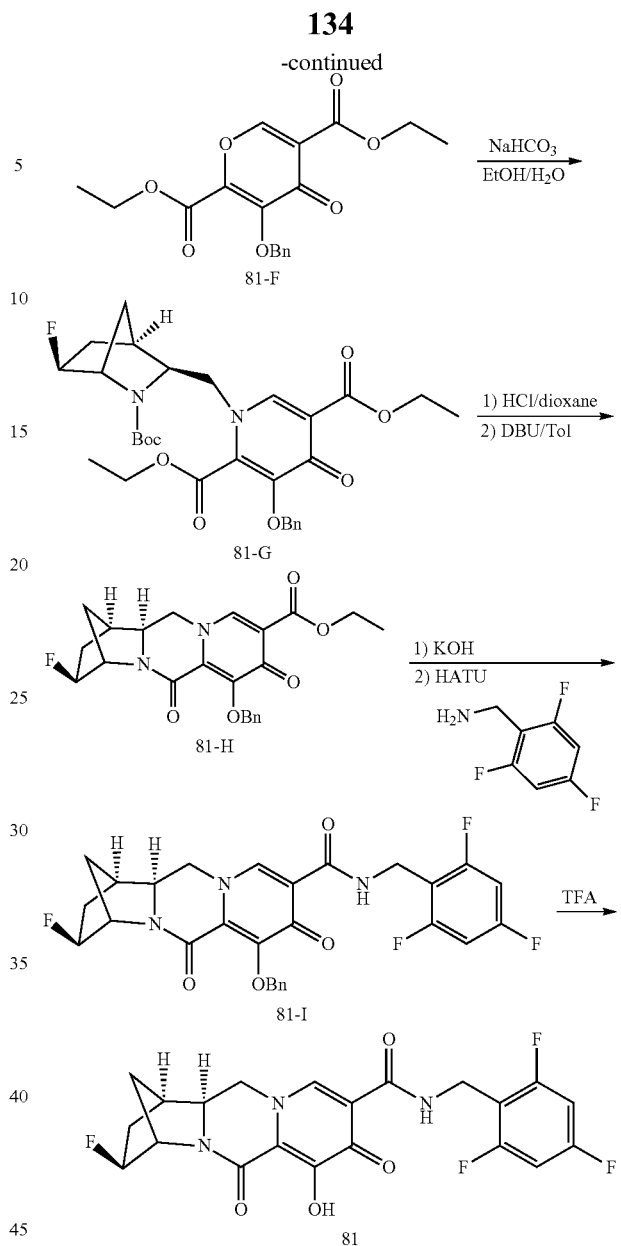

Step 1

A 100-mL round bottom flask was charged with 81-A (1.0 g, 3.7 mmol) in DCM (10 mL). The reaction mixture was cooled to 0° C. Diethylaminosulfur trifluoride (DAST) (0.58 mL, 4.1 mmol) was slowly added in. Then the reaction mixture was stirred at room temperature for one hour. The mixture was cooled back to 0° C. Saturated NaHCO$_3$ (5 mL) was added dropwise to quench the reaction. Then the reaction mixture was diluted with EtOAc (100 mL), washed with sat. NaHCO$_3$, brine, and dried over Na$_2$SO$_4$. After concentration, the residue was purified by flash chromatography using hexanes-EtOAc as eluents to afford 81-B. LCMS-ESI$^+$ (m/z): [M+H]$^+$ found: 274.

Step 2

A 100-mL round bottom flask was charged with 81-B (0.8 g, 3.0 mmol) in THF (10 mL). The reaction mixture was stirred at −78° C. 2.0 M LiBH$_4$ in THF (3.2 mL, 6.4 mmol) was slowly added in. Then the reaction mixture was warmed up and stirred at room temperature for 3 hours. Then the reaction mixture was diluted with EtOAc (100 mL) and treated slowly with water (H₂ evolution). After the two phases were separated, the aqueous fraction was extracted with EtOAc and the two organic fractions were combined, washed with water, and dried over Na₂SO₄. After concentration, the residue was purified by flash chromatography using hexanes-EtOAc as eluents to afford 81-C. LCMS-ESI⁺ (m/z): [M+H]⁺ found: 246.

Step 3

A 100-mL round bottom flask was charged with 81-C (0.57 g, 2.3 mmol), triphenylphosphine (1.3 g, 5.1 mmol) and phthalimide (0.55 g, 3.7 mmol) in THF (15 mL). Then the reaction mixture was cooled to 0° C. with stirring. Diisopropyl azodicarboxylate (DIAD) (1.0 mL, 5.1 mmol) was slowly added to the reaction mixture. The reaction mixture was stirred at room temperature for overnight. After concentration, the residue was purified by flash chromatography using hexanes-EtOAc as eluents to afford 81-D. LCMS-ESI⁺ (m/z): [M+H]⁺ found: 375.

Step 4

To a solution of 81-D (0.8 g, 2.1 mmol) EtOH (40 mL) was added hydrazine monohydrate (0.6 mL). The reaction mixture was heated to 70° C. with stirring for 3 hours. After filtration to remove the solid, the filtrate was concentrated to afford 81-E. LCMS-ESI⁺ (m/z): [M+H]⁺ found: 245.

Step 5

A 100-mL round bottom flask was charged with 81-E (0.49 g, 2.0 mmol) and 81-F (0.7 g, 2.0 mmol) in ethanol (7 mL). Sodium bicarbonate (0.34 g, 4.0 mmol) in water (7 mL) was added to the reaction mixture. Then the reaction mixture was stirred at room temperature for overnight. The mixture was diluted with EtOAc (50 mL) and washed with water (2×). The aqueous fractions were extracted with EtOAc (1×), and the organic fractions were combined, dried (Na₂SO₄), and concentrated. The crude 81-G was used for next step without further purification. LCMS-ESI⁺ (m/z): [M+H]⁺ found: 573.

Step 6

A 100-mL round bottom flask was charged with 81-G (1.1 g, 1.9 mmol) in 4 N HCl/dioxane (11 mL). Then the reaction mixture was stirred at room temperature for 1 hour. After concentration, 1.0 g intermediate was obtained. The intermediate and DBU (1.3 g, 8.8 mmol) were dissolved in toluene (10 mL). The reaction mixture was heated to 110° C. with stirring for 1 hour. After concentration, the residue was purified by flash chromatography using hexanes-EtOAc as eluents to afford 81-H. LCMS-ESI⁺ (m/z): [M+H]⁺ found: 413.

Step 7

A 100-mL round bottom flask was charged with 81-H (0.56 g, 1.4 mmol) in THF (5 mL) and MeOH (5 mL). 1 N KOH (4 mL) was added to the reaction mixture. Then the reaction mixture was stirred at room temperature for 1 hour. The reaction mixture was acidified by adding 1 N HCl (4 mL). After concentration, the residue was co-evaporated with toluene (3×). Half of the crude acid, 2,4,6-trifluobenzylamine (0.2 g, 1.3 mmol), N,N-diisopropylethylamine (DIPEA) (0.41 g, 3.1 mmol) and HATU (0.48 g, 1.25 mmol) were dissolved in DMF (10 mL). The reaction mixture was stirred at room temperature for 2 hours. The mixture was diluted with EtOAc (100 mL) and washed with saturated NaHCO₃ (2×), saturated NH₄Cl (2×) and dried over Na₂SO₄. After concentration, the crude was purified by column chromatography on silica gel with hexane-EtOAc to afford 81-I. LCMS-ESI⁺ (m/z): [M+H]⁺ found: 542.

Step 8

A 50-mL round bottom flask was charged with 81-I (0.31 g, 0.58 mmol) in TFA (3 mL). The reaction mixture was stirred at room temperature for 30 minutes. After concentration, the crude was purified by column chromatography on silica gel with EtOAc-MeOH to afford compound 81. ¹H-NMR (400 MHz, Chloroform-d) δ 10.29 (s, 1H), 8.31 (s, 1H), 6.65 (dd, J=8.7, 7.5 Hz, 2H), 5.05-4.75 (m, 2H), 4.65 (d, J=5.6 Hz, 2H), 4.11 (d, J=12.2 Hz, 1H), 3.83 (t, J=12.3 Hz, 1H), 3.56 (dd, J=12.3, 3.3 Hz, 1H), 2.77 (s, 1H), 2.25-1.97 (m, 2H), 1.95 (d, J=11.0 Hz, 2H), 1.77 (d, J=11.2 Hz, 1H). ¹⁹F-NMR (376 MHz, Chloroform-d) δ −108.98 (t, J=8.2 Hz), −112.03 (t, J=7.2 Hz), −168.00. LCMS-ESI⁺ (m/z): found: 452.

Example 82

Preparation of Compound 82

(1S,3R,4R,12aR)-3-fluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

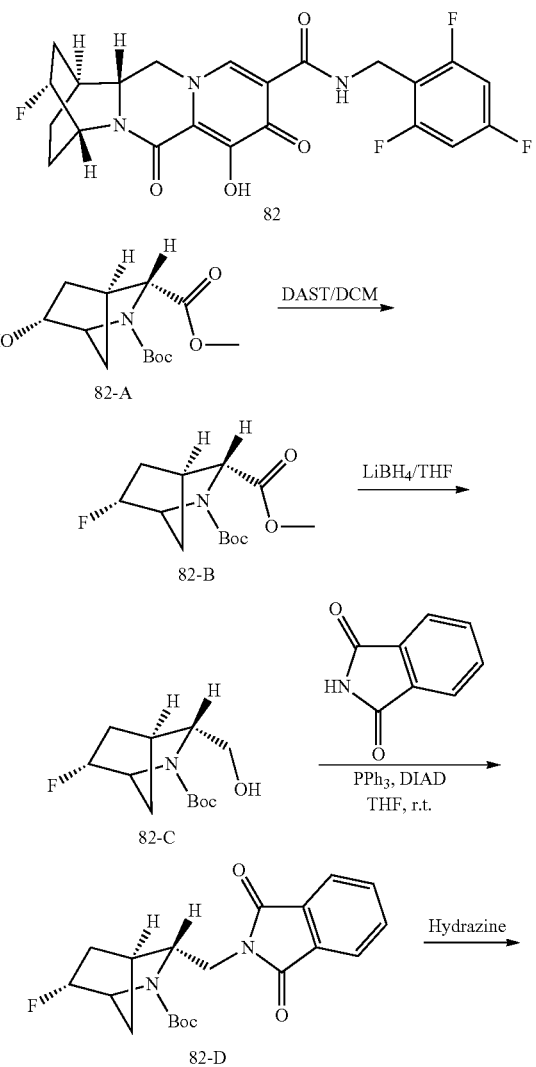

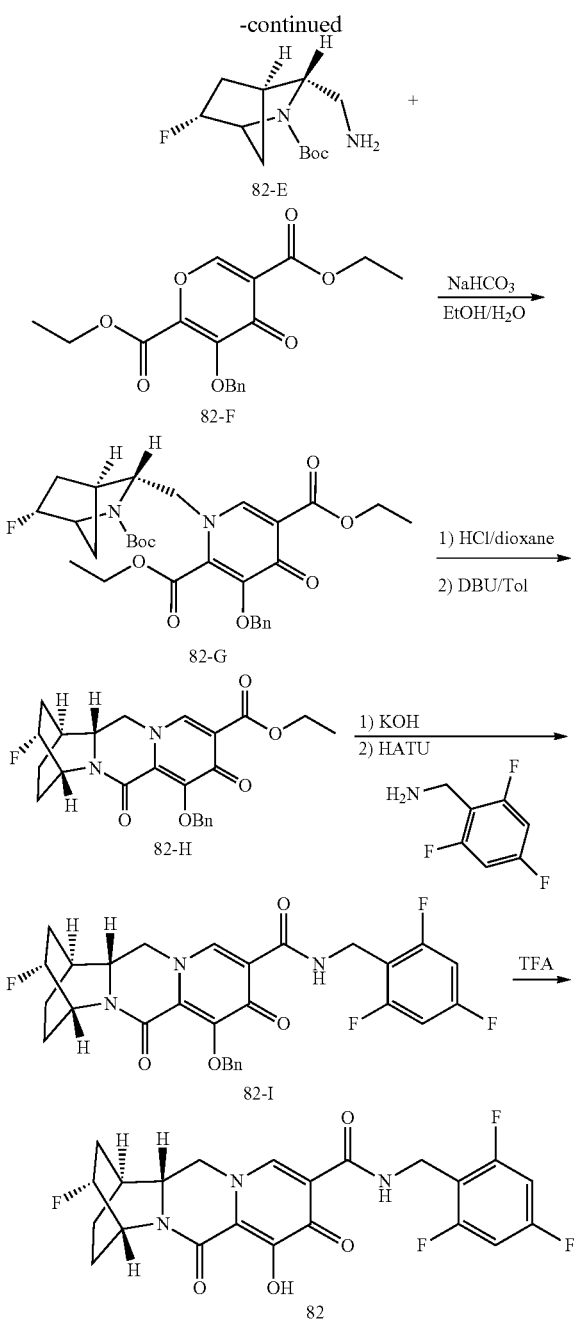

Step 1

A 100-mL round bottom flask was charged with 82-A (0.6 g, 2.1 mmol) in DCM (6 mL). The reaction mixture was cooled to 0° C. DAST (0.35 mL, 3.0 mmol) was slowly added in. Then the reaction mixture was stirred at room temperature for one hour. The mixture was cooled back to 0° C. Saturated NaHCO$_3$ (5 mL) was added drop wise to quench the reaction. Then the reaction mixture was diluted with EtOAc (100 mL), washed with sat. NaHCO$_3$, brine, and dried over Na$_2$SO$_4$. After concentration, the residue was purified by flash chromatography using hexanes-EtOAc as eluents to afford 82-B. LCMS-ESI$^+$ (m/z): [M+H]$^+$ found: 274.

Step 2

A 100-mL round bottom flask was charged with 82-B (0.4 g, 1.5 mmol) in THF (10 mL). The reaction mixture was stirred at −78° C. 2.0 M LiBH$_4$ in THF (1.6 mL, 3.2 mmol) was slowly added in. Then the reaction mixture was warmed up and stirred at room temperature for 3 hours. Then the reaction mixture was diluted with EtOAc (100 mL) and added water slowly (H$_2$ evolution). After the two phases were separated, the aqueous fraction was extracted with EtOAc and the two organic fractions were combined, washed with water and dried over Na$_2$SO$_4$. After concentration, the residue was purified by flash chromatography using hexanes-EtOAc as eluents to afford 82-C. LCMS-ESI$^+$ (m/z): [M+H]$^+$ found: 246.

Step 3

A 100-mL round bottom flask was charged with 82-C (0.25 g, 1.0 mmol), triphenylphosphine (0.59 g, 2.2 mmol) and phthalimide (0.24 g, 1.6 mmol) in THF (10 mL). Then the reaction mixture was cooled to 0° C. with stirring. DIAD (0.44 mL, 2.2 mmol) was slowly added to the reaction mixture. The reaction mixture was stirred at room temperature for overnight. After concentration, the residue was purified by flash chromatography using hexanes-EtOAc as eluents to afford 82-D. LCMS-ESI$^+$ (m/z): [M+H]$^+$ found: 375.

Step 4

To a solution of 82-D (0.35 g, 0.9 mmol) EtOH (20 mL) was added hydrazine monohydrate (0.3 mL). The reaction mixture was heated to 70° C. with stirring for 3 hours. After filtration to remove the solid, the filtrate was concentrated to afford 82-E. LCMS-ESI$^+$ (m/z): [M+H]$^+$ found: 245.

Step 5

A 100-mL round bottom flask was charged with 82-E (0.21 g, 0.87 mmol) and 82-F (0.3 g, 0.87 mmol) in ethanol (7 mL). Sodium bicarbonate (0.15 g, 1.7 mmol) in water (7 mL) was added to the reaction mixture. Then the reaction mixture was stirred at room temperature for overnight. The mixture was diluted with EtOAc (50 mL) and washed with water (2×). The aqueous fractions were extracted with EtOAc, and the organic fractions were combined, dried (Na$_2$SO$_4$), and concentrated. The crude 82-G was used for next step without further purification. LCMS-ESI$^+$ (m/z): [M+H]$^+$ found: 573.

Step 6

A 100-mL round bottom flask was charged with 82-G (0.49 g, 0.86 mmol) in 4 N HCl/dioxane (5 mL). Then the reaction mixture was stirred at room temperature for 1 hour. After concentration, 0.4 g intermediate was obtained. The intermediate and DBU (0.6 g, 4.0 mmol) were dissolved in toluene (10 mL). The reaction mixture was heated to 110° C. with stirring for 1 hour. After concentration, the residue was purified by flash chromatography using hexanes-EtOAc as eluents to afford 82-H. LCMS-ESI$^+$ (m/z): [M+H]$^+$ found: 413.

Step 7

A 100-mL round bottom flask was charged with 82-H (0.2 g, 0.49 mmol) in THF (5 mL) and MeOH (5 mL). 1 N KOH (1.5 mL) was added to the reaction mixture. Then the reaction mixture was stirred at room temperature for 1 hour. The reaction mixture was acidified by adding 1 N HCl (1.5 mL). After concentration, the residue was co-evaporated with toluene (3×). The crude acid, 2,4,6-trifluobenzylamine (0.15 g, 0.95 mmol), N,N-diisopropylethylamine (DIPEA) (0.31 g, 2.4 mmol) and HATU (0.36 g, 0.95 mmol) were dissolved in DCM (10 mL). The reaction mixture was stirred at room temperature for 2 hours. The mixture was diluted with EtOAc (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford 82-I. LCMS-ESI⁺ (m/z): [M+H]⁺ found: 542.

Step 8

A 50-mL round bottom flask was charged with 82-I (0.22 g, 0.41 mmol) in TFA (3 mL). The reaction mixture was stirred at room temperature for 30 minutes. After concentration, the crude was purified by column chromatography on silica gel with EtOAc-MeOH to afford compound 82. $^1$H-NMR (400 MHz, Chloroform-d) δ 10.25 (s, 1H), 8.28 (s, 1H), 6.65 (s, 2H), 5.15-4.77 (m, 2H), 4.65 (s, 2H), 4.32-3.41 (m, 2H), 2.78 (s, 1H), 1.86 (dd, J=144.8, 72.3 Hz, 6H). $^{19}$F-NMR (376 MHz, Chloroform-d) δ −108.98 (t, J=8.2 Hz), −112.03 (t, J=7.2 Hz), −168.00. LCMS-ESI⁺ (m/z): found: 452.

Example 83

Preparation of Compound 83

(1S,4R,12aS)-3,3-difluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

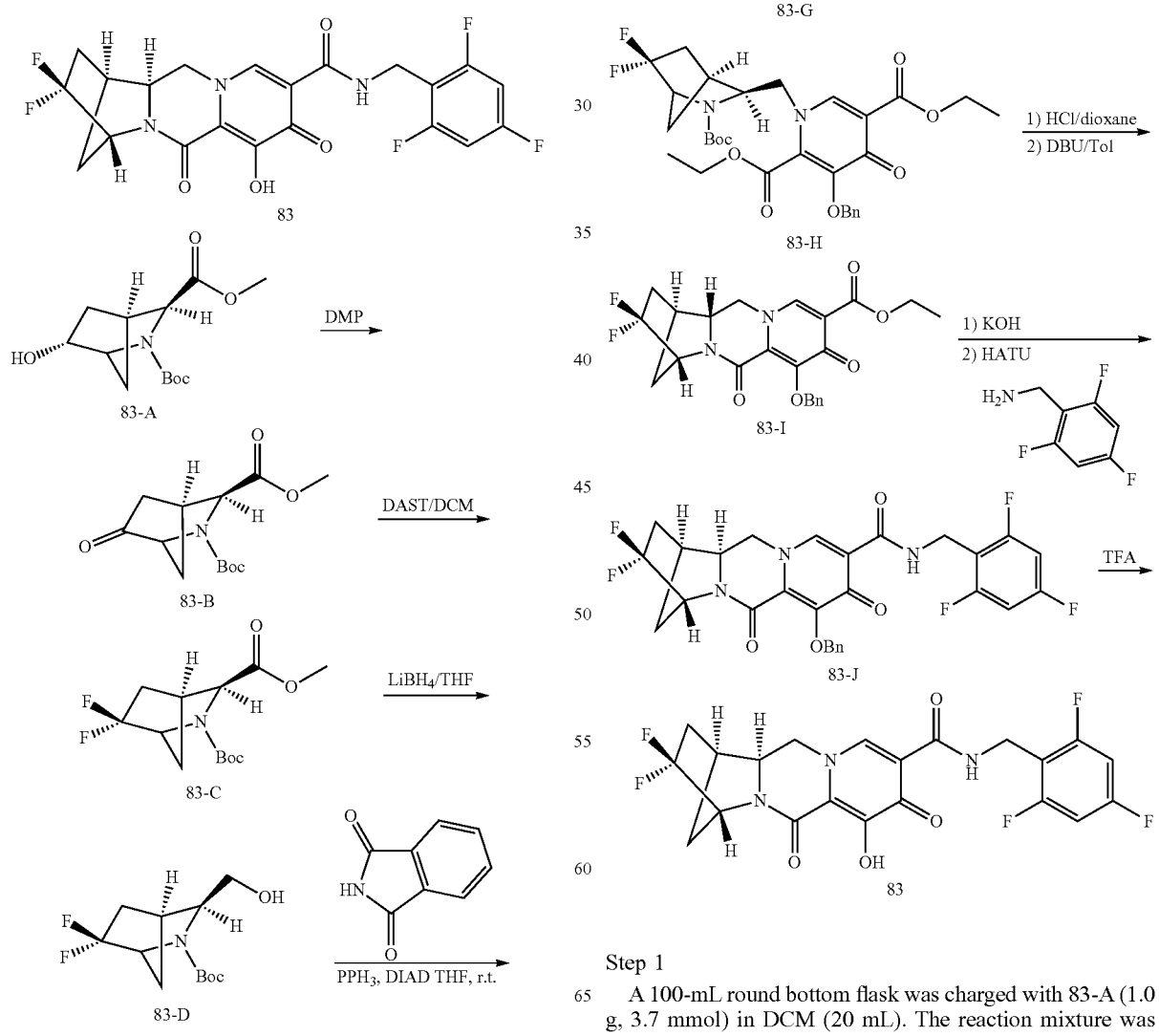

Step 1

A 100-mL round bottom flask was charged with 83-A (1.0 g, 3.7 mmol) in DCM (20 mL). The reaction mixture was cooled to 0° C. Dess-Martin periodinane (1.8 g, 4.2 mmol)

was slowly added in. Then the reaction mixture was stirred at room temperature for 3 hours. After concentration, the residue was purified by flash chromatography using hexanes-EtOAc as eluents to afford 83-B. LCMS-ESI⁺ (m/z): [M+H]⁺ found: 270.

Step 2

A 100-mL round bottom flask was charged with 83-B (0.85 g, 3.2 mmol) in DCM (15 mL). The reaction mixture was cooled to 0° C. DAST (1.5 mL, 11.3 mmol) was slowly added in. Then the reaction mixture was stirred at room temperature overnight. The mixture was cooled back to 0° C. Saturated NaHCO₃ (5 mL) was added dropwise to quench the reaction. Then the reaction mixture was diluted with EtOAc (100 mL), washed with sat. NaHCO₃, brine, and dried over Na₂SO₄. After concentration, the residue was purified by flash chromatography using hexanes-EtOAc as eluents to afford 83-C. LCMS-ESI⁺ (m/z): [M+H]⁺ found: 292.

Step 3

A 100-mL round bottom flask was charged with 83-C (0.44 g, 1.5 mmol) in THF (6 mL). The reaction mixture was stirred at −78° C. 2.0 M LiBH₄ in THF (1.6 mL, 3.2 mmol) was slowly added in. Then the reaction mixture was warmed up and stirred at room temperature for 3 hours. Then the reaction mixture was diluted with EtOAc (100 mL) and added water slowly (H₂ evolution). After the two phases were separated, the aqueous fraction was extracted with EtOAc and the two organic fractions were combined, washed with water, and dried over Na₂SO₄. After concentration, the residue was purified by flash chromatography using hexanes-EtOAc as eluents to afford 83-D. LCMS-ESI⁺ (m/z): [M+H]⁺ found: 264.

Step 4

A 100-mL round bottom flask was charged with 83-D (0.17 g, 0.65 mmol), triphenylphosphine (0.37 g, 1.4 mmol) and phthalimide (0.15 g, 1.0 mmol) in THF (10 mL). Then the reaction mixture was cooled to 0° C. with stirring. DIAD (0.28 mL, 1.4 mmol) was slowly added to the reaction mixture. The reaction mixture was stirred at room temperature for overnight. After concentration, the residue was purified by flash chromatography using hexanes-EtOAc as eluents to afford 83-E. LCMS-ESI⁺ (m/z): [M+H]⁺ found: 393.

Step 5

To a solution of 83-E (0.25 g, 0.64 mmol) EtOH (20 mL) was added hydrazine monohydrate (0.3 mL). The reaction mixture was heated to 70° C. with stirring for 3 hours. After filtration to remove the solid, the filtrate was concentrated to afford 83-F. LCMS-ESI⁺ (m/z): [M+H]⁺ found: 263.

Step 6

A 100-mL round bottom flask was charged with 83-F (0.18 g, 0.69 mmol) and 83-G (0.324 g, 0.69 mmol) in ethanol (7 mL). Sodium bicarbonate (0.12 g, 1.4 mmol) in water (7 mL) was added to the reaction mixture. Then the reaction mixture was stirred at room temperature overnight. The mixture was diluted with EtOAc (50 mL) and washed with water. The aqueous fractions were extracted with EtOAc, and the organic fractions were combined, dried (Na₂SO₄), and concentrated. The crude 83-H was used for next step without further purification. LCMS-ESI⁺ (m/z): [M+H]⁺ found: 591.

Step 7

A 100-mL round bottom flask was charged with 83-H (0.4 g, 0.68 mmol) in 4 N HCl/dioxane (3.8 mL). Then the reaction mixture was stirred at room temperature for 1 hour. After concentration, 0.35 g intermediate was obtained. The intermediate and DBU (0.51 g, 3.3 mmol) were dissolved in toluene (10 mL). The reaction mixture was heated to 110° C. with stirring for 1 hour. After concentration, the residue was purified by flash chromatography using hexanes-EtOAc as eluents to afford 83-I. LCMS-ESI⁺ (m/z): [M+H]⁺ found: 431.

Step 8

A 100-mL round bottom flask was charged with 83-I (0.2 g, 0.47 mmol) in THF (5 mL) and MeOH (5 mL). 1 N KOH (1.4 mL) was added to the reaction mixture. Then the reaction mixture was stirred at room temperature for 1 hour. The reaction mixture was acidified by adding 1 N HCl (1.4 mL). After concentration, the residue was co-evaporated with toluene (3×). The crude acid, 2,4,6-trifluobenzylamine (0.14 g, 0.91 mmol), N,N-diisopropylethylamine (DIPEA) (0.29 g, 2.2 mmol) and HATU (0.35 g, 0.91 mmol) were dissolved in DCM (10 mL). The reaction mixture was stirred at room temperature for 2 hours. The mixture was diluted with EtOAc (100 mL) and washed with saturated NaHCO₃ (2×), saturated NH₄Cl (2×) and dried over Na₂SO₄. After concentration, the crude was purified by column chromatography on silica gel with hexane-EtOAc to afford 83-J. LCMS-ESI⁺ (m/z): [M+H]⁺ found: 560.

Step 9

A 50-mL rbf was charged with 83-J (0.18 g, 0.32 mmol) in TFA (3 mL). The reaction mixture was stirred at room temperature for 30 minutes. After concentration, the crude was purified by column chromatography on silica gel with EtOAc-MeOH to afford compound 83 as a white solid. ¹H-NMR (400 MHz, Chloroform-d) δ 10.29 (d, J=6.1 Hz, 1H), 8.34 (s, 1H), 6.65 (dd, J=8.7, 7.5 Hz, 2H), 4.83 (s, 1H), 4.72-4.58 (m, 2H), 4.36-4.10 (m, 2H), 4.05 (t, J=11.5 Hz, 1H), 2.97 (d, J=4.4 Hz, 1H), 2.49-2.08 (m, 3H), 2.12-1.94 (m, 2H). ¹⁹F-NMR (376 MHz, Chloroform-d) δ −92.32 (ddd, J=225.6, 22.5, 9.1 Hz), −107.64−−109.54 (m), −112.05 (t, J=7.0 Hz), −114.67 (d, J=226.7 Hz). LCMS-ESI⁺ (m/z): found: 470.

Example 84

Preparation of Compound 84

(1S,2R,4S,12aR)-7-hydroxy-2-methyl-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

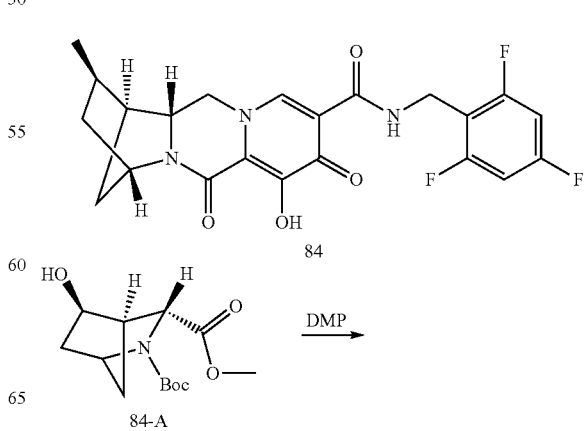

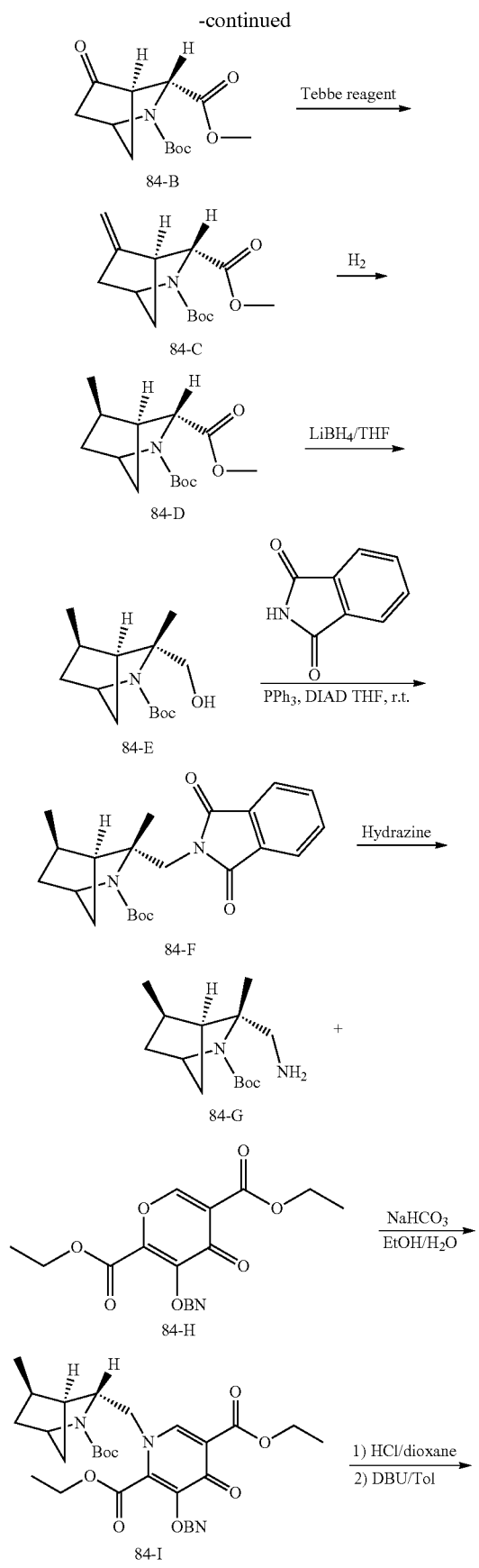

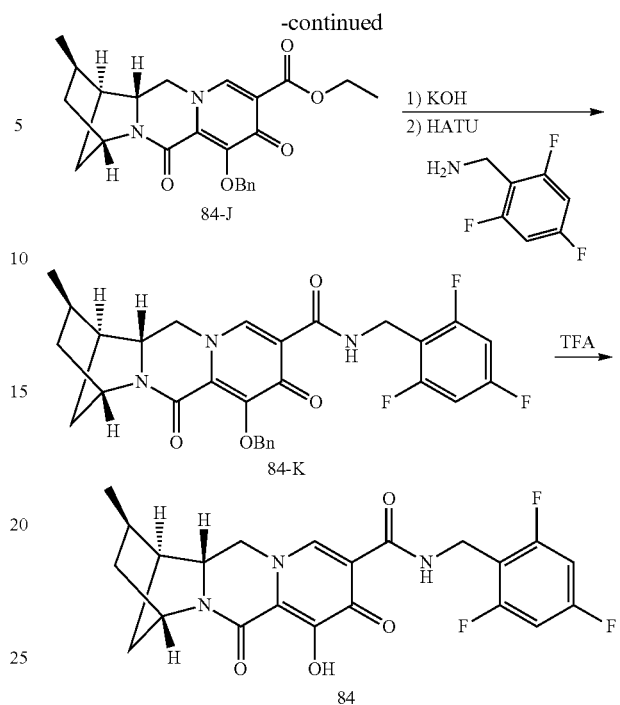

Step 1

A 100-mL round bottom flask was charged with 84-A (1.6 g, 5.9 mmol) in DCM (20 mL). The reaction mixture was cooled to 0° C. Dess-Martin periodinane (4.9 g, 11.7 mmol) was slowly added in. Then the reaction mixture was stirred at room temperature for 3 hours. After concentration, the residue was purified by flash chromatography using hexanes-EtOAc as eluents to afford 84-B. LCMS-ESI$^+$ (m/z): [M+H]$^+$ found: 270.

Step 2

A 100-mL round bottom flask was charged with 84-B (1.3 g, 4.8 mmol) in THF (30 mL). The reaction mixture was cooled to 0° C. Tebbe reagent (0.5 M in toluene, 19.4 mL, 9.7 mmol) was slowly added in. Then the reaction mixture was stirred at room temperature for 2 hours. The mixture was cooled back to 0° C. Saturated NaHCO$_3$ (5 mL) was added drop wise to quench the reaction. The reaction mixture was stirred at room temperature for another 15 minutes and filtered through celite. The filtered cake was washed with DCM (2×). The combined filtrates were concentrated in vacuum and the residue was purified by flash chromatography using hexanes-EtOAc as eluents to afford 84-C. LCMS-ESI$^+$ (m/z): [M+H]$^+$ found: 268.

Step 3

To a solution (purged with N$_2$) of 84-C (0.9 g, 3.4 mmol) in EtOH (20 mL) was added Pd/C (0.18 g). The mixture was stirred under H$_2$ for 3 hours. The mixture was filtered through celite and the filtrate was concentrated to afford 84-D. LCMS-ESI$^+$ (m/z): [M+H]$^+$ found: 270.

Step 4

A 100-mL round bottom flask was charged with 84-D (0.9 g, 3.3 mmol) in THF (6 mL). The reaction mixture was stirred at −78° C. 2.0 M LiBH$_4$ in THF (13.2 mL, 26.4 mmol) was slowly added in. Then the reaction mixture was warmed up and stirred at room temperature for 3 hours. Then the reaction mixture was diluted with EtOAc (100 mL) and added water slowly (H$_2$ evolution). After the two phases were separated, the aqueous fraction was extracted with EtOAc and the two organic fractions were combined, washed with water, and dried over Na$_2$SO$_4$. After concentration, the residue was purified by flash chromatography using hexanes-EtOAc as eluents to afford 84-E. LCMS-ESI$^+$ (m/z): [M+H]$^+$ found: 242.

Step 5

A 100-mL round bottom flask was charged with 84-E (0.4 g, 1.66 mmol), triphenylphosphine (0.96 g, 3.6 mmol) and phthalimide (0.39 g, 2.7 mmol) in THF (15 mL). Then the reaction mixture was cooled to 0° C. with stirring. DIAD (0.7 mL, 3.6 mmol) was slowly added to the reaction mixture. The reaction mixture was stirred at room temperature for overnight. After concentration, the residue was purified by flash chromatography using hexanes-EtOAc as eluents to afford 84-F. LCMS-ESI$^+$ (m/z): [M+H]$^+$ found: 371.

Step 6

To a solution of 84-F (0.55 g, 1.5 mmol) EtOH (20 mL) was added hydrazine monohydrate (0.3 mL). The reaction mixture was heated to 70° C. with stirring for 3 hours. After filtration to remove the solid, the filtrate was concentrated to afford 84-G. LCMS-ESI$^+$ (m/z): [M+H]$^+$ found: 241.

Step 7

A 100-mL round bottom flask was charged with 84-G (0.35 g, 1.4 mmol) and 84-H (0.5 g, 1.4 mmol) in ethanol (10 mL). Sodium bicarbonate (0.24 g, 2.8 mmol) in water (10 mL) was added to the reaction mixture. Then the reaction mixture was stirred at room temperature for overnight. The mixture was diluted with EtOAc (50 mL) and washed with water (2×). The aqueous fractions were extracted with EtOAc, and the organic fractions were combined, dried (Na$_2$SO$_4$), and concentrated. The crude 84-I was used for next step without further purification. LCMS-ESI$^+$ (m/z): [M+H]$^+$ found: 583.

Step 8

A 100-mL rbf was charged with 84-I (0.84 g, 1.4 mmol) in 4 N HCl/dioxane (8.2 mL). Then the reaction mixture was stirred at room temperature for 1 hour. After concentration, 0.74 g intermediate was obtained. The intermediate and DBU (1.1 g, 7.2 mmol) were dissolved in toluene (10 mL). The reaction mixture was heated to 110° C. with stirring for 1 hour. After concentration, the residue was purified by flash chromatography using hexanes-EtOAc as eluents to afford 84-J. LCMS-ESI$^+$ (m/z): [M+H]$^+$ found: 409.

Step 9

A 100-mL round bottom flask was charged with 84-J (0.4 g, 0.98 mmol) in THF (5 mL) and MeOH (5 mL). 1 N KOH (3.0 mL) was added to the reaction mixture. Then the reaction mixture was stirred at room temperature for 1 hour. The reaction mixture was acidified by adding 1 N HCl (3.0 mL). After concentration, the residue was co-evaporated with toluene (3×). The crude acid, 2,4,6-trifluobenzylamine (0.32 g, 1.96 mmol), N,N-diisopropylethylamine (DIPEA) (0.63 g, 4.9 mmol) and HATU (0.74 g, 1.9 mmol) were dissolved in DCM (10 mL). The reaction mixture was stirred at room temperature for 2 hours. The mixture was diluted with EtOAc (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford 84-K. LCMS-ESI$^+$ (m/z): [M+H]$^+$ found: 538.

Step 10

A 50-mL round bottom flask was charged with 84-K (0.5 g, 0.93 mmol) in TFA (6 mL). The reaction mixture was stirred at room temperature for 30 minutes. After concentration, the crude was purified by column chromatography on silica gel with EtOAc-MeOH to afford compound 84.

$^1$H-NMR (400 MHz, Chloroform-d) δ 10.37 (s, 1H), 8.28 (s, 1H), 6.65 (t, J=8.1 Hz, 2H), 4.80 (s, 1H), 4.77-4.52 (m, 3H), 4.08 (d, J=13.1 Hz, 1H), 3.88 (d, J=12.3 Hz, 1H), 2.47 (d, J=3.2 Hz, 1H), 2.35 (s, 1H), 2.16 (ddd, J=14.3, 11.2, 3.6 Hz, 1H), 1.93-1.57 (m, 3H), 1.29-1.19 (m, 1H), 1.17 (d, J=7.0 Hz, 3H). $^{19}$F-NMR (376 MHz, Chloroform-d) δ −109.24, −111.98. LCMS-ESI$^+$ (m/z): found: 448.

Example 85

Preparation of Compound 85

(6aS,7R,11S)-1-hydroxy-2,13-dioxo-N-(2,4,6-trifluorobenzyl)-6,6a,7,8,9,10,11,13-octahydro-2H-7,11-methanopyrido[1',2':4,5]pyrazino[1,2-a]azepine-3-carboxamide

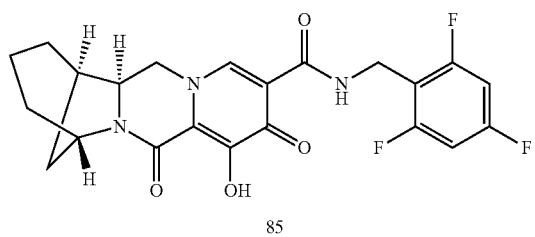

85

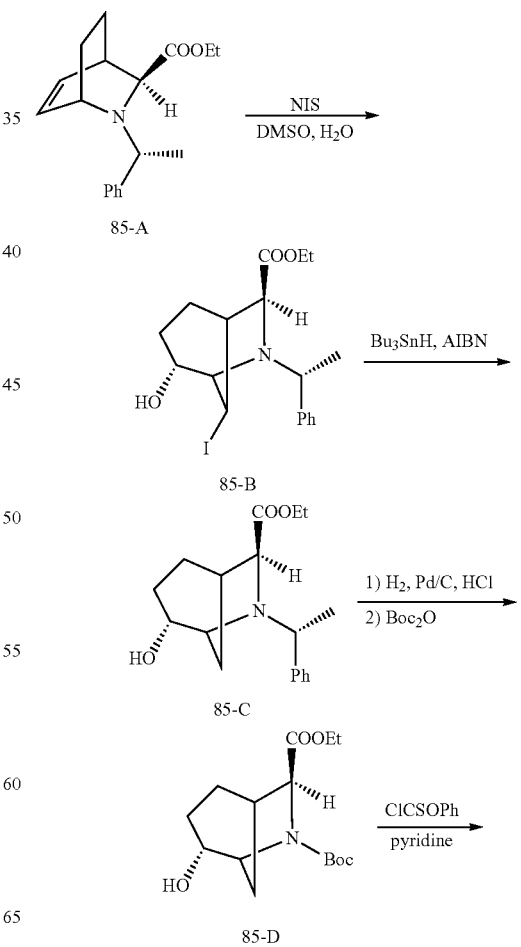

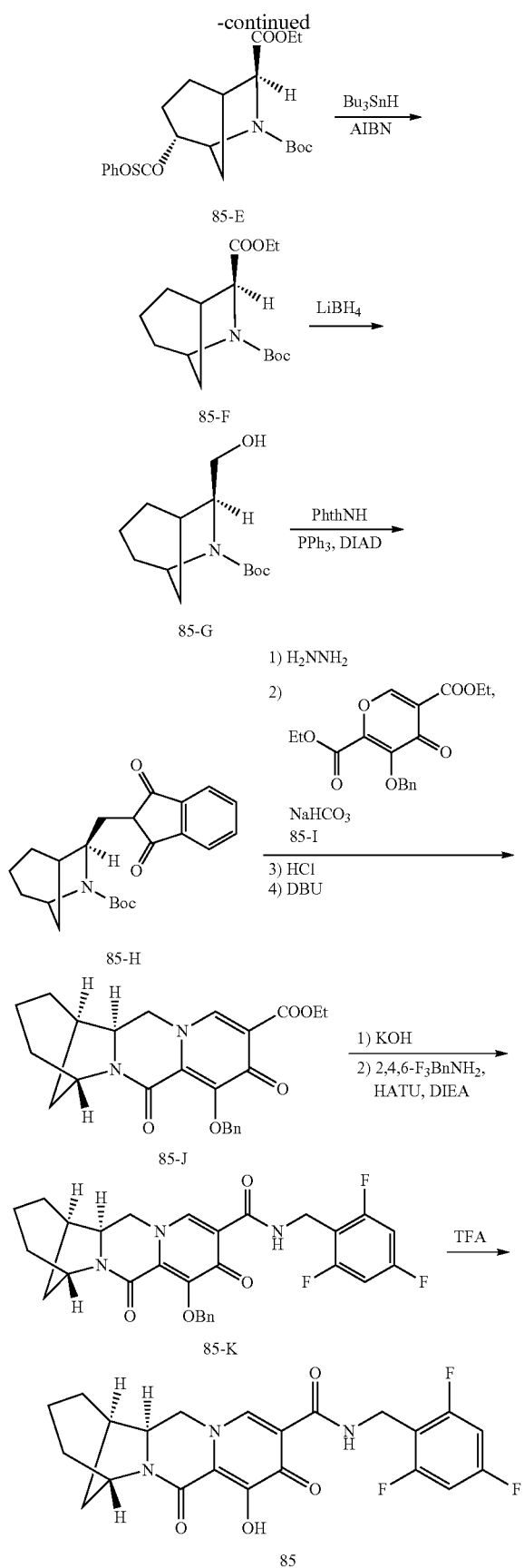

Step 1

A solution of 85-A (1100 mg, 3.855 mmol) in DMSO (6 mL) and water (0.75 mL) was stirred at room temperature as N-iodosuccinmide (885 mg, 3.934 mmol) was added. After 2 h, additional N-iodosuccinmide (88 mg, 0.391 mmol) was added and the resulting mixture was stirred at room temperature for 1.5 h. The dark brown reaction mixture was diluted with EtOAc, and washed with a mixture of 10% aq. $Na_2S_2O_3$ solution and aq. $NaHCO_3$ solution (~1:4 mixture) and then with water (with some brine). After the aqueous fractions were extracted with EtOAc, the organic fractions were combined, dried ($Na_2SO_4$), and concentrated. The residue was purified by flash chromatography using hexanes-EtOAc as eluents to obtain 85-B. $^1$H-NMR (400 MHz, $CDCl_3$) δ 7.51-7.44 (m, 2H), 7.33-7.17 (m, 3H), 4.22-4.05 (m, 2H), 4.02-3.86 (m, 2H), 3.77 (d, J=5.3 Hz, 1H), 3.54-3.44 (m, 1H), 3.27 (t, J=4.5 Hz, 1H), 2.75-2.66 (m, 1H), 2.30 (dddd, J=14.8, 13.1, 7.2, 5.8 Hz, 1H), 2.14 (dddd, J=14.8, 13.0, 6.1, 2.1 Hz, 1H), 1.97 (d, J=8.9 Hz, 1H), 1.58-1.46 (m, 1H), 1.45-1.34 (m, 4H), 1.24 (t, J=7.1 Hz, 3H). LCMS-ESI$^+$ (m/z): [M+H]$^+$ calculated for $C_{18}H_{25}INO_3$: 430.1; found: 430.0.

Step 2

A solution of 85-B (993 mg, 2.313 mmol), AIBN (305 mg, 1.857 mmol), and tributyltin hydride (1392 mg, 4.799 mmol) in toluene (15 mL) was stirred at 100° C. After 2 h, the reaction mixture was cooled to room temperature, diluted with EtOAc, and washed with water and brine. After the aqueous fractions were extracted with EtOAc, the organic fractions were combined, dried ($Na_2SO_4$), and concentrated. The residue was purified by flash chromatography using hexanes-EtOAc as eluents to obtain 85-C. $^1$H-NMR (400 MHz, $CDCl_3$) δ 7.57-7.49 (m, 2H), 7.32-7.23 (m, 2H), 7.23-7.15 (m, 1H), 4.24-4.02 (m, 2H), 3.97 (q, J=6.7 Hz, 1H), 3.83 (d, J=5.1 Hz, 1H), 3.48 (t, J=4.6 Hz, 1H), 3.19-3.04 (m, 1H), 2.58 (p, J=4.0 Hz, 1H), 2.30 (dddd, J=14.7, 13.1, 7.0, 4.5 Hz, 1H), 1.98 (d, J=11.2 Hz, 1H), 1.64 (tdd, J=13.3, 6.2, 2.6 Hz, 1H), 1.49-1.33 (m, 3H), 1.37 (d, J=6.7 Hz, 3H), 1.32-1.26 (m, 1H), 1.23 (t, J=7.2 Hz, 3H). LCMS-ESI$^+$ (m/z): [M+H]$^+$ calculated for $C_{18}H_{26}NO_3$: 304.2; found: 304.1.

Step 3

A mixture of 85-C (725 mg, 2.39 mmol) and 20% Pd(OH)$_2$/C (351 mg) in EtOH (25 mL) and 4 N HCl in dioxane (0.9 mL) was stirred under H$_2$ atmosphere. After 2 h, the reaction mixture was filtered, and the filtrate was concentrated. LCMS-ESI$^+$ (m/z): [M+H]$^+$ calculated for $C_{10}H_{18}NO_3$: 200.13; found: 200.1. After the residue was co-evaporated with toluene (×2), the residue and Boc$_2$O (720 mg, 3.299 mmol) in THF (15 mL) was stirred at room temperature as N,N-diisopropylethylamine (DIPEA) (1.2 mL, 6.889 mmol) was added. After 1 h, the reaction mixture was diluted with water and extracted with EtOAc (×2). After the organic extracts were washed with water, the combined extracts were dried (Na$_2$SO$_4$) and concentrated. The residue was purified by flash using hexanes-EtOAc as eluents to obtain 85-D which appears to be a mixture of rotamers. $^1$H-NMR (400 MHz, $CDCl_3$) δ 4.42-3.97 (m, 5H), 2.62 (d, J=5.6 Hz, 1H), 2.45-2.26 (m, 1H), 2.25-2.15 (m, 1H), 1.80 (td, J=13.7, 6.7 Hz, 1H), 1.66 (dd, J=12.3, 6.6 Hz, 2H), 1.55-1.70 (m, 2H), 1.47 (s, 2H), 1.42 (s, 7H), 1.28 (dt, J=9.5, 7.1 Hz, 3H). LCMS-ESI$^+$ (m/z): [M+H]$^+$ calculated for $C_{15}H_{26}NO_5$: 300.2; found: 299.7.

Step 4

To a solution of 85-D (568 mg, 1.897 mmol) and pyridine (0.25 mL, 3.091 mmol) in THF (5 mL) was added phenyl chlorothionoformate (0.3 mL, 2.169 mmol) at 0° C., which produced insoluble material quickly. After ~30 min at 0° C., additional pyridine (0.3 mL, 3.709 mmol) and phenyl chlorothionoformate (0.3 mL, 2.169 mmol) were added. After 1.5 h at 0° C. and 1 h at room temperature, the mixture was concentrated, and the residue was dissolved in EtOAc and water. After separation of two layers, the organic fraction was washed with ~0.1 N HCl, saturated aqueous $NaHCO_3$, and brine. After the aqueous fractions were extracted with EtOAc, the combined organic fractions were dried ($Na_2SO_4$), and concentrated. The residue was purified by flash chromatography using EtOAc/hexanes as eluents to afford 85-E. $^1$H-NMR (400 MHz, $CDCl_3$) δ 7.47-7.37 (m, 2H), 7.30 (t, J=6.9 Hz, 1H), 7.11 (dd, J=8.0, 4.0 Hz, 2H), 5.54 (dt, J=9.0, 4.9 Hz, 1H), 4.50 (dt, J=9.8, 5.3 Hz, 1H), 4.35 (dd, J=21.4, 5.0 Hz, 1H), 4.30-4.14 (m, 2H), 2.71 (s, 1H), 2.54 (s, 1H), 2.14-2.00 (m, 1H), 1.82 (m, 3H), 1.54 (m, 1H), 1.48 (s, 4.5H), 1.45 (s, 4.5H), 1.30 (dt, J=9.4, 7.1 Hz, 3H). LCMS-ESI$^+$ (m/z): [M+H]$^+$ calculated for $C_{22}H_{30}NO_6S$: 436.2; found: 435.8.

Step 5

A mixture of 85-E (602 mg, 1.382 mmol), AIBN (182 mg, 1.108 mmol), and tributyltin hydride (608 mg, 2.096 mmol) in toluene (8 mL) was stirred at 100° C. After 1 h, the reaction mixture was concentrated and the residue was dissolved in EtOAc before washing with water and brine. After the aqueous fractions were extracted with EtOAc, the combined organic fractions were dried ($Na_2SO_4$) and concentrated. The residue was purified with flash chromatography using EtOAc/hexanes as eluents to give 85-F which appears to be a mixture of rotamers. $^1$H-NMR (400 MHz, $CDCl_3$) δ 4.37-4.06 (m, 4H), 2.69-2.53 (m, 1H), 2.11 (m, 1H), 1.97 (m, 0.65H), 1.93-1.80 (m, 1.35H), 1.54 (s, 5H), 1.46 (s, 3.15H), 1.42 (s, 5.85H), 1.27 (m, 3H). LCMS-ESI$^+$ (m/z): [M-$C_4H_8$+H]$^+$ calculated for $C_{11}H_{18}NO_4$: 228.1; found: 227.9.

Step 6

85-F (420 mg) was repurified and the purified 85-F in THF (3 mL) was stirred at 0° C. as 2.0 M $LiBH_4$ in THF (1.5 mL) was added. After 5 min, the mixture was stirred at room temperature for 17 h and additional 2.0 M $LiBH_4$ in THF (1.5 mL) was added at room temperature. After 23 h at room temperature, additional 2.0 M $LiBH_4$ in THF (3 mL) was added and the resulting mixture was stirred for ~72 h. After the reaction mixture was stirred at 0° C. as water was slowly added and further diluted with water, the product was extracted with EtOAc (×2). The extracts were washed with water, combined, dried ($Na_2SO_4$), and concentrated. The residue was purified by flash chromatography using hexane-EtOAc as eluents to give 85-G. $^1$H-NMR (400 MHz, $CDCl_3$) δ 4.12 (t, J=5.3 Hz, 1H), 3.99 (dd, J=12.0, 7.9 Hz, 1H), 3.85 (dd, J=8.0, 4.7 Hz, 1H), 3.73 (dd, J=11.9, 1.4 Hz, 1H), 2.28 (d, J=4.6 Hz, 1H), 1.90-1.73 (m, 2H), 1.68-1.45 (m, 6H), 1.47 (s, 9H), 1.43-1.33 (m, 1H). LCMS-ESI$^+$ (m/z): [M-$C_4H_8$+H]$^+$ calculated for $C_9H_{16}NO_3$: 186.1; found: 186.0.

Step 7

A solution of 85-G (198 mg, 0.820 mmol), phthalimide (200 mg, 1.359 mmol), and $PPh_3$ (488 mg, 1.861 mmol) in THF (10 mL) was stirred at 0° C. bath as DIAD (0.36 mL, 1.828 mmol) was added. After 30 min at 0° C., the mixture was stirred at room temperature for 17 h. The reaction mixture was concentrated and the residue was purified by flash chromatography using hexane-EtOAc as eluents to 85-H which appears to be a mixture of rotamers. $^1$H-NMR (400 MHz, $CDCl_3$) δ 7.82 (dd, J=5.4, 3.1 Hz, 2H), 7.69 (dd, J=5.4, 3.1 Hz, 2H), 4.46 (s, 1H), 4.19 (m, 2H), 3.95 (s, 1H), 2.31-2.14 (m, 1H), 2.05 (d, J=16.5 Hz, 1H), 1.84 (m, 2H), 1.79-1.70 (m, 1H), 1.66 (m, 1H), 1.61-1.30 (m, 12H). LCMS-ESI$^+$ (m/z): [M+H]$^+$ calculated for $C_{21}H_{27}N_2O_4$: 371.2; found: 370.8.

Step 8

To a solution of 85-H (270 mg, 0.729 mmol) in EtOH (12 mL) was added hydrazine hydrate (0.145 mL, 3.083 mmol) at room temperature and the resulting solution was stirred at 70° C. After 1.5 h, the mixture was cooled to 0° C. and diluted with ether (30 mL) before stirring for 1 h at 0° C. The mixture was filtered and the filtrate was concentrated. The residue was dissolved in $CH_2Cl_2$ and filtered to remove some insoluble material. The resulting filtrate was concentrated. The residue, combined with 85-I (257 mg, 0.742 mmol), and $NaHCO_3$ (131 mg, 1.559 mmol) in water (3 mL) and EtOH (3 mL) was stirred at room temperature. After 1 h, the mixture was diluted with water and extracted with EtOAc (×2). After the extracts were washed with water, the organic extracts were combined, dried ($Na_2SO_4$), and concentrated. To a solution of the residue in $CH_2Cl_2$ (2 mL) was added 4 N HCl in dioxane (6 mL). After 1.5 h at room temperature, the solution was concentrated and co-evaporated with toluene. A mixture of the residue and DBU (0.6 mL, 4.012 mmol) in toluene (5 mL) was stirred at 100° C. bath. After 1 h, additional DBU (0.3 mL, 2.006 mmol) was added and the mixture was stirred another 1 h at 100° C. After the mixture was concentrated, the residue was purified by flash chromatography using EtOAc-20% MeOH/EtOAc as eluents to give 85-J. $^1$H-NMR (400 MHz, $CDCl_3$) δ 8.08 (s, 1H), 7.71-7.62 (m, 2H), 7.36-7.29 (m, 2H), 7.29-7.23 (m, 1H), 5.44 (d, J=9.8 Hz, 1H), 5.10 (d, J=9.8 Hz, 1H), 4.44-4.28 (m, 3H), 4.23 (t, J=13.0 Hz, 1H), 3.99 (ddt, J=10.2, 6.3, 3.6 Hz, 2H), 2.44-2.36 (m, 1H), 2.29 (dt, J=11.6, 5.3 Hz, 1H), 1.84 (dt, J=10.8, 5.3 Hz, 2H), 1.77-1.61 (m, 3H), 1.57 (d, J=11.7 Hz, 1H), 1.48 (ddd, J=20.9, 12.3, 5.5 Hz, 1H), 1.38 (t, J=7.1 Hz, 3H). LCMS-ESI$^+$ (m/z): [M+H]$^+$ calculated for $C_{24}H_{27}N_2O_5$: 423.2; found: 423.3.

Step 9

A mixture of 85-J (214 mg, 0.507 mmol) in THF (4 mL) and MeOH (4 mL) was stirred at room temperature as 1 N KOH (1.1 mL) was added. After 30 min, the reaction mixture was concentrated to ~1 mL, acidified with 1 N HCl (~1.2 mL), and diluted with brine before extraction with $CH_2Cl_2$ (20 mL×2). The combined extracts were dried ($Na_2SO_4$) and concentrated to obtain the crude acid. LCMS-ESI$^+$ (m/z): [M+H]$^+$ calculated for $C_{22}H_{23}N_2O_5$: 395.2; found: 395.3.

A mixture of the crude acid (199 mg, 0.505 mmol), 2,4,6-trifluorobenzyl amine (130 mg, 0.807 mmol), and HATU (304 mg, 0.800 mmol) in $CH_2Cl_2$ (6 mL) was stirred at room temperature as N,N-diisopropylethylamine (DIPEA) (0.62 mL, 3.559 mmol) was added. After 30 min, the reaction mixture was concentrated and the residue was dissolved in EtOAc, washed with saturated aqueous $NH_4Cl$ (×2), saturated aqueous $NaHCO_3$ (×2), and brine. After the aqueous fractions were extracted with EtOAc, two organic fractions were combined, dried ($Na_2SO_4$) and concentrated. The residue was purified by flash using EtOAc-20% MeOH/EA as eluents to obtain 85-K. $^1$H-NMR (400 MHz, $CDCl_3$) δ 10.40 (t, J=5.7 Hz, 1H), 8.42 (s, 1H), 7.68-7.54 (m, 2H), 7.33 (ddd, J=7.7, 6.3, 1.5 Hz, 2H), 7.30-7.26 (m, 1H), 6.74-6.60 (m, 2H), 5.37 (d, J=10.0 Hz, 1H), 5.17 (d, J=10.0 Hz, 1H), 4.76-4.57 (m, 2H), 4.46 (dd, J=6.0, 4.3 Hz, 1H), 4.34 (t, J=12.4 Hz, 1H), 4.07 (dd, J=12.4, 3.6 Hz, 1H), 3.91 (dt, J=12.4, 3.9 Hz, 1H), 2.52-2.44 (m, 1H), 2.32 (dd, J=11.8, 6.2 Hz, 1H), 1.92 (dt, J=10.7, 5.4 Hz, 1H), 1.83-1.70 (m, 3H), 1.67 (d, J=11.7 Hz, 1H), 1.52 (dddt, J=25.5, 17.0, 11.8, 5.3 Hz, 2H). $^{19}$F-NMR (376 MHz, $CDCl_3$) δ −109.15

(dq, J=15.0, 7.5, 7.1 Hz, 1H), −111.85 (t, J=6.8 Hz, 2F). LCMS-ESI+ (m/z): [M+H]+ calculated for $C_{29}H_{27}F_3N_3O_4$: 538.2; found: 538.3.

Step 10

85-K (187 mg, 0.348 mmol) was dissolved in trifluoroacetic acid (3 mL) at room temperature and stirred at room temperature. After 1 h, the solution was concentrated and the residue was dissolved in $CH_2Cl_2$. After the solution was washed with 0.1 N HCl, the aqueous fraction was extracted with $CH_2Cl_2$ (×2). The organic fractions were combined, dried ($Na_2SO_4$), and concentrated. The residue was purified by flash chromatography using $CH_2Cl_2$-20% MeOH in $CH_2Cl_2$ as eluents to obtain 150 mg (96%) of compound 85. Compound 85 was further purified by recrystallization from methanol (10 mL) to give compound 85. ¹H-NMR (400 MHz, $CDCl_3$) δ 12.09 (s, 1H), 10.39 (t, J=5.7 Hz, 1H), 8.36 (s, 1H), 6.74-6.48 (m, 2H), 4.64 (d, J=5.7 Hz, 2H), 4.59 (dd, J=6.1, 4.4 Hz, 1H), 4.36-4.18 (m, 2H), 4.12 (dt, J=12.4, 4.1 Hz, 1H), 2.68-2.47 (m, 1H), 2.25-2.10 (m, 1H), 2.10-1.98 (m, 1H), 1.98-1.66 (m, 4H), 1.66-1.48 (m, 2H). ¹⁹F-NMR (376 MHz, $CDCl_3$) δ −109.23 (ddd, J=15.1, 8.6, 6.0 Hz, 1F), −112.02 (t, J=6.9 Hz, 2F). LCMS-ESI+ (m/z): [M+H]+ calculated for $C_{22}H_{21}F_3N_3O_4$: 448.2; found: 448.3.

Example 86

Preparation of Compound 86

(1R,3S,4R,12aS)-7-hydroxy-3-methyl-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

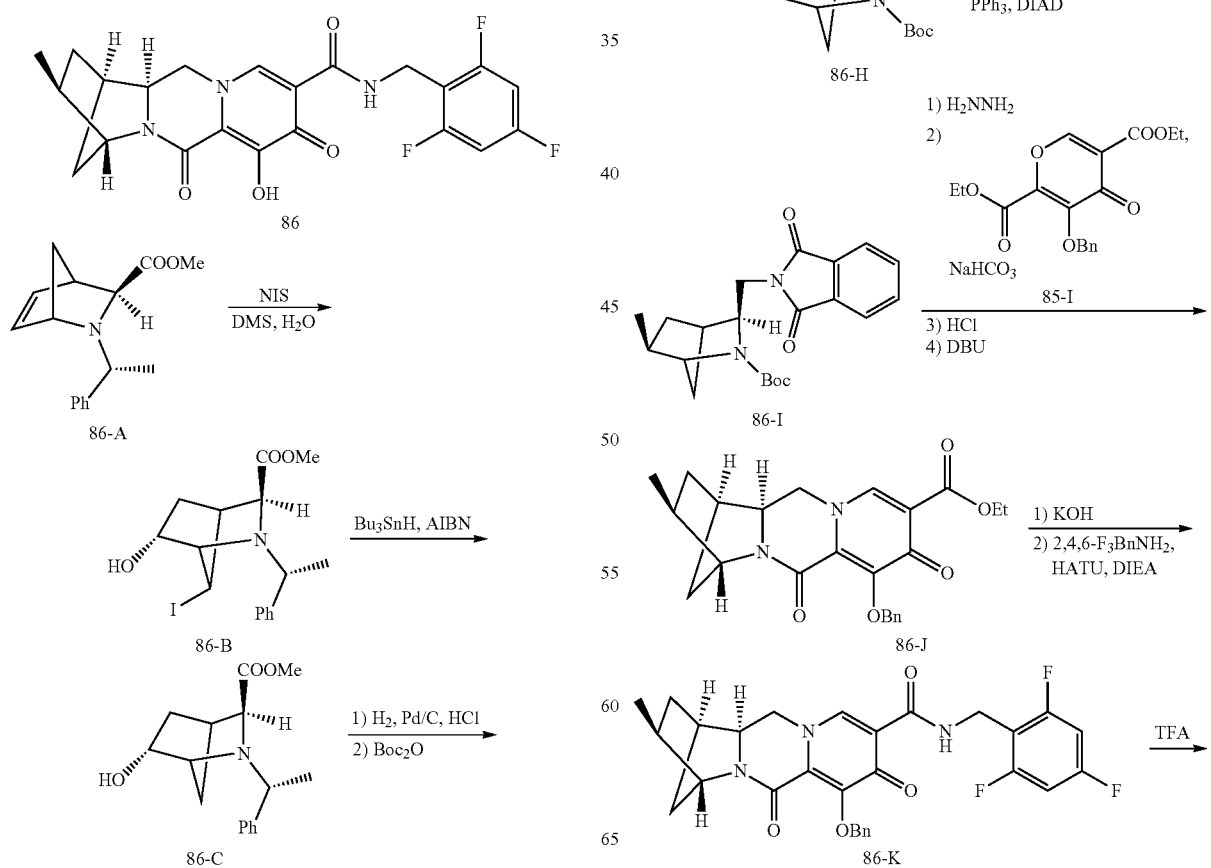

-continued

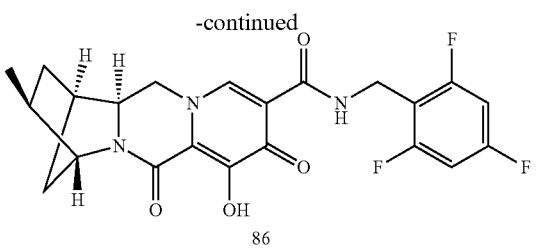
86

Step 1

A solution of 86-A (10.160 g, 39.48 mmol) in DMSO (52 mL) and water (6.5 mL) was stirred at room temperature as N-iodosuccinmide (8.888 g, 39.50 mmol) was added. After 30 min, the dark brown reaction mixture was diluted with EtOAc, and washed with saturated aqueous NaHCO$_3$ solution, 10% aqueous Na$_2$S$_2$O$_3$ solution], and brine. After the aqueous fractions were extracted with EtOAc, the organic fractions were combined, dried (Na$_2$SO$_4$), and concentrated. The residue was purified by flash chromatography using hexanes-EtOAc as eluents to obtain 86-B as a white solid. $^1$H-NMR (400 MHz, CDCl$_3$) δ 7.33-7.19 (m, 5H), 4.25-4.12 (m, 1H), 3.79 (q, J=1.6 Hz, 1H), 3.72 (q, J=6.5 Hz, 1H), 3.51 (s, 1H), 3.47 (s, 3H), 3.31 (dd, J=3.9, 1.6 Hz, 1H), 2.76-2.69 (m, 1H), 2.13 (ddd, J=14.3, 7.8, 1.7 Hz, 1H), 2.08-1.97 (m, 1H), 1.91 (dtd, J=14.1, 4.0, 1.5 Hz, 1H), 1.42 (d, J=6.5 Hz, 3H). LCMS-ESI$^+$ (m/z): [M+H]$^+$ calculated for C$_{16}$H$_{21}$INO$_3$: 402.1; found: 402.0.

Step 2

A solution of 86-B (12.468 g, 31.07 mmol), azobisisobutyronitrile (AIBN) (4.082 g, 24.86 mmol), and tributyltin hydride (18.047 g 62.22 mmol) in toluene (150 mL) was stirred at 100° C. After 30 min, the reaction mixture was cooled to room temperature, diluted with EtOAc, and washed with water and brine. After the aqueous fractions were extracted with EtOAc, the organic fractions were combined, dried (Na$_2$SO$_4$), and concentrated. The residue was purified by flash chromatography twice using hexanes-EtOAc as eluents to obtain 86-C. $^1$H-NMR (400 MHz, CDCl$_3$) δ 7.39-7.31 (m, 2H), 7.31-7.24 (m, 2H), 7.24-7.17 (m, 1H), 4.11 (s, 1H), 3.72 (s, 1H), 3.49 (s, 3H), 3.33 (d, J=3.4 Hz, 1H), 3.27 (d, J=6.4 Hz, 1H), 2.65-2.51 (m, 1H), 1.92 (ddd, J=13.6, 6.8, 2.4 Hz, 1H), 1.69-1.50 (m, 2H), 1.47 (d, J=10.1 Hz, 1H), 1.41 (d, J=6.6 Hz, 3H), 1.21-1.07 (m, 1H). LCMS-ESI$^+$ (m/z): [M+H]$^+$ calculated for C$_{16}$H$_{22}$NO$_3$: 276.2; found: 276.1.

Step 3

A mixture of 86-C (4.187 g, 15.21 mmol) and 20% Pd(OH)$_2$/C (1.022 g) in EtOH (100 mL) and 4 N HCl in dioxane (5.7 mL) was stirred under H$_2$ atmosphere. After 1.5 h, the reaction mixture was filtered, and the filtrate was concentrated. After the residue was co evaporated with toluene, the residue was used for the next step. LCMS-ESI$^+$ (m/z): [M+H]$^+$ calculated for C$_8$H$_{14}$NO$_3$: 172.1; found: 172.1.

After the residue was co-evaporated with toluene, the residue and Boc$_2$O (5.712 g, 26.17 mmol) in THF (45 mL) was stirred at room temperature as N,N-diisopropylethylamine (DIPEA) (8 mL, 45.93 mmol) was added. After 30 min, the reaction mixture was diluted with water and extracted with EtOAc (×2). After the organic extracts were washed with water, the combined extracts were dried (Na$_2$SO$_4$) and concentrated. The residue was purified by flash chromatography using hexanes-EtOAc as eluents to obtain 86-D. $^1$H NMR spectrum suggests a mixture of rotamers. $^1$H-NMR (400 MHz, CDCl$_3$) δ 4.20 (d, J=7.6 Hz, 1H), 4.19-4.10 (m, 2H), 4.08 (d, J=3.5 Hz, 1H), 3.72 (s, 3H), 2.74 (d, J=5.6 Hz, 1H), 1.97 (ddd, J=13.6, 6.9, 2.8 Hz, 1H), 1.88-1.78 (m, 1H), 1.79-1.50 (m, 1H), 1.46 (s, 3H), 1.38 (s, 6H), 1.31 (d, J=13.3 Hz, 1H). LCMS-ESI$^+$ (m/z): [M+H]$^+$ calculated for C$_{13}$H$_{22}$NO$_5$: 272.2; found: 271.6.

Step 4

A solution of 86-D (1659 mg, 6.115 mmol) in CH$_2$Cl$_2$ (35 mL) was stirred at 0° C. bath as Dess-Martin periodinane (5.183 g, 12.22 mmol) was added in portions. After 5 min, the mixture was stirred at room temperature. After 2 h, the reaction mixture was cooled in an ice bath, quenched with water, and filtered. The filtrate was washed with saturated NaHCO$_3$, dried (Na$_2$SO$_4$), and concentrated. The residue was purified by flash chromatography using hexanes-EtOAc as eluents to give 86-E. $^1$H NMR spectrum suggests two rotamers. $^1$H-NMR (400 MHz, CDCl$_3$) δ 4.43 (d, J=3.8 Hz, 0.5H), 4.39 (s, 1H), 4.26 (s, 0.5H), 3.75 (s, 3H), 3.10 (s, 1H), 2.24 (d, J=4.5 Hz, 0.5H), 2.19 (d, J=4.4 Hz, 0.5H), 2.12 (d, J=4.4 Hz, 0.5H), 2.07 (d, J=4.2 Hz, 0.5H), 2.01 (dd, J=4.5, 2.2 Hz, 0.5H), 1.98 (dt, J=4.3, 1.9 Hz, 0.5H), 1.80 (s, 0.5H), 1.77 (s, 0.5H), 1.46 (s, 4.5H), 1.40 (d, J=2.8 Hz, 4.5H). LCMS-ESI$^+$ (m/z): [M-C$_4$H$_8$+H]$^+$ calculated for C$_9$H$_{12}$NO$_5$: 214.1; found: 213.8.

Step 5

A solution of 86-E (528 mg, 1.961 mmol) in THF (12 mL) was stirred at 0° C. as 0.5 M solution of Tebbe reagent in toluene (7.9 mL, 3.95 mmol) was added dropwise. After addition, the brown solution was allowed to warm to room temperature slowly and was stirred at room temperature for 2.5 h. The reaction mixture was stirred at 0° C. bath as the reaction was quenched carefully by the addition of saturated aqueous NaHCO$_3$ solution. After the mixture was diluted with CH$_2$Cl$_2$ and stirred at room temperature for 15 minutes, the resulting mixture was filtered through celite pad and the filter cake was washed with CH$_2$Cl$_2$. After the two fractions in the filtrate were separated, the aq. fraction was extracted with CH$_2$Cl$_2$, and the organic fractions were combined, dried (Na$_2$SO$_4$), and concentrated. The residue was purified by flash chromatography using hexanes-EtOAc as eluents to give 86-F. $^1$H NMR spectrum suggests two rotamers. $^1$H-NMR (400 MHz, CDCl$_3$) δ 5.13 (s, 0.6H), 5.04 (s, 0.4H), 4.82-4.71 (m, 1H), 4.55 (s, 0.6H), 4.43 (s, 0.4H), 4.29 (d, J=3.7 Hz, 0.4H), 4.24 (d, J=3.7 Hz, 0.6H), 3.71 (s, 3H), 2.84 (s, 1H), 2.14 (m, 2H), 1.75 (s, 0.6H), 1.74-1.70 (s, 0.4H), 1.55 (m, 1H), 1.45 (s, 3.6H), 1.37 (s, 5.4H). LCMS-ESI$^+$ (m/z): [M+H]$^+$ calculated for C$_{14}$H$_{22}$NO$_4$: 268.2; found: 267.6.

Step 6

A mixture of 86-F (333 mg, 1.246 mmol) and 20% Pd(OH)$_2$/C (53 mg) in EtOH (5 mL) was stirred under H$_2$ atmosphere. After 30 min, the mixture was filtered and the filtrate was concentrated to give 86-G. $^1$H NMR spectrum suggests two rotamers. $^1$H-NMR (400 MHz, CDCl$_3$) δ 4.20 (m, 1H), 4.08 (m, 1H), 3.71 (two s, 3H), 2.68 (m, 1H), 2.06 (m, 1H), 1.80-1.63 (m, 2H), 1.63-1.51 (m, 1H), 1.44 (s, 4H), 1.38 (s, 5H), 1.13 (m, 3H), 0.92 (m, 1H). LCMS-ESI$^+$ (m/z): [M+H]$^+$ calculated for C$_{14}$H$_{24}$NO$_4$: 270.2; found: 269.7.

Step 7

A solution of 86-G (336 mg, 1.482 mmol) in THF (5 mL) was stirred at 0° C. as 2.0 M LiBH$_4$ in THF (1.5 mL) was added. After 5 min, the mixture was stirred at room temperature. After 2 h, additional 2.0 M LiBH$_4$ in THF (1.5 mL) was added. After 21 h at room temperature, additional 2.0 M LiBH$_4$ in THF (3 mL) was added. After 3 h at room temperature, the solution was heated at 35° C. for 18 h. The reaction mixture was cooled to 0° C. and quenched carefully with water. After the mixture was extracted with EtOAc (×2), the two organic fractions were washed with water, combined, dried (Na$_2$SO$_4$), and concentrated. The residue was purified by flash chromatography using hexanes-EtOAc to give 86-H. $^1$H-NMR (400 MHz, CDCl$_3$) δ 4.95-4.09 (br, 1H), 4.05 (s, 1H), 3.82 (dd, J=11.5, 7.7 Hz, 1H), 3.76-3.69 (m, 1H), 3.66 (d, J=11.5 Hz, 1H), 2.45 (d, J=4.1 Hz, 1H), 2.03 (dqdd, J=11.4, 7.0, 4.5, 2.6 Hz, 1H), 1.77-1.57 (m, 2H), 1.48 (dd, J=10.1, 1.8 Hz, 1H), 1.45 (s, 9H), 1.00 (d, J=6.9 Hz, 3H), 0.93 (ddd, J=13.2, 4.7, 2.6 Hz, 1H). LCMS-ESI$^+$ (m/z): [M+H]$^+$ calculated for C$_{13}$H$_{24}$NO$_3$: 242.2; found: 241.7.

Step 8

A solution of 86-H (218 mg, 0.903 mmol), phthalimide (218 mg, 1.482 mmol), and PPh$_3$ (535 mg, 2.040 mmol) in THF (10 mL) was stirred at 0° C. bath as DIAD (0.40 mL, 2.032 mmol) was added. After 10 min at 0° C., the mixture was stirred at room temperature for 19 h. The reaction mixture was concentrated and the residue was purified by flash chromatography using hexane-EtOAc as eluents to give 86-I. $^1$H NMR suggests two rotamers. $^1$H-NMR (400 MHz, CDCl$_3$) δ 7.82 (dt, J=7.3, 3.6 Hz, 2H), 7.70 (d, J=5.3 Hz, 2H), 4.53-4.26 (m, 1H), 4.26-3.89 (m, 2H), 3.89-3.65 (m, 1H), 2.28 (m, 1H), 2.04 (m, 1H), 1.82-1.65 (m, 2H), 1.66-1.43 (m, 7H), 1.38 (s, 4H), 1.19-1.01 (m, 3H). LCMS-ESI$^+$ (m/z): [M+H]$^+$ calculated for C$_{21}$H$_{27}$N$_2$O$_4$: 371.2; found: 370.8.

Step 9

To a solution of 86-I (319 mg, 0.861 mmol) in EtOH (12 mL) was added hydrazine hydrate (0.17 mL, 3.494 mmol) at room temperature and the resulting solution was stirred at 70° C. bath. After 1.5 h, the mixture was cooled to 0° C. and diluted with ether (25 mL) before stirring for 1 h at 0° C. The mixture was filtered and the filtrate was concentrated. The residue was dissolved in CH$_2$Cl$_2$ and filtered to remove some insoluble material. The resulting filtrate was concentrated to give crude amine. LCMS-ESI$^+$ (m/z): [M+H]$^+$ calculated for C$_{13}$H$_{25}$N$_2$O$_2$: 241.2; found: 240.9.

After the crude amine was co-evaporated with toluene, a mixture of the crude amine, 85-I (300 mg, 0.866 mmol), and NaHCO$_3$ (150 mg, 1.845 mmol) in water (3 mL) and EtOH (3 mL) was stirred at room temperature. After 2 h, the mixture was diluted with water and extracted with EtOAc (×2). After the extracts were washed with water, the organic extracts were combined, dried (Na$_2$SO$_4$), and concentrated. To a solution of the residue in CH$_2$Cl$_2$ (2 mL) was added 4 N HCl in dioxane (6 mL). After 1.5 h at room temperature, the solution was concentrated and co-evaporated with toluene. A mixture of the residue and DBU (0.65 mL, 4.347 mmol) in toluene (6 mL) was stirred at 100° C. After 1 h, additional DBU (0.65 mL, 4.347 mmol) was added and the mixture was stirred at 100° C. Additional DBU (0.65 mL, 4.347 mmol) was added after 1 h and the mixture was stirred another 2.5 h at 100° C. The mixture was diluted with CH$_2$Cl$_2$ and washed with water containing 3 mL of 1 N HCl. The organic fraction was dried (Na$_2$SO$_4$) and concentrated. The residue was purified by flash chromatography using EtOAc-20% MeOH/EtOAc as eluents to give 86-J. $^1$H-NMR (400 MHz, CDCl$_3$) δ 8.09 (s, 1H), 7.70-7.62 (m, 2H), 7.37-7.27 (m, 3H), 5.48 (d, J=9.9 Hz, 1H), 5.16 (d, J=9.9 Hz, 1H), 4.53 (s, 1H), 4.38 (m, 2H), 4.11 (m, 1H), 3.97 (dd, J=12.2, 3.0 Hz, 1H), 3.88 (dt, J=12.2, 3.0 Hz, 1H), 2.63 (d, J=4.2 Hz, 1H), 2.28 (qd, J=7.2, 3.1 Hz, 1H), 2.00-1.88 (m, 1H), 1.80-1.56 (m, 2H), 1.39 (t, J=7.1 Hz, 3H), 1.07 (d, J=6.9 Hz, 3H), 1.04 (dd, J=5.0, 2.5 Hz, 1H). LCMS-ESI$^+$ (m/z): [M+H]$^+$ calculated for C$_{24}$H$_{27}$N$_2$O$_5$: 423.2; found: 423.2.

Step 10

A mixture of 86-J (83 mg, 0.196 mmol) in THF (2 mL) and EtOH (2 mL) was stirred at room temperature as 1 N KOH (0.4 mL) was added. After 30 min, the reaction mixture was diluted with water and washed with CH$_2$Cl$_2$. After the aqueous fraction was acidified with 1 N HCl 0.45 mL), the product was extracted with CH$_2$Cl$_2$ (×2). The combined extracts were dried (Na$_2$SO$_4$) and concentrated to obtain the crude acid. LCMS-ESI$^+$ (m/z): [M+H]$^+$ calculated for C$_{22}$H$_{23}$N$_2$O$_5$: 395.2; found: 395.2.

A mixture of the crude acid (69 mg, 0.175 mmol), 2,4,6-trifluorobenzyl amine (42 mg, 0.261 mmol), and HATU (106 mg, 0.279 mmol) in CH$_2$Cl$_2$ (3 mL) was stirred at room temperature as N,N-diisopropylethylamine (DIPEA) (0.25 mL, 1.435 mmol) was added. After 30 min, the reaction mixture was concentrated and the residue was dissolved in EtOAc, washed with saturated aqueous NH$_4$Cl (×2), saturated aqueous NaHCO$_3$ (×2), and brine. After the aqueous fractions were extracted with EtOAc, two organic fractions were combined, dried (Na$_2$SO$_4$) and concentrated. The residue was purified by flash chromatography using EtOAc-20% MeOH/EtOAc as eluents to obtain 86-K. $^1$H-NMR (400 MHz, CDCl$_3$) δ 10.40 (t, J=5.7 Hz, 1H), 8.40 (s, 1H), 7.66-7.51 (m, 2H), 7.36-7.29 (m, 2H), 7.29-7.23 (m, 1H), 6.71-6.61 (m, 2H), 5.36 (d, J=10.0 Hz, 1H), 5.18 (d, J=10.0 Hz, 1H), 4.73-4.58 (m, 2H), 4.53 (s, 1H), 4.22-4.11 (m, 1H), 4.03 (dd, J=12.4, 3.1 Hz, 1H), 3.81 (dt, J=12.3, 3.1 Hz, 1H), 2.68-2.59 (m, 1H), 2.29 (dddd, J=11.4, 7.1, 4.7, 2.4 Hz, 1H), 1.94 (ddd, J=13.5, 11.2, 4.6 Hz, 1H), 1.88-1.67 (m, 2H), 1.06 (d, J=7.0 Hz, 3H), 1.03-1.09 (m, 1H). $^{19}$F-NMR (376 MHz, CDCl$_3$) δ −109.14 (ddd, J=15.2, 8.7, 6.2 Hz, 1F), −111.86 (t, J=7.0 Hz, 2F). LCMS-ESI$^+$ (m/z): [M+H]$^+$ calculated for C$_{29}$H$_{27}$F$_3$N$_3$O$_4$: 538.2; found: 538.1.

Step 11

86-K (61 mg, 0.113 mmol) was dissolved in trifluoroacetic acid (2 mL) and stirred at room temperature. After 1 h, the solution was concentrated and the residue was dissolved in CH$_2$Cl$_2$. After the solution was washed with 0.1 N HCl, the aqueous fraction was extracted with CH$_2$Cl$_2$ (×2). The organic fractions were combined, dried (Na$_2$SO$_4$), and concentrated. The residue was purified by flash chromatography using CH$_2$Cl$_2$-20% MeOH in CH$_2$Cl$_2$ as eluents to obtain compound 86. $^1$H-NMR (400 MHz, CDCl$_3$) δ 12.02 (s, 1H), 10.40 (t, J=5.7 Hz, 1H), 8.35 (s, 1H), 6.63 (t, J=8.1 Hz, 2H), 4.62 (d, J=5.7 Hz, 2H), 4.59 (s, 1H), 4.22 (dd, J=12.2, 3.5 Hz, 1H), 4.13 (t, J=11.9 Hz, 1H), 4.05 (dt, J=12.0, 3.1 Hz, 1H), 2.77-2.70 (m, 1H), 2.31 m, 1H), 2.09-1.93 (m, 1H), 1.93-1.81 (m, 2H), 1.10 (ddd, J=13.9, 5.0, 2.1 Hz, 1H), 1.02 (d, J=6.9 Hz, 3H). $^{19}$F-NMR (376 MHz, CDCl$_3$) δ −109.22 (ddd, J=15.1, 8.7, 6.1 Hz, 1F), −112.05 (t, J=6.9 Hz, 2F). LCMS-ESI$^+$ (m/z): [M+H]$^+$ calculated for C$_{22}$H$_{21}$F$_3$N$_3$O$_4$: 448.2; found: 448.3.

Example 87

Preparation of cis-5-aminotetrahydro-2H-pyran-3-ol

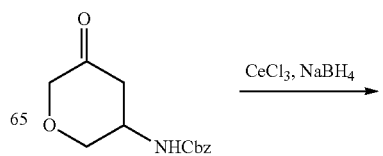

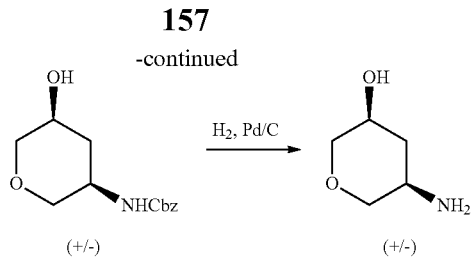

(+/-)       (+/-)

Step 1

A solution of benzyl (5-oxotetrahydro-2H-pyran-3-yl)carbamate (740 mg, 3.0 mmol) and cerium(III) chloride heptahydrate (1.12 g, 3.0 mmol) in 20 mL methanol was cooled to 0° C. and sodium borohydride (120 mg, 3.2 mmol) was then added portionwise. The reaction mixture was allowed to stir at 0° C. for 45 minutes and then quenched by slow addition of 1 mL acetone followed by 3 hours stirring at room temperature. The reaction mixture was partitioned between water and dichloromethane and the aqueous phase extracted into dichloromethane followed by 2-butanol. The combined organic phases were dried over magnesium sulfate, filtered, concentrated, and the residue purified by flash chromatography (0-100% EtOAc/hexanes) to afford the desired cis-benzyl ((3R,5S)-5-hydroxytetrahydro-2H-pyran-3-yl)carbamate. $^1$H-NMR (400 MHz, Chloroform-d) δ 7.39-7.26 (m, 5H), 6.06 (br s, 1H), 5.07 (s, 2H), 3.86-3.70 (m, 2H), 3.69-3.47 (m, 4H), 2.00-1.89 (m, 1H), 1.76 (d, J=13.5 Hz, 1H). The undesired trans-isomer was also isolated.

Step 2

To a solution of cis-benzyl ((3R,5S)-5-hydroxytetrahydro-2H-pyran-3-yl)carbamate (290 mg, 1.16 mmol) in 5 mL 1:1 DCM:EtOH was added 10 wt % Pd/C (255 mg). This mixture was stirred under balloon pressure hydrogen for 18 hours and palladium removed by filtration thru celite with ethanol rinse. Upon concentration of filtrate, the cis-5-aminotetrahydro-2H-pyran-3-ol was afforded and carried on as crude.

Example 88

Preparation of Compound 88

'(2R,5S,13aR)—N-(3-chloro-2-fluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

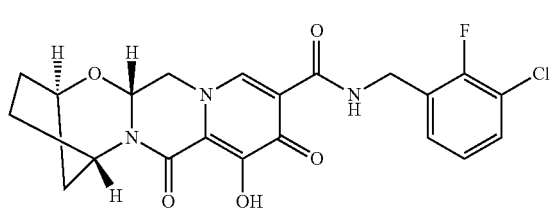

Compound 88 was prepared in a similar manner to compound 15 using (3-chloro-2-fluorophenyl)methanamine in place of (4-fluorophenyl)methanamine. $^1$H-NMR (400 MHz, Chloroform-d) δ 10.43 (br s, 1H), 8.34 (br s, 1H), 7.32-7.24 (m, 2H), 7.02 (t, J=7.9 Hz, 1H), 5.36 (d, J=9.4 Hz, 1H), 5.30 (s, 2H), 4.70 (d, J=6.0 Hz, 3H), 4.24 (d, J=12.0 Hz, 1H), 4.00 (dd, J=12.7, 9.5 Hz, 1H), 2.18-1.96 (m, 4H), 1.96-1.83 (m, 1H), 1.60 (dt, J=12.4, 3.1 Hz, 1H). LCMS-ESI$^+$ (m/z): [M+H]$^+$ calculated for $C_{21}H_{19}ClFN_3O_5$: 448.11; found: 448.2.

Example 89

Preparation of Compound 89

(2R,5S,13aR)—N-(2,5-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide

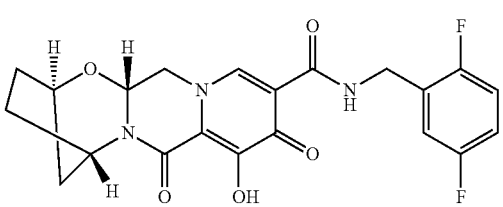

Compound 89 was prepared in a similar manner to compound 15 using (2,5-difluorophenyl)methanamine in place of (4-fluorophenyl)methanamine. $^1$H-NMR (400 MHz, Chloroform-d) δ 10.32 (t, J=5.8 Hz, 1H), 8.31 (br s, 1H), 7.15-6.89 (m, 2H), 6.86 (d, J=8.5 Hz, 1H), 5.40 (d, J=9.3 Hz, 1H), 5.24 (s, 1H), 4.67-4.51 (m, 3H), 4.35-4.28 (m, 1H), 3.99-3.90 (m, 1H), 2.16-1.85 (m, 5H), 1.60-1.50 (m, 1H). LCMS-ESI$^+$ (m/z): [M+H]$^+$ calculated for $C_{21}H_{19}F_2N_3O_5$: 432.14; found: 432.2.

Example 90

Preparation of Compound 90

(1R,4S,12aR)—N-(3-chloro-2-fluorobenzyl)-7-hydroxy-6,8-dioxo-1,2,3,4,6,8,12,12a-octahydro-1,4-methanodipyrido[1,2-a:1',2'-d]pyrazine-9-carboxamide

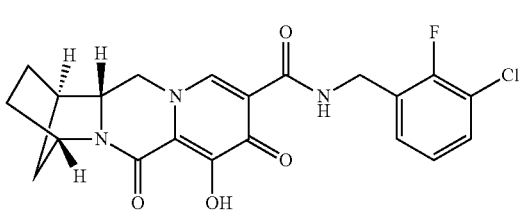

Compound 90 was prepared in a similar manner to compound 41 using (3-chloro-2-fluorophenyl)methanamine in place of (2,4,6-trifluorophenyl)methanamine. $^1$H-NMR (400 MHz, Chloroform-d) δ 9.22 (s, 1H), 8.79 (s, 1H), 7.39-7.28 (m, 2H), 7.06 (t, J=8.0 Hz, 1H), 4.89 (s, 1H), 4.70-4.56 (m, 3H), 4.06-3.83 (m, 2H), 3.04-2.88 (m, 1H), 2.77 (s, 1H), 1.97-1.58 (m, 6H). LCMS-ESI$^+$ (m/z): [M+H]$^+$ calculated for $C_{21}H_{19}ClFN_3O_4$: 432.11; found: 432.2.

Example 91

Preparation of Compound 91

(1R,4S,12aR)-7-hydroxy-6,8-dioxo-N-(2,3,4-trifluorobenzyl)-1,2,3,4,6,8,12,12a-octahydro-1,4-methanodipyrido[1,2-a:1',2'-d]pyrazine-9-carboxamide

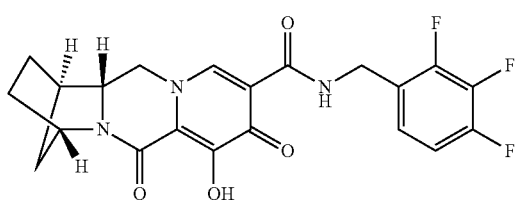

91

Compound 91 was prepared in a similar manner to compound 41 using (2,3,4-trifluorophenyl)methanamine in place of (2,4,6-trifluorophenyl)methanamine. $^1$H-NMR (400 MHz, Chloroform-d) δ 10.25 (s, 1H), 8.45 (s, 1H), 7.10 (d, J=5.1 Hz, 1a), 6.90 (d, J=8.7 Hz, 1H), 4.89 (s, 1H), 4.63 (s, 2H), 4.22 (d, J=11.6 Hz, 1H), 3.93-3.73 (m, 2H), 2.71 (s, 1H), 1.97-1.57 (m, 6H). LCMS-ESI$^+$ (m/z): [M+H]$^+$ calculated for $C_{21}H_{18}F_3N_3O_4$: 434.13; found: 434.2.

Example 92

Preparation of Compound 92

(1R,4S,12aR)—N-(4-chloro-2-fluorobenzyl)-7-hydroxy-6,8-dioxo-1,2,3,4,6,8,12,12a-octahydro-1,4-methanodipyrido[1,2-a:1',2'-d]pyrazine-9-carboxamide

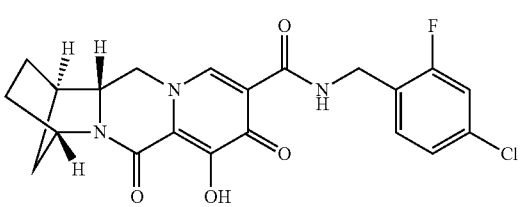

92

Compound 92 was prepared in a similar manner to compound 41 using (4-chloro-2-fluorophenyl)methanamine in place of (2,4,6-trifluorophenyl)methanamine. $^1$H-NMR (400 MHz, Chloroform-d) δ 10.28 (s, 1H), 8.41 (s, 1H), 7.29 (s, 1H), 7.11-6.95 (m, 2H), 4.85 (s, 1H), 4.57 (s, 2H), 4.22 (d, J=10.2 Hz, 1H), 3.81 (q, J=13.9, 13.1 Hz, 2H), 2.68 (s, 1H), 1.99-1.50 (m, 6H). LCMS-ESI$^+$ (m/z): [M+H]$^+$ calculated for $C_{21}H_{19}ClFN_3O_4$: 432.11; found: 432.2.

Example 93

Preparation of Compound 93

(1R,4S,12aR)—N-(2-chloro-4,6-difluorobenzyl)-7-hydroxy-6,8-dioxo-1,2,3,4,6,8,12,12a-octahydro-1,4-methanodipyrido[1,2-a:1',2'-d]pyrazine-9-carboxamide

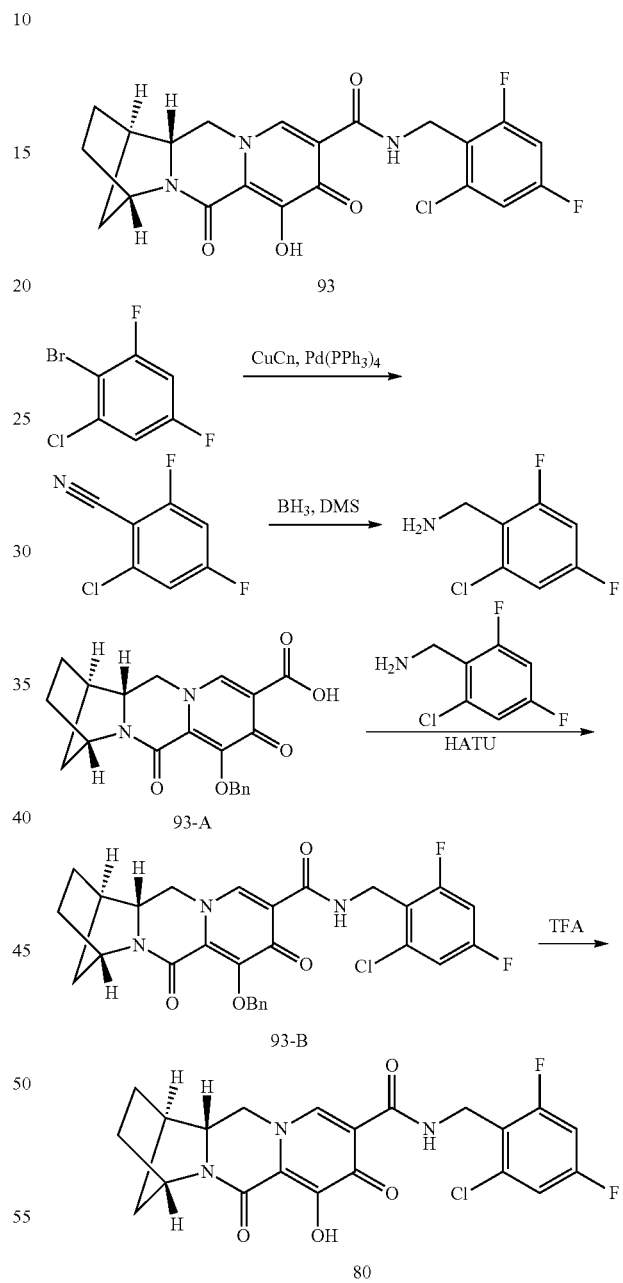

Step 1

A 5 mL microwave vial was charged with 2-bromo-1-chloro-3,5-difluorobenzene (540 mg, 2.4 mmol), cuprous cyanide (436 mg, 4.87 mmol), tetrakis(triphenylphosphine) palladium (63 mg, 0.05 mmol), sealed, and evacuated/backfilled with nitrogen. To this was added 5 mL degassed DMF. The sealed vessel was heated at 110° C. for 18 hours, diluted with ethyl acetate, and washed sequentially with twice 9:1 NH$_4$OH:NH$_4$Cl$_{(aq)}$, twice 5% LiCl$_{(aq)}$, and brine. The organic phase was then dried over magnesium sulfate, filtered, and concentrated. The crude residue was purified by flash chromatography (100% hexanes) to afford 2-chloro-4,6-difluorobenzonitrile. $^1$H-NMR (400 MHz, Chloroform-d) δ 7.13 (dt, J=8.0, 1.9 Hz, 1H), 6.93 (td, J=8.5, 2.3 Hz, 1H).
Step 2

To a solution of 2-chloro-4,6-difluorobenzonitrile (210 mg, 1.2 mmol) in 2.4 mL THF was added a 2M solution of borane-DMS in THF (0.6 mL). This reaction mixture was allowed to stir at refluxing temperature for 18 hours resulting in a loss of all solvent. The residue was re-dissolved in 3 mL THF, cooled to 0° C., a 6M solution of HCl$_{(aq)}$ was carefully added, and the mixture returned to reflux for 30 minutes. The reaction mixture was once again cooled to 0° C. and treated with 4M NaOH$_{(aq)}$. The aqueous phase was extracted with DCM, combined organic phases dried over magnesium sulfate, filtered, and concentrated. The crude residue was purified by flash chromatography (0-10% MeOH/DCM) to afford (2-chloro-4,6-difluorophenyl)methanamine. $^1$H-NMR (400 MHz, Chloroform-d) δ 6.95 (dt, J=8.3, 2.1 Hz, 1H), 6.76 (td, J=9.4, 2.5 Hz, 1H), 3.94 (d, J=1.9 Hz, 2H).
Steps 3 and 4

A solution of 93-A (74 mg, 0.11 mmol), (2-chloro-4,6-difluorophenyl)methanamine (48.5 mg, 0.27 mmol), HATU (100 mg, 0.26 mmol), and N,N-diisopropylethylamine (0.1 mL, 0.57 mmol) in 1 mL dichloromethane was stirred at room temperature for one hour at which point complete disappearance of 93-A and formation of 93-B was observed by LCMS. TFA (0.65 M) was added and the mixture was stirred at room temperature for one hour, at which point 1 mL DMF was added. The reaction mixture and then concentrated and purified by preparative HPLC (ACN/H$_2$O+ 0.1% TFA) to afford compound 93. $^1$H-NMR (400 MHz, DMSO-d$_6$) δ 10.41 (t, J=5.7 Hz, 1H), 8.33 (s, 1H), 7.41-7.26 (m, 2H), 4.72-4.57 (m, 3H), 4.43 (dd, J=12.5, 3.6 Hz, 1H), 3.94 (t, J=12.4 Hz, 2H), 3.77 (dd, J=12.4, 3.6 Hz, 3H), 1.87-1.67 (m, 3H), 1.67-1.45 (m, 2H), 1.43 (d, J=10.4 Hz, 1H). LCMS-ESI$^+$ (m/z): [M+H]$^+$ calculated for C$_{21}$H$_{18}$ClF$_2$N$_3$O$_4$: 450.10; found: 450.2.

Example 94

Preparation of Compound 94

(1R,4S,12aR)—N-benzyl-7-hydroxy-6,8-dioxo-1,2,3,4,6,8,12,12a-octahydro-1,4-methanodipyrido[1,2-a:1',2'-d]pyrazine-9-carboxamide

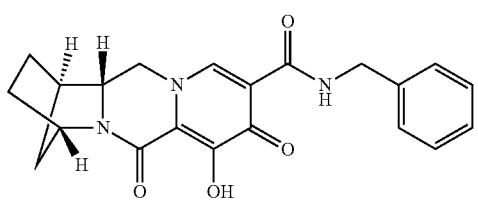

Compound 94 was prepared in a similar manner to compound 41 using phenylmethanamine in place of (2,4,6-trifluorophenyl)methanamine. $^1$H-NMR (400 MHz, Chloroform-d) δ 10.37 (s, 1H), 8.26 (s, 1H), 7.37-7.19 (m, 5H), 4.55 (d, J=4.8 Hz, 1H), 4.34 (d, J=5.7 Hz, 1H), 4.23 (d, J=9.8 Hz, 1H), 4.09 (d, J=28.2 Hz, 1H), 3.78 (d, J=10.9 Hz, 1H), 3.64 (d, J=13.2 Hz, 1H), 3.14-3.01 (m, 1H), 1.91-1.49 (m, 4H). LCMS-ESI$^+$ (m/z): [M+H]$^+$ calculated for C$_{21}$H$_{21}$N$_3$O$_4$: 380.16; found: 380.2.

Example 95

Preparation of chiral tert-butyl 3-((1,3-dioxoisoindolin-2-yl)methyl)-2-azabicyclo[2.1.1]hexane-2-carboxylates 95-A and 95-B

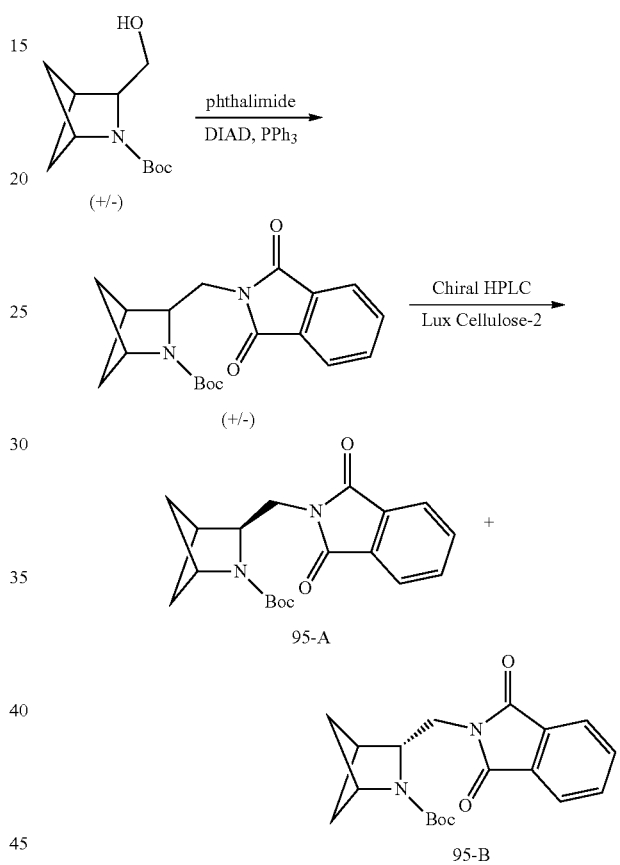

Absolute stereochemistries unknown

Step 1

To a 0° C. solution of racemic tert-butyl 3-(hydroxymethyl)-2-azabicyclo[2.1.1]hexane-2-carboxylate (285 mg, 1.34 mmol), triphenylphosphine (425 mg, 1.62 mmol), and phthalimide (240 mg, 1.62 mmol) in 9 mL THF was added dropwise a solution of diisopropyl azodicarboxylate (0.35 mL, 1.8 mmol) in 1 ml THF. The reaction mixture was warmed to room temperature, stirred for 90 minutes, concentrated onto silica, and purified by flash chromatography (0-25% EtOAc/hexanes) to afford tert-butyl 3-((1,3-dioxoisoindolin-2-yl)methyl)-2-azabicyclo[2.1.1]hexane-2-carboxylate as a racemic mixture. LCMS-ESI$^+$ (m/z): [M+H]$^+$ calculated for C$_{19}$H$_{23}$N$_2$O$_4$: 343.2; found: 342.8.
Step 2

Racemic tert-butyl 3-((1,3-dioxoisoindolin-2-yl)methyl)-2-azabicyclo[2.1.1]hexane-2-carboxylate (655 mg, 1.91 mmol) was separated by chiral HPLC on a Lux Cellulose-2 column using an acetronitrile eluent to afford chiral 95-A

Example 96

Preparation of Compound 96

(1R,3R,11 aS)-6-hydroxy-5,7-dioxo-N-(2,4,6-trifluorobenzyl)-2,3,5,7,11,11a-hexahydro-1H-1,3-methanopyrido[1,2-a]pyrrolo[1,2-d]pyrazine-8-carboxamide

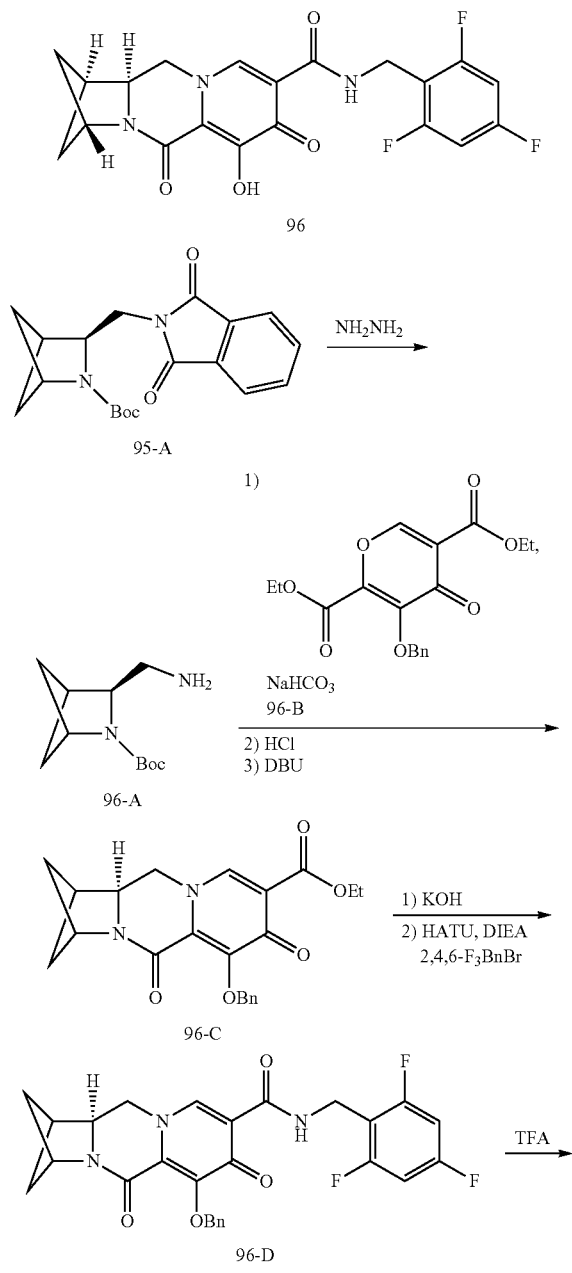

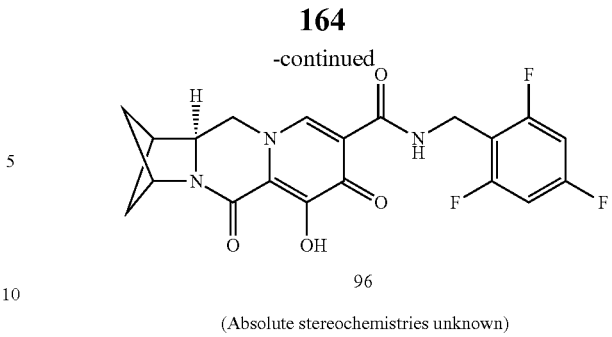

(Absolute stereochemistries unknown)

Step 1

To a solution of intermediate 95-A (141 mg, 0.41 mmol, 98% ee, unknown absolute stereochemistry) in 9 mL ethanol was added hydrazine hydrate (0.5 mL, 10.3 mmol) and stirred at 70° C. for 18 hours to afford 96-A of unknown absolute stereochemistry. Solids were removed by filtration and the filtrate concentrated and carried on as crude.

Step 2

A mixture of crude 96-A (0.41 mmol assumed), 96-B (430 mg, 1.25 mmol), and sodium bicarbonate (69 mg, 0.82 mmol) in 2 mL water and 2 mL ethanol were stirred at room temperature for 18 hours, after which the reaction mixture was diluted with water and thrice extracted to ethyl acetate. The combined organic phases were dried over magnesium sulfate, filtered, concentrated. The crude residue (222 mg) was dissolved in 1.5 mL DCM and 4 N HCl in dioxane (4 mL) was added and stirred for 90 minutes at room temperature. The mixture was concentrated to dryness and coevaporated with toluene. The crude residue and DBU (0.3 mL, 2.0 mmol) in 6 mL methanol was stirred at 50° C. for 90 minutes. The reaction mixture was then concentrated onto silica gel and purified by flash chromatography (0-10% MeOH/DCM) to afford 96-C. LCMS-ESI$^+$ (m/z): [M+H]$^+$ calculated for $C_{22}H_{22}N_2O_5$: 395.16; found: 395.2.

Step 3

A mixture of 96-C (112 mg, 0.28 mmol), 1M aqueous potassium hydroxide (1 mL), 4 mL methanol, and 4 mL THF was stirred at room temperature for 3 hours, at which point the mixture was diluted with dichloromethane, acidified by addition of 1M aqueous hydrogen chloride, and the organic phase extracted to dichloromethane. The combined organics were dried, filtered, and concentrated from toluene. After drying under vacuum, the residue was suspended in 1.5 mL DCM and trifluorobenzylamine (62 mg, 0.38 mmol), HATU (220 mg, 0.58 mmol), and N,N-diisopropylethylamine (DIPEA) (0.15 mL, 0.86 mmol) were added. This reaction mixture was stirred at room temperature for 2 hours to afford 96-D which was carried forward as crude.

Step 4

Trifluoroacetic acid (1.7 mL, 22.2 mmol) was added to the crude reaction solution containing 96-D from the prior step and the reaction mixture allowed to stir at room temperature for 90 minutes. 1 mL of DMF was then added, the reaction mixture concentrated down to ~1 mL, filtered, and purified by preparative HPLC (ACN/water+0.1% TFA) to afford compound 96 (unknown absolute stereochemistry). $^1$H-NMR (400 MHz, DMSO-d$_6$) δ 10.45-10.35 (m, 1H), 8.39 (s, 1H), 7.23-7.09 (m, 2H), 4.67 (dd, J=12.6, 4.8 Hz, 2H), 4.53 (d, J=5.5 Hz, 2H), 4.20 (dd, J=11.9, 3.8 Hz, 1H), 4.05-3.95 (m, 1H), 2.96-2.88 (m, 1H), 2.16 (d, J=7.0 Hz, 1H), 1.97 (d, J=7.0 Hz, 1H), 1.68-1.60 (m, 1H), 1.53-1.45 (m, 1H). LCMS-ESI$^+$ (m/z): [M+H]$^+$ calculated for $C_{20}H_{16}F_3N_3O_4$: 420.12; found: 420.2.

Example 97

Preparation of Compound 97

(1S,3S,11aR)-6-hydroxy-5,7-dioxo-N-(2,4,6-trifluorobenzyl)-2,3,5,7,11,11a-hexahydro-1H-1,3-methanopyrido[1,2-a]pyrrolo[1,2-d]pyrazine-8-carboxamide

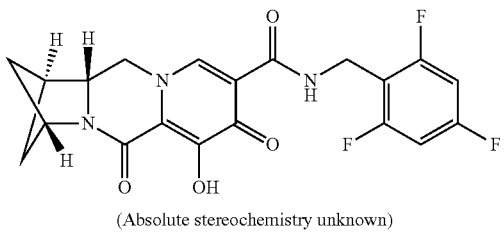

(Absolute stereochemistry unknown)

Compound 97 (49% ee, unknown absolute stereochemistry) was prepared in a similar manner to compound 96 using intermediate 95-B (49% ee, unknown absolute stereochemistry) in place of enantiomerically opposite intermediate 95-A. $^1$H-NMR (400 MHz, DMSO-d$_6$) δ 10.39 (t, J=5.7 Hz, 1H), 8.42 (s, 1H), 7.25-7.13 (m, 2H), 4.73-4.66 (m, 2H), 4.54 (d, J=5.7 Hz, 2H), 4.20 (dd, J=12.3, 3.9 Hz, 1H), 4.01 (t, J=12.4 Hz, 1H), 2.93 (dd, J=6.7, 3.4 Hz, 1H), 2.19-2.14 (m, 1H), 1.97 (d, J=8.3 Hz, 1H), 1.65 (dd, J=10.4, 7.9 Hz, 1H), 1.49 (dd, J=10.5, 7.7 Hz, 1H). LCMS-ESI$^+$ (m/z): [M+H]$^+$ calculated for C$_{20}$H$_{16}$F$_3$N$_3$O$_4$: 420.12; found: 420.2.

Example 98

Preparation of Compound 98

(1S,4R,12aR)-3,3-difluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

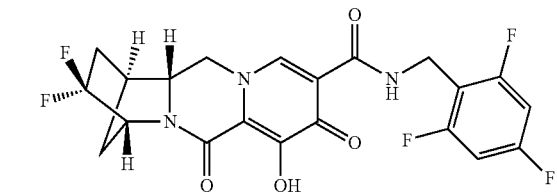

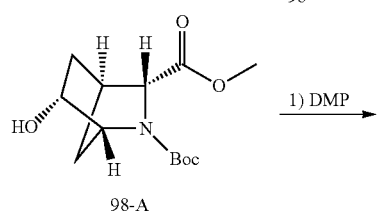

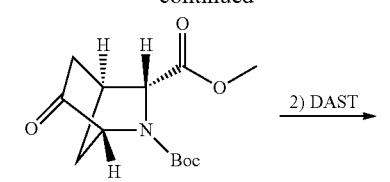

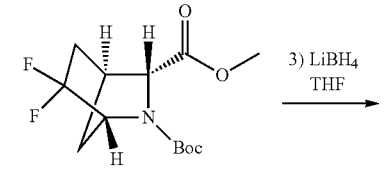

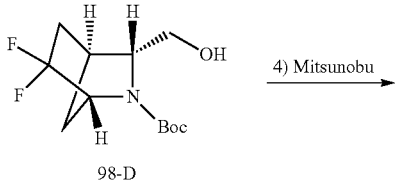

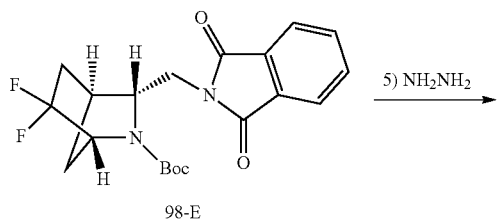

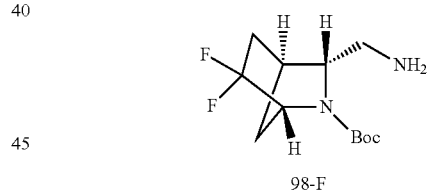

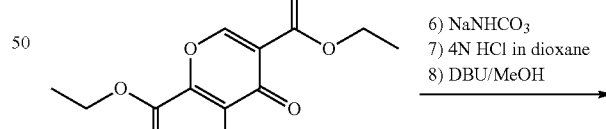

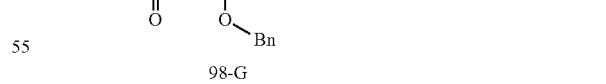

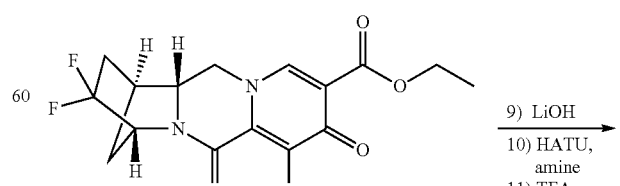

-continued

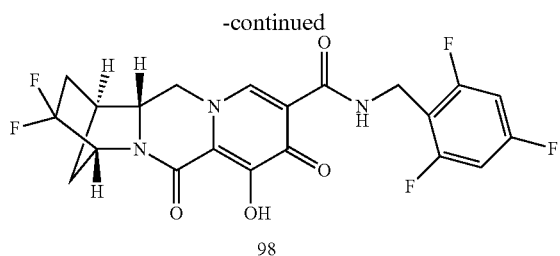

98

Step 1

98-A (0.5 g, 1.87 mmol) was dissolved in DCM (20 mL) and cooled to 0° C. under Nitrogen. Dess-Martin Periodinane (1.59 g, 3.74 mmol) was added slowly. The mixture was stirred for 2 h at room temperature, quenched with $Na_2S_2O_3$/$NaHCO_3$ (7:1) aqueous saturated solution (160 mL) and stirred vigorously until two layers were separated. The crude product was twice extracted with DCM. The combined organic layers was dried over sodium sulfate and concentrated. The crude product was purified by flash chromatography on silica gel with 0-20% MeOH/DCM to afford 98-B. $^1$H-NMR (400 MHz, Chloroform-d) δ 4.34-4.05 (m, 1H), 3.97-3.75 (m, 1H), 3.69 (s, 3H), 2.89 (dd, J=4.4, 2.1 Hz, 1H), 2.30-1.97 (m, 3H), 1.56 (d, J=11.3 Hz, 1H), 1.35 (s, 9H). LCMS-ESI$^+$ (m/z): [M+H]$^+$ calculated for $C_{13}H_{19}NO_5$: 269.13; found: 270.78.

Step 2

A solution of 98-B (504 mg, 1.87 mmol) in DCM (15 mL) was stirred at 0° C. DAST (1 ml) was added drop wise to the reaction mixture. After overnight stirring at room temperature, the reaction mixture was cooled back to 0° C. Saturated $NaHCO_3$ (10 mL) was added slowly. The mixture was extracted with twice with DCM and dried over $Na_2SO_4$. After concentrating, the residue was purified by flash chromatography 0-50% EtOAc/hexanes to give 98-C. $^1$H-NMR (400 MHz, Chloroform-d) δ 4.45-4.18 (m, 1H), 3.85 (m, 1H), 3.72 (d, J=1.5 Hz, 3H), 2.72 (ddd, J=5.1, 3.2, 1.6 Hz, 1H), 2.27-1.52 (m, 4H), 1.41 (d, J=21.9 Hz, 9H). $^{19}$F-NMR (376 MHz, Chloroform-d) δ −91.72--93.99 (m), −113.65--115.98 (m). LCMS-ESI$^+$ (m/z): [M+H]$^+$ calculated for $C_{13}H_{19}F_2NO_4$: 291.13; found: 291.55.

Step 3

98-C (476 mg, 1.634 mmol) in THF (20 mL) was stirred at 0° C. as 2.0 M LiBH$_4$ in THF (2.4 mL, 4.8 mmol) was added. The mixture was warmed to room temperature and stirred for 4 h. The reaction mixture was quenched with ice and diluted with EtOAc and saturated NH$_4$Cl (some H$_2$ evolution). After the two phases were separated, the organic fraction was washed with brine, dried (Na$_2$SO$_4$), and concentrated. The crude product of 98-D was used as is for the next step. LCMS-ESI (m/z): [M+H]$^+$ calculated for $C_{12}H_{19}F_2NO_3$: 263.13; found: 164.10.

Step 4

98-D (1.634 mmol), phthalimide (0.36 g, 2.4 5 mmol), and PPh$_3$ (0.855 g, 3.26 mmol) in THF (10 mL) was stirred at 0° C. bath as DIAD (0.642 mL, 3.26 mmol) was added. After addition, the mixture was stirred at 0° C. for 30 min and then at room temperature for 16 h. It was diluted with EtOAc, and saturated NH$_4$Cl. After stirring for 5 min, a solid was filtered off and the two phases were separated. The organic phase was washed with brine, dried (Na$_2$SO$_4$), and concentrated. The crude product was purified by flash chromatography with 0-50% EA/Hex as eluents to give 98-E. $^1$H-NMR suggests a mixture of two rotamers. $^1$H-NMR (400 MHz, Chloroform-d) δ 7.89-7.80 (m, 2H), 7.78-7.66 (m, 2H), 5.02 (ddt, J=16.6, 12.5, 6.3 Hz, 1H), 4.24 (d, J=71.8 Hz, 1H), 4.10-3.92 (m, 1H), 3.83-3.51 (m, 2H), 2.46 (s, 1H), 2.21-1.98 (m, 2H), 1.87-1.62 (m, 2H), 1.31 (d, J=8.5 Hz, 9H); $^{19}$F-NMR (376 MHz, Chloroform-d) δ −91.22--93.58 (m), −113.20--115.45 (m). LCMS-ESI$^+$ (m/z): [M+H]$^+$ calculated for $C_{20}H_{22}F_2N_2O_4$: 392.15; found: 393.3.

Step 5

To a solution of 98-E (696 mg, 1.774 mmol) in EtOH (10 mL) was added hydrazine hydrate (1 mL) at room temperature and the resulting solution was stirred at room temperature for 2 h. The mixture was diluted with ethyl ether (30 mL) and stirred at 0° C. for 60 min before filtration. The filtrate was concentrated and the residue was dissolved in CH$_2$Cl$_2$ and filtered. The filtrate was concentrated and purified by flash chromatography on silica gel with 0-20% MeOH (0.2% TEA)/DCM to give 98-F. $^1$H-NMR (400 MHz, Chloroform-d) δ 4.91 (p. J=6.2 Hz, 1H), 4.29-3.97 (m, 1H), 3.36-2.93 (m, 2H), 2.49 (qt, J=8.8, 5.2 Hz, 2H), 2.08 (dddd, J=25.5, 14.0, 7.1, 4.9 Hz, 1H), 1.89-1.49 (m, 4H), 1.41 and 1.21 (d, J=6.2 Hz, 9H). $^{19}$F-NMR (376 MHz, Chloroform-d) δ −91.63--93.16 (m), −113.11--115.08 (m). LCMS-ESI$^+$ (m/z): [M+H]$^+$ calculated for $C_{12}H_{20}F_2N_2O_2$: 262.15; found: 262.8.

Step 6, 7 and 8

The mixture of 98-G (375.8 mg, 1.55 mmol), 98-E (370 mg, 1.41 mmol), and NaHCO$_3$ (261 mg, 3.10 mmol) in water (5 mL) and EtOH (5 mL) was stirred at room temperature for 2 h. The mixture was diluted with brine and extracted with EtOAc (×2). The extracts were combined, dried (Na$_2$SO$_4$), concentrated, and dried in vacuo to afford crude A. LCMS-ESI$^+$ (m/z): [M+H]$^+$ 591.59. Crude A (1.38 mmol) in CH$_2$Cl$_2$ (5 mL) was added 4 N HCl in dioxane (5 mL). After 2 h at room temperature, mixture was concentrated to dryness. It was co-evaporated with toluene once and dried in vacuo to afford crude B. B (1.38 mmol+0.442 mmol) and DBU (3 mL, 11 mmol) in anhydrous MeOH (15 mL) were stirred at 50° C. bath for 40 min. The mixture was concentrated. The residue was purified by flash chromatography (80 g column) using 0-20% MeOH/DCM as eluents to give 98-H. LCMS-ESI$^+$ (m/z): [M+H]$^+$ calculated for $C_{23}H_{22}F_2N_2O_5$: 444.15; found: 445.36 (90%), 431.18 (10%).

Steps 9, 10 and 11

The remaining steps were performed using procedures similar to Example 41 to afford desired compound 98. $^1$H-NMR (400 MHz, Chloroform-d) δ 10.29 (d, J=6.1 Hz, 1H), 8.34 (s, 1H), 6.65 (dd, J=8.7, 7.5 Hz, 2H), 4.83 (s, 1H), 4.72-4.58 (m, 2H), 4.36-4.10 (m, 2H), 4.05 (t, J=11.5 Hz, 1H), 2.97 (d, J=4.4 Hz, 1H), 2.49-2.08 (m, 3H), 2.12-1.94 (m, 1H). $^{19}$F-NMR (376 MHz, Chloroform-d) δ −92.08--93.57 (m, 1F), −108.92 (ddd, J=15.1, 8.8, 6.3 Hz, 1F), −109.30--110.65 (m, 1F), −112.16 (p, J=7.3 Hz, 2F). LCMS-ESI$^+$ (m/z): [M+H]$^+$ calculated for $C_{21}H_{16}F_5N_3O_4$: 469.11; found: 470.23.

Example 99

Preparation of Compound 99

(1R,3S,4R,12aR)-7-hydroxy-3-methyl-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

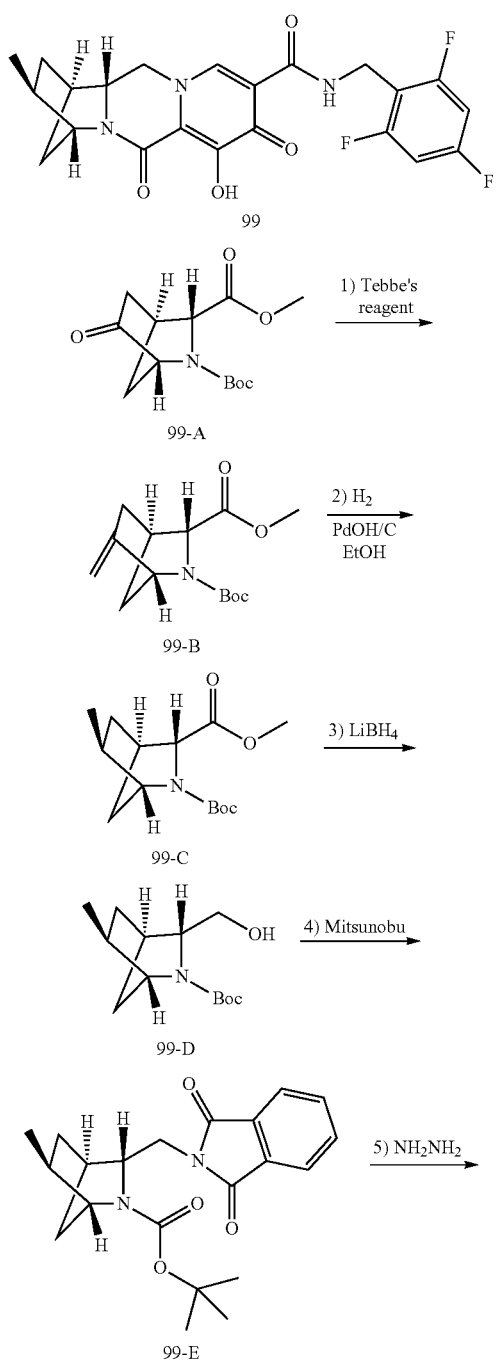

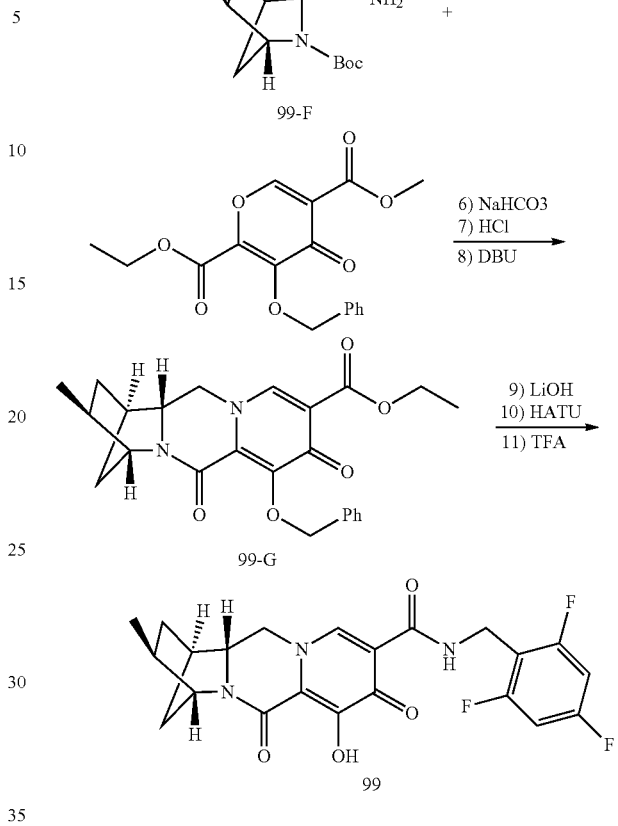

Step 1

To a stirred solution of 99-A (1 g, 3.71 mmol) in THF (20 mL) was added dropwise a solution of the Tebbe reagent (0.5 M in toluene, 14.85 mL, 7.42 mmol) at 0° C. After addition, the brown solution was allowed to warm to room temperature slowly and was stirred at room temperature for 2 h. The reaction was quenched carefully by the addition of saturated NaHCO$_3$ solution at 0° C., and the mixture was stirred at room temperature for 15 minutes. The mixture was filtered through celite, and the filter cake was washed with ether and DCM (1:1) twice. After separated layers, the organics were combined and concentrated in vacuo, and the residue was purified by column chromatography on silica gel column with 0-50% EtOAc/hexanes to afford 99-B. $^1$H-NMR (400 MHz, Chloroform-d) δ 5.06 (dt, J=48.6, 2.6 Hz, 1H), 4.73 (d, J=7.0 Hz, 1H), 4.42 (d, J=61.8 Hz, 1H), 3.81 (d, J=48.2 Hz, 1H), 3.73 (d, J=1.6 Hz, 3H), 2.74 (dd, J=9.4, 4.4 Hz, 1H), 2.38 (ddt, J=13.5, 4.5, 2.5 Hz, 1H), 2.18-2.06 (m, 1H), 1.99 (dt, J=10.2, 2.4 Hz, 1H), 1.58 (s, 1H), 1.42 (d, J=25.5 Hz, 9H). LCMS-ESI$^+$ (m/z): [M+H]$^+$ calculated for C$_{14}$H$_{21}$NO$_4$: 267.15; found: 267.65.

Step 2

A mixture of 99-B (675 mg, 2.506 mmol) and 20% Pd(OH)$_2$/C (500 mg) in EtOH (50 mL) was stirred under H$_2$ atmosphere. The mixture was filtered through Celite and the filtrate was concentrated to give 99-C. $^1$H-NMR (400 MHz, Chloroform-d) δ 4.23-3.99 (m, 1H), 3.77-3.64 (m, 4H), 2.55 (d, J=4.8 Hz, 1H), 2.14-1.86 (m, 3H), 1.42 (d, J=24.2 Hz, 9H), 0.96 (d, J=6.6 Hz, 3H), 0.85 (ddd, J=12.5, 4.8, 2.4 Hz, 1H). LCMS-ESI$^+$ (m/z): [M+H]$^+$ calculated for C$_{14}$H$_{23}$NO$_4$: 269.16; found: 269.69.

Step 3

99-C (670 mg, 2.488 mmol) in THF (20 mL) was stirred at 0° C. as 2.0 M LiBH$_4$ in THF (3.7 mL, 7.46 mmol) was added. The mixture was warmed to room temperature and stirred for 4 h. The reaction mixture was quenched with ice and diluted with EtOAc and saturated NH$_4$Cl (some H$_2$ evolution). After two phases were separated, the organic fraction was washed with brine, dried (Na$_2$SO$_4$), and concentrated. The crude alcohol 99-D was used as is for the next step. LCMS-ESI$^+$ (m/z): [M+H]$^+$ calculated for C$_{13}$H$_{23}$NO$_3$: 241.17; found: 241.76.

Steps 4 and 5

Steps 4 and 5 were performed using procedures similar to those in Example 41 to afford 99-F. LCMS-ESI$^+$ (m/z): [M+H]$^+$ calculated for C$_{13}$H$_{24}$N$_2$O$_2$: 240.18; found: 241.2.

Step 6, 7 and 8

Steps 6, 7 and 8 were performed using procedures similar to that of Example 41 to give 99-G. LCMS-ESI$^+$ (m/z): [M+H]$^+$ calculated for C$_{24}$H$_{26}$N$_2$O$_5$: 422.18; found: 423.21.

Step 9, 10 and 11

The remaining steps were performed using procedures similar to Example 41 to afford compound 99. $^1$H-NMR (400 MHz, Chloroform-d) δ 11.71 (s, 1H), 10.36 (t, J=5.7 Hz, 1H), 8.28 (s, 1H), 6.63 (t, J=8.1 Hz, 2H), 4.63 (t, J=5.4 Hz, 3H), 4.12 (dd, J=12.3, 3.5 Hz, 1H), 3.83 (t, J=12.3 Hz, 1H), 3.67 (dd, J=12.3, 3.4 Hz, 1H), 2.64-2.52 (m, 1H), 2.30 (ddq, J=10.5, 7.2, 3.6 Hz, 1H), 2.13 (td, J=12.1, 4.4 Hz, 1H), 1.82-1.63 (m, 2H), 1.24 (d, J=3.3 Hz, 1H), 1.04 (d, J=6.9 Hz, 4H), 0.90-0.79 (m, 1H). $^{19}$F-NMR (376 MHz, Chloroform-d) δ −109.20 (ddd, J=15.0, 8.8, 6.2 Hz), −112.03 (t, J=7.0 Hz). LCMS-ESI$^+$ (m/z): [M+H]$^+$ calculated for C$_{22}$H$_{20}$F$_3$N$_3$O$_4$: 447.14; found: 448.32.

Example 100

Preparation of Compound 100

(1R,4R,12aS)—N-(2,4-difluorobenzyl)-7-hydroxy-6,8-dioxo-1,2,3,4,6,8,12,12a-octahydro-1,4-ethanodipyrido[1,2-a:1',2'-d]pyrazine-9-carboxamide

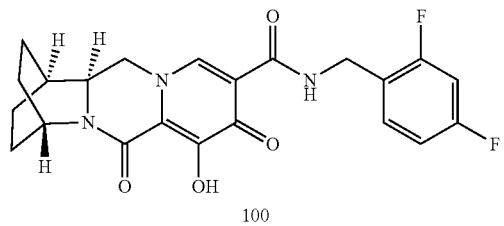

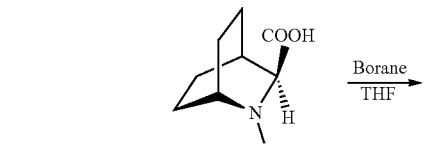

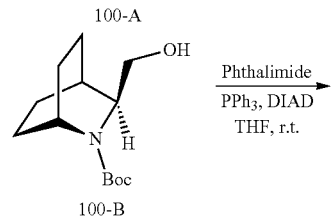

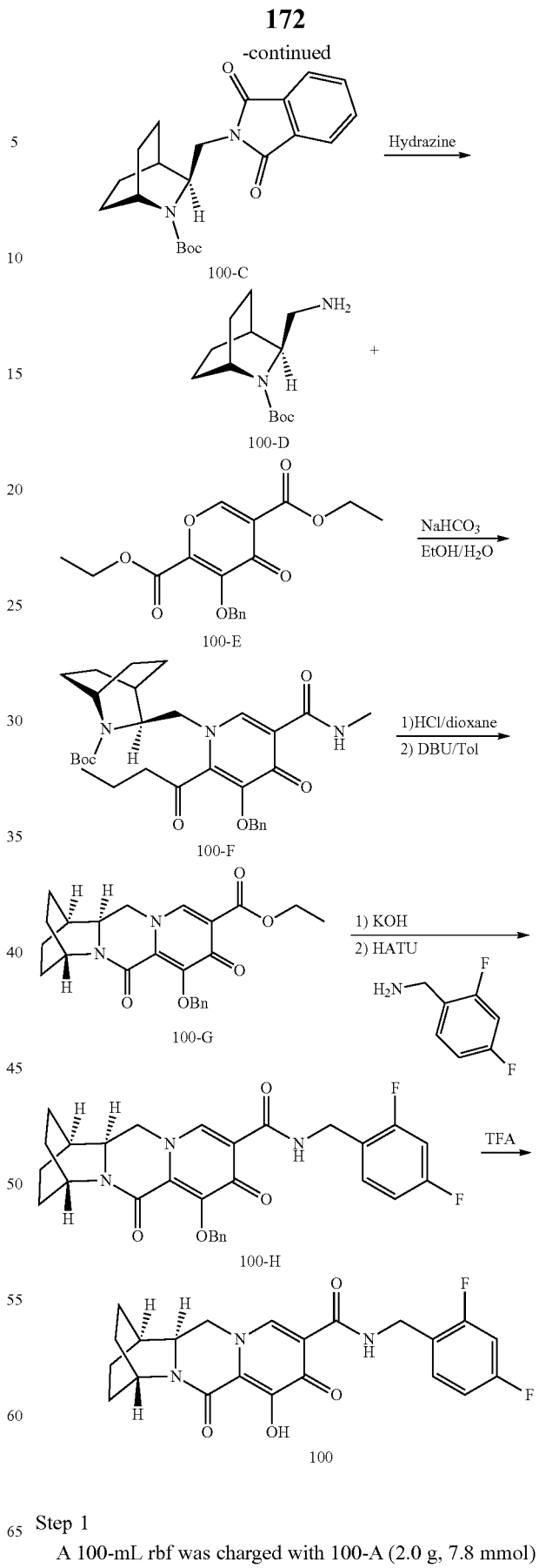

Step 1

A 100-mL rbf was charged with 100-A (2.0 g, 7.8 mmol) in THF (20 mL). The reaction mixture was cooled to 0° C.

Borane dimethyl sulfide (2 N in THF, 17.6 mL) was slowly added in. Then the reaction mixture was stirred at room temperature for overnight. The reaction mixture was cooled back to 0° C. Methanol (8 mL) was added drop wise to quench the reaction. After concentration, the residue was purified by Combi Flash (40 g column, cartridge used) using hexanes-EA as eluents to afford 100-B. LCMS-ESI$^+$ (m/z): [M+H]$^+$ found: 242.
Step 2

A 100-mL rbf was charged with 100-B (1.8 g, 7.4 mmol), triphenylphosphine (4.3 g, 16.2 mmol) and phthalimide (1.8 g, 12.2 mmol) in THF (30 mL). Then the reaction mixture was cooled to 0° C. with stirring. DIAD (3.2 mL, 16.2 mmol) was slowly added to the reaction mixture. The reaction mixture was stirred at room temperature for overnight. After concentration, the residue was purified by Combi Flash (80 g column, cartridge used) using hexanes-EA as eluents to afford 100-C. LCMS-ESI$^+$ (m/z): [M+H]$^+$ found: 371.
Step 3

To a solution of 100-C (2.5 g, 6.8 mmol) in EtOH (50 mL) was added hydrazine monohydrate (1.7 mL). The reaction mixture was heated to 70° C. with stirring for 3 hours. After filtration to remove the solid, the filtrate was concentrated to afford 100-D. LCMS-ESI$^+$ (m/z): [M+H]$^+$ found: 241.
Step 4

A 100-mL rbf was charged with 100-D (1.6 g, 6.7 mmol) and 100-E (2.3 g, 6.7 mmol) in ethanol (30 mL). Sodium bicarbonate (1.2 g, 1.4 mmol) in water (30 mL) was added to the reaction mixture. Then the reaction mixture was stirred at room temperature for overnight. The mixture was diluted with EA (200 mL) and washed with water (2×). The aqueous fractions were extracted with EA (1×), and the organic fractions were combined, dried (Na$_2$SO$_4$), and concentrated. The crude 100-F was used for next step without further purification. LCMS-ESI$^+$ (m/z): [M+H]$^+$ found: 569.
Step 5

A 100-mL rbf was charged with 100-F (3.7 g, 6.5 mmol) in 4 N HCl/dioxane (38 mL). Then the reaction mixture was stirred at room temperature for 1 hour. After concentration, 3.2 g intermediate was obtained. The intermediate and DBU (5.1 g, 33.8 mmol) were dissolved in toluene (100 mL). The reaction mixture was heated to 110° C. with stirring for 1 hour. After concentration, the residue was purified by Combi Flash (80 g column, cartridge used) using hexanes-EA as eluents to afford 100-G. LCMS-ESI$^+$ (m/z): [M+H]$^+$ found: 423.
Step 6

A 100-mL rbf was charged with 100-G (2.0 g, 4.7 mmol) in THF (20 mL) and MeOH (20 mL). 1 N KOH (18.9 mL) was added to the reaction mixture. Then the reaction mixture was stirred at room temperature for 1 hour. The reaction mixture was acidified by adding 1 N HCl (18.9 mL). After concentration, the residue was co-evaporated with toluene (3×). The crude acid (0.28 g, 0.72 mmol), 2, 4-difluobenzylamine (0.2 g, 1.44 mmol), N,N-diisopropylethylamine (DIPEA) (0.47 g, 3.6 mmol) and HATU (0.55 g, 1.44 mmol) were dissolved in DCM (20 mL). The reaction mixture was stirred at room temperature for 2 hours. The mixture was diluted with EA (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford 100-H. LCMS-ESI$^+$ (m/z): [M+H]$^+$ found: 520.
Step 7

A 50-mL rbf was charged with 100-H (0.36 g, 0.69 mmol) in TFA (5 mL). The reaction mixture was stirred at room temperature for 30 minutes. After concentration, the crude was purified by column chromatography on silica gel with EtOAc-MeOH to afford compound 100. $^1$H-NMR (400 MHz, Chloroform-d) δ 12.25 (m, 1H), 10.47 (t, J=5.9 Hz, 1H), 8.30 (s, 1H), 7.58-7.29 (m, 1H), 6.98-6.50 (m, 2H), 4.62 (dd, J=14.8, 4.9 Hz, 3H), 4.22 (t, J=12.2 Hz, 1H), 4.14-4.07 (m, 1H), 3.96 (dd, J=12.2, 3.1 Hz, 1H), 2.26-1.44 (m, 9H). $^{19}$F-NMR (376 MHz, Chloroform-d) δ -112.38 (t, J=7.7 Hz), -114.78 (q, J=8.5 Hz). LCMS-ESI$^+$ (m/z): found: 430.

Example 101

Preparation of Compound 101

(1R,4R,12aS)-7-hydroxy-6,8-dioxo-N-(2,4,6-trifluorobenzyl)-1,2,3,4,6,8,12,12a-octahydro-1,4-ethanodipyrido[1,2-a:1',2'-d]pyrazine-9-carboxamide

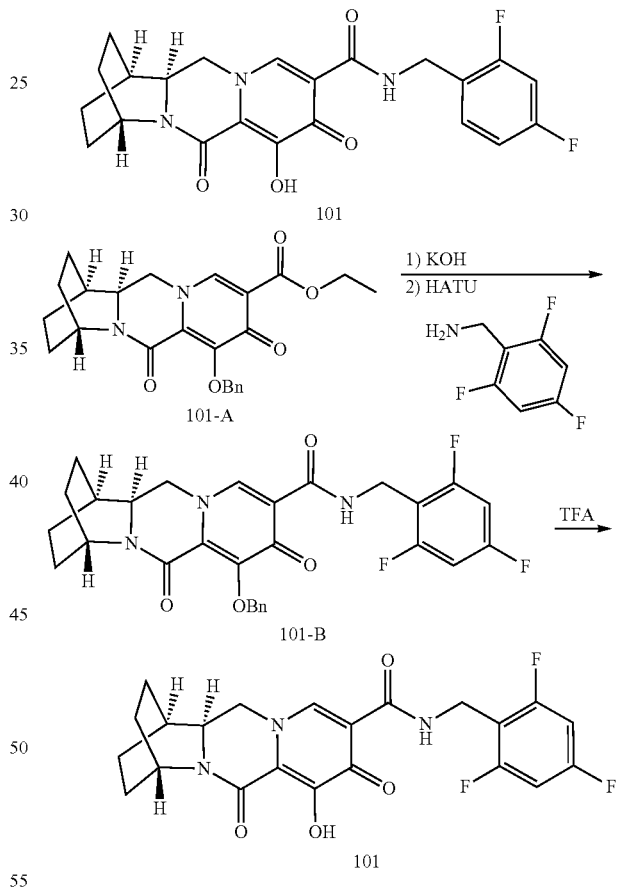

Step 1

A 100-mL rbf was charged with 101-A (0.3 g, 0.72 mmol) in THF (2 mL) and MeOH (2 mL). 1 N KOH (2.1 mL) was added to the reaction mixture. Then the reaction mixture was stirred at room temperature for 1 hour. The reaction mixture was acidified by adding 1 N HCl (2.1 mL). After concentration, the residue was co-evaporated with toluene (3×). The crude acid (0.72 mmol), 2, 4, 6-trifluobenzylamine (0.23 g, 1.44 mmol), N,N-diisopropylethylamine (DIPEA) (0.47 g, 3.6 mmol) and HATU (0.55 g, 1.44 mmol) were dissolved in DCM (20 mL). The reaction mixture was stirred at room temperature for 2 hours. The mixture was diluted with EA (100 mL) and washed with saturated NaHCO$_3$ (2×), saturated NH$_4$Cl (2×) and dried over Na$_2$SO$_4$. After concentration, the crude was purified by column chromatography on silica gel with hexane-EtOAc to afford 101-B. LCMS-ESI$^+$ (m/z): [M+H]$^+$ found: 538.

Step 2

A 50-mL rbf was charged with 101-B (0.36 g, 0.67 mmol) in TFA (5 mL). The reaction mixture was stirred at room temperature for 30 minutes. After concentration, the crude was purified by column chromatography on silica gel with EtOAc-MeOH to afford compound 101. $^1$H-NMR (400 MHz, Chloroform-d) δ 12.11 (s, 1H), 10.40 (t, J=5.8 Hz, 1H), 8.28 (s, 1H), 6.91-6.39 (m, 2H), 4.62 (ddd, J=25.0, 6.5, 2.8 Hz, 3H), 4.21 (t, J=12.2 Hz, 1H), 4.09 (dd, J=12.5, 3.0 Hz, 1H), 3.93 (dd, J=12.2, 3.1 Hz, 1H), 2.35-1.39 (m, 9H). $^{19}$F NMR (376 MHz, Chloroform-d) δ −112.38 (t, J=7.7 Hz), −114.78 (q, J=8.5 Hz). LCMS-ESI$^+$ (m/z): found: 448.

Example 102

Preparation of Compound 102

(1S,4S,12aR)-7-hydroxy-6,8-dioxo-N-(2,4,6-trifluorobenzyl)-1,2,3,4,6,8,12,12a-octahydro-1,4-ethanodipyrido[1,2-a:1',2'-d]pyrazine-9-carboxamide

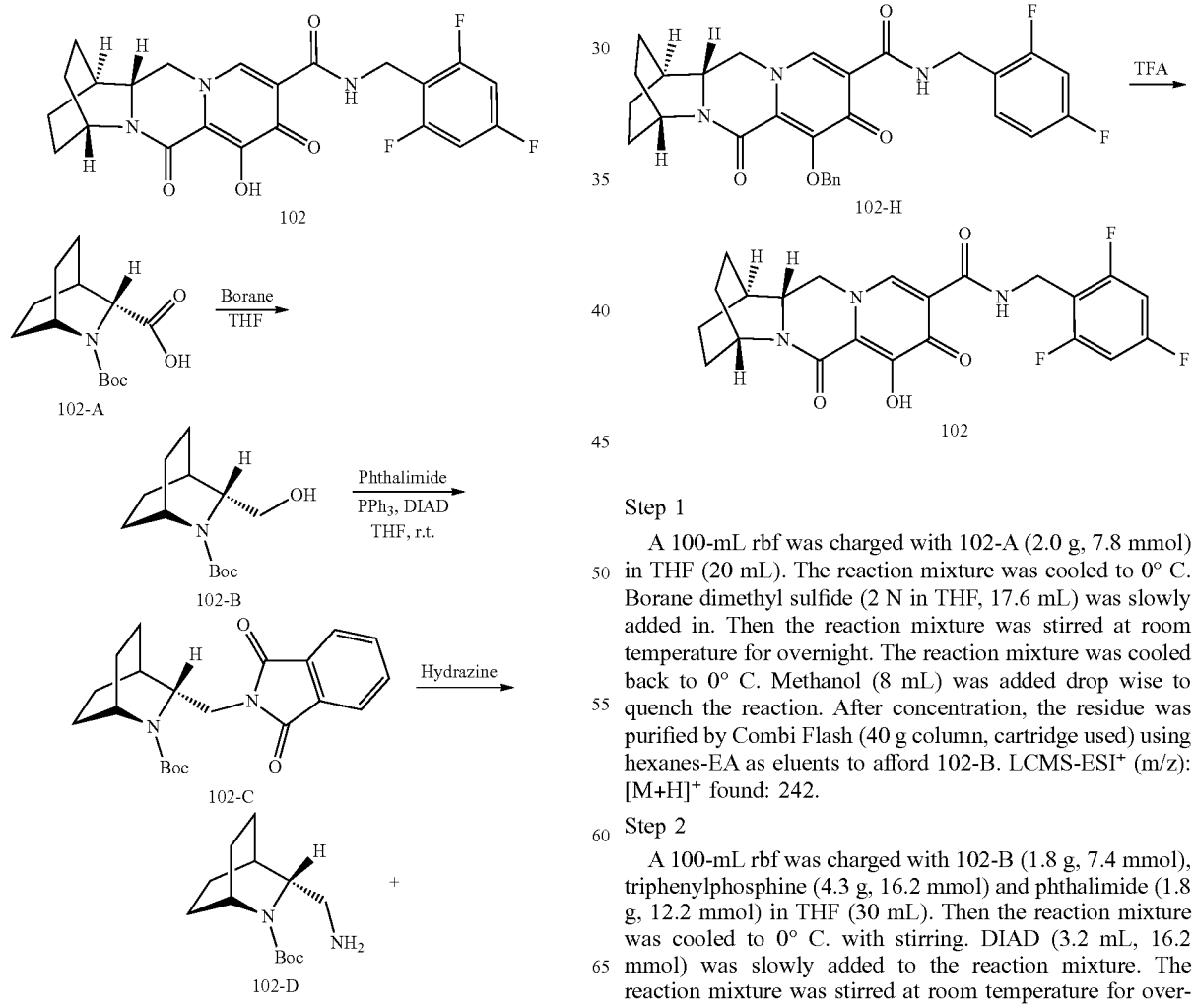

Step 1

A 100-mL rbf was charged with 102-A (2.0 g, 7.8 mmol) in THF (20 mL). The reaction mixture was cooled to 0° C. Borane dimethyl sulfide (2 N in THF, 17.6 mL) was slowly added in. Then the reaction mixture was stirred at room temperature for overnight. The reaction mixture was cooled back to 0° C. Methanol (8 mL) was added drop wise to quench the reaction. After concentration, the residue was purified by Combi Flash (40 g column, cartridge used) using hexanes-EA as eluents to afford 102-B. LCMS-ESI$^+$ (m/z): [M+H]$^+$ found: 242.

Step 2

A 100-mL rbf was charged with 102-B (1.8 g, 7.4 mmol), triphenylphosphine (4.3 g, 16.2 mmol) and phthalimide (1.8 g, 12.2 mmol) in THF (30 mL). Then the reaction mixture was cooled to 0° C. with stirring. DIAD (3.2 mL, 16.2 mmol) was slowly added to the reaction mixture. The reaction mixture was stirred at room temperature for overnight. After concentration, the residue was purified by Combi Flash (80 g column, cartridge used) using hexanes-EA as eluents to afford 102-C. LCMS-ESI+ (m/z): [M+H]+ found: 371.

Step 3

To a solution of 102-C (2.5 g, 6.8 mmol) in EtOH (50 mL) was added hydrazine monohydrate (1.7 mL). The reaction mixture was heated to 70° C. with stirring for 3 hours. After filtration to remove the solid, the filtrate was concentrated to afford 102-D. LCMS-ESI+ (m/z): [M+H]+ found: 241.

Step 4

A 100-mL rbf was charged with 102-D (1.6 g, 6.7 mmol) and 102-E (2.3 g, 6.7 mmol) in ethanol (30 mL). Sodium bicarbonate (1.2 g, 1.4 mmol) in water (30 mL) was added to the reaction mixture. Then the reaction mixture was stirred at room temperature for overnight. The mixture was diluted with EA (200 mL) and washed with water (2×). The aqueous fractions were extracted with EA (1×), and the organic fractions were combined, dried ($Na_2SO_4$), and concentrated. The crude 102-F was used for next step without further purification. LCMS-ESI+ (m/z): [M+H]+ found: 569.

Step 5

A 100-mL rbf was charged with 102-F (3.7 g, 6.5 mmol) in 4 N HCl/dioxane (38 mL). Then the reaction mixture was stirred at room temperature for 1 hour. After concentration, 3.2 g intermediate was obtained. The intermediate and DBU (5.1 g, 33.8 mmol) were dissolved in toluene (100 mL). The reaction mixture was heated to 110° C. with stirring for 1 hour. After concentration, the residue was purified by Combi Flash (80 g column, cartridge used) using hexanes-EA as eluents to afford 102-G. LCMS-ESI+ (m/z): [M+H]+ found: 423.

Step 6

A 100-mL rbf was charged with 102-G (0.3 g, 0.72 mmol) in THF (2 mL) and MeOH (2 mL). 1 N KOH (2.1 mL) was added to the reaction mixture. Then the reaction mixture was stirred at room temperature for 1 hour. The reaction mixture was acidified by adding 1 N HCl (2.1 mL). After concentration, the residue was co-evaporated with toluene (3×). The crude acid (0.72 mmol), 2, 4, 6-trifluobenzylamine (0.23 g, 1.44 mmol), N,N-diisopropylethylamine (DIPEA) (0.47 g, 3.6 mmol) and HATU (0.55 g, 1.44 mmol) were dissolved in DCM (20 mL). The reaction mixture was stirred at room temperature for 2 hours. The mixture was diluted with EA (100 mL) and washed with saturated $NaHCO_3$ (2×), saturated $NH_4Cl$ (2×) and dried over $Na_2SO_4$. After concentration, the crude was purified by column chromatography on silica gel with hexane-EtOAc to afford 102-H. LCMS-ESI+ (m/z): [M+H]+ found: 538.

Step 7

A 50-mL rbf was charged with 102-H (0.36 g, 0.67 mmol) in TFA (5 mL). The reaction mixture was stirred at room temperature for 30 minutes. After concentration, the crude was purified by column chromatography on silica gel with EtOAc-MeOH to afford compound 102. $^1$H-NMR (400 MHz, Chloroform-d) δ 12.13 (s, 1H), 10.40 (t, J=5.8 Hz, 1H), 8.28 (s, 1H), 6.64 (t, J=8.1 Hz, 2H), 4.89-4.41 (m, 3H), 4.22 (t, J=12.2 Hz, 1H), 4.09 (dd, J=12.3, 3.1 Hz, 1H), 3.95 (dd, J=12.1, 4.1 Hz, 1H), 2.45-1.60 (m, 9H). $^{19}$F-NMR (376 MHz, Chloroform-d) δ -109.26 (ddd, J=15.1, 8.8, 6.3 Hz), -111.99 (t, J=6.9 Hz). LCMS-ESI+ (m/z): found: 448.

Example 103

Preparation of Compound 103

(1R,4R,12aR)-2,3-difluoro-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide

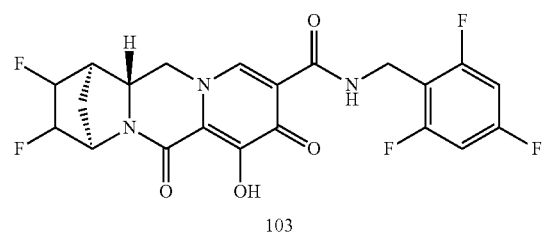

103

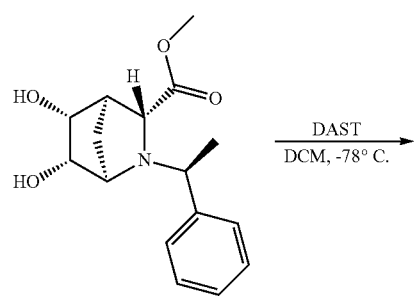

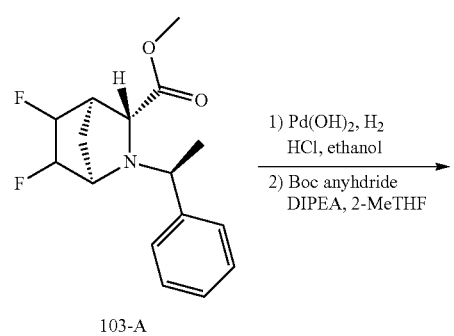

103-A

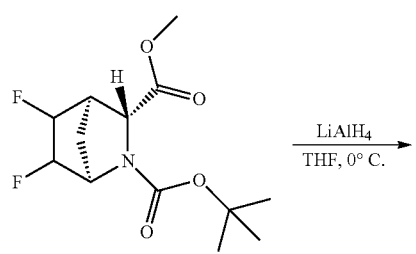

103-B

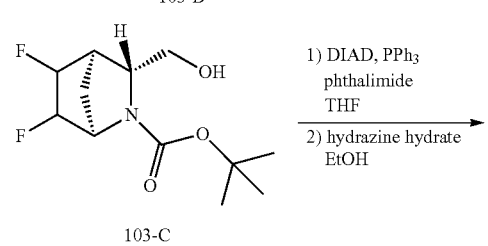

103-C

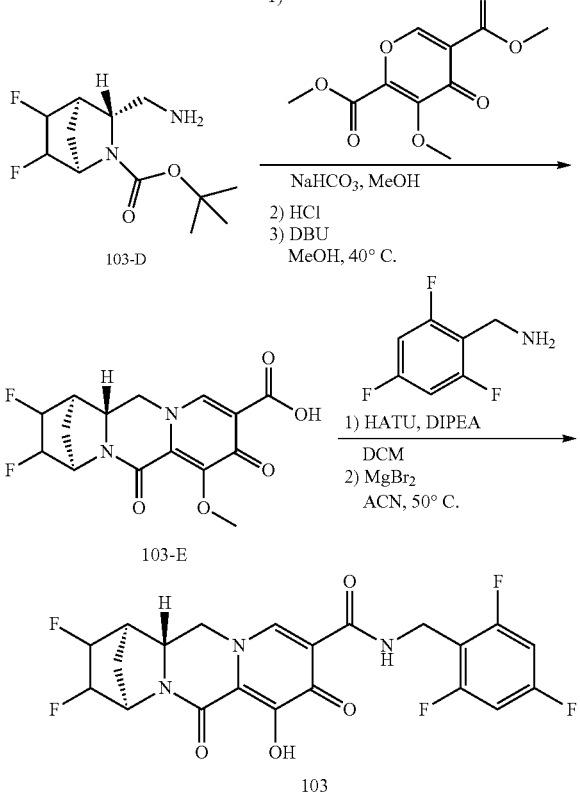

Step 1

A solution of (1R,3R,4R,5R,6S)-methyl 5,6-dihydroxy-2-((S)-1-phenylethyl)-2-azabicyclo[2.2.1]heptane-3-carboxylate (2.0 g, 6.9 mmol) in DCM (27 mL) was cooled to −78° C. in a dry ice/acetone bath. To this solution was added DAST (2.18 ml, 16.48 mmol) via plastic tipped pipette. The solution was stirred at −78° C. for 30 minutes after which time it was removed from the bath, let warm slowly to room temperature, and stirred at room temperature for one hour. The reaction was quenched by slow addition of the reaction mixture to a stirring solution of saturated sodium bicarbonate (150 mL) via plastic tipped pipette. The layers were separated and the aqueous layer was back-extracted with dichloromethane. The combined organic layers were dried over magnesium sulfate, filtered and concentrated in vacuo. The crude product was purified by silica gel chromatography (7-28% ethyl acetate/hexane) to provide 103-A. $^1$H-NMR (400 MHz, Chloroform-d) δ 7.43-7.16 (m, 5H), 5.01-4.60 (m, 2H), 3.85 (q, J=7.1, 6.6 Hz, 1H), 3.55 (s, 2H), 3.53-3.42 (m, 2H), 2.76 (dq, J=5.1, 2.0 Hz, 1H), 2.19-2.07 (m, 1H), 2.03-1.88 (m, 1H), 1.39 (d, J=6.7 Hz, 3H).

Steps 2 and 3

To a solution of 103-A (0.96 g, 3.24 mmol) in Ethanol (36.01 ml) and 1.25M HCl-ethanol (4.09 ml) was added 20% PdOH/C (1.14 g, 1.62 mmol) the suspension was stirred under an atmosphere of hydrogen for 22 hours. After filtering through Celite, the cake was washed with EtOH, the filtrate was concentrated under vacuum to dryness to afford the crude deprotected product which was assumed to be 3.24 mmol for next step. LCMS-ESI$^+$ (m/z): [M+H]$^+$ calculated for $C_8H_{12}F_2NO_2$: 192.08; found: 192.110.

To the crude residue (0.62 g, 3.24 mmol) and Di-tert-butyl dicarbonate (1.06 g, 4.86 mmol) in 2-Methyltetrahydrofuran (32.43 ml) was added N,N-diisopropylethylamine (0.56 ml, 0 mol). Upon completion, the reaction mixture was diluted with water, extracted into EtOAC (2×) and the organic fractions were washed with water, combined, dried (Na$_2$SO$_4$), and concentrated. The residue was purified by silica column chromatography (0-55% EtOAc/Hexanes) to afford 103-B. $^1$H-NMR (400 MHz, Chloroform-d) δ 5.12-5.01 (m, 1H), 4.92 (s, 1H), 4.49 (s, 1H), 4.14 (d, J=14.7 Hz, 1H), 3.75 (s, 3H), 2.91 (s, 1H), 2.24-1.98 (m, 2H), 1.47 (s, 5H), 1.38 (s, 5H). LCMS-ESI$^+$ (m/z): [M+H]$^+$ calculated for $C_{13}H_{20}F_2NO_4$: 292.13; found: 291.75.

Step 4

A solution of 103-B (0.68 g, 2.33 mmol) in THF (15 ml) was stirred in an ice bath as 1.0 M LiBH$_4$ in THF (4.65 ml) was added and the resulting mixture was stirred at 0° C. for 30 minutes at which time it was shown to be complete by TLC. The reaction mixture was carefully treated with water (0.3 mL), then with NaOH (~15%, 3.5M, 0.3 mL), then finally with additional water (0.9 mL). The mixture was stirred at room temperature for 15 minutes, and the ppt that formed was filtered, washed with diethyl ether and the supernate was concentrated to afford 103-C. $^1$H-NMR (400 MHz, Chloroform-d) δ 4.83 (s, 1H), 4.56 (d, J=10.5 Hz, 1H), 4.37 (s, 1H), 3.78-3.47 (m, 3H), 2.76 (s, 1H), 2.36-2.18 (m, 1H), 2.17-1.98 (m, 1H), 1.55 (s, 1H), 1.48 (s, 9H).

Steps 5 and 6

A mixture of 103-C (0.59 g, 2.25 mmol), phthalimide (0.53 g, 3.6 mmol) and triphenylphosphine (1.3 g, 4.95 mmol) in THF (11 ml) was cooled in an ice bath. Diisopropyl Azodicarboxylate (0.97 ml, 4.95 mmol) was added. The mixture was then warmed up to room temperature and stirred for 14 h and then concentrated in vacuo. The residue was dissolved in ether, stirred for 1 h, then the solids were filtered off and the filtrate was concentrated. The residue was purified by silica column chromatography (10-31-91% EtOAc/hexanes) to afford the protected amino compound (assumed 2.25 mmol of product). LCMS-ESI$^+$ (m/z): [M+H]$^+$ calculated for $C_{20}H_{23}F_2N_2O_4$: 393.15; found: 392.77.

A solution of the protected amino compound (0.88 g, 2.25 mmol) and hydrazine hydrate (0.46 ml, 9.52 mmol) in ethanol (22 ml) was stirred at 60° C. for 2 h. The reaction mixture was cooled in an ice bath, ether (10 ml) was added and the mixture was stirred for 30 min. The solid formed was filtered off and the filtrate was concentrated under vacuum to dryness to give 103-D. $^1$H-NMR (400 MHz, Chloroform-d) δ 5.17-4.61 (m, 2H), 4.37 (s, 1H), 3.80 (s, 1H), 3.11-2.77 (m, 1H), 2.01 (s, 2H), 1.87 (s, 1H), 1.83 (d, J=7.4 Hz, 1H), 1.46 (s, 9H), 1.30 (d, J=6.4 Hz, 1H), 1.27 (d, J=6.3 Hz, 3H). LCMS-ESI$^+$ (m/z): [M+H]$^+$ calculated for $C_{12}H_{20}F_2N_2O_2$: 263.15; found: 262.86.

Steps 7, 8 and 9

Compound 103 was prepared in a similar manner to compound 60 using 103-D in place of 41-E and using (2,4,6-trifluorophenyl)methanamine in place of (2,3-dichlorophenyl)methanamine. A single diastereomer resulted. The stereochemistry of the fluorines is unknown. $^1$H-NMR (400 MHz, Chloroform-d) δ 8.08 (s, 1H), 6.46-6.27 (m, 2H), 4.95 (d, J=53.5 Hz, 1H), 4.65 (d, J=54.9 Hz, 1H), 4.45 (s, 1H), 4.33 (d, J=5.6 Hz, 2H), 3.84 (t, J=3.6 Hz, 2H), 2.75 (s, 1H), 2.28 (p, J=1.9 Hz, 2H), 2.20 (s, 1H), 1.91 (dd, J=33.3, 15.2 Hz, 1H), 0.95 (s, 1H). LCMS-ESI$^+$ (m/z): [M+H]$^+$ calculated for $C_{21}H_{17}F_5N_3O_4$: 470.11; found: 0.470.13.

Antiviral Assay

Example 104

Antiviral Assays in MT4 Cells

For the antiviral assay utilizing MT4 cells, 0.4 µL of 189X test concentration of 3-fold serially diluted compound in DMSO was added to 40 µL of cell growth medium (RPMI 1640, 10% FBS, 1% penicilline/Streptomycine, 1% L-Glutamine, 1% HEPES) in each well of 384-well assay plates (10 concentrations) in quidruplicate.

1 mL aliquots of $2\times10^6$ MT4 cells are pre-infected for 1 and 3 hours respectively at 37° C. with 25 µL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 µL of 2000 (for MT4) cells is added to each well of the assay plates.

Assay plates were then incubated in a 37° C. incubator. After 5 days of incubation, 25 µL of 2× concentrated CellTiter-Glo™ Reagent (catalog # G7573, Promega Biosciences, Inc., Madison, Wis.) was added to each well of the assay plate. Cell lysis was carried out by incubating at room temperature for 2-3 minutes, and then chemiluminescence was read using the Envision reader (PerkinElmer).

Compounds of the present invention demonstrate antiviral activity in this assay as depicted in Table 1 below. Accordingly, the compounds of the invention may be useful for treating the proliferation of the HIV virus, treating AIDS, or delaying the onset of AIDS or ARC symptoms.

TABLE 1

| Compound Number | nM in MT-4 | |
| --- | --- | --- |
| | $EC_{50}$ | $CC_{50}$ |
| 1 | 2.6 | 5819 |
| 2 | 2.2 | 3111 |
| 3 | 2.0 | 38446 |
| 4 | 14.8 | 45769 |
| 5 | 8.1 | 10452 |
| 6 | 5.3 | 53192 |
| 7 | 3.5 | 15610 |
| 8 | 2.5 | 13948 |
| 9 | 5.1 | 13451 |
| 10 | 6.1 | 3670 |
| 11 | 4.9 | 10274 |
| 12 | 5.9 | 3337 |
| 13 | 46.0 | 12666 |
| 14 | 65.5 | 4939 |
| 15 | 2.2 | 16268 |
| 16 | 1.5 | 13633 |
| 17 | 5.9 | 6613 |
| 18 | 4.1 | 10263 |
| 19 | 2.8 | 38690 |
| 20 | 3.3 | 27990 |
| 21 | 38.3 | 13010 |
| 22 | 64.3 | 4433 |
| 23 | 2.3 | 13444 |
| 24 | 6.1 | 12074 |
| 25 | 26.2 | 5233 |
| 26 | 10.3 | 8836 |
| 27 | 4.4 | 8751 |
| 28 | 15.6 | 18687 |
| 29 | 13.9 | 9446 |
| 30 | 4.0 | 6828 |
| 31 | 9.0 | 4525 |
| 32 | 14.0 | 4684 |
| 33 | 43.5 | 3971 |
| 34 | 422.1 | 3585 |
| 35 | 157.0 | 15546 |
| 36 | 7.6 | 11424 |
| 37 | 10.2 | 19486 |
| 38 | 1.7 | 10223 |
| 39 | 3.6 | 12174 |
| 40 | 2.4 | 9560 |
| 41 | 2.1 | 15675 |
| 42 | 2.5 | 3544 |
| 43 | 6.9 | 10321 |
| 44 | 2.3 | 9869 |
| 45 | 2.4 | 15765 |
| 46 | 2.6 | 19295 |
| 47 | 1.9 | 11301 |
| 48 | 2.7 | 13967 |
| 49 | 33.3 | 52219 |
| 50/51 (racemic mixture) | 1.9 | 37173 |
| 52 | 15.0 | 12943 |
| 53 | 14.3 | 3347 |
| 54 | 15.6 | 3236 |
| 55 | 1.5 | 11100 |
| 56 | 3.1 | 17238 |
| 57 | 2.3 | 11751 |
| 58 | 1.5 | 7694 |
| 59 | 3.1 | 22200 |
| 60 | 2.1 | 3308 |
| 61 | 1.8 | 25881 |
| 62 | 9.2 | 3492 |
| 63 | 2.5 | 3164 |
| 64 | 3.5 | 3332 |
| 65 | 2.4 | 2508 |
| 66 | 9.4 | 11848 |
| 67 | 10.7 | 2981 |
| 68 | 2.7 | 4175 |
| 69 | 1.9 | 4767 |
| 70 | 5.1 | 8413 |
| 71 | 2.6 | 4660 |
| 72 | 4.3 | 6255 |
| 73 | 1.8 | 9194 |
| 74 | 29.3 | 4340 |
| 75 | 2.8 | 5292 |
| 76 | 17.8 | 34581 |
| 77 | 5.6 | 10145 |
| 78 | 5.6 | 3198 |
| 79 | 3.4 | 12092 |
| 80 | 4.6 | 5045 |
| 81 | 1.9 | 12298 |
| 82 | 2.9 | 30434 |
| 83 | 1.9 | 27501 |
| 84 | 2.9 | 9727 |
| 85 | 2.0 | 10378 |
| 86 | 2.3 | 22405 |
| 88 | 2.9 | 3230 |
| 89 | 8.4 | 4629 |
| 90 | 5.7 | 8086 |
| 91 | 5.0 | 7183 |
| 92 | 18.6 | 4553 |
| 93 | 2.2 | 6158 |
| 94 | 11.5 | 51173 |
| 96 | 2.6 | 26586 |
| 97 | 2.1 | 17341 |
| 98 | 2.4 | 17947 |
| 99 | 2.0 | 8475 |
| 100 | 2.2 | 11580 |
| 101 | 2.1 | 11585 |
| 102 | 2.3 | 12042 |
| 103 | 10.3 | 35127 |

Example 105

Human PXR Activation Assay

Luciferase Reporter Gene Assay.

A stably transformed tumor cell line (DPX2) was plated on 96-well microtiter plates. DPX2 cells harbor the human PXR gene (NR1I2) and a luciferase reporter gene linked to two promoters identified in the human CYP3A4 gene, namely XREM and PXRE. The cells were treated with six concentrations of each compound (0.15~50 µM) and incubated for 24 hours. The number of viable cells was determined and the reporter gene activity was assessed. Positive control: Rifampicin at 6 concentrations (0.1~20 µM). % $E_{max}$ relative to the maximum fold induction by 10 or 20 µM RIF was calculated for test compounds according to the following equation which adjusts for the DMSO background: % $E_{max}$=(Fold induction−1)/(Maximum fold induction by RIF−1)×100%.

TABLE 2

| Compound Number | % $E_{max}$ at 15 µM |
|---|---|
| 2 | 4.5 |
| 3 | 7.5 |
| 4 | 3 |
| 5 | 32 |
| 6 | 0 |
| 7 | 6 |
| 8 | 7 |
| 9 | 7 |
| 10 | 19 |
| 15 | 20 |
| 16 | 17 |
| 17 | 7 |
| 18 | 4 |
| 19 | 2 |
| 20 | 2 |
| 23 | 45 |
| 28 | 6 |
| 29 | 3 |
| 32 | 14 |
| 33 | 17 |
| 36 | 3 |
| 37 | 2 |
| 38 | 7 |
| 39 | 6 |
| 40 | 0 |
| 41 | 11.5 |
| 42 | 21 |
| 43 | 18 |
| 44 | 4 |
| 45 | 19 |
| 46 | 34 |
| 47 | 11 |
| 48 | 5 |
| 54 | 2 |
| 55 | 24 |
| 56 | 3 |
| 57 | 3 |
| 58 | 1 |
| 59 | 4 |
| 60 | 3 |
| 61 | 1 |
| 63 | 13 |
| 64 | 8 |
| 66 | 0 |
| 67 | 0 |
| 68 | 6 |
| 69 | 5 |
| 70 | 10 |
| 71 | 3 |
| 72 | 4 |
| 73 | 7 |
| 75 | 0 |
| 77 | 11 |
| 79 | 0 |
| 80 | 2 |
| 81 | 1 |
| 82 | 1 |
| 83 | 1 |
| 84 | 21 |
| 85 | 77 |
| 86 | 30 |
| 88 | 27 |

TABLE 2-continued

| Compound Number | % $E_{max}$ at 15 µM |
|---|---|
| 89 | 5 |
| 90 | 11 |
| 91 | 3 |
| 92 | 3 |
| 93 | 9 |
| 96 | 11 |
| 97 | 9 |
| 98 | 0 |
| 99 | 17 |
| 100 | 45 |
| 102 | 123 |
| 103 | 0 |

Example 106

OCT2 Inhibition Assay

The dose dependent inhibition of OCT2 mediated uptake of a model substrate $^{14}$C-Tetraethylammonium (TEA) by test compounds was studied in wild-type and OCT2-transfected MDCKII cells at 7 concentrations from 0.014 µM to 10 µM.

MDCKII cells were maintained in minimal essential medium (MEM) with 1% Pen/Strep, 10% fetal bovine serum, and 0.25 mg/mL hygromycin B in an incubator set at 37° C., 90% humidity and 5% $CO_2$. 24 hours prior to assay, media containing 5 mM sodium butyrate were added to MDCKII cells in flasks, and cells were grown to 80-90% confluence. On assay day, cells were trypsinized and resuspended in Krebs-Henseleit Buffer (KHB), pH 7.4 at 5×10$^6$ million cells/mL. Cells were preincubated for 15 min in assay plate before addition of test compound or substrate.

Test compounds were serially diluted in DMSO and then spiked (2 µL) into in 0.4 mL KHB buffer containing wild-type or OCT2-transfected cells and incubated for 10 minutes. Assay was initiated with the addition of 0.1 mL of 100 µM $^{14}$C-TEA in KHB buffer (20 µM final concentration after mixing). The concentration of TEA is based on the $K_m$. After 10 minutes of incubation, the assay mixture was quenched with addition of 0.5 mL of ice-cold IX PBS buffer. Samples were then centrifuged at 1000 rpm for 5 min and supernatants were removed. Wash steps were repeated four times with ice-cold PBS. Finally, the cell pellets were lysed with 0.2N NaOH and let sit at room temperature for at least 30 min to ensure complete lysis. Samples were then counted on liquid scintillation counter and dpm counts were used to perform the following calculations. The % inhibition was calculated as follows: % inhibition=[1−{[OCT2]$_i$−[WT]$_{ni}$}/{[OCT2]$_{ni}$−[WT]$_{ni}$}]*100 where, [OCT2]$_i$ represents the dpm count in the presence of test compound for either OCT2 cells, [OCT2]$_{ni}$ represents the dpm count in the absence of test compound for OCT2 cells and [WT]$_{ni}$ represents the dpm count in the absence of test compound for wild type cells, respectively.

TABLE 3

| Compound Number | IC$_{50}$ (nM) |
|---|---|
| 2 | 240 |
| 3 | 250 |
| 5 | 2230 |
| 11 | 10000 |

TABLE 3-continued

| Compound Number | IC$_{50}$ (nM) |
|---|---|
| 13 | 610 |
| 36 | 10000 |
| 39 | 358 |
| 40 | 204 |
| 41 | 2823 |
| 42 | 487 |
| 45 | 137 |
| 47 | 6200 |
| 48 | 4909 |
| 55 | 476 |
| 63 | 42 |
| 64 | 94 |
| 77 | 3830 |
| 82 | 10000 |
| 83 | 10000 |
| 96 | 1357 |
| 98 | 3726 |
| 99 | 1506 |
| 100 | 450 |

The data in Tables 1, 2 and 3 represent an average over time of each assays for each compound. For certain compounds, multiple assays have been conducted over the life of the project. Thus, the data reported in Tables 1, 2 and 3 include the data reported in the priority documents, as well as data from assays run in the intervening period.

Example 107

Pharmacokinetic Analysis Following Oral or Intravenous Administration to Beagle Dogs Pharmacokinetic analysis was performed on various test compounds following intravenous or oral administration to beagle dogs.

For pharmacokinetic analysis of intravenously administered compounds, the test compounds were formulated in 5% Ethanol, 55% PEG 300, and 40% water at 0.1 mg/mL for IV infusion. For pharmacokinetic analysis of orally administered compounds, the test compounds were formulated as an aqueous suspension in 0.1% Tween 20, 0.5% HPMC LV100 in Di Water at 1 mg/kg.

Each dosing group consisted of 3 male, non-naïve purebred beagle dogs. At dosing, the animals weighed between 10 to 13 kg. The animals were fasted overnight prior to dose administration and up to 4 hr after dosing. For studies of intravenous administration, the test article was administered to the animals by intravenous infusion over 30 min. The rate of infusion was adjusted according to the body weight of each animal to deliver a dose of 0.5 mg/kg. For studies of oral administration, the test article was administered according to the body weight of each animal to deliver a dose of 1 mg/kg.

For pharmacokinetic analysis of intravenously administered compounds, serial venous blood samples (approximately 1 mL each) were taken from each animal at 0, 0.250, 0.483, 0.583, 0.750, 1.00, 1.50, 2.00, 4.00, 8.00, 12.0, and 24.0 hours after dosing. The blood samples were collected into Vacutainer™ tubes containing EDTA-K2 as the anticoagulant and were immediately placed on wet ice pending centrifugation for plasma. An LC/MS/MS method was used to measure the concentration of the test compound in plasma. An aliquot of 100 μL of each plasma sample was added to a clean 96 well plate, and 400 μL of cold acetonitrile/internal standard solution (ACN)/(ISTD) was added. After protein precipitation, an aliquot of 110 μL of the supernatant was transferred to a clean 96-well plate and diluted with 300 μL of water. An aliquot of 25 μL of the above solution was injected into a TSQ Quantum Ultra LC/MS/MS system utilizing a Hypersil Gold C$_{18}$ HPLC column (50×3.0 mm, 5 μm; Thermo-Hypersil Part #25105-053030). An Agilent 1200 series binary pump (P/N G1312A Bin Pump) was used for elution and separation, and an HTS Pal autosampler (LEAP Technologies, Carrboro, N.C.) was used for sample injection. A TSQ Quantum Ultra triple quadrupole mass spectrometer was utilized in selective reaction monitoring mode (Thermo Finnigan, San Jose, Calif.). Liquid chromatography was performed using two mobile phases: mobile phase A contained 1% acetonitrile in 2.5 mM ammonium formate aqueous solution with pH of 3.0, and mobile phase B contained 90% acetonitrile in 10 mM ammonium formate with pH of 4.6. Non-compartmental pharmacokinetic analysis was performed on the plasma concentration-time data. The resulting data are shown in the first three columns of Table 4. In Table 4, CL refers to clearance, which characterizes the rate at which drug is removed from plasma. The lower the clearance of a drug is, the longer the elimination half-life is in the body. V$_{ss}$ refers to the steady state volume of distribution and indicates how well a drug is distributed into the tissues. The larger the V$_{ss}$ is, the longer the elimination half-life is in the body. MRT refers to mean residence time, which is a measure of the average time molecules exist in the body.

For pharmacokinetic analysis of orally administered compounds, serial venous blood samples (approximately 0.3 mL each) were taken from each animal at time points of 0, 0.25, 0.50, 1.0, 2.0, 4.0, 6.0, 8.0, 12.0 and 24.0 hours after dosing. Blood samples were collected, prepared and analyzed in a similar way to the intranveous studies described above. Non-compartmental pharmacokinetic analysis was performed on the plasma concentration-time data. The resulting data are shown in the last three columns of Table 4. In Table 4, F (%) refers to oral bioavailability. C$_{max}$ refers to the peak plasma concentration of the compound after administration. AUC refers to area under the curve and is a measure of total plasma exposure of the indicated compound.

TABLE 4

| Compound # | CL (L/h/kg) | V$_{ss}$ (L/kg) | MRT (h) | F (%) aqueous suspension | C$_{max}$ (μM) aqueous suspension | AUC (μM * h) aqueous suspension |
|---|---|---|---|---|---|---|
| 98 | 0.047 | 0.16 | 3.3 | n/a | n/a | n/a |
| 83 | 0.161 | 0.38 | 2.4 | n/a | n/a | n/a |
| 55 | 0.058 | 0.24 | 4.2 | n/a | n/a | n/a |
| 77 | 0.300 | 0.64 | 2.2 | n/a | n/a | n/a |
| 41 | 0.015 | 0.11 | 7.5 | 10.7 | 2.4 | 16.3 |
| 42 | 0.020 | 0.15 | 7.1 | 28.0 | 4.5 | 28.6 |
| 47 | 0.014 | 0.10 | 7.4 | 12.6 | 2.8 | 20.4 |
| 8 | 0.498 | 0.87 | 1.8 | n/a | n/a | n/a |
| 7 | 0.510 | 1.20 | 2.3 | n/a | n/a | n/a |
| 3 | 0.047 | 0.23 | 4.9 | 18.7 | 1.2 | 9.2 |
| 2 | 0.030 | 0.20 | 6.5 | 40.7 | 7.8 | 66.1 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having Formula (I):

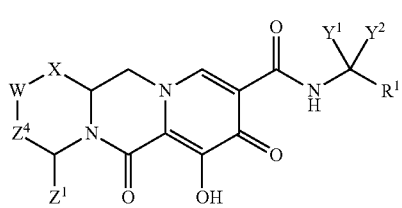

or a stereoisomer or pharmaceutically acceptable salt thereof,
wherein:
X is —$NZ^3$—;
W is —$CHZ^2$—;
$Z^2$ is hydrogen;
$Z^1$ and $Z^3$, taken together, form -L-, wherein L is —$C(R^a)_2$—;
$Z^4$ is —$CH_2CH_2$—;
$Y^1$ and $Y^2$ are each independently hydrogen, $C_{1-3}$alkyl or $C_{1-3}$haloalkyl;
$R^1$ is phenyl substituted with one, two or three halogens; and
each $R^a$ is, independently, hydrogen, halogen, hydroxy or $C_{1-4}$alkyl.

2. The compound of claim 1, wherein the compound is selected from the group consisting of:

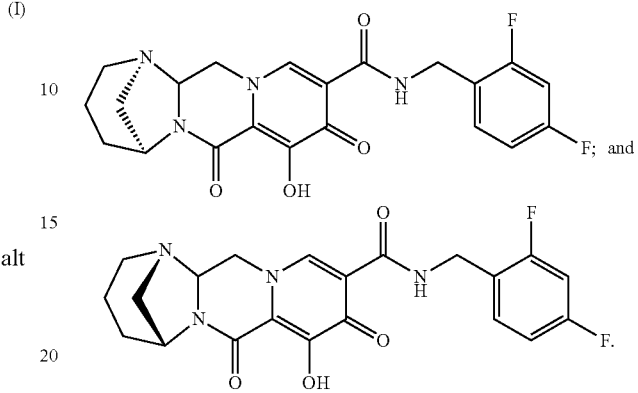

3. A pharmaceutical composition comprising a compound of claim 1, or a stereoisomer or pharmaceutically acceptable salt thereof, and a pharmaceutically acceptable carrier, diluent or excipient.

* * * * *